(12) United States Patent
Glick et al.

(10) Patent No.: US 10,961,270 B2
(45) Date of Patent: *Mar. 30, 2021

(54) COMPOUNDS AND COMPOSITIONS FOR TREATING CONDITIONS ASSOCIATED WITH STING ACTIVITY

(71) Applicant: Innate Tumor Immunity, Inc., Princeton, NJ (US)

(72) Inventors: Gary Glick, Ann Arbor, MI (US); Shomir Ghosh, Brookline, MA (US); Edward James Olhava, Newton, MA (US); William R. Roush, Tequesta, FL (US); Roger Jones, Martinsville, NJ (US)

(73) Assignee: Innate Tumor Immunity, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/778,281

(22) Filed: Jan. 31, 2020

(65) Prior Publication Data

US 2020/0165288 A1 May 28, 2020

Related U.S. Application Data

(63) Continuation of application No. 15/748,685, filed as application No. PCT/US2017/013066 on Jan. 11, 2017, now Pat. No. 10,604,542.

(60) Provisional application No. 62/436,759, filed on Dec. 20, 2016, provisional application No. 62/277,273, filed on Jan. 11, 2016.

(51) Int. Cl.

| | | |
|---|---|---|
| *A61K 31/7084* | (2006.01) | |
| *C07H 21/00* | (2006.01) | |
| *C07H 21/02* | (2006.01) | |
| *A61K 39/395* | (2006.01) | |
| *C07K 16/28* | (2006.01) | |
| *A61K 39/00* | (2006.01) | |

(52) U.S. Cl.
CPC ......... *C07H 21/00* (2013.01); *A61K 31/7084* (2013.01); *A61K 39/3955* (2013.01); *C07H 21/02* (2013.01); *C07K 16/2818* (2013.01); *A61K 2039/505* (2013.01)

(58) Field of Classification Search
None
See application file for complete search history.

(56) References Cited

U.S. PATENT DOCUMENTS

| | | |
|---|---|---|
| 9,549,944 B2 | 1/2017 | Dubensky, Jr. et al. |
| 9,840,533 B2 | 12/2017 | Patel et al. |
| 10,604,542 B2 * | 3/2020 | Glick ..................... C07H 21/00 |
| 2014/0205653 A1 | 7/2014 | Dubensky, Jr. et al. |
| 2015/0010613 A1 | 1/2015 | Dubensky, Jr. et al. |
| 2015/0056224 A1 | 2/2015 | Dubensky, Jr. et al. |
| 2017/0044206 A1 | 2/2017 | Altman et al. |

FOREIGN PATENT DOCUMENTS

| | | |
|---|---|---|
| WO | WO 2013/185052 A1 | 12/2013 |
| WO | WO 2014/093936 A1 | 6/2014 |
| WO | WO 2014/179335 A1 | 11/2014 |
| WO | WO 2014/189805 A1 | 11/2014 |
| WO | WO 2015/077354 A1 | 5/2015 |
| WO | WO 2015/077534 A1 | 5/2015 |
| WO | WO 2016/096174 A1 | 6/2016 |
| WO | WO 2016/096577 A1 | 6/2016 |
| WO | WO 2017/027645 A1 | 2/2017 |
| WO | WO 2017/027646 A1 | 2/2017 |
| WO | WO 2017/161349 A1 | 9/2017 |

* cited by examiner

*Primary Examiner* — Traviss C McIntosh, III
(74) *Attorney, Agent, or Firm* — Elliott Korsen

(57) ABSTRACT

This disclosure features chemical entities (e.g., a compound that modulates (e.g., agonizes) Stimulator of Interferon Genes (STING), or a pharmaceutically acceptable salt, and/or hydrate, and/or cocrystal, and/or drug combination of the compound) that are useful, e.g., for treating a condition, disease or disorder in which a decrease or increase in STING activity (e.g., a decrease, e.g., a condition, disease or disorder associated with repressed or impaired STING signaling) contributes to the pathology and/or symptoms and/or progression of the condition, disease or disorder (e.g., cancer) in a subject (e.g., a human). This disclosure also features compositions as well as other methods of using and making the same.

7 Claims, No Drawings

COMPOUNDS AND COMPOSITIONS FOR TREATING CONDITIONS ASSOCIATED WITH STING ACTIVITY

CROSS REFERENCE TO RELATED APPLICATIONS

This application is a continuation of U.S. application Ser. No. 15/748,685, filed Jan. 30, 2018, now allowed, which is a 371 application of PCT/US2017/013066, filed Jan. 11, 2017, which claims benefit to U.S. Provisional Application No. 62/436,759, filed Dec. 20, 2016 and U.S. Provisional Application No. 62/277,273, filed on Jan. 11, 2016, each of which is incorporated herein by reference in its entirety.

TECHNICAL FIELD

This disclosure features chemical entities (e.g., a compound that modulates (e.g., agonizes) Stimulator of Interferon Genes (STING), or a pharmaceutically acceptable salt, and/or hydrate, and/or cocrystal, and/or drug combination of the compound) that are useful, e.g., for treating a condition, disease or disorder in which a decrease or increase in STING activity (e.g., a decrease, e.g., a condition, disease or disorder associated with repressed or impaired STING signaling) contributes to the pathology and/or symptoms and/or progression of the condition, disease or disorder (e.g., cancer) in a subject (e.g., a human). This disclosure also features compositions as well as other methods of using and making the same.

BACKGROUND

STING, also known as transmembrane protein 173 (TMEM173) and MPYS/MITA/ERIS, is a protein that in humans is encoded by the TMEM173 gene. STING has been shown to play a role in innate immunity. STING induces type I interferon production when cells are infected with intracellular pathogens, such as viruses, mycobacteria and intracellular parasites. Type I interferon, mediated by STING, protects infected cells and nearby cells from local infection in an autocrine and paracrine manner. The STING pathway is a pathway that is involved in the detection of cytosolic DNA.

The STING signaling pathway is activated by cyclic dinucleotides (CDNs), which may be produced by bacteria or produced by antigen presenting cells in response to sensing cytosolic DNA. Unmodified CDNs have been shown to induce type I interferon and other co-regulated genes, which in turn facilitate the development of a specific immune response (see, e.g., Wu and Sun, et al., Science 2013, 339, 826-830). WO 2015/077354 discloses the use of STING agonists for the treatment of cancer.

SUMMARY

This disclosure features chemical entities (e.g., a compound that modulates (e.g., agonizes) Stimulator of Interferon Genes (STING), or a pharmaceutically acceptable salt, and/or hydrate, and/or cocrystal, and/or drug combination of the compound) that are useful, e.g., for treating a condition, disease or disorder in which a decrease or increase in STING activity (e.g., a decrease, e.g., a condition, disease or disorder associated with repressed or impaired STING signaling) contributes to the pathology and/or symptoms and/or progression of the condition, disease or disorder (e.g., cancer) in a subject (e.g., a human).

In certain embodiments, the chemical entities described herein induce an immune response in a subject (e.g., a human). In certain embodiments, the chemical entities described herein induce STING-dependent type I interferon production in a subject (e.g., a human). This disclosure also features compositions as well as other methods of using and making the same.

An "agonist" of STING includes compounds that, at the protein level, directly bind or modify STING such that an activity of STING is increased, e.g., by activation, stabilization, altered distribution, or otherwise.

Certain compounds described herein that agonize STING to a lesser extent than a STING full agonist can function in assays as antagonists as well as agonists. These compounds antagonize activation of STING by a STING full agonist because they prevent the full effect of STING interaction. However, the compounds also, on their own, activate some STING activity, typically less than a corresponding amount of the STING full agonist. Such compounds may be referred to as "partial agonists of STING".

In some embodiments, the compounds described herein are agonists (e.g. full agonists) of STING. In other embodiments, the compounds described herein are partial agonists of STING.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

While not wishing to be bound by theory, it is believed that the partial agonists of STING described herein provide advantages with regard to treating the disorders described herein. By way of example, the partial agonists of STING described herein exhibit intrinsic activities that are expected to be both (i) high enough to induce an anti-tumor response (i.e., kill one or more tumor cells) and (ii) low enough to reduce the likelihood of producing toxicity-related side effects. As discussed above, partial agonists can antagonize activation of STING by a STING full agonist because they prevent the full effect of STING interaction, thereby reducing the activity of the STING full agonist. It is believed that this antagonism can also modulate (e.g., reduce) the toxicity profile of the STING full agonist.

Accordingly, this disclosure contemplates methods in which the partial agonists of STING described herein are combined with one (or more) full agonists of STING (e.g., as described anywhere herein) to provide therapeutic drug combinations that are both efficacious and exhibit relatively low toxicity.

In one aspect, compounds of Formula A, or a pharmaceutically acceptable salt thereof, are featured:

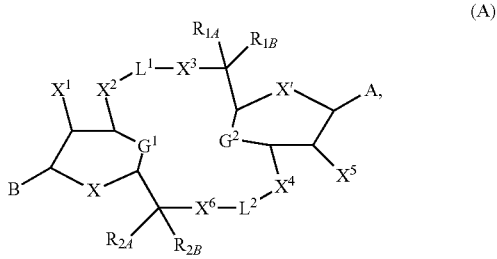

(A)

in which A, B, X, X', $G^1$, $G^2$, $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein. $X^1$ and $X^5$ can each be independently "up" or "down."

In another aspect, compounds of Formula B, or a pharmaceutically acceptable salt thereof, are featured:

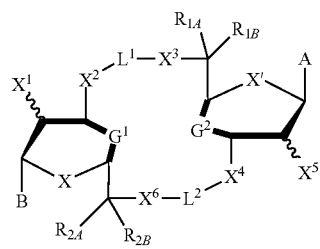

(B)

in which A, B, X, X', $G^1$, $G^2$, $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein. $X^1$ and $X^5$ can each be independently "up" or "down."

In one aspect, compounds of Formula I, or a pharmaceutically acceptable salt thereof, are featured:

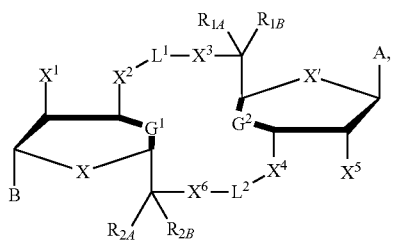

(I)

in which A, B, X, X', $G^1$, $G^2$, $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein.

In one aspect, compounds of Formula A', or a pharmaceutically acceptable salt thereof, are featured:

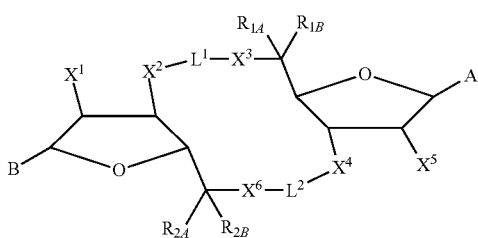

(A')

in which A, B, X, X', $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein. $X^1$ and $X^5$ can each be independently "up" or "down."

In another aspect, compounds of Formula B', or a pharmaceutically acceptable salt thereof, are featured:

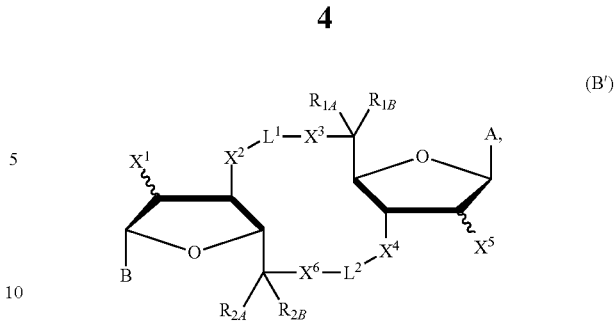

(B')

in which A, B, X, X', $X^1$, $X^2$, $X^3$, $X^4$, $X^5$, $X^6$, $L^1$, $L^2$, $R_{1A}$, $R_{1B}$, $R_{2A}$, and $R_{2B}$ can be as defined anywhere herein. $X^1$ and $X^5$ can each be independently "up" or "down."

In another aspect, compounds of Formula I-A, or a pharmaceutically acceptable salt thereof, are featured:

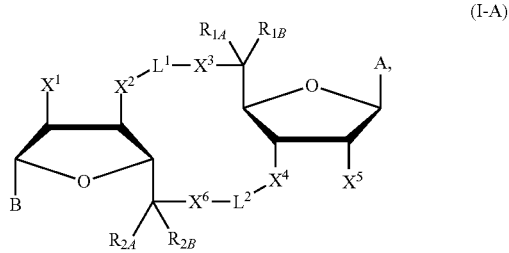

(I-A)

in which A, B, X, X', $X^1$, $X^2$, $X^3$, $X^4$, $X^5$, $X^6$, L, $L^2$, $R_{1A}$, $R_{1B}$, $R_{2A}$, and $R_{2B}$ can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing) STING activity are featured that include contacting STING with a chemical entity described herein (e.g., a compound described generically or specifically herein or a pharmaceutically acceptable salt thereof or compositions containing the same). Methods include in vitro methods, e.g., contacting a sample that includes one or more cells comprising STING (e.g., innate immune cells, e.g., mast cells, macrophages, dendritic cells (DCs), and natural killer cells) with the chemical entity. The contacting can, in some cases, induce an immune response sufficient to kill at least one of the one or more cancer cells. Methods can also include in vivo methods; e.g., administering the chemical entity to a subject (e.g., a human) having a disease in which repressed or impaired STING signaling contributes to the pathology and/or symptoms and/or progression of the disease (e.g., cancer; e.g., a refractory cancer).

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same).

In a further aspect, methods of inducing an immune response (e.g., an innate immune response) in a subject in need thereof are featured that include administering to the subject an effective amount of a chemical entity described herein (e.g., a compound described generically or specifically herein or a pharmaceutically acceptable salt thereof or compositions containing the same).

In another aspect, methods of inducing induce STING-dependent type I interferon production in a subject in need thereof are featured that include administering to the subject an effective amount of a chemical entity described herein (e.g., a compound described generically or specifically herein or a pharmaceutically acceptable salt thereof or compositions containing the same).

In a further aspect, methods of treatment of a disease in which repressed or impaired STING signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which repressed or impaired STING signaling contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment that include administering to a subject a chemical entity described herein (e.g., a compound described generically or specifically herein or a pharmaceutically acceptable salt thereof or compositions containing the same), wherein the chemical entity is administered in an amount effective to treat a disease in which repressed or impaired STING signaling contributes to the pathology and/or symptoms and/or progression of the disease, thereby treating the disease.

Embodiments can include one or more of the following features.

The chemical entity can be administered in combination with one or more additional cancer therapies (e.g., surgery, radiotherapy, chemotherapy, toxin therapy, immunotherapy, cryotherapy or gene therapy, or a combination thereof; e.g., chemotherapy that includes administering one or more (e.g., two, three, four, five, six, or more) additional chemotherapeutic agents. Non-limiting examples of additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a vinca alkaloid and/or a taxane; e.g., Vincristine, Vinblastine, Vinorelbine and/or Vindesine Taxol, Paclltaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumumab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1-PD-L1, PD-1-PD-L2, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TLIA, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL 12, Phosphatidylserine, TIM3, Phosphatidylserine-TIM3, SIRPA-CD47, VEGF, Neuropilin, CD160, CD30, and CD155 (e.g., CTLA-4 or PD1 or PD-L1).

The subject can have cancer; e.g., the subject has undergone and/or is undergoing and/or will undergo one or more cancer therapies.

Non-limiting examples of cancer include melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma. In certain embodiments, the cancer can be a refractory cancer.

The chemical entity can be administered intratumorally.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "STING" is meant to include, without limitation, nucleic acids, polynucleotides, oligonucleotides, sense and antisense polynucleotide strands, complementary sequences, peptides, polypeptides, proteins, homologous and/or orthologous STING molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21*st ed.;* Lippincott Williams & Wilkins: Philadelphia, Pa., 2005; *Handbook of Pharmaceutical Excipients,* 6*th ed.*; Rowe et al., Eds.; The Pharmaceutical Press and the American Pharmaceutical Association: 2009; *Handbook of Pharmaceutical Additives,* 3*rd ed.*; Ash and Ash Eds.; Gower Publishing Company: 2007; *Pharmaceutical Preformulation and Formulation,* 2*nd ed.*; Gibson Ed.; CRC Press LLC: Boca Raton, Fla., 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a divalent alkyl (e.g., —CH$_2$—).

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent. Examples of aryl groups include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the accompanying drawings and the description below. Other features and advantages of the invention will be apparent from the description and drawings, and from the claims.

DETAILED DESCRIPTION

This disclosure features chemical entities (e.g., a compound that modulates (e.g., agonizes) Stimulator of Interferon Genes (STING), or a pharmaceutically acceptable salt, and/or hydrate, and/or cocrystal, and/or drug combination of the compound) that are useful, e.g., for treating a condition, disease or disorder in which a decrease or increase in STING activity (e.g., a decrease, e.g., a condition, disease or disorder associated with repressed or impaired STING signaling) contributes to the pathology and/or symptoms and/or progression of the condition, disease or disorder (e.g., cancer) in a subject (e.g., a human).

In certain embodiments, the chemical entities described herein induce an immune response in a subject (e.g., a human). In certain embodiments, the chemical entities described herein induce STING-dependent type I interferon production in a subject (e.g., a human). This disclosure also features compositions as well as other methods of using and making the same.

Formula I Compounds

In one aspect, compounds of Formula A, or a pharmaceutically acceptable salt thereof, are featured:

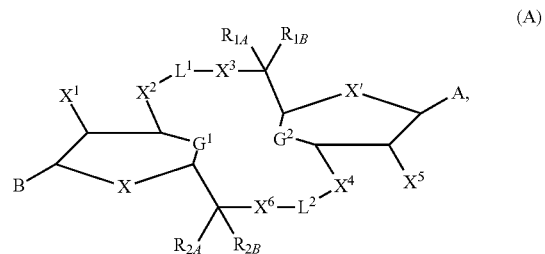

(A)

wherein:

A and B are each independently selected from the group consisting of Formulae (i), (ii), (iii), and (iv):

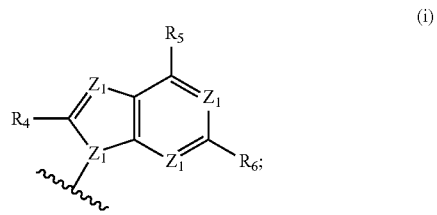

(i)

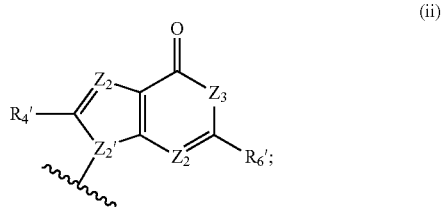

(ii)

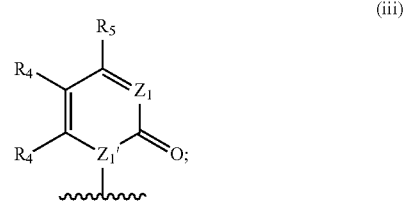

(iii)

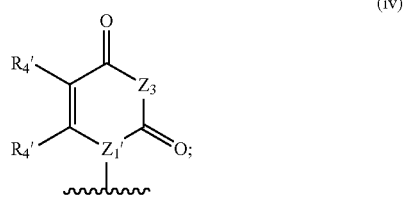

(iv)

X and X' are each independently selected from the group consisting of O, S, S(O), SO$_2$, CH$_2$, CHF, CF$_2$, CH$_2$O, OCH$_2$, CH$_2$CH$_2$, CH=CH, NR$^3$, and N(O$^-$)R$^3$;

G$^1$ is a bond connecting (i) the carbon directly attached to X$^2$ and (ii) the carbon directly attached to C(R$^{2A}$)(R$^{2B}$)(X$^6$); or is C(R$^{G1A}$)(R$^{G1B}$);

G$^2$ is a bond connecting (i) the carbon directly attached to X$^4$ and (ii) the carbon directly attached to C(R$^{1A}$)(R$^{1B}$)(X$^3$); or is C(R$^{G2A}$)(R$^{G2B}$);

X$^1$ and X$^5$ are each independently selected from the group consisting of H, C$_{1-4}$ alkyl, C$_{1-4}$ haloalkyl, halo (e.g., F), —CN, —NO$_2$, —N$_3$, —OH, —OR$^{a1}$, —SH, —SR$^{a1}$, —C(O)H, —C(O)R$^{a1}$, —C(O)NR$^{c1}$R$^{d1}$, —C(O)OH, —C(O)OR$^{a1}$, —OC(O)H, —OC(O)R$^{a1}$, —OC(O)NR$^{b1}$R$^{c1}$, —C(=NR$^{c1}$)NR$^{b1}$R$^{c1}$, —NR$^{d1}$C(=NR$^{e1}$)NR$^{b1}$R$^{c1}$, —NR$^{b1}$R$^{c1}$, —$^+$NR$^{b1}$R$^{c1}$R$^{d1}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, —NR$^{d1}$S(O)$_2$NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$;

X$^2$, X$^3$, X$^4$ and X$^6$ are each independently selected from the group consisting of O, S, and N—R$^3$;

L$^1$ is

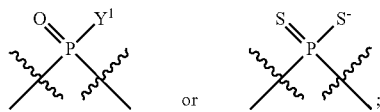

or

L$^2$ is

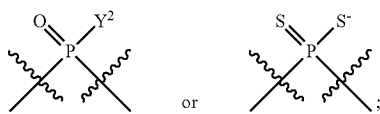

or;

Y$^1$ and Y$^2$ are each independently selected from the group consisting of —OH, —OR$^{a1}$, O$^-$, —SH, —SR$^{a1}$, S$^-$; and —NR$^{b1}$R$^{c1}$;

R$^{1A}$ and R$^{1B}$ are each independently selected from the group consisting of H; halo; C$_{1-4}$ alkyl; C$_{1-4}$ haloalkyl; C$_{2-4}$ alkenyl; C$_{2-4}$ alkynyl; and C$_{3-5}$ cycloalkyl, which is optionally substituted with from 1-4 independently selected C$_{1-4}$ alkyl; or R$^{1A}$ and R$^{1B}$, together with the carbon atom to which each is attached, form a C$_{3-5}$ cycloalkyl or heterocyclyl, including from 4-5 ring atoms, wherein from 1-2 (e.g., 1) ring atoms are independently selected from the group consisting of nitrogen and oxygen (e.g., oxetane), wherein the C$_{3-5}$ cycloalkyl or heterocyclyl ring can each be optionally substituted with from 1-4 independently selected C$_{1-4}$ alkyl;

R$^{2A}$ and R$^{2B}$ are each independently selected from the group consisting of H; halo; C$_{1-4}$ alkyl; C$_{1-4}$ haloalkyl; C$_{2-4}$ alkenyl; C$_{2-4}$ alkynyl; and C$_{3-5}$ cycloalkyl, which is optionally substituted with from 1-4 independently selected C$_{1-4}$ alkyl; or R$^{2A}$ and R$^{2B}$, together with the carbon atom to which each is attached, form a C$_{3-5}$ cycloalkyl or heterocyclyl, including from 4-5 ring atoms, wherein from 1-2 (e.g., 1) ring atoms are independently selected from the group consisting of nitrogen and oxygen (e.g., oxetane), wherein the C$_{3-5}$ cycloalkyl or heterocyclyl ring can each be optionally substituted with from 1-4 independently selected C$_{1-4}$ alkyl, Z$_1$ is N or C—R$^4$;
Z$_{1'}$ is N or C—H;
Z$_2$ is N or C—R$^{4'}$;
Z$_{2'}$ is N or C—H;
Z$_3$ is N—R$^3$ or C—R$^4$;

each occurrence of R$^{a1}$ is independently selected from the group consisting of:
C$_{1-10}$ alkyl optionally substituted with from 1-3 R$^A$;
C$_{1-10}$ haloalkyl optionally substituted with from 1-3 R$^A$;
C$_{2-10}$ alkenyl optionally substituted with from 1-3 R$^B$,
C$_{2-10}$ alkynyl optionally substituted with from 1-3 R$^B$,
C$_{3-10}$ cycloalkyl optionally substituted with from 1-5 R$^C$;
(C$_{3-10}$ cycloalkyl)-C$_{1-6}$ alkylene, wherein the alkylene serves as the point of attachment, and wherein the C$_{3-10}$ cycloalkyl optionally substituted with from 1-5 R$^C$;
heterocyclyl, including from 3-10 ring atoms, wherein from 1-3 ring atoms are independently selected from the group consisting of nitrogen, oxygen and sulfur, and which is optionally substituted with from 1-5 R$^C$;
(heterocyclyl as defined above)-C$_{1-6}$ alkylene, wherein the alkylene serves as the point of attachment, and wherein the heterocyclyl is optionally substituted with from 1-5 R$^C$;
C$_{6-10}$ aryl optionally substituted with from 1-5 R$^D$;
heteroaryl including from 5-10 ring atoms, wherein from 1-4 ring atoms are independently selected from the group consisting of nitrogen, oxygen and sulfur, and which is optionally substituted with from 1-5 R$^D$; and
(heteroaryl as defined above)-C$_{1-6}$ alkylene, wherein the alkylene serves as the point of attachment, and wherein the heteroaryl optionally substituted with from 1-5 R$^D$;

each occurrence of R$^3$, R$^{b1}$, R$^{c1}$, R$^{d1}$, and R$^{e1}$ is independently selected from the group consisting of: H; R$^{a1}$; —C(O)H, —C(O)R$^{a1}$, —C(O)NR$^{c1}$R$^{d1}$, —C(O)OR$^{a1}$, —OC(O)H, —C(=NR$^{c1}$)NR$^{b1}$R$^{c1}$, —NR$^{d1}$C(=NR$^{e1}$)NR$^{b1}$R$^{c1}$, —NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$; or R$^{b1}$ and R$^{c1}$ taken together with the nitrogen atom to which each is attached form a heterocyclyl, including from 3-10 ring atoms, wherein from 1-3 ring atoms are independently selected from the group consisting of nitrogen, oxygen and sulfur, and which is optionally substituted with from 1-5 R$^C$; (e.g., azetidinyl, morpholino, piperidinyl);

each occurrence of R$^{G1A}$, R$^{G1B}$, R$^{G1A}$(R$^{G2A}$), R$^{G1B}$ (R$^{G2B}$), R$^4$, R$^{4'}$, R$^5$, R$^6$, and R$^{6'}$ is independently selected from the group consisting of: H; R$^{a1}$; halo, —CN, —NO$_2$, —N$_3$, —OH, —OR$^{a1}$, —SH, —SR$^{a1}$, —C(O)H, —C(O)R$^{a1}$, —C(O)NR$^{c1}$R$^{d1}$, —C(O)OH, —C(O)OR$^{a1}$, —OC(O)H, —OC(O)R$^{a1}$, —OC(O)NR$^{b1}$R$^{c1}$, —C(=NR$^{e1}$)NR$^{b1}$R$^{c1}$, —NR$^{d1}$C(=NR$^{e1}$)NR$^{b1}$R$^{c1}$, —NR$^{b1}$R$^{c1}$, —N$^+$R$^{b1}$R$^{c1}$R$^{d1}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, —NR$^{d1}$S(O)$_2$NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$;

each occurrence of R$^A$ is independently selected from the group consisting of: —CN; —OH; C$_{1-6}$ alkoxy; C$_{1-6}$ haloalkoxy; —C(O)NRR', wherein R' and R" are each independently selected from H and C$_{1-4}$ alkyl; —C(O)OH; —C(O)O(C$_{1-6}$ alkyl); and —NR"R'", wherein R" and R'" are each independently selected from the group consisting of H, C$_{1-4}$ alkyl, —SO$_2$(C$_{1-6}$ alkyl), —C(O)(C$_{1-6}$ alkyl), and —C(O)O(C$_{1-6}$ alkyl);

each occurrence of R$^B$ is independently selected from the group consisting of: halo; —CN; —OH; C$_{1-6}$ alkoxy; C$_{1-6}$ haloalkoxy; —C(O)NRR', wherein R' and R" are each independently selected from H and C$_{1-4}$ alkyl; —C(O)OH; —C(O)O(C$_{1-6}$ alkyl); and —NR"R'", wherein R" and R'" are each each independently selected from the group consisting of H, $C_{1-4}$ alkyl, —$SO_2(C_{1-6}$ alkyl), —$C(O)(C_{1-6}$ alkyl), and —$C(O)O(C_{1-6}$ alkyl);

each occurrence of $R^C$ is independently selected from the group consisting of: $C_{1-6}$ alkyl; $C_{1-4}$ haloalkyl; halo; —CN; —OH; oxo; $C_{1-6}$ alkoxy; $C_{1-6}$ haloalkoxy; —C(O)NR'R", wherein R' and R" are each independently selected from H and $C_{1-4}$ alkyl; —$C(O)(C_{1-6}$ alkyl); —C(O)OH; —C(O)O($C_{1-6}$ alkyl); and —NR"R''', wherein R" and R''' are each independently selected from the group consisting of H, $C_{1-4}$ alkyl, —$SO_2(C_{1-6}$ alkyl), —$C(O)(C_{1-6}$ alkyl), and —C(O)O ($C_{1-6}$ alkyl);

each occurrence of $R^D$ is independently selected from the group consisting of:

$C_{1-6}$ alkyl optionally substituted with from 1-2 substituents independently selected from the group consisting of: —OH, $C_{1-4}$ alkoxy; $C_{1-4}$ haloalkoxy; —$NH_2$, —NH($C_{1-4}$ alkyl), and —N($C_{1-4}$ alkyl)$_2$;
$C_{1-4}$ haloalkyl;
$C_{2-4}$ alkenyl;
$C_{2-4}$ alkynyl;
halo;
—CN;
—$NO_2$;
—$N_3$;
—OH;
$C_{1-6}$ alkoxy;
$C_{1-6}$ haloalkoxy;
—C(O)NR'R", wherein R' and R" are each independently selected from H and $C_{1-4}$ alkyl;
—$SO_2$NR'R", wherein R' and R" are each independently selected from H and $C_{1-4}$ alkyl;
—$C(O)(C_{1-4}$ alkyl);
—C(O)OH;
—C(O)O($C_{1-6}$ alkyl);
—$SO_2(C_{1-6}$ alkyl),
—NR"R''', wherein R" and R''' are each independently selected from the group consisting of H, $C_{1-4}$ alkyl, —$SO_2(C_{1-6}$ alkyl), —$C(O)(C_{1-6}$ alkyl), and —C(O)O ($C_{1-6}$ alkyl);
($C_{3-10}$ cycloalkyl)-(CH$_2$)$_{0-2}$, wherein the CH$_2$ (when present) serves as the point of attachment, and wherein the $C_{3-10}$ cycloalkyl is optionally substituted with from 1-5 independently selected $C_{1-4}$ alkyl;
(heterocyclyl as defined above)-(CH$_2$)$_{0-2}$, wherein the CH$_2$ (when present) serves as the point of attachment, and wherein the heterocyclyl is optionally substituted with from 1-5 independently selected $C_{1-4}$ alkyl;
(phenyl)-(CH$_2$)$_{0-2}$, wherein the CH$_2$ (when present) serves as the point of attachment, and wherein the phenyl is optionally substituted with from 1-5 substituents independently selected from halo, $C_{1-4}$ alkyl, —$CF_3$, —$OCH_3$, —$SCH_3$, —$OCF_3$, —$NO_2$, —$N_3$, —$NH_2$, —NH($C_{1-4}$ alkyl), —N($C_{1-4}$ alkyl)$_2$, —$C(O)(C_{1-4}$ alkyl), —C(O)OH, —C(O)O($C_{1-4}$ alkyl), —$SO_2(CH_3)$, and cyclopropyl; and (heteroaryl as defined above)-(CH$_2$)$_{0-2}$, wherein the CH$_2$ (when present) serves as the point of attachment, and wherein the phenyl is optionally substituted with from 1-5 substituents independently selected from halo, $C_{1-4}$ alkyl, —$CF_3$, —$OCH_3$, —$SCH_3$, —$OCF_3$, —$NO_2$, —$N_3$, —$NH_2$, —NH($C_{1-4}$ alkyl), —N($C_{1-4}$ alkyl)$_2$, —$C(O)(C_{1-4}$ alkyl), —C(O)OH, —C(O)O($C_{1-4}$ alkyl), —$SO_2(CH_3)$, and cyclopropyl; and provided at least one of $X^2$, $X^3$, $X^4$ and $X^6$ is N—$R^3$.

In some embodiments, it is further provided that the compound is not:

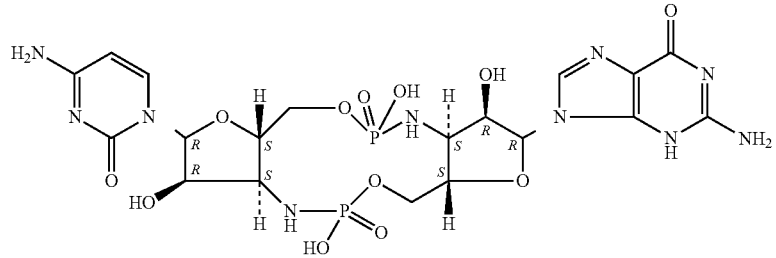

Variables X, X', $G^1$, and $G^2$

In some embodiments, the compounds have formula (B). In some embodiments, the compounds have formula (I).

In some embodiments, X and X' are each O. In some embodiments, $G^1$ is a bond connecting (i) the carbon directly attached to $X^2$ and (ii) the carbon directly attached to $C(R^{2A})(R^{2B})(X^6)$. In some embodiments, $G^2$ is a bond connecting (i) the carbon directly attached to $X^4$ and (ii) the carbon directly attached to $C(R^{1A})(R^{1B})(X^3)$.

In some embodiments, X and X' are each O, $G^1$ is a bond connecting (i) the carbon directly attached to $X^2$ and (ii) the carbon directly attached to $C(R^{2A})(R^{2B})(X^6)$, $G^2$ is a bond connecting (i) the carbon directly attached to $X^4$ and (ii) the carbon directly attached to $C(R^{1A})(R^{1B})(X^3)$, and the compound has formula (A'), (B'), or (I-A) described previously.

Variable A and B

In some embodiments, A and B are each independently selected from the group consisting of formula (i) and formula (ii). In certain embodiments, A has formula (i), and B has formula (ii). In other embodiments, A has formula (ii), and B has formula (ii). In still other embodiments, A has formula (i), and B has formula (i).

In some embodiments, each occurrence of $Z^1$ is N, and $Z^{1'}$ is N. In some embodiments, $R^5$ is —$NR^{b1}R^{c1}$ (e.g., —$NH_2$ or —$NHR^{c1}$). In some embodiments, each occurrence of $Z^1$ is N, $Z^{1'}$ is N, and $R^5$ is —$NR^{b1}R^{c1}$ (e.g., —$NH_2$ or —$NHR^{c1}$). In certain of these embodiments, $R^4$ and/or $R^6$ is H; or $R^4$ is other than H, and $R^6$ is H.

In some embodiments, each occurrence of $Z^1$ is N, and $Z^{1'}$ is N. In some embodiments, $R^5$ is —OH. In some embodiments, each occurrence of $Z^1$ is N, $Z^{1'}$ is N, and $R^5$ is —OH. In certain of these embodiments, $R^6$ is H. In certain of these embodiments, $R^4$ is H; in other embodiments, $R^4$ is other than H. For example, each occurrence of $Z^1$ is N; $Z^{1'}$ is N; $R^5$ is —OH; $R^6$ is H; and $R^4$ is H.

In some embodiments, each occurrence of $Z^2$ is N, $Z^{2'}$ is. N, and $Z^3$ is N—$R^3$ (e.g., N—H). In some embodiments, $R^{6'}$ is —$NR^{b1}R^{c1}$ (e.g., —$NH_2$ or —$NHR^{c1}$). In some embodiments, each occurrence of $Z^2$ is N, $Z^{2'}$ is. N, $Z^3$ is N—$R^3$ (e.g., N—H), and $R^{6'}$ is —$NR^{b1}R^{c1}$ (e.g., —$NH_2$ or —$NHR^{c1}$). In certain of these embodiments, $R^{4'}$ is H; in other embodiments, $R^{4'}$ is other than H.

In certain of the foregoing embodiments, each occurrence of $R^{b1}$ and $R^{c1}$ or each occurrence of $R^{c1}$ is independently selected from the group consisting of: H; $R^{a1}$; —C(O)H, —C(O)$R^{a1}$, —C(O)NRR', wherein R and R' are each independently selected from H and $C_{1-4}$ alkyl; —C(O)O$R^{a1}$, —OC(O)H, —S(O)$R^{a1}$, and —S(O)$_2R^{a1}$; In certain of the foregoing embodiments, each occurrence of $R^{b1}$ and $R^{c1}$ or each occurrence of $R^{c1}$ is independently selected from the group consisting of: H; $C_{1-6}$ (e.g., $C_{1-4}$) alkyl optionally substituted with from 1-3 $R^4$; —SO$_2$($C_{1-6}$ alkyl); —C(O)H; —C(O)($C_{1-6}$ alkyl optionally substituted with from 1-3 $R^4$); —C(O)NRR', wherein R and R' are each independently selected from H and $C_{1-4}$ alkyl optionally substituted with from 1-3 $R^4$; and —C(O)O($C_{1-6}$ alkyl optionally substituted with from 1-3 $R^4$).

In certain of the foregoing embodiments, each occurrence of $R^{b1}$ and $R^{c1}$ or each occurrence of $R^{c1}$ is independently selected from the group consisting of: H; $C_{1-6}$ (e.g., $C_{1-4}$) alkyl; —SO$_2$($C_{1-6}$ alkyl); —C(O)H; —C(O)($C_{1-6}$ alkyl); —C(O)NRR', wherein R and R' are each independently selected from H and $C_{1-4}$ alkyl; and —C(O)O($C_{1-6}$ alkyl).

Variables $X^2$, $X^3$, $X^4$ and $X^6$

In some embodiments, two of $X^2$, $X^3$, $X^4$ and $X^6$ (e.g., $X^2$ and $X^4$; or $X^3$ and $X^6$) are N—$R^3$ (e.g., N—H). In certain embodiments, $X^2$ and $X^4$ are N—$R^3$ (e.g., N—H). In other embodiments, $X^3$ and $X^6$ are N—$R^3$ (e.g., N—H).

In certain embodiments, two of $X^2$, $X^3$, $X^4$ and $X^6$ (e.g., $X^2$ and $X^4$; or $X^3$ and $X^6$) are N—$R^3$ (e.g., N—H), and the others are O. In certain embodiments, $X^2$ and $X^4$ are N—$R^3$ (e.g., N—H), and the others are O. In other embodiments, $X^3$ and $X^6$ are N—$R^3$ (e.g., N—H), and the others are O.

Variables $X^1$ and $X^5$

In some embodiments, $X^1$ is —OH, —O$R^{a1}$, —F, —SH, —$SR^{a1}$, —OC(O)H, —OC(O)$R^{a1}$, —OC(O)$NR^{b1}R^{c1}$, —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$ (in certain embodiments, $X^1$ is other than —F).

In certain embodiments, $X^1$ is —OH, —O$R^{a1}$, —OC(O)H, —OC(O)$R^{a1}$, —OC(O)$NR^{b1}R^{c1}$, —F, —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$ (in certain embodiments, $X^1$ is other than —F).

In certain embodiments, $X^1$ is —F, —OH, —O$R^{a1}$, —OC(O)H, —OC(O)$R^{a1}$, or —OC(O)$NR^{b1}R^{c1}$ (in certain embodiments, $X^1$ is other than —F).

In certain embodiments, $X^1$ is —F, —OH or —O$R^{a1}$ (in certain embodiments, $X^1$ is other than —F).

In certain embodiments, $X^1$ is —OH.

In certain embodiments, $X^1$ is —OH, —O$R^{a1}$, —OC(O)H, —OC(O)$R^{a1}$, or —OC(O)$NR^{b1}R^{c1}$ (e.g., —OH or —O$R^{a1}$; e.g., —OH), and two of $X^2$, $X^3$, $X^4$ and $X^6$ (e.g., $X^2$ and $X^4$; or $X^3$ and $X^6$) are N—$R^3$ (e.g., N—H). In certain embodiments, two of $X^2$, $X^3$, $X^4$ and $X^6$ (e.g., $X^2$ and $X^4$; or $X^3$ and $X^6$) are N—$R^3$ (e.g., N—H), and the others are O.

In other embodiments, $X^1$ is —$NO_2$, —$N_3$, —$NR^{d1}C(=NR^{e1})NR^{b1}R^{c1}$, —$NR^{b1}R^{c1}$, —$^+NR^{b1}R^{c1}R^{d1}$, —$NR^{d1}C(O)H$, —$NR^{d1}C(O)R^{a1}$, —$NR^{d1}C(O)OR^{a1}$, —$NR^{d1}C(O)NR^{b1}R^{c1}$, —$NR^{d1}S(O)R^{a1}$, —$NR^{d1}S(O)_2R^{a1}$, or —$NR^{d1}S(O)_2NR^{b1}R^{c1}$; e.g., —$NR^{b1}R^{c1}$ or —$^+NR^{b1}R^{c1}R^{d1}$; e.g., —$NH_2$, —$^+NH_3$, or $NHR^{c1}$.

In some embodiments, $X^1$ is H, —OH, —O$R^{a1}$, —SH, —$SR^{a1}$, —OC(O)H, —OC(O)$R^{a1}$, —OC(O)$NR^{b1}R^{c1}$, $C_{1-4}$ alkyl, $C_{1-4}$ haloalkyl (e.g., $CF_3$), halo (e.g., F), —CN, —C(O)H, —C(O)$R^{a1}$, —C(O)$NR^{c1}R^{d1}$, —C(O)OH, —C(O)O$R^{a1}$, —C(=$NR^{e1}$)$NR^{b1}R^{c1}$, —S(O)$R^{a1}$, —S(O)$NR^{b1}R^{c1}$, —S(O)$_2R^{a1}$, or —S(O)$_2NR^{b1}R^{c1}$ (in certain embodiments, $X^1$ is other than H; e.g., $X^1$ is —OH, —O$R^{a1}$, —SH, —$SR^{a1}$, —OC(O)H, —OC(O)$R^{a1}$, —OC(O)$NR^{b1}R^{c1}$, $C_{1-4}$ alkyl, $C_{1-4}$ haloalkyl (e.g., $CF_3$), halo (e.g., F), —CN, —C(O)H, —C(O)$R^{a1}$, —C(O)$NR^{c1}R^{d1}$, —C(O)OH, —C(O)O$R^{a1}$, —C(=$NR^{e1}$)$NR^{b1}R^{c1}$, —S(O)$R^{a1}$, —S(O)$NR^{b1}R^{c1}$, —S(O)$_2R^{a1}$, or —S(O)$_2NR^{b1}R^{c1}$).

In certain embodiments, $X^1$ is H, —OH, —O$R^{a1}$, —SH, —$SR^{a1}$, —OC(O)H, —OC(O)$R^{a1}$, —OC(O)$NR^{b1}R^{c1}$, $C_{1-4}$ alkyl, $C_{1-4}$ haloalkyl (e.g., $CF_3$), halo (e.g., F), —CN, or —S(O)$_2R^{a1}$ (in certain embodiments, $X^1$ is other than H; e.g., $X^1$ is —OH, —O$R^{a1}$, —SH, —$SR^{a1}$, —OC(O)H, —OC(O)$R^{a1}$, —OC(O)$NR^{b1}R^{c1}$, $C_{1-4}$ alkyl, $C_{1-4}$ haloalkyl (e.g., $CF_3$), halo (e.g., F), —CN, or —S(O)$_2R^{a1}$).

In certain embodiments, $X^1$ is —F, —OH, —O$R^{a1}$, —OC(O)H, —OC(O)$R^{a1}$, or —OC(O)$NR^{b1}R^{c1}$. For example, $X^1$ can be —F, —OH, or —O$R^{a1}$ (e.g., $R^{a1}$ can be $C_{1-10}$ alkyl, e.g., $C_{1-4}$ alkyl). As another example, $X^1$ can be —F or —OH.

In certain embodiments, $X^1$ is —OH, —O$R^{a1}$, —SH, —$SR^{a1}$, —OC(O)H, —OC(O)$R^{a1}$, or —OC(O)$NR^{b1}R^{c1}$.

In certain embodiments, $X^1$ is —OH, —O$R^{a1}$, —OC(O)H, —OC(O)$R^{a1}$, or —OC(O)$NR^{b1}R^{c1}$. For example, $X^1$ can be —OH or —O$R^{a1}$ (e.g., $R^{a1}$ can be $C_{1-10}$ alkyl, e.g., $C_{1-4}$ alkyl). As another example, $X^1$ can be —OH.

In certain embodiments, $X^1$ is H, $C_{1-4}$ alkyl, $C_{1-4}$ haloalkyl (e.g., $CF_3$), halo (e.g., F), —CN, —C(O)H, —C(O)$R^{a1}$, —C(O)$NR^{c1}R^{d1}$, —C(O)OH, —C(O)O$R^{a1}$, —C(=$NR^{d1}$)$NR^{b1}R^{c1}$, —S(O)$R^{a1}$, —S(O)$NR^{b1}R^{c1}$, —S(O)$_2R^{a1}$, or —S(O)$_2NR^{b1}R^{c1}$ (in certain embodiments, $X^1$ is other than H; e.g., $X^L$ is $C_{1-4}$ alkyl, $C_{1-4}$ haloalkyl (e.g., $CF_3$), halo (e.g., F), —CN, —C(O)H, —C(O)$R^{a1}$, —C(O)$NR^{c1}R^{d1}$, —C(O)OH, —C(O)O$R^{a1}$, —C(=$NR^{e1}$)$NR^{b1}R^{c1}$, —S(O)$R^{a1}$, —S(O)$NR^{b1}R^{c1}$, —S(O)$_2R^{a1}$, or —S(O)$_2NR^{b1}R^{c1}$).

In certain embodiments, $X^1$ is H, $C_{1-4}$ alkyl, $C_{1-4}$ haloalkyl (e.g., $CF_3$), halo (e.g., F), —CN, or —S(O)$_2R^{a1}$.

In certain embodiments, $X^1$ is $C_{1-4}$ alkyl, $C_{1-4}$ haloalkyl (e.g., $CF_3$), halo (e.g., F), —CN, or —S(O)$_2R^{a1}$.

In certain embodiments, $X^1$ is H, $C_{1-4}$ alkyl, $C_{1-4}$ haloalkyl (e.g., $CF_3$), or halo (e.g., F).

In certain embodiments, $X^1$ is $C_{1-4}$ alkyl, $C_{1-4}$ haloalkyl (e.g., $CF_3$), or halo (e.g., F).

In certain embodiments, $X^1$ is H or halo (e.g., F).

In certain embodiments, $X^1$ is halo (e.g., —F).

In certain of the foregoing embodiments, two of $X^2$, $X^3$, $X^4$ and $X^1$ (e.g., $X^2$ and $X^4$; or $X^3$ and $X^6$) c N—$R^3$ (e.g., N—H). In certain of the foregoing embodiments, two of $X^2$, $X^3$, $X^4$ and $X^6$ (e.g., $X^2$ and $X^4$; or $X^3$ and $X^6$) are N—$R^3$ (e.g., N—H), and the others are O.

In some embodiments, $X^1$ is —OH, —O$R^{a1}$, —SH, —$SR^{a1}$, —OC(O)H, —OC(O)$R^{a1}$, —OC(O)$NR^{b1}R^{c1}$, $C_{1-4}$ alkyl, $C_{1-4}$ haloalkyl (e.g., $CF_3$), halo (e.g., F), —CN, —C(O)H, —C(O)$R^{a1}$, —C(O)$NR^{c1}R^{d1}$, —C(O)OH, —C(O)O$R^{a1}$, —C(=$NR^{e1}$)$NR^{b1}R^{c1}$, —S(O)$R^{a1}$, —S(O)$NR^{b1}R^{c1}$, —S(O)$_2R^{a1}$, and —S(O)$_2NR^{b1}R^{c1}$.

In certain embodiments, $X^1$ is —OH, —O$R^{a1}$, $C_{1-4}$ alkyl, $C_{1-4}$ haloalkyl (e.g., $CF_3$), halo (e.g., F), —CN, and —S(O)$_2R^{a1}$.

In certain embodiments, $X^1$ is —OH, —O$R^{a1}$, —SH, —$SR^{a1}$, —OC(O)H, —OC(O)$R^{a1}$, or —OC(O)$NR^{b1}R^{c1}$.

For example, $X^1$ can be —OH, —OR$^{a1}$, —OC(O)H, —OC(O)R$^{a1}$, or —OC(O)NR$^{b1}$R$^{c1}$; e.g., $X^1$ can be —OH or —OR$^{a1}$ (e.g., —OH).

In other embodiments, $X^1$ is $C_{1-4}$ alkyl, $C_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, or —S(O)$_2$NR$^{b1}$R$^{c1}$. For example, $X^1$ can be $C_{1-4}$ alkyl, $C_{1-4}$ haloalkyl (e.g., CF$_3$), halo (e.g., F), —CN, or —S(O)$_2$R$^{a1}$. As another example, $X^1$ can be $C_{1-4}$ alkyl, $C_{1-4}$ haloalkyl (e.g., CF$_3$), or halo (e.g., F). As a further example, $X^1$ can be halo (e.g., —F).

In certain of the foregoing embodiments, two of $X^2$, $X^3$, $X^4$ and $X^6$ (e.g., $X^2$ and $X^4$; or $X^3$ and $X^6$) c N—R$^3$ (e.g., N—H). In certain of the foregoing embodiments, two of $X^2$, $X^3$, $X^4$ and $X^6$ (e.g., $X^2$ and $X^4$; or $X^3$ and $X^6$) are N—R$^3$ (e.g., N—H), and the others are O.

In some embodiments, the carbon directly attached to $X^1$ has the (R)-configuration.

In some embodiments, the carbon directly attached to $X^1$ has the (S)-configuration.

In some embodiments, $X^5$ is —OH, —OR$^{a1}$, —F, —SH, —SR$^{a1}$, —OC(O)H, —OC(O)R$^{a1}$, —OC(O)NR$^{b1}$R$^{c1}$, —NO$_2$, —N$_3$, —NR$^{d1}$C(=NR$^{e1}$)NR$^{b1}$R$^{c1}$, —NR$^{b1}$R$^{c1}$, —$^+$NR$^{b1}$R$^{c1}$R$^{d1}$, NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, or —NR$^{d1}$S(O)$_2$NR$^{b1}$R$^{c1}$ (in certain embodiment, $X^5$ is other than —F).

In certain embodiments, $X^5$ is —OH, —OR$^{a1}$, —OC(O)H, —OC(O)R$^{a1}$, —OC(O)NR$^{b1}$R$^{c1}$, —F, —NO$_2$, —N$_3$, —NR$^{d1}$C(=NR$^{e1}$)NR$^{b1}$R$^{c1}$, —NR$^{b1}$R$^{c1}$, —$^+$NR$^{b1}$R$^{c1}$R$^{d1}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, or —NR$^{d1}$S(O)$_2$NR$^{b1}$R$^{c1}$ (in certain embodiment, $X^5$ is other than —F).

In certain embodiments, $X^5$ is —F, —OH, —OR$^{a1}$, —OC(O)H, —OC(O)R$^{a1}$, or —OC(O)NR$^{b1}$R$^{c1}$ (in certain embodiment, $X^5$ is other than —F).

In certain embodiments, $X^5$ is —F, —OH or —OR$^{a1}$ (in certain embodiment, $X^5$ is other than —F).

In certain embodiments, $X^5$ is —OH.

In certain embodiments, $X^5$ is —OH, —OR$^{a1}$, —OC(O)H, —OC(O)R$^{a1}$, or —OC(O)NR$^{b1}$R$^{c1}$ (e.g., —OH or —OR$^{a1}$; e.g., —OH), and two of $X^2$, $X^3$, $X^4$ and $X^6$ (e.g., $X^2$ and $X^4$; or $X^3$ and $X^6$) are N—R$^3$ (e.g., N—H). In certain embodiments, two of $X^2$, $X^3$, $X^4$ and $X^6$ (e.g., $X^2$ and $X^4$; or $X^3$ and $X^6$) are N—R$^3$ (e.g., N—H), and the others are O.

In other embodiments, $X^5$ is —NO$_2$, —N$_3$, —NR$^{d1}$C(=NR$^{e1}$)NR$^{b1}$R$^{c1}$, —NR$^{b1}$R$^{c1}$, —$^+$NR$^{b1}$R$^{c1}$R$^{d1}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, or —NR$^{d1}$S(O)$_2$NR$^{b1}$R$^{c1}$; e.g., —NR$^{b1}$R$^{c1}$ or —$^+$NR$^{b1}$R$^{c1}$R$^{d1}$; e.g., —NH$_2$, —$^+$NH$_3$, or NHR$^{c1}$.

In some embodiments, $X^5$ is H, —OH, —OR$^{a1}$, —SH, —SR$^{a1}$, —OC(O)H, —OC(O)R$^{a1}$, —OC(O)NR$^{b1}$R$^{c1}$, $C_{1-4}$ alkyl, $C_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, or —S(O)$_2$NR$^{b1}$R$^{c1}$ (in certain embodiments, $X^1$ is other than H; e.g., $X^5$ is —OH, —OR$^{a1}$, —SH, —SR$^{a1}$, —OC(O)H, —OC(O)R$^{a1}$, —OC(O)NR$^{b1}$R$^{c1}$, $C_{1-4}$ alkyl, $C_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, or —S(O)$_2$NR$^{b1}$R$^{c1}$).

In certain embodiments, $X^5$ is H, —OH, —OR$^{a1}$, —SH, —SR$^{a1}$, —OC(O)H, —OC(O)R$^{a1}$, —OC(O)NR$^{b1}$R$^{c1}$, $C_{1-4}$ alkyl, $C_{1-4}$ haloalkyl (e.g., CF$_3$), halo (e.g., F), —CN, or —S(O)$_2$R$^{a1}$ (in certain embodiments, $X^5$ is other than H).

In certain embodiments, $X^5$ is —F, —OH, —OR$^{a1}$, —OC(O)H, —OC(O)R$^{a1}$, or —OC(O)NR$^{b1}$R$^{c1}$. For example, $X^5$ can be —F, —OH, or —OR$^{a1}$ (e.g., R$^{a1}$ can be $C_{1-10}$ alkyl, e.g., $C_{1-4}$ alkyl). As another example, $X^5$ can be —F or —OH.

In certain embodiments, $X^5$ is —OH, —OR$^{a1}$, —SH, —SR$^{a1}$, —OC(O)H, —OC(O)R$^{a1}$, or —OC(O)NR$^{b1}$R$^{c1}$.

In certain embodiments, $X^5$ is —OH, —OR$^{a1}$, —OC(O)H, —OC(O)R$^{a1}$, or —OC(O)NR$^{b1}$R$^{c1}$. For example, $X^5$ can be —OH or —OR$^{a1}$ (e.g., R$^{a1}$ can be $C_{1-10}$ alkyl, e.g., $C_{1-4}$ alkyl). As another example, $X^5$ can be —OH.

In certain embodiments, $X^5$ is H, $C_{1-4}$ alkyl, $C_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, or —S(O)$_2$NR$^{b1}$R$^{c1}$ (in certain embodiments, $X^5$ is other than H; e.g., $X^5$ is $C_{1-4}$ alkyl, $C_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, or —S(O)$_2$NR$^{b1}$R$^{c1}$).

In certain embodiments, $X^5$ is H, $C_{1-4}$ alkyl, $C_{1-4}$ haloalkyl (e.g., CF$_3$), halo (e.g., F), —CN, or —S(O)$_2$R$^{a1}$.

In certain embodiments, $X^5$ is $C_{1-4}$ alkyl, $C_{1-4}$ haloalkyl (e.g., CF$_3$), halo (e.g., F), —CN, or —S(O)$_2$R$^{a1}$.

In certain embodiments, $X^5$ is H, $C_{1-4}$ alkyl, $C_{1-4}$ haloalkyl (e.g., CF$_3$), or halo (e.g., F).

In certain embodiments, $X^5$ is $C_{1-4}$ alkyl, $C_{1-4}$ haloalkyl (e.g., CF$_3$), or halo (e.g., F).

In certain embodiments, $X^5$ is H or halo (e.g., F).

In certain embodiments, $X^5$ is halo (e.g., —F).

In certain of the foregoing embodiments, two of $X^2$, $X^3$, $X^1$ and $X^6$ (e.g., $X^2$ and $X^4$; or $X^3$ and $X^6$) c N—R$^3$ (e.g., N—H). In certain of the foregoing embodiments, two of $X^2$, $X^3$, $X^1$ and $X^6$ (e.g., $X^2$ and $X^4$; or $X^3$ and $X^6$) are N—R$^3$ (e.g., N—H), and the others are O.

In some embodiments, $X^5$ is —OH, —OR$^{a1}$, —SH, —SR$^{a1}$, —OC(O)H, —OC(O)R$^{a1}$, —OC(O)NR$^{b1}$R$^{c1}$, $C_{1-4}$ alkyl, $C_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$ R$^{c1}$, S(O)$_2$R$^{a1}$, and —S(O)$_2$NR$^{b1}$R$^{c1}$.

In certain embodiments, $X^5$ is —OH, —OR$^{a1}$, $C_{1-4}$ alkyl, $C_{1-4}$ haloalkyl (e.g., CF$_3$), halo (e.g., F), —CN, and —S(O)$_2$R$^{a1}$.

In certain embodiments, $X^5$ is —OH, —OR$^{a1}$, —SH, —SR$^{a1}$, —OC(O)H, —OC(O)R$^{a1}$, or —OC(O)NR$^{b1}$R$^{c1}$. For example, $X^5$ can be —OH, —OR$^{a1}$, —OC(O)H, —OC(O)R$^{a1}$, or —OC(O)NR$^{b1}$R$^{c1}$; e.g., $X^1$ can be —OH or —OR$^{a1}$ (e.g., —OH).

In other embodiments, $X^5$ is $C_{1-4}$ alkyl, $C_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, or —S(O)$_2$NR$^{b1}$R$^{c1}$. For example, $X^5$ can be $C_{1-4}$ alkyl, $C_{1-4}$ haloalkyl (e.g., CF$_3$), halo (e.g., F), —CN, or —S(O)$_2$R$^{a1}$. As another example, $X^5$ can be $C_{1-4}$ alkyl, $C_{1-4}$ haloalkyl (e.g., CF$_3$), or halo (e.g., F). As a further example, $X^5$ can be halo (e.g., —F).

In certain of the foregoing embodiments, two of $X^2$, $X^3$, $X^4$ and $X^6$ (e.g., $X^2$ and $X^4$; or $X^3$ and $X^6$) are N—R$^3$ (e.g., N—H). In certain of the foregoing embodiments, two of $X^2$, $X^3$, $X^1$ and $X^6$ (e.g., $X^2$ and $X^4$; or $X^3$ and $X^6$) are N—R$^3$ (e.g., N—H), and the others are O.

In some embodiments, the carbon directly attached to $X^5$ has the (R)-configuration.

In some embodiments, the carbon directly attached to $X^5$ has the (S)-configuration.

In some embodiments, $X^1$ and $X^5$ are each independently selected from —OH, —OR$^{a1}$, —F, —SH, —SR$^{a1}$, —OC(O)H, —OC(O)R$^{a1}$, —OC(O)NR$^{b1}$R$^{c1}$, —NO$_2$, —N$_3$, —NR$^{d1}$C(=NR$^{e1}$)NR$^{b1}$R$^{c1}$, —NR$^{b1}$R$^{c1}$, —$^+$NR$^{b1}$R$^{c1}$R$^{d1}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, or —NR$^{d1}$S(O)$_2$NR$^{b1}$R$^{c1}$ (in certain embodiment, $X^1$ and/or $X^5$ is other than —F). $X^1$ and $X^5$ can be the same or different.

In certain embodiments, $X^1$ and $X^5$ are each independently selected from —OH, —OR$^{a1}$, —OC(O)H, —OC(O)R$^{a1}$, —OC(O)NR$^{b1}$R$^{c1}$, —F, —NO$_2$, —N$_3$, —NR$^{d1}$C(=NR$^{e1}$)NR$^{b1}$R$^{c1}$, —NR$^{b1}$R$^{c1}$, —$^+$NR$^{b1}$R$^{c1}$R$^{d1}$, —NR$^{d1}$C(O)H, —NR$^{d1}$C(O)R$^{a1}$, —NR$^{d1}$C(O)OR$^{s1}$, —NR$^{d1}$C(O)NR$^{b1}$R$^{c1}$, —NR$^{d1}$S(O)R$^{a1}$, —NR$^{d1}$S(O)$_2$R$^{a1}$, or —NR$^{d1}$S(O)$_2$NR$^{b1}$R$^{c1}$ (in certain embodiment, $X^5$ is other than —F).

In certain embodiments, $X^1$ and $X^5$ are each independently selected from —F, —OH, —OR$^{a1}$, —OC(O)H, —OC(O)R$^{a1}$, or —OC(O)NR$^{b1}$R$^{c1}$ (in certain embodiment, $X^5$ is other than —F).

In certain embodiments, $X^1$ and $X^5$ are each independently selected from —F, —OH or —OR$^{a1}$ (in certain embodiment, $X^5$ is other than —F).

In certain embodiments, $X^1$ and $X^5$ are each —OH.

In certain embodiments, $X^1$ and $X^5$ are each independently selected from —OH, —OR$^{a1}$, —OC(O)H, —OC(O)R$^{a1}$, or —OC(O)NR$^{b1}$R$^{c1}$ (e.g., —OH or —OR$^{a1}$; e.g., —OH), and at least one (e.g., two) of $X^2$, $X^3$, $X^4$ and $X^6$ is other than O (e.g., N—R$^3$). In certain embodiments, two of $X^2$, $X^3$, $X^4$ and $X^6$ (e.g., $X^2$ and $X^4$) are N—R$^3$ (e.g., N—H), and the others are O.

In other embodiments, $X^1$ and $X^5$ are each independently selected from —NO$_2$, —N$_3$, —NR$^{d1}$C(=NR$^{e1}$)NR$^{b1}$R$^{c1}$, —NR$^{b1}$R$^{c1}$, —$^+$NR$^{b1}$R$^{c1}$R$^{d1}$, —NR$^{d1}$C(O)H, —NR$^{d1}$C(O)R$^{a1}$, —NR$^{d1}$C(O)OR$^{a1}$, —NR$^{d1}$C(O)NR$^{b1}$R$^{c1}$, —NR$^{d1}$S(O)R$^{a1}$, —NR$^{d1}$S(O)$_2$R$^{a1}$, or —NR$^{d1}$S(O)$_2$NR$^{b1}$R$^{c1}$; e.g., —NR$^{b1}$R$^{c1}$ or —$^+$NR$^{b1}$R$^{c1}$R$^{d1}$; e.g., —NH$_2$, —$^+$NH$_3$, or NHR$^{c1}$.

In some embodiments, $X^1$ and $X^5$ are each independently selected from H, —OH, —OR$^{a1}$, —SH, —SR$^{a1}$, —OC(O)H, —OC(O)R$^{a1}$, —OC(O)NR$^{b1}$R$^{c1}$, C$_{1-4}$ alkyl, C$_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$ (in certain embodiments, $X^1$ and $X^5$ are each other than H; e.g., $X^1$ and $X^5$ are each independently selected from —OH, —OR$^{a1}$, —SH, —SR$^{a1}$, —OC(O)H, —OC(O)R$^{a1}$, —OC(O)NR$^{b1}$R$^{c1}$, C$_{1-4}$ alkyl, C$_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$).

In certain embodiments, $X^1$ and $X^5$ are each independently selected from H, —OH, —OR$^{a1}$, —SH, —SR$^{a1}$, —OC(O)H, —OC(O)R$^{a1}$, —OC(O)NR$^{b1}$R$^{c1}$, C$_{1-4}$ alkyl, C$_{1-4}$ haloalkyl (e.g., CF$_3$), halo (e.g., F), —CN, and —S(O)$_2$R$^{a1}$ (in certain embodiments, $X^1$ and $X^5$ are each other than H; e.g., $X^1$ and $X^5$ are each independently selected from —OH, —OR$^{a1}$, —SH, —SR$^{a1}$, —OC(O)H, —OC(O)R$^{a1}$, —OC(O)NR$^{b1}$R$^{c1}$, C$_{1-4}$ alkyl, CIA haloalkyl (e.g., CF$_3$), halo (e.g., F), —CN, and —S(O)$_2$R$^{a1}$).

In certain embodiments, $X^1$ and $X^5$ are each independently selected from —F, —OH, —OR$^{a1}$, —OC(O)H, —OC(O)R$^{a1}$, and —OC(O)NR$^{b1}$R$^{c1}$. For example, $X^1$ and $X^5$ are each independently selected from —F, —OH, and —OR$^{a1}$ (e.g., R$^{a1}$ can be C$_{1-10}$ alkyl, e.g., C$_{1-4}$ alkyl). As another example, $X^1$ and $X^5$ are each independently selected from —F and —OH.

In certain embodiments, $X^1$ and $X^5$ are each independently selected from —OH, —OR$^{a1}$, —SH, —SR$^{a1}$, —OC(O)H, —OC(O)R$^{a1}$, and —OC(O)NR$^{b1}$R$^{c1}$.

In certain embodiments, $X^1$ and $X^5$ are each independently selected from —OH, —OR$^{a1}$, —OC(O)H, —OC(O)R$^{a1}$, and —OC(O)NR$^{b1}$R$^{c1}$c. For example, $X^1$ and $X^5$ are each independently selected from —OH and —OR$^{a1}$ (e.g., R$^{a1}$ can be C$_{1-10}$ alkyl, e.g., C$_{1-4}$ alkyl). As another example, $X^1$ and $X^5$ are each —OH.

In certain embodiments, $X^1$ and $X^5$ are each independently selected from H, Ca-4 alkyl, C$_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$ (in certain embodiments, $X^1$ and $X^5$ are each other than H; e.g., $X^1$ and $X^5$ are each independently selected from C$_{1-4}$ alkyl, C$_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$).

In certain embodiments, $X^1$ and $X^5$ are each independently selected from H, C$_{1-4}$ alkyl, C$_{1-4}$ haloalkyl (e.g., CF$_3$), halo (e.g., F), —CN, and —S(O)$_2$R$^{a1}$.

In certain embodiments, $X^1$ and $X^5$ are each independently selected from C$_{1-4}$ alkyl, C$_{1-4}$ haloalkyl (e.g., CF$_3$), halo (e.g., F), —CN, and —S(O)$_2$R$^{r1}$.

In certain embodiments, $X^1$ and $X^5$ are each independently selected from H, C$_{1-4}$ alkyl, C$_{1-4}$ haloalkyl (e.g., CF$_3$), and halo (e.g., F).

In certain embodiments, $X^1$ and $X^5$ are each independently selected from C$_{1-4}$ alkyl, C$_{1-4}$ haloalkyl (e.g., CF$_3$), and halo (e.g., F).

In certain embodiments, $X^1$ and $X^5$ are each independently selected from H and halo (e.g., F).

In certain embodiments, $X^1$ and $X^5$ are each an independently selected halo (e.g., —F).

In certain of the foregoing embodiments, two of $X^2$, $X^3$, $X^4$ and $X^6$ (e.g., $X^2$ and $X^4$; or $X^3$ and $X^6$) c N—R$^3$ (e.g., N—H). In certain of the foregoing embodiments, two of $X^2$, $X^3$, $X^4$ and $X^6$ (e.g., $X^2$ and $X^4$; or $X^3$ and $X^6$) are N—R$^3$ (e.g., N—H), and the others are O.

In some embodiments, $X^1$ and $X^5$ are each independently selected from —OH, —OR$^{a1}$, —SH, —SR$^{a1}$, —OC(O)H, —OC(O)R$^{a1}$, —OC(O)NR$^{b1}$R$^{c1}$, C$_{1-4}$ alkyl, C$_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR, —C(=NR$^{e1}$)NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$.

In certain embodiments, $X^1$ and $X^5$ are each independently selected from —OH, —OR$^{a1}$, C$_{1-4}$ alkyl, C$_{1-4}$ haloalkyl (e.g., CF$_3$), halo (e.g., F), —CN, and —S(O)$_2$R$^1$.

In certain embodiments, $X^1$ and $X^5$ are each independently selected from —OH, —OR$^{a1}$, —SH, —SR$^{a1}$, —OC(O)H, —OC(O)R$^{a1}$, or —OC(O)NR$^{b1}$R$^{c1}$. For example, $X^1$ and $X^5$ can each be independently selected from —OH, —OR$^{a1}$, —OC(O)H, —OC(O)R$^{a1}$, or —OC(O)NR$^{b1}$R$^{c1}$; e.g., $X^1$ and $X^5$ can each be independently selected from —OH or —OR$^{a1}$ (e.g., —OH).

In other embodiments, $X^1$ and $X^5$ are each independently selected from C$_{1-4}$ alkyl, C$_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, or —S(O)$_2$NR$^{b1}$R$^{c1}$.

For example, $X^1$ and $X^5$ can each be independently selected from $C_{1-4}$ alkyl, $C_{1-4}$ haloalkyl (e.g., $CF_3$), halo (e.g., F), —CN, or —S(O)$_2$R$^{a1}$. As another example, $X^1$ and $X^5$ can each be independently selected from $C_{1-4}$ alkyl, $C_{1-4}$ haloalkyl (e.g., $CF_3$), or halo (e.g., F). As a further example, $X^1$ and $X^5$ can each be halo (e.g., —F).

In certain of the foregoing embodiments, two of $X^2$, $X^3$, $X^4$ and $X^6$ (e.g., $X^2$ and $X^4$; or $X^3$ and $X^6$) are N—R$^3$ (e.g., N—H). In certain of the foregoing embodiments, two of $X^2$, $X^3$, $X^4$ and $X^1$ (e.g., $X^2$ and $X^4$; or $X^3$ and $X^6$) are N—R$^3$ (e.g., N—H), and the others are O.

In some of the foregoing embodiments, $X^1$ and $X^5$ are the same (e.g., $X^1$ and $X^5$ are both —OH; or $X^1$ and $X^5$ are both halo (e.g., $X^1$ and $X^5$ are both —F); or $X^1$ and $X^5$ are both —OR$^{a1}$, in which R$^{a1}$ can be $C_{1-10}$ alkyl, e.g., $C_{1-4}$ alkyl).

In some of the foregoing embodiments, $X^1$ and $X^5$ are different (e.g., one of $X^1$ and $X^5$ is —OH, and the other is halo (e.g., —F); or one of $X^1$ and $X^5$ is —OH, and the other is —OR$^{a1}$, in which R$^{a1}$ can be $C_{1-10}$ alkyl, e.g., $C_{1-4}$ alkyl; or one of $X^1$ and $X^5$ is —OR$^{a1}$, in which R$^{a1}$ can be $C_{1-10}$ alkyl, e.g., $C_{1-4}$ alkyl, and the other is halo (e.g., —F)).

In some embodiments, the carbon directly attached to $X^1$ and the carbon directly attached to $X^5$ both have the (R)-configuration.

In some embodiments, the carbon directly attached to $X^1$ and the carbon directly attached to $X^5$ both have the (S)-configuration.

In some embodiments, the carbon directly attached to $X^1$ and the carbon directly attached to $X^5$ have opposite configurations (i.e., one has the (R)-configuration, and the other has the (S)-configuration).

Variables $L^1$ and $L^2$

In some embodiments, $L^1$ is

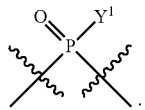

In some embodiments, $Y^1$ is —OH, —OR$^{a1}$, O$^-$, —SH, —SR$^{a1}$, or S. In certain embodiments, $Y^1$ is —OH, —OR$^{a1}$, or O$^-$ (e.g., —OR$^{a1}$ or O$^-$). In other embodiments, $Y^1$ is S$^-$. In certain of these embodiments, $L^1$ has the RP configuration, or $L^1$ has the SP configuration.

In some embodiments, $L^2$ is

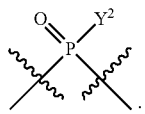

In some embodiments, $Y^2$ is —OH, —OR$^{a1}$, O$^-$, —SH, —SR$^{a1}$, or —S$^-$. In certain embodiments, $Y^2$ is —OH, —OR$^{a1}$, or O$^-$ (e.g., —OR$^{a1}$ or O$^-$). In other embodiments, $Y^2$ is —SH or —S$^-$. In certain of these embodiments, $L^2$ has the RP configuration, or $L^2$ has the SP configuration.

In some embodiments, $L^1$ is

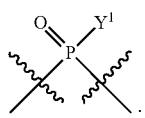

and $L^2$ is

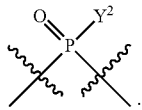

$Y^1$ and $Y^2$ can be the same or different. In some embodiments, $Y^1$ and $Y^2$ are each independently selected from is —OH, —OR$^{a1}$, O$^-$, —SH, —SR$^{a1}$, or S; e.g., —OR$^{a1}$ or O$^-$; e.g., —SH or S$^-$, e.g., —S$^-$.

In certain embodiments, $Y^1$ and $Y^2$ are each —O$^-$.

In certain embodiments, $Y^1$ and $Y^2$ are each —SH or —S$^-$, e.g., —S$^-$. In certain of these embodiments, $L^1$ and $L^2$ both have the RP configuration or both have the SP configuration.

In other of these embodiments, one of $L^1$ and $L^2$ has the RP configuration, and the other has the SP configuration.

Variables $R^{1A}$ and $R^{1B}$ and $R^{2A}$ and $R^{2B}$

In some embodiments, $R^{1A}$ and $R^{1B}$ are each H. In some embodiments, $R^{2A}$ and $R^{2B}$ are each H. In some embodiments, $R^{1A}$ and $R^{1B}$ are each H, and $R^{2A}$ and $R^{2B}$ are each H.

Variables $R^3$, $R^{b1}$, $R^{c1}$, $R^{d1}$, and $R^{e1}$

In some embodiments, each occurrence of $R^3$, $R^{b1}$, $R^{c1}$, $R^{d1}$, and $R^{e1}$ (or each occurrence of $R^{b1}$ and $R^{e1}$; or each occurrence of $R^{c1}$ and $R^{d1}$; or each occurrence of $R^3$; or each occurrence of $R^{e1}$) is independently selected from the group consisting of: H; $R^{a1}$; —C(O)H, —C(O)R$^{a1}$, —C(O)NR$^{c1}$R$^{d1}$, —C(O)OR$^{a1}$, —OC(O)H, —S(O)R$^{a1}$, and —S(O)$_2$R$^{a1}$; or $R^{b1}$ and $R^{d1}$ taken together with the nitrogen atom to which each is attached form a heterocyclyl, including from 3-10 (e.g., 3-6, 4-6, 5-6) ring atoms, wherein from 1-3 ring atoms are independently selected from the group consisting of nitrogen, oxygen and sulfur, and which is optionally substituted with from 1-5 R$^C$; (e.g., azetidinyl, morpholino, piperidinyl).

In certain embodiments, each occurrence of $R^3$, $R^{b1}$, $R^{c1}$, $R^{d1}$, and $R^{e1}$ (or each occurrence of $R^{b1}$ and $R^{e1}$; or each occurrence of $R^{c1}$ and $R^{d1}$; or each occurrence of $R^3$; or each occurrence of $R^{e1}$) is independently selected from the group consisting of: H; $R^{a1}$; —C(O)H, —C(O)R$^{a1}$, —C(O)NRR', wherein R and R' are each independently selected from H and $C_{1-4}$ alkyl optionally substituted with from 1-3 $R^A$; —C(O)OR$^{a1}$, —OC(O)H, —S(O)R$^{a1}$, and —S(O)$_2$R$^{a1}$; or $R^{b1}$ and $R^{c1}$ taken together with the nitrogen atom to which each is attached form a heterocyclyl, including from 3-10 (e.g., 3-6, 4-6, 5-6) ring atoms, wherein from 1-3 ring atoms are independently selected from the group consisting of nitrogen, oxygen and sulfur, and which is optionally substituted with from 1-5 R$^C$; (e.g., azetidinyl, morpholino, piperidinyl).

In certain embodiments, each occurrence of $R^3$, $R^{b1}$, $R^{c1}$, $R^{d1}$, and $R^{e1}$ (or each occurrence of $R^{b1}$ and $R^{e1}$; or each occurrence of $R^{c1}$ and $R^{d1}$; or each occurrence of $R^3$; or each occurrence of $R^{e1}$) is independently selected from the group consisting of: H; $C_{1-6}$ (e.g., $C_{1-4}$) alkyl optionally substituted with from 1-3 $R^A$; —SO$_2$($C_{1-6}$ alkyl); —C(O)H; —C(O)($C_{1-6}$ alkyl optionally substituted with from 1-3 $R^A$); —C(O)NRR', wherein R and R' are each independently selected from H and $C_{1-4}$ alkyl optionally substituted with from 1-3 $R^A$; and —C(O)O($C_{1-6}$ alkyl optionally substituted with from 1-3 $R^A$); or $R^{b1}$ and $R^{c1}$ taken together with the nitrogen atom to which each is attached form a heterocyclyl, including from 3-10 (e.g., 3-6, 4-6, 5-6) ring atoms, wherein from 1-3 ring atoms are independently selected from the group consisting of nitrogen, oxygen and sulfur, and which is optionally substituted with from 1-5 $R^C$; (e.g., azetidinyl, morpholino, piperidinyl).

In certain embodiments, each occurrence of $R^3$, $R^{b1}$, $R^{c1}$, $R^{d1}$, and $R^{e1}$ (or each occurrence of $R^{b1}$ and $R^{e1}$; or each occurrence of $R^{c1}$ and $R^{d1}$; or each occurrence of $R^3$; or each occurrence of $R^{e1}$) is independently selected from the group consisting of: H; $C_{1-6}$ (e.g., $C_{1-4}$) alkyl; —$SO_2(C_{1-6}$ alkyl); —C(O)H; —C(O)($C_{1-6}$ alkyl); —C(O)NRR', wherein R and R' are each independently selected from H and $C_{1-4}$ alkyl; and —C(O)O($C_{1-6}$ alkyl); or $R^{b1}$ and $R^{c1}$ taken together with the nitrogen atom to which each is attached form a heterocyclyl, including from 3-10 (e.g., 3-6, 4-6, 5-6) ring atoms, wherein from 1-3 ring atoms are independently selected from the group consisting of nitrogen, oxygen and sulfur, and which is optionally substituted with from 1-5 $R^C$; (e.g., azetidinyl, morpholino, piperidinyl).

In certain embodiments, each occurrence of $R^3$, $R^{b1}$, $R^{c1}$, $R^{d1}$, and $R^{e1}$ (or each occurrence of $R^{b1}$ and $R^{e1}$; or each occurrence of $R^{e1}$ and $R^{d1}$; or each occurrence of $R^3$; or each occurrence of $R^{e1}$) is independently selected from the group consisting of: H; $R^{a1}$; —C(O)H, —C(O)$R^{a1}$, —C(O)NR$^{c1}$R$^{d1}$, —C(O)O$R^{a1}$, —OC(O)H, —S(O)$R^{a1}$, and —S(O)$_2R^{a1}$.

In certain embodiments, each occurrence of $R^3$, $R^{b1}$, $R^{c1}$, $R^{d1}$, and $R^{e1}$ (or each occurrence of $R^{b1}$ and $R^{e1}$; or each occurrence of $R^{c1}$ and $R^{d1}$; or each occurrence of $R^3$; or each occurrence of $R^{e1}$) is independently selected from the group consisting of: H; $R^{a1}$; —C(O)H, —C(O)$R^{a1}$, —C(O)NRR', wherein R and R' are each independently selected from H and $C_{1-4}$ alkyl optionally substituted with from 1-3 $R^4$; —C(O)O$R^{a1}$, —OC(O)H, —S(O)$R^{a1}$, and —S(O)$_2R^{a1}$.

In certain embodiments, each occurrence of $R^3$, $R^{b1}$, $R^{c1}$, $R^{d1}$, and $R^{e1}$ (or each occurrence of $R^{b1}$ and $R^{e1}$; or each occurrence of $R^{c1}$ and $R^{d1}$; or each occurrence of $R^3$; or each occurrence of $R^{e1}$) is independently selected from the group consisting of: H; $C_{1-6}$ (e.g., $C_{1-4}$) alkyl optionally substituted with from 1-3 $R^4$; —$SO_2(C_{1-6}$ alkyl); —C(O)H; —C(O)($C_{1-6}$ alkyl optionally substituted with from 1-3 $R^4$); —C(O)NRR', wherein R and R' are each independently selected from H and $C_{1-4}$ alkyl optionally substituted with from 1-3 $R^4$; and —C(O)O($C_{1-6}$ alkyl optionally substituted with from 1-3 $R^4$).

In certain embodiments, each occurrence of $R^3$, $R^{b1}$, $R^{c1}$, $R^{d1}$, and $R^{e1}$ (or each occurrence of $R^{b1}$ and $R^{e1}$; or each occurrence of $R^{c1}$ and $R^{d1}$; or each occurrence of $R^3$; or each occurrence of $R^{e1}$) is independently selected from the group consisting of: H; $C_{1-6}$ (e.g., $C_{1-4}$) alkyl; —$SO_2(C_{1-6}$ alkyl); —C(O)H; —C(O)($C_{1-6}$ alkyl); —C(O)NRR', wherein R and R' are each independently selected from H and $C_{1-4}$ alkyl; and —C(O)O($C_{1-6}$ alkyl).

In certain embodiments, $R^{b1}$ and $R^{c1}$ taken together with the nitrogen atom to which each is attached form a heterocyclyl, including from 3-10 (e.g., 3-6, 4-6, 5-6) ring atoms, wherein from 1-3 ring atoms are independently selected from the group consisting of nitrogen, oxygen and sulfur, and which is optionally substituted with from 1-5 $R^C$; (e.g., azetidinyl, morpholino, piperidinyl).

Non-Limiting Combinations

[A] In some embodiments:

$X^1$ and $X^5$ are each independently selected from the group consisting of —OH, —O$R^{a1}$, —OC(O)H, —OC(O)$R^{a1}$, or —OC(O)NR$^{b1}$R$^{c1}$;

two of $X^2$, $X^3$, $X^4$ and $X^6$ are N—$R^3$ (e.g., N—H);

$L^1$ is

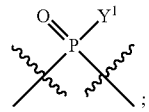

$L^2$ is

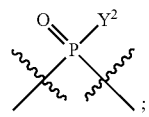

$Y^1$ and $Y^2$ are each independently selected from —OH, —O$R^{a1}$, O$^-$, —SH, —S$R^{a1}$, or S; and A and B are each independently selected from the group consisting of: formula (i) and formula (ii).

Embodiments can include any one or more of the following features.

A can have formula (i), and B can have formula (ii); or A can have formula (ii), and B can have formula (ii); or A can have formula (i), and B can have formula (i); or A can have formula (ii), and B can have formula (i). $Z^1$ can be N, and $Z^{1'}$ can be N. In certain embodiments, $R^5$ can be —NR$^{b1}$R$^{c1}$ (e.g., —NH$_2$ or —NHR$^{c1}$; e.g., in certain embodiments, $R^4$ and/or $R^6$ is H; or $R^4$ is other than H, and $R^6$ is H). In other embodiments, $R^5$ is —OH, and $R^6$ is H (e.g., in certain embodiments, $R^4$ is H; in other embodiments, $R^4$ is other than H). Each occurrence of $Z^2$ can be N, $Z^{2'}$ can be N, and $Z^3$ can be N—$R^3$ (e.g., N—H). $R^{6'}$ can be —NR$^{b1}$R$^{c1}$ (e.g., —NH$_2$ or —NHR$^{c1}$; e.g., in certain embodiments, $R^{4'}$ is H; in other embodiments, $R^{4'}$ is other than H).

$X^1$ and $X^5$ can each be independently selected from the group consisting of —OH, or —O$R^{a1}$ (e.g., $R^{a1}$ can be $C_{1-10}$ alkyl, e.g., $C_{1-4}$ alkyl); e.g., $X^1$ and $X^5$ can each be —OH. Two of $X^2$, $X^3$, $X^4$ and $X^6$ can be N—$R^3$ (e.g., N—H), and the others can be O. $Y^1$ and $Y^2$ can each be O$^-$; or $Y^1$ and $Y^2$ can each be SH or S$^-$. $L^1$ and $L^2$ can both have the RP configuration or both have the Sp configuration; or one of $L^1$ and $L^2$ can have the RP configuration, and the other can have the SP configuration. $R^{1A}$ and $R^{1B}$ can each be H, and $R^{2A}$ and $R^{2B}$ can each be H.

Each occurrence of $R^{b1}$ and $R^{c1}$ or each occurrence of R can be independently selected from the group consisting of: H; $C_{1-6}$ (e.g., $C_{1-4}$) alkyl; —$SO_2(C_{1-4}$ alkyl); —C(O)H; —C(O)($C_{1-6}$ alkyl); —C(O)NRR', wherein R' and R" are each independently selected from H and $C_{1-4}$ alkyl; and —C(O)O($C_{1-6}$ alkyl).

[B] In some embodiments:

$X^1$ and $X^5$ are each independently selected from the group consisting of H, $C_{1-4}$ alkyl, $C_{1-4}$ haloalkyl (e.g., CF$_3$), halo (e.g., F), —CN, —C(O)H, —C(O)$R^{a1}$, —C(O)NR$^{c1}$R$^{d1}$, —C(O)OH, —C(O)O$R^{a1}$, —C(=NR$^{e1}$)NR$^{b1}$R$^{c1}$, —S(O)$R^{a1}$, —S(O)NR$^{b1}$R$^{c1}$, —S(O)$_2R^{a1}$, and —S(O)$_2$NR$^{b1}$R$^{c1}$;

two of $X^2$, $X^3$, $X^4$ and $X^1$ are N—$R^3$ (e.g., N—H);

$L^1$ is

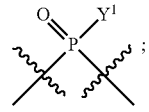

$L^2$ is

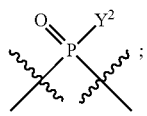

Y and $Y^2$ are each independently selected from —OH, —OR$^{a1}$, O⁻, —SH, —SR$^{a1}$, or S; and A and B are each independently selected from the group consisting of:

(i)

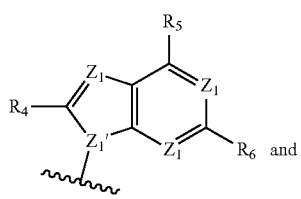 and (ii)

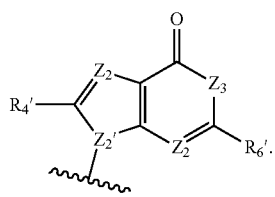

A can have formula (i), and B can have formula (ii); or A can have formula (ii), and B can have formula (ii); or A can have formula (i), and B can have formula (i); or A can have formula (ii), and B can have formula (i). $Z^1$ can be N, and $Z^{1'}$ can be N. In certain embodiments, $R^5$ can be —NR$^{b1}$R$^{c1}$ (e.g., —NH$_2$ or —NHR$^{c1}$; e.g., in certain embodiments, $R^4$ and/or $R^6$ is H; or $R^4$ is other than H, and $R^6$ is H). In other embodiments, $R^5$ is —OH, and $R^6$ is H (e.g., in certain embodiments, $R^4$ is H; in other embodiments, $R^4$ is other than H). Each occurrence of $Z^2$ can be N, $Z^{2'}$ can be. N, and $Z^3$ can be N—$R^3$ (e.g., N—H). $R^{6'}$ can be —NR$^{b1}$R$^{c1}$ (e.g., —NH$_2$ or —NHR$^{c1}$; e.g., in certain embodiments, $R^{4'}$ is H; in other embodiments, $R^{4'}$ is other than H).

$X^1$ and $X^5$ can each be independently selected from the group consisting of H, $C_{1-4}$ alkyl, $C_{1-4}$ haloalkyl (e.g., CF$_3$), halo (e.g., F), —CN, and —S(O)$_2$R$^{a1}$ (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., CF$_3$), halo (e.g., F), —CN, and —S(O)$_2$R$_{a1}$).

In certain embodiments, $X^1$ and $X^5$ can each be independently selected from the group consisting of H, $C_{1-4}$ alkyl, $C_{1-4}$ haloalkyl (e.g., CF$_3$), and halo (e.g., F) (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., CF$_3$), and halo (e.g., F)).

For example, $X^1$ and $X^5$ can each be independently selected from the group consisting of H and halo (e.g., F); or $X^1$ and $X^5$ can each be an independently selected halo (e.g., F).

Each occurrence of $R^{b1}$ and $R^{c1}$ or each occurrence of R can be independently selected from the group consisting of: H; $C_{1-6}$ (e.g., $C_{1-4}$) alkyl; —SO$_2$(C$_{1-6}$ alkyl); —C(O)H; —C(O)(C$_{1-6}$ alkyl); —C(O)NRR', wherein R' and R" are each independently selected from H and $C_{1-4}$ alkyl; and —C(O)O(C$_{1-6}$ alkyl).

[C] In some embodiments, the compound has formula (I):

(II)

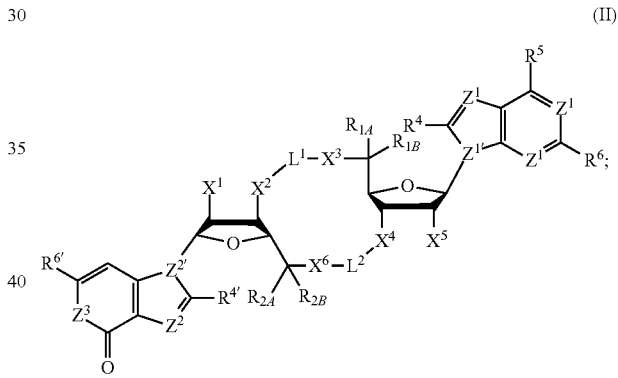

or formula (II-A)

(II-A)

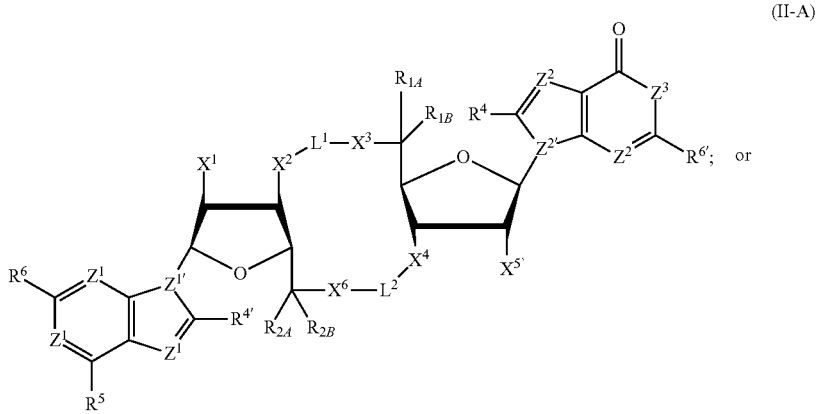

or formula (III):

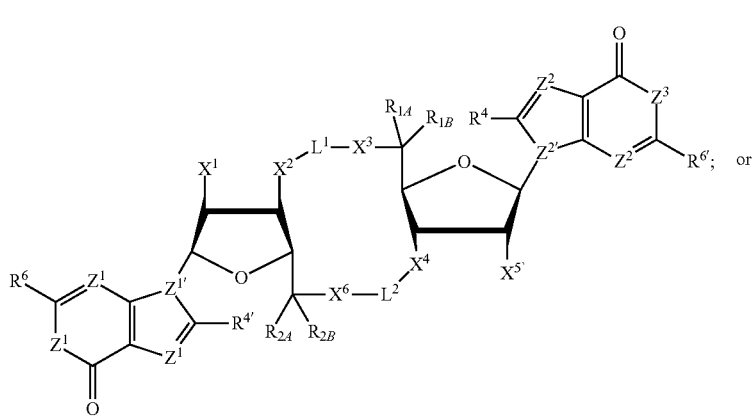

or formula (IV):

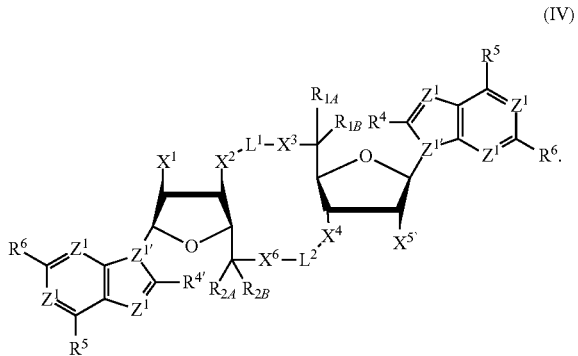

[D] In some embodiments of formula (II), (II-A), (III), or (IV):
$X^1$ and $X^5$ are each independently selected from the group consisting of —OH, —OR$^{a1}$, —OC(O)H, —OC(O)R$^{a1}$, or —OC(O)NR$^{b1}$R$^{c1}$;
two of $X^2$, $X^3$, $X^4$ and $X^1$ are N—R$^3$ (e.g., N—H);
$L^1$ is

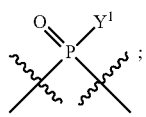

$L^2$ is

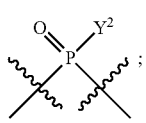

$Y^1$ and $Y^2$ are each independently selected from —OH, —OR$^{a1}$, O$^-$, —SH, —SR$^{a1}$, or S; and optionally:
each occurrence of $Z^1$ is N, $Z^{1'}$ is N, and $R^5$ is —NR$^{b1}$R$^{c1}$ (e.g., —NH$_2$ or —NHR$^{c1}$); and in certain of these embodiments, $R^4$ and/or $R^6$ is H; or $R^4$ is other than H, and $R^6$ is H; and/or each occurrence of $Z^1$ is N, $Z^{1'}$ is N, and $R^5$ is —OH; in certain of these embodiments, $R^6$ is H; in certain of these embodiments, $R^4$ is H; in other embodiments, $R^4$ is other than H; and/or each occurrence of $Z^2$ is N, $Z^{2'}$ is N, $Z^3$ is N—R$^3$ (e.g., N—H), and $R^{6'}$ is —NR$^{b1}$R$^{c1}$ (e.g., —NH$_2$ or —NHR$^{c1}$); and in certain of these embodiments, $R^{4'}$ is H; in other embodiments, $R^{4'}$ is other than H.

$X^1$ and $X^5$ can each be independently selected from the group consisting of —OH, or is —OR$^{a1}$ (e.g., R$^{a1}$ can be C$_{1-10}$ alkyl, e.g., C$_{1-4}$ alkyl); e.g., $X^1$ and $X^5$ can each be —OH. Two of $X^2$, $X^3$, $X^4$ and $X^6$ can be N—R$^3$ (e.g., N—H), and the others can be O. $Y^1$ and $Y^2$ can each be O$^-$; or $Y^1$ and $Y^2$ can each be SH or S$^-$. $L^1$ and $L^2$ can both have the RP configuration or both have the SP configuration; or one of $L^1$ and $L^2$ can have the RP configuration, and the other can have the SP configuration. $R^{1A}$ and $R^{1B}$ can each be H, and $R^{2A}$ and $R^{2B}$ can each be H.

Each occurrence of R$^{b1}$ and R$^{c1}$ or each occurrence of R$^{c1}$ can be independently selected from the group consisting of: H; C$_{1-6}$ (e.g., C$_{1-4}$) alkyl; —SO$_2$(C$_{1-6}$ alkyl); —C(O)H; —C(O)(C$_{1-6}$ alkyl); —C(O)NRR', wherein R' and R" are each independently selected from H and C$_{1-4}$ alkyl; and —C(O)O(C$_{1-4}$ alkyl).

[E] In some embodiments of formula (II), (II-A), (III), or (IV):
$X^1$ and $X^5$ are each independently selected from the group consisting of H, C$_{1-4}$ alkyl, C$_{1-4}$ haloalkyl (e.g., CF$_3$), halo (e.g., F), —CN, —C(O)H, —C(O)R$^{a1}$, —C(O)NR$^{c1}$R$^{d1}$, C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$;
two of $X^2$, $X^3$, $X^4$ and $X^6$ are N—R$^3$ (e.g., N—H);
$L^1$ is

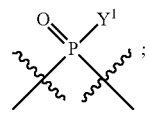

$L^2$ is

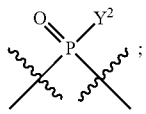

$Y^1$ and $Y^2$ are each independently selected from —OH, —OR$^{a1}$, O⁻, —SH, —SR$^{a1}$, or S; and optionally:

each occurrence of $Z^1$ is N, $Z^{1'}$ is N, and $R^5$ is —NR$^{b1}$R$^{c1}$ (e.g., —NH$_2$ or —NHR$^{c1}$); and in certain of these embodiments, $R^4$ and/or $R^6$ is H; or $R^4$ is other than H, and $R^6$ is H; and/or each occurrence of $Z^1$ is N, $Z^{1'}$ is N, and $R^5$ is —OH; in certain of these embodiments, $R^6$ is H; in certain of these embodiments, $R^4$ is H; in other embodiments, $R^4$ is other than H; and/or each occurrence of $Z^2$ is N, $Z^{2'}$ is. N, $Z^3$ is N—R$^3$ (e.g., N—H), and $R^{6'}$ is —NR$^{b1}$R$^{c1}$ (e.g., —NH$_2$ or —NHR$^{c1}$); and in certain of these embodiments, $R^{4'}$ is H; in other embodiments, $R^{4'}$ is other than H.

$X^1$ and $X^5$ can each be independently selected from the group consisting of H, $C_{1-4}$ alkyl, $C_{1-4}$ haloalkyl (e.g., CF$_3$), halo (e.g., F), —CN, and —S(O)$_2$R (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., CF$_3$), halo (e.g., F), —CN, and —S(O)$_2$R$^1$).

In certain embodiments, $X^1$ and $X^5$ can each be independently selected from the group consisting of H, $C_{1-4}$ alkyl, $C_{1-4}$ haloalkyl (e.g., CF$_3$), and halo (e.g., F) (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., CF$_3$), and halo (e.g., F)).

For example, $X^1$ and $X^5$ can each be independently selected from the group consisting of H and halo (e.g., F); or $X^1$ and $X^5$ can each be an independently selected halo (e.g., F).

Each occurrence of R$^{b1}$ and R$^{c1}$ or each occurrence of R$^{c1}$ can be independently selected from the group consisting of: H; $C_{1-6}$ (e.g., $C_{1-4}$) alkyl; —SO$_2$($C_{1-6}$ alkyl); —C(O)H; —C(O)($C_{1-6}$ alkyl); —C(O)NRR', wherein R' and R" are each independently selected from H and $C_{1-4}$ alkyl; and —C(O)O($C_{1-6}$ alkyl).

[F] In some embodiments of formula (II), (II-A), (III), or (IV):

$X^1$ and $X^5$ are each independently selected from the group consisting of is —OH, —OR$^{a1}$, —OC(O)H, —OC(O)R$^{a1}$, or —OC(O)NR$^{b1}$R$^{c1}$;

$X^2$ and $X^4$ are each an independently selected N—R$^3$ (e.g., N—H);

$X^3$ and $X^6$ are O;

$L^1$ is

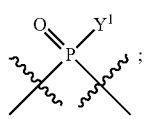

$L^2$ is

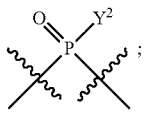

$Y^1$ and $Y^2$ are each independently selected from —OH, —OR$^{a1}$, O⁻, —SH, —SR$^{a1}$, or S; and optionally:

each occurrence of $Z^1$ is N, $Z^{1'}$ is N, and $R^5$ is —NR$^{b1}$R$^{c1}$ (e.g., —NH$_2$ or —NHR$^{c1}$); and in certain of these embodiments, $R^4$ and/or $R^6$ is H; or $R^4$ is other than H, and $R^6$ is H; and/or each occurrence of $Z^1$ is N, $Z^{1'}$ is N, and $R^5$ is —OH; in certain of these embodiments, $R^6$ is H; in certain of these embodiments, $R^4$ is H; in other embodiments, $R^4$ is other than H; and/or each occurrence of $Z^2$ is N, $Z^{2'}$ is. N, $Z^3$ is N—R$^3$ (e.g., N—H), and $R^{6'}$ is —NR$^{b1}$R$^{c1}$ (e.g., —NH$_2$ or —NHR$^{c1}$); and in certain of these embodiments, $R^{4'}$ is H; in other embodiments, $R^{4'}$ is other than H.

$X^1$ and $X^5$ can each be independently selected from the group consisting of —OH, or —OR$^{a1}$ (e.g., R$^{a1}$ can be $C_{1-10}$ alkyl, e.g., $C_{1-4}$ alkyl); e.g., $X^1$ and $X^5$ can each be —OH. Two of $X^2$, $X^3$, $X^4$ and $X^6$ can be N—R$^3$ (e.g., N—H), and the others can be O. $Y^1$ and $Y^2$ can each be O⁻; or $Y^1$ and $Y^2$ can each be SH or S⁻. $L^1$ and $L^2$ can both have the RP configuration or both have the SP configuration; or one of $L^1$ and $L^2$ can have the R$_P$ configuration, and the other can have the SP configuration. R$^{1A}$ and R$^{1B}$ can each be H, and R$^2$ and R$^{2B}$ can each be H.

Each occurrence of R$^{b1}$ and R$^{c1}$ or each occurrence of R$^{c1}$ can be independently selected from the group consisting of: H; $C_{1-6}$ (e.g., $C_{1-4}$) alkyl; —SO$_2$($C_{1-6}$ alkyl); —C(O)H; —C(O)($C_{1-6}$ alkyl); —C(O)NRR', wherein R' and R" are each independently selected from H and $C_{1-4}$ alkyl; and —C(O)O($C_{1-6}$ alkyl).

[G] In some embodiments of formula (II), (II-A), (III), or (IV):

$X^1$ and $X^5$ are each independently selected from the group consisting of —OH, —OR$^{a1}$, —OC(O)H, —OC(O)R$^{a1}$, or —OC(O)NR$^{b1}$R$^{c1}$;

$X^3$ and $X^6$ are each an independently selected N—R$^3$ (e.g., N—H);

$X^2$ and $X^4$ are O;

$L^1$ is

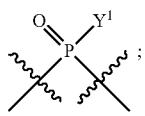

$L^2$ is

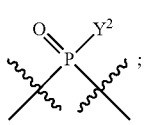

$Y^1$ and $Y^2$ are each independently selected from —OH, —OR$^{a1}$, O⁻, —SH, —SR$^{a1}$, or S; and optionally:

each occurrence of $Z^1$ is N, $Z^{1'}$ is N, and $R^5$ is —$NR^{b1}R^{c1}$ (e.g., —$NH_2$ or —$NHR^{c1}$); and in certain of these embodiments, $R^4$ and/or $R^6$ is H; or $R^4$ is other than H, and $R^6$ is H; and/or each occurrence of $Z^1$ is N, $Z^{1'}$ is N, and $R^5$ is —OH; in certain of these embodiments, $R^6$ is H; in certain of these embodiments, $R^4$ is H; in other embodiments, $R^4$ is other than H; and/or each occurrence of $Z^2$ is N, $Z^{2'}$ is. N, $Z^3$ is N—$R^3$ (e.g., N—H), and $R^{6'}$ is —$NR^{b1}R^{c1}$ (e.g., —$NH_2$ or —$NHR^{c1}$); and in certain of these embodiments, $R^{4'}$ is H; in other embodiments, $R^{4'}$ is other than H.

$X^1$ and $X^5$ can each be independently selected from the group consisting of —OH, or —$OR^{a1}$ (e.g., $R^{a1}$ can be $C_{1-10}$ alkyl, e.g., $C_{1-4}$ alkyl); e.g., $X^1$ and $X^5$ can each be —OH. Two of $X^2$, $X^3$, $X^4$ and $X^6$ can be N—$R^3$ (e.g., N—H), and the others can be O. $Y^1$ and $Y^2$ can each be O⁻; or $Y^1$ and $Y^2$ can each be SH or S⁻. $L^1$ and $L^2$ can both have the RP configuration or both have the $S_P$ configuration; or one of $L^1$ and $L^2$ can have the RP configuration, and the other can have the $S_P$ configuration. $R^{1A}$ and $R^{1B}$ can each be H, and $R^{2A}$ and $R^{2B}$ can each be H.

Each occurrence of $R^{b1}$ and $R^{c1}$ or each occurrence of $R^{c1}$ can be independently selected from the group consisting of: H; $C_{1-6}$ (e.g., $C_{1-4}$) alkyl; —$SO_2(C_{1-6}$ alkyl); —C(O)H; —C(O)($C_{1-6}$ alkyl); —C(O)NRR', wherein R' and R" are each independently selected from H and $C_{1-4}$ alkyl; and —C(O)O($C_{1-6}$ alkyl).

[H] In some embodiments of formula (II), (II-A), (III), or (IV):

$X^1$ and $X^5$ are each independently selected from the group consisting of H, $C_{1-4}$ alkyl, $C_{1-4}$ haloalkyl (e.g., $CF_3$), halo (e.g., F), —CN, —C(O)H, —C(O)$R^{a1}$, —C(O)$NR^{c1}R^{d1}$, —C(O)OH, —C(O)$OR^{a1}$, —C(=$NR^{e1}$)$NR^{b1}R^{c1}$, —S(O)$R^{a1}$, —S(O)$NR^{b1}R^{c1}$, —$S(O)_2R^{a1}$, and —$S(O)_2NR^{b1}R^{c1}$;

$X^2$ and $X^4$ are each an independently selected N—$R^3$ (e.g., N—H);

$X^3$ and $X^1$ are O;

$L^1$ is

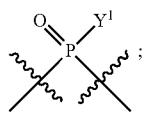

$L^2$ is

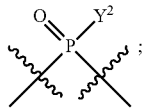

$Y^1$ and $Y^2$ are each independently selected from —OH, —$OR^{a1}$, O⁻, —SH, —$SR^{a1}$, or S; and optionally:

each occurrence of $Z^1$ is N, $Z^{1'}$ is N, and $R^5$ is —$NR^{b1}R^{c1}$ (e.g., —$NH_2$ or —$NHR^{c1}$); and in certain of these embodiments, $R^4$ and/or $R^6$ is H; or $R^4$ is other than H, and $R^6$ is H; and/or each occurrence of $Z^1$ is N, $Z^{1'}$ is N, and $R^5$ is —OH; in certain of these embodiments, $R^6$ is H; in certain of these embodiments, $R^4$ is H; in other embodiments, $R^4$ is other than H; and/or each occurrence of $Z^2$ is N, $Z^{2'}$ is. N, $Z^3$ is N—$R^3$ (e.g., N—H), and $R^{a1}$ is —$NR^{b1}R^{c1}$ (e.g., —$NH_2$ or —$NHR^{c1}$);

and in certain of these embodiments, $R^{4'}$ is H; in other embodiments, $R^{4'}$ is other than H.

$X^1$ and $X^5$ can each be independently selected from the group consisting of H, $C_{1-4}$ alkyl, $C_{1-4}$ haloalkyl (e.g., $CF_3$), halo (e.g., F), —CN, and —$S(O)_2R^{a1}$ (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., $CF_3$), halo (e.g., F), —CN, and —$S(O)_2R^{a1}$).

In certain embodiments, $X^1$ and $X^5$ can each be independently selected from the group consisting of H, $C_{1-4}$ alkyl, $C_{1-4}$ haloalkyl (e.g., $CF_3$), and halo (e.g., F) (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., $CF_3$), and halo (e.g., is F)).

For example, $X^1$ and $X^5$ can each be independently selected from the group consisting of H and halo (e.g., F); or $X^1$ and $X^5$ can each be an independently selected halo (e.g., F).

Each occurrence of $R^{b1}$ and $R^{c1}$ or each occurrence of $R^{c1}$ can be independently selected from the group consisting of: H; $C_{1-6}$ (e.g., $C_{1-4}$) alkyl; —$SO_2(C_{1-6}$ alkyl); —C(O)H; —C(O)($C_{1-6}$ alkyl); —C(O)NRR', wherein R' and R" are each independently selected from H and $C_{1-4}$ alkyl; and —C(O)O($C_{1-6}$ alkyl).

[I] In some embodiments of formula (II), (II-A), (III), or (IV):

$X^1$ and $X^5$ are each independently selected from the group consisting of is are each independently selected from the group consisting of H, $C_{1-4}$ alkyl, $C_{1-4}$ haloalkyl (e.g., $CF_3$), halo (e.g., F), —CN, —C(O)H, —C(O)$R^{a1}$, —C(O)$NR^{c1}R^{d1}$, —C(O)OH, —C(O)$OR^{a1}$, —C(=$NR^{e1}$)$NR^{b1}R^{c1}$, —S(O)$R^{a1}$, —S(O)$NR^{b1}R^{c1}$, —$S(O)_2R^{a1}$, and —$S(O)_2NR^{b1}R^{c1}$;

$X^3$ and $X^6$ are each an independently selected N—$R^3$ (e.g., N—H);

$X^2$ and $X^4$ are O;

$L^1$ is

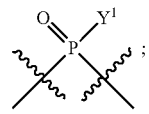

$L^2$ is

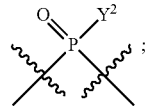

$Y^1$ and $Y^2$ are each independently selected from —OH, —$OR^{a1}$, O⁻, —SH, —$SR^{a1}$, or S; and optionally:

each occurrence of $Z^1$ is N, $Z^{1'}$ is N, and $R^5$ is —$NR^{b1}R^{c1}$ (e.g., —$NH_2$ or —$NHR^{c1}$); and in certain of these embodiments, $R^4$ and/or $R^6$ is H; or $R^4$ is other than H, and $R^6$ is H; and/or each occurrence of $Z^1$ is N, $Z^{1'}$ is N, and $R^5$ is —OH; in certain of these embodiments, $R^6$ is H; in certain of these embodiments, $R^4$ is H; in other embodiments, $R^4$ is other than H; and/or each occurrence of $Z^2$ is N, $Z^{2'}$ is. N, $Z^3$ is N—$R^3$ (e.g., N—H), and $R^{6'}$ is —$NR^{b1}R^{c1}$ (e.g., —$NH_2$ or —$NHR^{c1}$);

and in certain of these embodiments, $R^{4'}$ is H; in other embodiments, $R^{4'}$ is other than H.

$X^1$ and $X^5$ can each be independently selected from the group consisting of H, $C_{1-4}$ alkyl, $C_{1-4}$ haloalkyl (e.g., $CF_3$), halo (e.g., F), —CN, and —$S(O)_2R^{a1}$ (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., $CF_3$), halo (e.g., F), —CN, and —$S(O)_2R^{a1}$).

In certain embodiments, $X^1$ and $X^5$ can each be independently selected from the group consisting of H, $C_{1-4}$ alkyl, $C_{1-4}$ haloalkyl (e.g., $CF_3$), and halo (e.g., F) (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., $CF_3$), and halo (e.g., F)).

For example, $X^1$ and $X^5$ can each be independently selected from the group consisting of H and halo (e.g., F); or $X^1$ and $X^5$ can each be an independently selected halo (e.g., F).

Each occurrence of $R^{b1}$ and $R^{d1}$ or each occurrence of $R^{e1}$ can be independently selected from the group consisting of: H; $C_{1-6}$ (e.g., $C_{1-4}$) alkyl; —$SO_2(C_{1-6}$ alkyl); —C(O)H; —C(O)($C_{1-6}$ alkyl); —C(O)NRR', wherein R' and R'' are each independently selected from H and $C_{1-4}$ alkyl; and —C(O)O($C_{1-6}$ alkyl).

[J] In some embodiments, the compound has formula (VI):

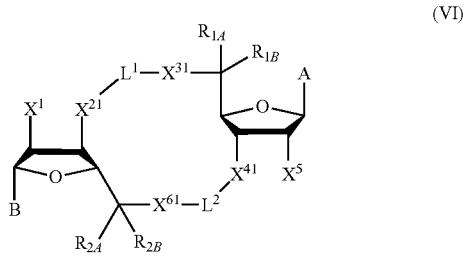

(VI)

in which, $X^1$ and $X^5$ are each independently selected from the group consisting of is —OH, —$OR^{a1}$, —OC(O)H, —OC(O)$R^{a1}$, or —OC(O)$NR^{b1}R^{c1}$;

$X^{21}$ and $X^{41}$ are each an independently selected N—$R^3$ (e.g., N—H);

$X^{31}$ and $X^{61}$ are O;

$L^1$ is

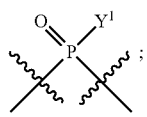

$L^2$ is

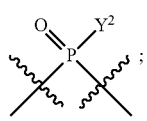

$Y^1$ and $Y^2$ are each independently selected from —OH, —$OR^{a1}$, $O^-$, —SH, —$SR^{a1}$, or S; and A and B are each independently selected from the group consisting of: formula (i) and formula (ii).

A can have formula (i), and B can have formula (ii); or A can have formula (ii), and B can have formula (ii); or A can have formula (i), and B can have formula (i); or A can have formula (ii), and B can have formula (i). $Z^1$ can be N, and $Z^{1'}$ can be N. In certain embodiments, $R^5$ can be —$NR^{b1}R^{c1}$ (e.g., —$NH_2$ or —$NHR^{c1}$; e.g., in certain embodiments, $R^4$ and/or $R^6$ is H; or $R^4$ is other than H, and $R^6$ is H). In other embodiments, $R^5$ is —OH, and $R^6$ is H (e.g., in certain embodiments, $R^4$ is H; in other embodiments, $R^4$ is other than H). Each occurrence of $Z^2$ can be N, $Z^{2'}$ can be. N, and $Z^3$ can be N—$R^3$ (e.g., N—H). $R^{6'}$ can be —$NR^{b1}R^{c1}$ (e.g., —$NH_2$ or —$NHR^{c1}$; e.g., in certain embodiments, $R^{4'}$ is H; in other embodiments, $R^{4'}$ is other than H).

$X^1$ and $X^5$ can each be independently selected from the group consisting of —OH, or —$OR^{a1}$ (e.g., $R^{a1}$ can be $C_{1-10}$ alkyl, e.g., $C_{1-4}$ alkyl); e.g., $X^1$ and $X^5$ can each be —OH. Two of $X^2$, $X^3$, $X^4$ and $X^1$ can be N—$R^3$ (e.g., N—H), and the others can be O. $Y^1$ and $Y^2$ can each be $O^-$; or $Y^1$ and $Y^2$ can each be SH or $S^-$. $L^1$ and $L^2$ can both have the RP configuration or both have the $S_P$ configuration; or one of $L^1$ and $L^2$ can have the RP configuration, and the other can have the $S_P$ configuration. $R^{1A}$ and $R^{1B}$ can each be H, and $R^{2A}$ and $R^{2B}$ can each be H.

Each occurrence of $R^{b1}$ and $R^{c1}$ or each occurrence of $R^{c1}$ can be independently selected from the group consisting of: H; $C_{1-6}$ (e.g., $C_{1-4}$) alkyl; —$SO_2(C_{1-6}$ alkyl); —C(O)H; —C(O)($C_{1-6}$ alkyl); —C(O)NRR', wherein R' and R'' are each independently selected from H and $C_{1-4}$ alkyl; and —C(O)O($C_{1-6}$ alkyl).

[K] In some embodiments, the compound has formula (VI), in which:

$X^1$ and $X^5$ are each independently selected from the group consisting of —OH, —$OR^{a1}$, —OC(O)H, —OC(O)$R^{a1}$, or —OC(O)$NR^{b1}R^{c1}$;

$X^{31}$ and $X^{61}$ are each an independently selected N—$R^3$ (e.g., N—H);

$X^{21}$ and $X^{41}$ are O;

$L^1$ is

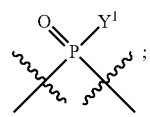

$L^2$ is

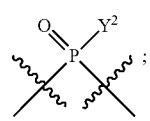

$Y^1$ and $Y^2$ are each independently selected from —OH, —$OR^{a1}$, $O^-$, —SH, —$SR^{a1}$, or S; and A and B are each independently selected from the group consisting of:

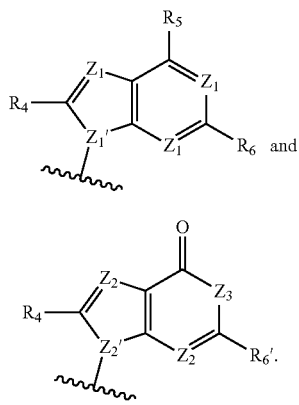

(i)

(ii)

A can have formula (i), and B can have formula (ii); or A can have formula (ii), and B can have formula (ii); or A can have formula (i), and B can have formula (i); or A can have formula (ii), and B can have formula (i). $Z^1$ can be N, and $Z^{1'}$ can be N. In certain embodiments, $R^5$ can be —NR$^{b1}$R$^{c1}$ (e.g., —NH$_2$ or —NHR$^{c1}$; e.g., in certain embodiments, $R^4$ and/or $R^6$ is H; or $R^4$ is other than H, and $R^6$ is H). In other embodiments, $R^5$ is —OH, and $R^6$ is H (e.g., in certain embodiments, $R^4$ is H; in other embodiments, $R^4$ is other than H). Each occurrence of $Z^2$ can be N, $Z^{2'}$ can be N, and $Z^3$ can be N—$R^3$ (e.g., N—H). $R^6$ can be —NR$^{b1}$R$^{c1}$ (e.g., —NH$_2$ or —NHR$^{c1}$; e.g., in certain embodiments, $R^{4'}$ is H; in other embodiments, $R^{4'}$ is other than H).

$X^1$ and $X^5$ can each be independently selected from the group consisting of —OH, or —OR$^{a1}$ (e.g., $R^{a1}$ can be $C_{1-10}$ alkyl, e.g., $C_{1-4}$ alkyl); e.g., $X^1$ and $X^5$ can each be —OH. Two of $X^2$, $X^3$, $X^4$ and $X^6$ can be N—$R^3$ (e.g., N—H), and the others can be O. $Y^1$ and $Y^2$ can each be O$^-$; or $Y^1$ and $Y^2$ can each be SH or S$^-$. $L^t$ and $L^2$ can both have the RP configuration or both have the $S_P$ configuration; or one of $L^1$ and $L^2$ can have the RP configuration, and the other can have the $S_P$ configuration. $R^{1A}$ and $R^{1B}$ can each be H, and $R^{2A}$ and $R^{2B}$ can each be H.

Each occurrence of $R^{b1}$ and $R^{c1}$ or each occurrence of $R^{c1}$ can be independently selected from the group consisting of: H; $C_{1-6}$ (e.g., $C_{1-4}$) alkyl; —SO$_2$($C_{1-6}$ alkyl); —C(O)H; —C(O)($C_{1-6}$ alkyl); —C(O)NRR', wherein R' and R" are each independently selected from H and $C_{1-4}$ alkyl; and —C(O)O($C_{1-6}$ alkyl).

[L] In some embodiments, the compound has formula (VI), in which:
wherein,
$X^1$ and $X^5$ are each independently selected from the group consisting of H, $C_{1-4}$ alkyl, $C_{1-4}$ haloalkyl (e.g., CF$_3$), halo (e.g., F), —CN, —C(O)H, —C(O)R$^{a1}$, —C(O)NR$^{c1}$R$^{d1}$, —C(O)OH, —C(O)OR$^{a1}$, —C(=NR$^{e1}$)NR$^{b1}$R$^{c1}$, —S(O)R$^{a1}$, —S(O)NR$^{b1}$R$^{c1}$, —S(O)$_2$R$^{a1}$, and —S(O)$_2$NR$^{b1}$R$^{c1}$;
$X^{21}$ and $X^{41}$ are each an independently selected N—$R^3$ (e.g., N—H);
$X^{31}$ and $X^{61}$ are O;
$L^1$ is

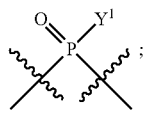

$L^2$ is

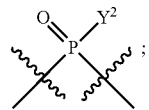

$Y^1$ and $Y^2$ are each independently selected from —OH, —OR$^{a1}$, O$^-$, —SH, —SR$^{a1}$, or S; and
A and B are each independently selected from the group consisting of:

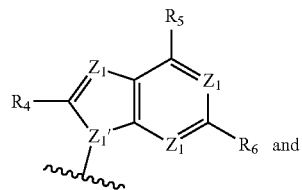

(i)

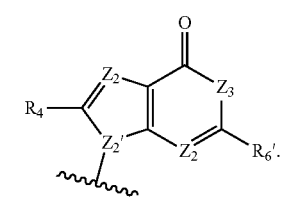

(ii)

A can have formula (i), and B can have formula (ii); or A can have formula (ii), and B can have formula (ii); or A can have formula (i), and B can have formula (i); or A can have formula (ii), and B can have formula (i). $Z^1$ can be N, and $Z^{1'}$ can be N. In certain embodiments, $R^5$ can be —NR$^{b1}$R$^{c1}$ (e.g., —NH$_2$ or —NHR$^{c1}$; e.g., in certain embodiments, $R^4$ and/or $R^6$ is H; or $R^4$ is other than H, and $R^6$ is H). In other embodiments, $R^5$ is —OH, and $R^6$ is H (e.g., in certain embodiments, $R^4$ is H; in other embodiments, $R^4$ is other than H). Each occurrence of $Z^2$ can be N, $Z^{2'}$ can be. N, and $Z^3$ can be N—$R^3$ (e.g., N—H). $R^{6'}$ can be —NR$^{b1}$R$^{c1}$ (e.g., —NH$_2$ or —NHR$^{c1}$; e.g., in certain embodiments, $R^{4'}$ is H; in other embodiments, $R^{4'}$ is other than H).

$X^1$ and $X^5$ can each be independently selected from the group consisting of H, $C_{1-4}$ alkyl, $C_{1-4}$ haloalkyl (e.g., CF$_3$), halo (e.g., F), —CN, and —S(O)$_2$R$^{a1}$ (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., CF$_3$), halo (e.g., F), —CN, and —S(O)$_2$R$^{a1}$).

In certain embodiments, $X^1$ and $X^5$ can each be independently selected from the group consisting of H, $C_{1-4}$ alkyl, $C_{1-4}$ haloalkyl (e.g., CF$_3$), and halo (e.g., F) (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., CF$_3$), and halo (e.g., F)).

For example, $X^1$ and $X^5$ can each be independently selected from the group consisting of H and halo (e.g., F); or $X^1$ and $X^5$ can each be an independently selected halo (e.g., F).

Each occurrence of $R^{b1}$ and $R^{c1}$ or each occurrence of $R^{c1}$ can be independently selected from the group consisting of: H; $C_{1-6}$ (e.g., $C_{1-4}$) alkyl; —SO$_2$(C s alkyl); —C(O)H;

—C(O)($C_{1-6}$ alkyl); —C(O)NRR', wherein R' and R" are each independently selected from H and $C_{1-4}$ alkyl; and —C(O)O($C_{1-6}$ alkyl).

[M] In some embodiments, the compound has formula (VI), in which:

$X^1$ and $X^5$ are each independently selected from the group consisting of is are each independently selected from the group consisting of H, $C_{1-4}$ alkyl, $C_{1-4}$ haloalkyl (e.g., $CF_3$), halo (e.g., F), —CN, —C(O)H, —C(O)$R^{a1}$, —C(O)NR$^{c1}$R$^{a1}$, —C(O)OH, —C(O)O$R^{a1}$, —C(=N$R^{e1}$)NR$^{b1}$R$^{c1}$, —S(O)$R^{a1}$, —S(O)NR$^{b1}$R$^{c1}$, —S(O)$_2$R$^{a1}$, and —S(O)$_2$NR$^{b1}$R$^{c1}$;

$X^{31}$ and $X^{61}$ are each an independently selected N—$R^3$ (e.g., N—H);

$X^{21}$ and $X^{41}$ are O;

$L^1$ is

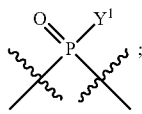

$L^2$ is

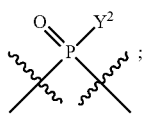

$Y^1$ and $Y^2$ are each independently selected from —OH, —OR$^{a1}$, O$^-$, —SH, —SR$^{a1}$, or S; and A and B are each independently selected from the group consisting of:

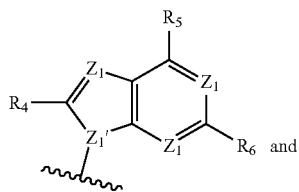

(i)

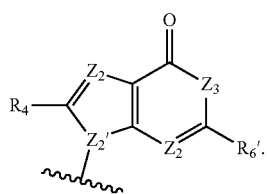

(ii)

A can have formula (i), and B can have formula (ii); or A can have formula (ii), and B can have formula (ii); or A can have formula (i), and B can have formula (i); or A can a have formula (ii), and B can have formula (i). $Z^1$ can be N, and $Z^{1'}$ can be N. In certain embodiments, $R^5$ can be —NR$^{b1}$R$^{c1}$ (e.g., —NH$_2$ or —NHR$^{c1}$; e.g., in certain embodiments, $R^4$ and/or $R^6$ is H; or $R^4$ is other than H, and $R^6$ is H). In other embodiments, $R^5$ is —OH, and $R^6$ is H (e.g., in certain embodiments, $R^4$ is H; in other embodiments, $R^4$ is other than H). Each occurrence of $Z^2$ can be N, $Z^{2'}$ can be N, and $Z^3$ can be N—$R^3$ (e.g., N—H). $R^{6'}$ can be —NR$^{b1}$R$^{c1}$ (e.g., —NH$_2$ or —NHR$^{c1}$; e.g., in certain embodiments, $R^{4'}$ is H; in other embodiments, $R^{4'}$ is other than H).

$X^1$ and $X^5$ can each be independently selected from the group consisting of H, $C_{1-4}$ alkyl, $C_{1-4}$ haloalkyl (e.g., $CF_3$), halo (e.g., F), —CN, and —S(O)$_2$R$^{a1}$ (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., $CF_3$), halo (e.g., F), —CN, and —S(O)$_2$R$^{a1}$).

In certain embodiments, $X^1$ and $X^5$ can each be independently selected from the group consisting of H, $C_{1-4}$ alkyl, $C_{1-4}$ haloalkyl (e.g., $CF_3$), and halo (e.g., F) (in certain embodiments, each of $X^1$ and $X^5$ is other than H; e.g., $X^1$ and $X^5$ can each be independently selected from the group consisting of $C_{1-4}$ alkyl, $C_{1-4}$ haloalkyl (e.g., $CF_3$), and halo (e.g., F)).

For example, $X^1$ and $X^5$ can each be independently selected from the group consisting of H and halo (e.g., F); or $X^1$ and $X^5$ can each be an independently selected halo (e.g., F).

Each occurrence of R$^{b1}$ and R$^{c1}$ or each occurrence of R$^{c1}$ can be independently selected from the group consisting of: H; $C_{1-6}$ (e.g., $C_{1-4}$) alkyl; —SO$_2$($C_{1-6}$ alkyl); —C(O)H; —C(O)($C_{1-6}$ alkyl); —C(O)NRR', wherein R' and R" are each independently selected from H and $C_{1-4}$ alkyl; and —C(O)O($C_{1-6}$ alkyl).

[N] In some embodiments:

$X^1$ and $X^5$ are each independently selected from the group consisting of halo (e.g., —F), —OH, —OR$^{a1}$, —OC(O)H, —OC(O)R$^{a1}$, or —OC(O)NR$^{b1}$R$^{c1}$;

two of $X^2$, $X^3$, $X^1$ and $X^6$ are N—$R^3$ (e.g., N—H);

$L^1$ is

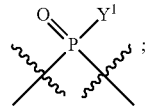

$L^2$ is

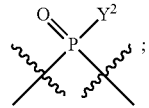

$Y^1$ and $Y^2$ are each independently selected from —OH, —OR$^{a1}$, O$^-$, —SH, —SR$^{a1}$, or S; and A and B are each independently selected from the group consisting of: formula (i) and formula (ii).

A can have formula (i), and B can have formula (ii); or A can have formula (ii), and B can have formula (ii); or A can have formula (i), and B can have formula (i); or A can have formula (ii), and B can have formula (i). $Z^1$ can be N, and $Z^{1'}$ can be N. In certain embodiments, $R^5$ can be —NR$^{b1}$R$^{c1}$ (e.g., —NH$_2$ or —NHR$^{c1}$; e.g., in certain embodiments, $R^4$ and/or $R^6$ is H; or $R^4$ is other than H, and $R^6$ is H). In other embodiments, $R^5$ is —OH, and $R^6$ is H (e.g., in certain embodiments, $R^4$ is H; in other embodiments, $R^4$ is other than H). Each occurrence of $Z^2$ can be N, $Z^{2'}$ can be N, and $Z^3$ can be N—$R^3$ (e.g., N—H). $R^{6'}$ can be —NR$^{b1}$R$^{c1}$ (e.g., —NH$_2$ or —NHR$^{c1}$; e.g., in certain embodiments, $R^{4'}$ is H; in other embodiments, $R^{4'}$ is other than H).

Each of $X^1$ and $X^5$ can each be independently selected from the group consisting of halo (e.g., —F), —OH, and —OR$^{a1}$ (e.g., R$^{a1}$ can be C$_{1-10}$ alkyl, e.g., C$_{1-4}$ alkyl). In certain embodiments, each of X$^1$ and X$^5$ can each be independently selected from the group consisting of: halo (e.g., —F) and —OH. For example, one of X$^1$ and X$^5$ can be halo (e.g., —F), and the other can be —OH.

Each occurrence of R$^{b1}$ and Ret or each occurrence of R$^{c1}$ can be independently selected from the group consisting of: H; C$_{1-6}$ (e.g., C$_{1-4}$) alkyl; —SO$_2$(C$_{1-6}$ alkyl); —C(O)H; —C(O)(C$_{1-6}$ alkyl); —C(O)NRR', wherein R' and R'' are each independently selected from H and C$_{1-4}$ alkyl; and —C(O)O(C$_{1-6}$ alkyl).

[O] In some embodiments of formula (II), (II-A), (III), or (IV):

X$^1$ and X$^5$ are each independently selected from the group consisting of halo (e.g., —F), —OH, —OR$^{a1}$, —OC(O)H, —OC(O)R$^{a1}$, or —OC(O)NR$^{b1}$R$^{c1}$;

two of X$^2$, X$^3$, X$^4$ and X$^6$ are N—R$^3$ (e.g., N—H);

L$^1$ is

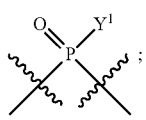

L$^2$ is

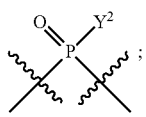

Y$^1$ and Y$^2$ are each independently selected from —OH, —OR$^{a1}$, O$^-$, —SH, —SR$^{a1}$, or S; and optionally:

each occurrence of Z$^1$ is N, Z$^{1'}$ is N, and R$^5$ is —NR$^{b1}$R$^{c1}$ (e.g., —NH$_2$ or —NHR$^{c1}$); and in certain of these embodiments, R$^4$ and/or R$^6$ is H; or R$^4$ is other than H, and R$^6$ is H; and/or each occurrence of Z$^1$ is N, Z$^{1'}$ is N, and R$^5$ is —OH; in certain of these embodiments, R$^6$ is H; in certain of these embodiments, R$^4$ is H; in other embodiments, R is other than H; and/or each occurrence of Z$^2$ is N, Z$^{2'}$ is. N, Z$^3$ is N—R$^3$ (e.g., N—H), and R$^{6'}$ is —NR$^{b1}$R$^{c1}$ (e.g., —NH$_2$ or —NHR$^{c1}$); and in certain of these embodiments, R$^{4'}$ is H; in other embodiments, R$^{4'}$ is other than H.

Each of X$^1$ and X$^5$ can each be independently selected from the group consisting of halo (e.g., —F), —OH, and —OR$^{a1}$ (e.g., R$^{a1}$ can be C$_{1-10}$ alkyl, e.g., C$_{1-4}$ alkyl). In certain embodiments, each of X$^1$ and X$^5$ can each be independently selected from the group consisting of: halo (e.g., —F) and —OH. For example, one of X$^1$ and X$^5$ can be halo (e.g., —F), and the other can be —OH.

Each occurrence of R$^{b1}$ and R$^{c1}$ or each occurrence of R$^{c1}$ can be independently selected from the group consisting of: H; C$_{1-6}$ (e.g., C$_{1-4}$) alkyl; —SO$_2$(C$_{1-4}$ alkyl); —C(O)H; —C(O)(C$_{1-6}$ alkyl); —C(O)NRR', wherein R' and R'' are each independently selected from H and C$_{1-4}$ alkyl; and —C(O)O(C$_{1-6}$ alkyl).

[P] In some embodiments of formula (II), (II-A), (III), or (IV):

X$^1$ and X$^5$ are each independently selected from the group consisting of is halo (e.g., —F), —OH, —OR$^{a1}$, —OC(O)H, —OC(O)R$^{a1}$, or —OC(O)NR$^{b1}$R$^{c1}$;

X$^2$ and X$^4$ are each an independently selected N—R$^3$ (e.g., N—H);

X$^3$ and X$^6$ are O;

L$^1$ is

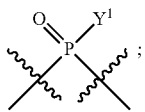

L$^2$ is

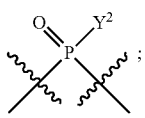

Y$^1$ and Y$^2$ are each independently selected from —OH, —OR$^{a1}$, O$^-$, —SH, —SR$^{a1}$, or S; and optionally:

each occurrence of Z$^1$ is N, Z$^{1'}$ is N, and R$^5$ is —NR$^{b1}$R$^{c1}$ (e.g., —NH$_2$ or —NHR$^{c1}$); and in certain of these embodiments, R$^4$ and/or R$^6$ is H; or R$^4$ is other than H, and R$^6$ is H; and/or each occurrence of Z$^1$ is N, Z$^{1'}$ is N, and R$^5$ is —OH; in certain of these embodiments, R$^6$ is H; in certain of these embodiments, R$^4$ is H; in other embodiments, R$^4$ is other than H; and/or each occurrence of Z$^2$ is N, Z$^{2'}$ is. N, Z$^3$ is N—R$^3$ (e.g., N—H), and R$^{6'}$ is —NR$^{b1}$R$^{c1}$ (e.g., —NH$_2$ or —NHR$^{c1}$); and in certain of these embodiments, R$^{4'}$ is H; in other embodiments, R$^{4'}$ is other than H.

Each of X$^1$ and X$^5$ can each be independently selected from the group consisting of halo (e.g., —F), —OH, and —OR$^{a1}$ (e.g., R$^{a1}$ can be C$_{1-10}$ alkyl, e.g., C$_{1-4}$ alkyl). In certain embodiments, each of X$^1$ and X$^5$ can each be independently selected from the group consisting of: halo (e.g., —F) and —OH. For example, one of X$^1$ and X$^5$ can be halo (e.g., —F), and the other can be —OH.

Each occurrence of R$^{b1}$ and R$^{c1}$ or each occurrence of R$^{c1}$ can be independently selected from the group consisting of: H; C$_{1-6}$ (e.g., C$_{1-4}$) alkyl; —SO$_2$(C$_{1-6}$ alkyl); —C(O)H; —C(O)(C$_{1-6}$ alkyl); —C(O)NRR', wherein R' and R'' are each independently selected from H and C$_{1-4}$ alkyl; and —C(O)O(C$_{1-6}$ alkyl).

[Q] In some embodiments of formula (II), (II-A), (III), or (IV):

X$^1$ and X$^5$ are each independently selected from the group consisting of halo (e.g., —F), —OH, —OR$^{a1}$, —OC(O)H, —OC(O)R$^{a1}$, or —OC(O)NR$^{b1}$R$^{c1}$;

X$^3$ and X$^6$ are each an independently selected N—R$^3$ (e.g., N—H);

X$^2$ and X$^4$ are O;

L$^1$ is

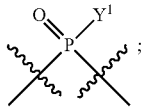

$L^2$ is

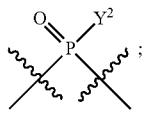

$Y^1$ and $Y^2$ are each independently selected from —OH, —OR$^{a1}$, O$^-$, —SH, —SR$^{a1}$, or S; and optionally:

each occurrence of $Z^1$ is N, $Z^{1'}$ is N, and $R^5$ is —NR$^{b1}$R$^{c1}$ (e.g., —NH$_2$ or —NHR$^{c1}$); and in certain of these embodiments, $R^4$ and/or $R^6$ is H; or $R^4$ is other than H, and $R^6$ is H; and/or each occurrence of $Z^1$ is N, $Z^{1'}$ is N, and $R^5$ is —OH; in certain of these embodiments, $R^6$ is H; in certain of these embodiments, $R^4$ is H; in other embodiments, $R^4$ is other than H; and/or each occurrence of $Z^2$ is N, $Z^{2'}$ is. N, $Z^3$ is N—R$^3$ (e.g., N—H), and $R^{6'}$ is —NR$^{b1}$R$^{c1}$ (e.g., —NH$_2$ or —NHR$^{c1}$); and in certain of these embodiments, $R^{4'}$ is H; in other embodiments, $R^{4'}$ is other than H.

Each of $X^1$ and $X^5$ can each be independently selected from the group consisting of halo (e.g., —F), —OH, and —OR$^{a1}$ (e.g., R$^{a1}$ can be C$_{1-10}$ alkyl, e.g., C$_{1-4}$ alkyl). In certain embodiments, each of $X^1$ and $X^5$ can each be independently selected from the group consisting of: halo (e.g., —F) and —OH. For example, one of $X^1$ and $X^5$ can be halo (e.g., —F), and the other can be —OH.

Each occurrence of R$^{b1}$ and R$^{c1}$ or each occurrence of R$^{c1}$ can be independently selected from the group consisting of: H; C$_{1-6}$ (e.g., C$_{1-4}$) alkyl; —SO$_2$(C$_{1-6}$ alkyl); —C(O)H; —C(O)(C$_{1-6}$ alkyl); —C(O)NRR', wherein R' and R" are each independently selected from H and C$_{1-4}$ alkyl; and —C(O)O(C$_{1-6}$ alkyl).

[R] In some embodiments, the compound has formula (VI):

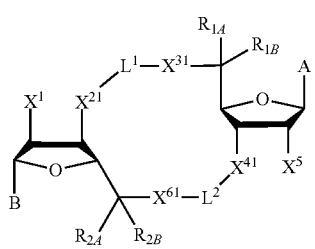

in which, $X^1$ and $X^5$ are each independently selected from the group consisting of is halo (e.g., —F), —OH, —OR$^{a1}$, —OC(O)H, —OC(O)R$^{a1}$, or —OC(O)NR$^{b1}$R$^{c1}$;

$X^{21}$ and $X^{41}$ are each an independently selected N—R$^3$ (e.g., N—H);

$X^{31}$ and $X^{61}$ are O;

$L^1$ is

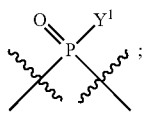

$L^2$ is

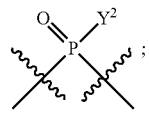

$Y^1$ and $Y^2$ are each independently selected from —OH, —OR$^{a1}$, O$^-$, —SH, —SR$^{a1}$, or S; and A and B are each independently selected from the group consisting of: formula (i) and formula (ii).

A can have formula (i), and B can have formula (ii); or A can have formula (ii), and B can have formula (ii); or A can have formula (i), and B can have formula (i); or A can have formula (ii), and B can have formula (i). $Z^1$ can be N, and $Z^{1'}$ can be N. In certain embodiments, $R^5$ can be —NR$^{b1}$R$^{c1}$ (e.g., —NH$_2$ or —NHR$^{c1}$; e.g., in certain embodiments, $R^4$ and/or $R^6$ is H; or $R^4$ is other than H, and $R^6$ is H). In other embodiments, $R^5$ is —OH, and $R^6$ is H (e.g., in certain embodiments, $R^4$ is H; in other embodiments, $R^4$ is other than H).

Each occurrence of $Z^2$ can be N, $Z^{2'}$ can be N, and $Z^3$ can be N—R$^3$ (e.g., N—H). $R^{6'}$ can be —NR$^{b1}$R$^{c1}$ (e.g., —NH$_2$ or —NHR$^{c1}$; e.g., in certain embodiments, $R^{4'}$ is H; in other embodiments, $R^{4'}$ is other than H).

Each of $X^1$ and $X^5$ can each be independently selected from the group consisting of halo (e.g., —F), —OH, and —OR$^{a1}$ (e.g., R$^{a1}$ can be C$_{1-10}$ alkyl, e.g., C$_{1-4}$ alkyl). In certain embodiments, each of $X^1$ and $X^5$ can each be independently selected from the group consisting of: halo (e.g., —F) and —OH. For example, one of $X^1$ and $X^5$ can be halo (e.g., —F), and the other can be —OH.

Each occurrence of R$^{b1}$ and R$^{c1}$ or each occurrence of R$^{c1}$ can be independently selected from the group consisting of: H; C$_{1-6}$ (e.g., C$_{1-4}$) alkyl; —SO$_2$(C$_{1-6}$ alkyl); —C(O)H; —C(O)(C$_{1-6}$ alkyl); —C(O)NRR', wherein R' and R" are each independently selected from H and C$_{1-4}$ alkyl; and —C(O)O(C$_{1-6}$ alkyl).

[S] In some embodiments, the compound has formula (VI), in which:

$X^1$ and $X^5$ are each independently selected from the group consisting of halo (e.g., —F), —OH, —OR$^{a1}$, —OC(O)H, —OC(O)R$^{a1}$, or —OC(O)NR$^{b1}$R$^{c1}$;

$X^{31}$ and $X^{61}$ are each an independently selected N—R$^3$ (e.g., N—H);

$X^{21}$ and $X^{41}$ are O;

$L^1$ is

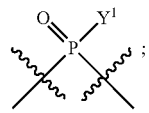

$L^2$ is

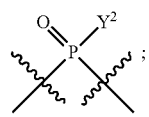

$Y^1$ and $Y^2$ are each independently selected from —OH, —OR$^{a1}$, O$^-$, —SH, —SR$^{a1}$, or S; and A and B are each independently selected from the group consisting of:

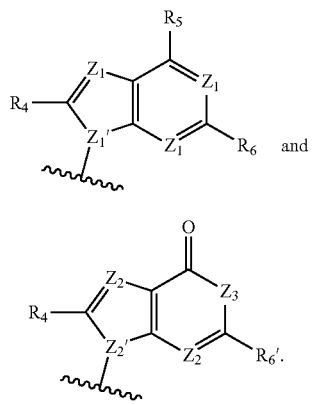

A can have formula (i), and B can have formula (ii); or A can have formula (ii), and B can have formula (ii); or A can have formula (i), and B can have formula (i); or A can have formula (ii), and B can have formula (i). $Z^1$ can be N, and $Z^{1'}$ can be N. In certain embodiments, $R^5$ can be —$NR^{b1}R^{c1}$ (e.g., —$NH_2$ or —$NHR^{c1}$; e.g., in certain embodiments, $R^4$ and/or $R^6$ is H; or $R^4$ is other than H, and $R^6$ is H). In other embodiments, $R^5$ is —OH, and $R^6$ is H (e.g., in certain embodiments, $R^4$ is H; in other embodiments, $R^4$ is other than H).

Each occurrence of $Z^2$ can be N, $Z^{2'}$ can be N, and $Z^3$ can be N—$R^3$ (e.g., N—H). $R^{6'}$ can be —$NR^{b1}R^{c1}$ (e.g., —$NH_2$ or —$NHR^{c1}$; e.g., in certain embodiments, $R^{4'}$ is H; in other embodiments, $R^{4'}$ is other than H).

Each of $X^1$ and $X^5$ can each be independently selected from the group consisting of halo (e.g., —F), —OH, and —$OR^{a1}$ (e.g., $R^{a1}$ can be $C_{1-10}$ alkyl, e.g., $C_{1-4}$ alkyl). In certain embodiments, each of $X^1$ and $X^5$ can each be independently selected from the group consisting of: halo (e.g., —F) and —OH. For example, one of $X^1$ and $X^5$ can be halo (e.g., —F), and the other can be —OH.

Each occurrence of $R^{b1}$ and $R^{c1}$ or each occurrence of $R^{c1}$ can be independently selected from the group consisting of: H; $C_{1-6}$ (e.g., $C_{1-4}$) alkyl; —$SO_2(C_{1-6}$ alkyl); —C(O)H; —C(O)($C_{1-6}$ alkyl); —C(O)NRR', wherein R' and R" are each independently selected from H and $C_{1-4}$ alkyl; and —C(O)O($C_{1-6}$ alkyl).

Representative and non-limiting examples of formula I compounds are shown in Table 1.

TABLE 1

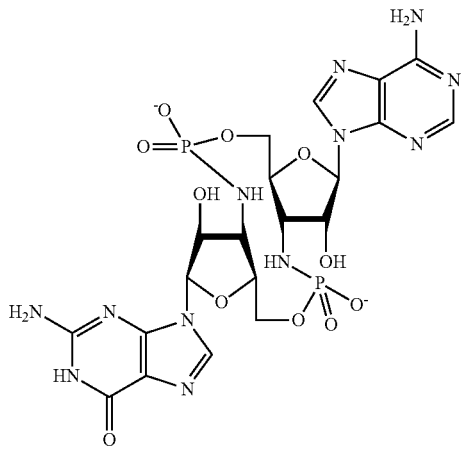

41

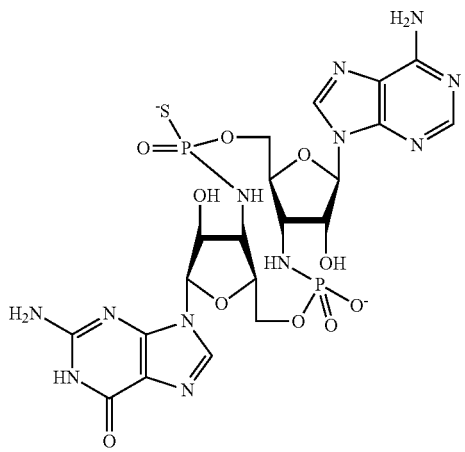

42

TABLE 1-continued
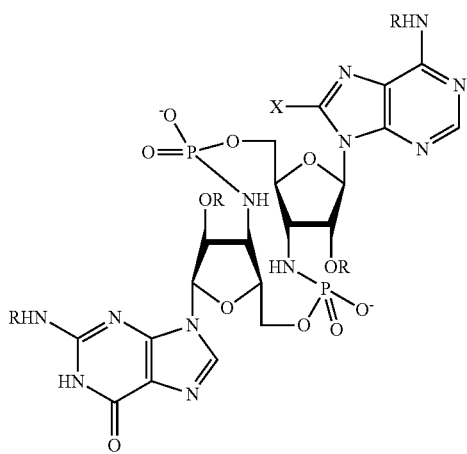
43
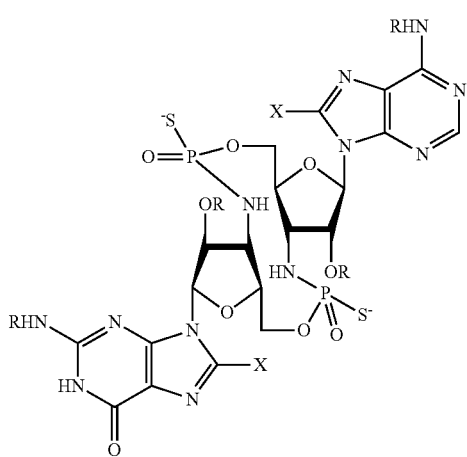
44
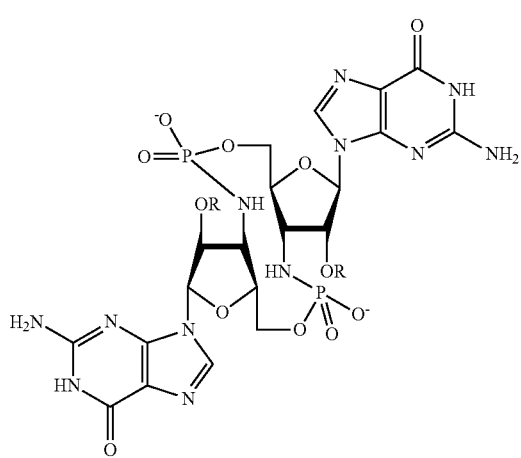
45

TABLE 1-continued
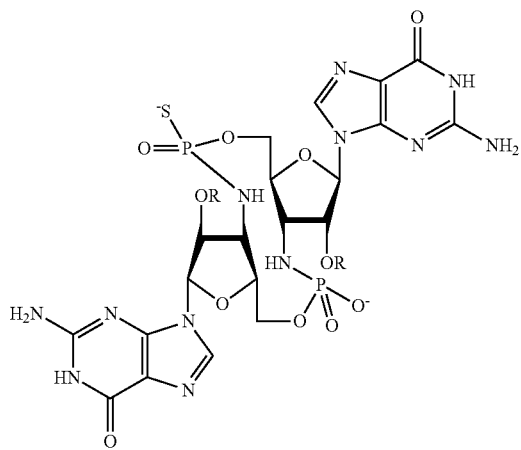
46
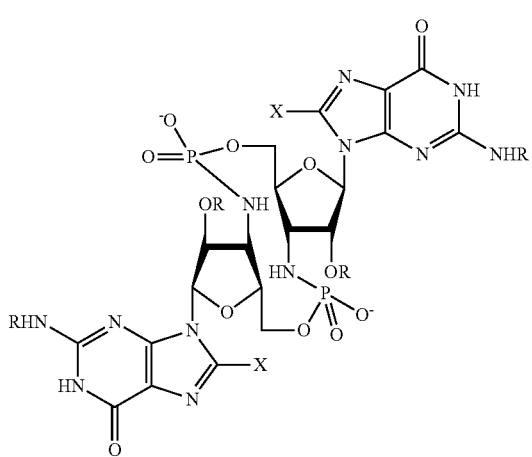
47
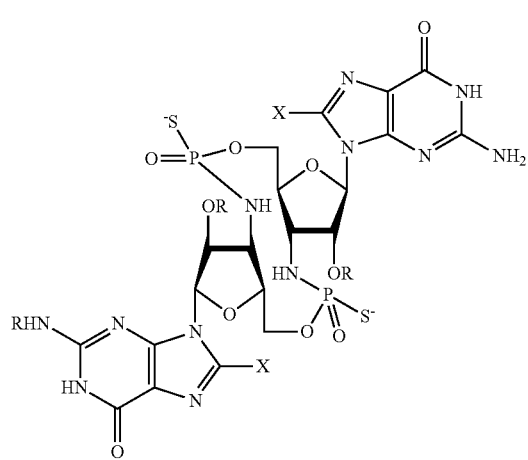
48

TABLE 1-continued
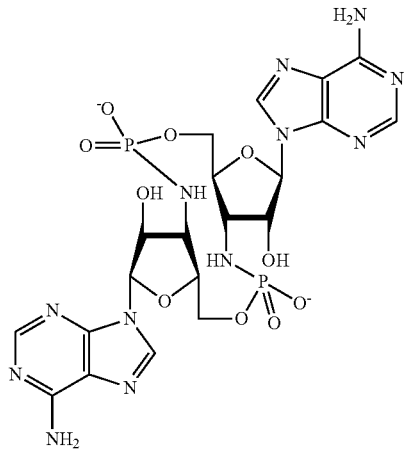
49
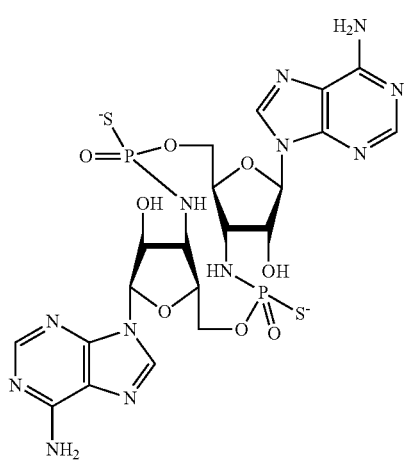
50
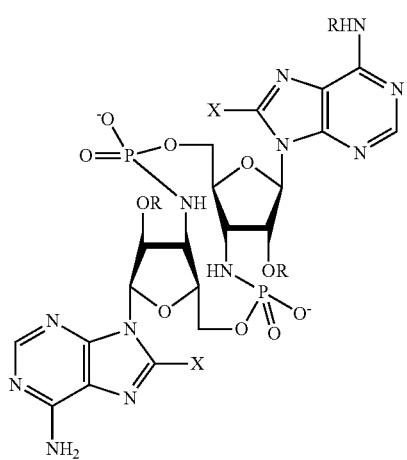
51

TABLE 1-continued
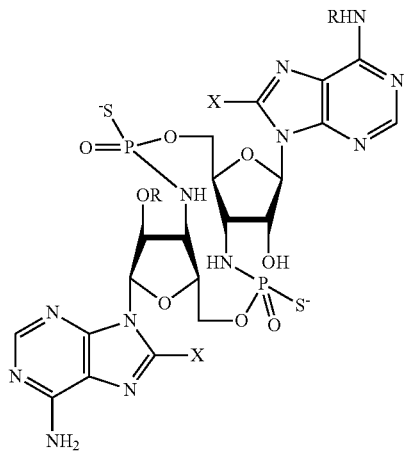
52
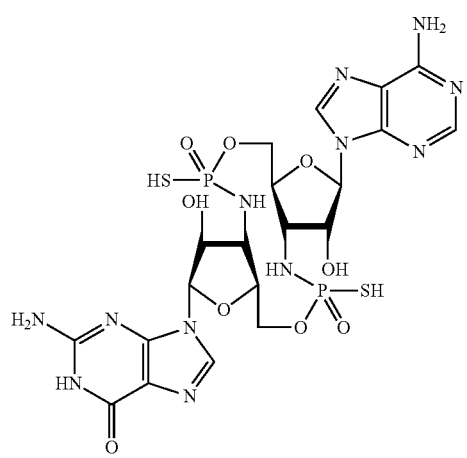
53
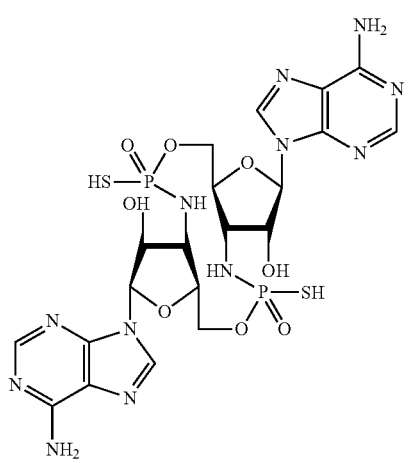
54

TABLE 1-continued
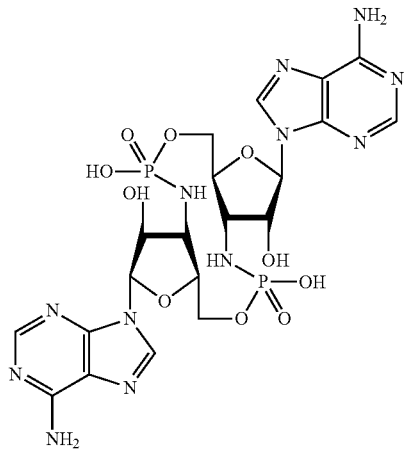
55
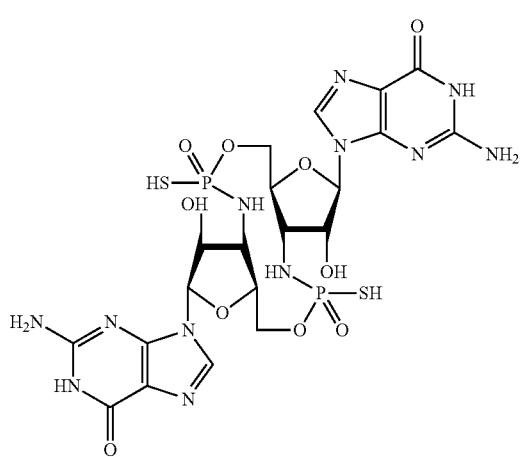
56
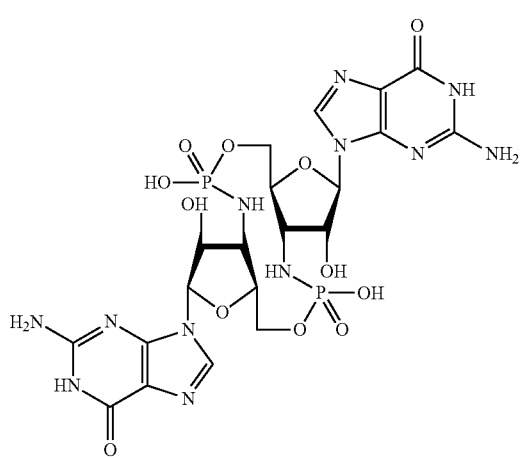
57

TABLE 1-continued
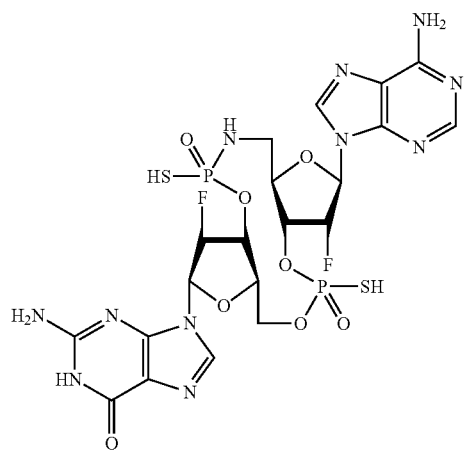
58
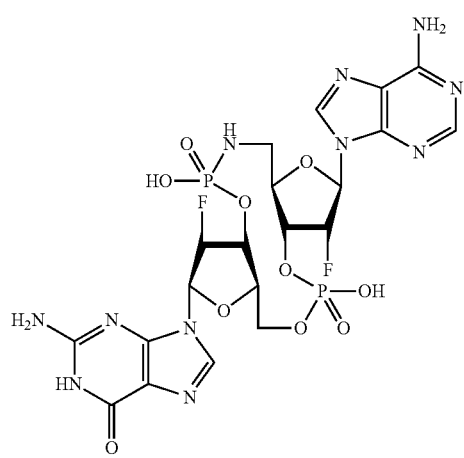
59
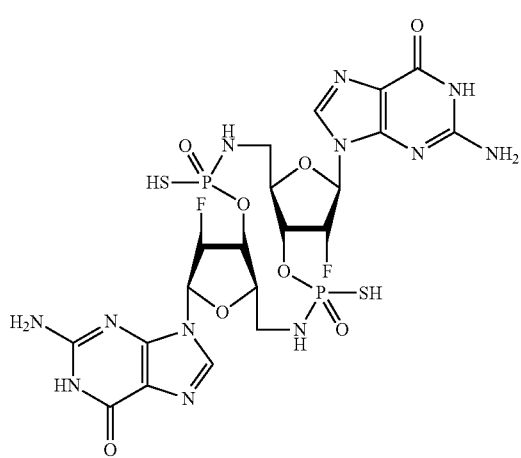
60

TABLE 1-continued
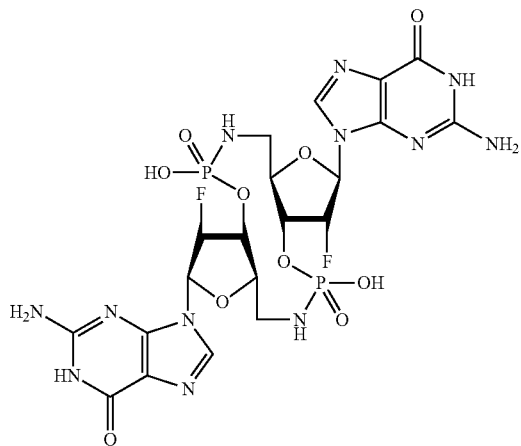
61
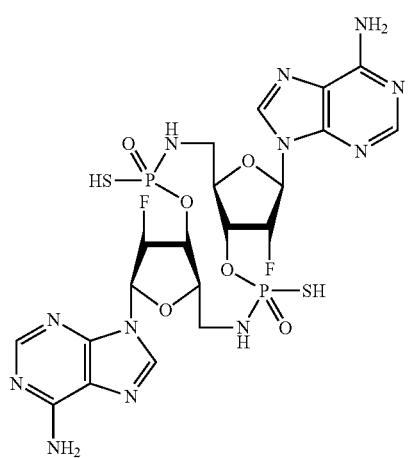
62
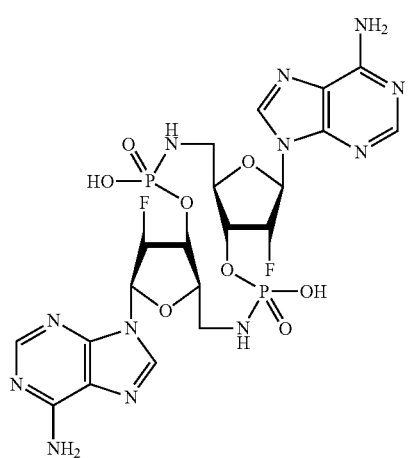
63

TABLE 1-continued
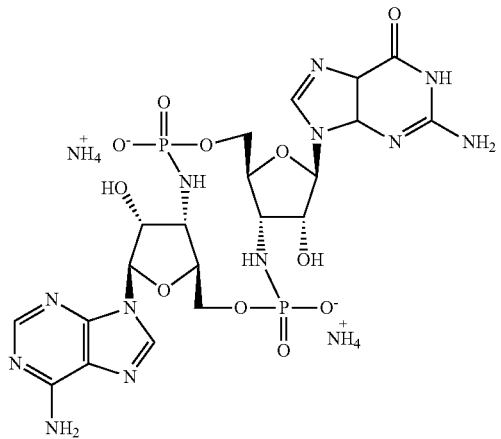
71
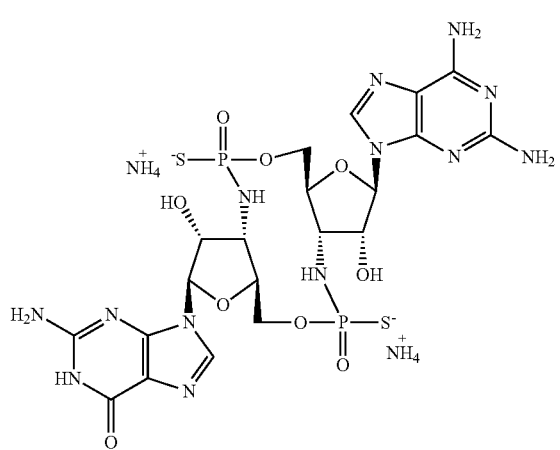
72
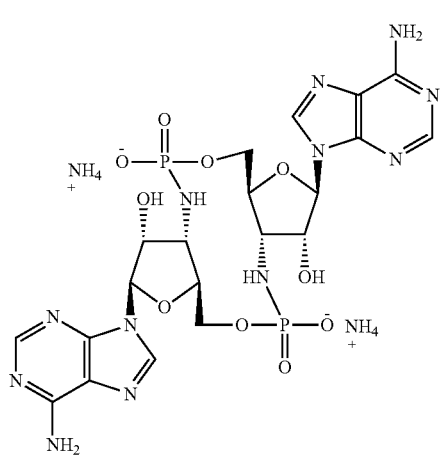
73

TABLE 1-continued
| | |
|---|---|
| 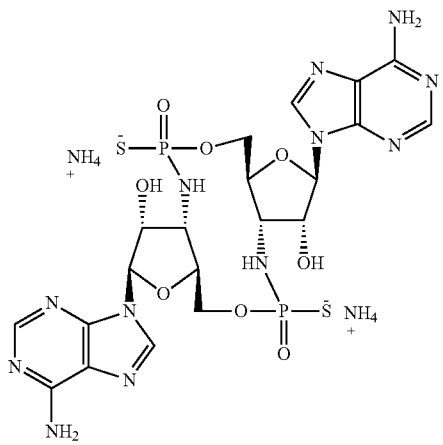 | 74 |
| 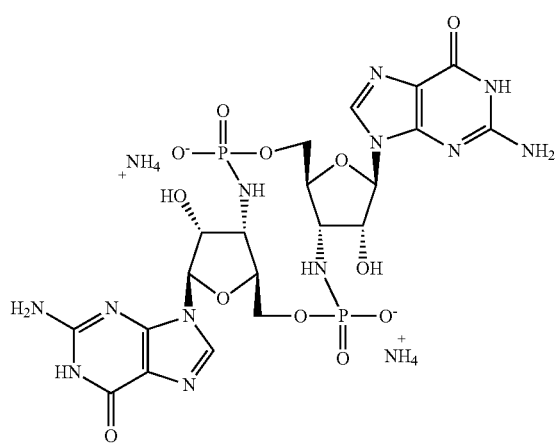 | 75 |
| 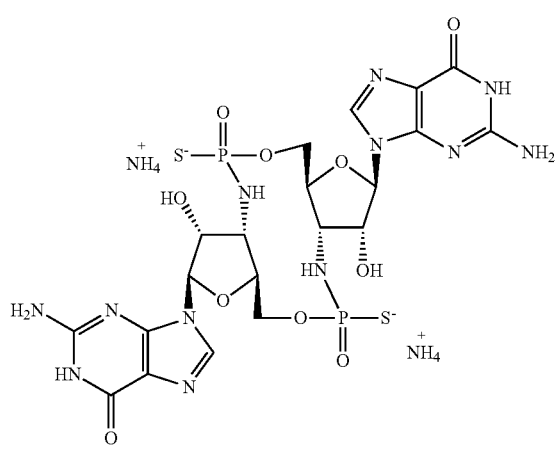 | 76 |

TABLE 1-continued
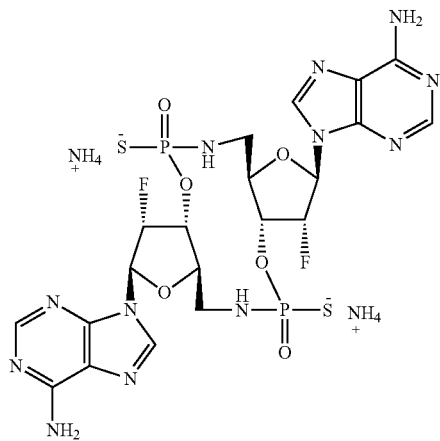
77
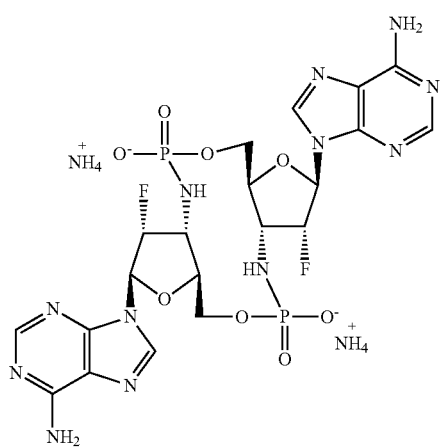
78
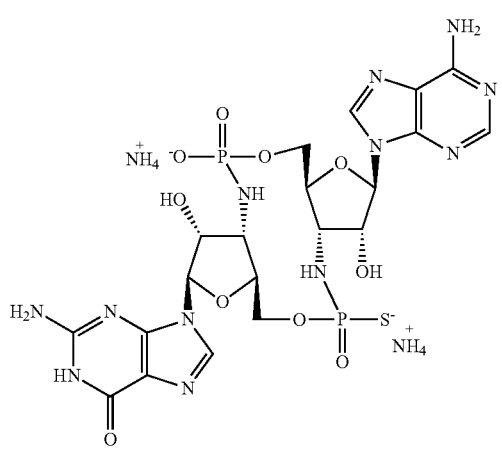
72-0A1

TABLE 1-continued

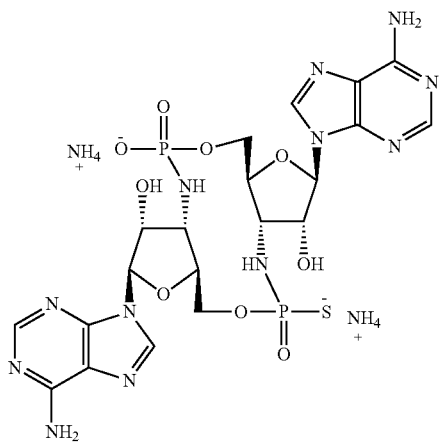

74-0B0

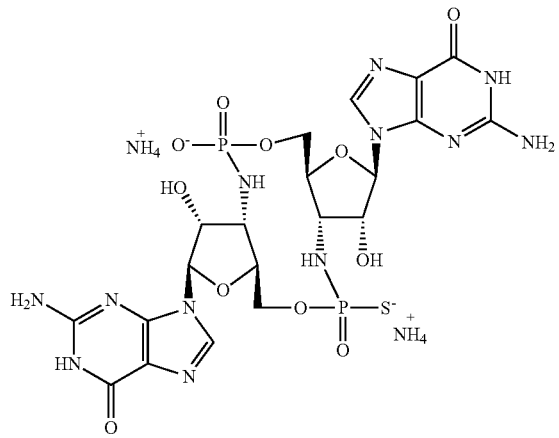

76-0A1

Pharmaceutical Compositions and Administration

General

In some embodiments, a chemical entity (e.g., a compound that modulates (e.g., agonizes) STING, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-L-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%~100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, $22^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more is pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in STING activity (e.g., a decrease, e.g., repressed or impaired STING signaling) contributes to the pathology and/or symptoms and/or progression of the condition, disease or disorder (e.g., immune disorders, cancer) are provided. In certain embodiments, the chemical entities described herein induce an immune response in a subject (e.g., a human). In certain embodiments, the chemical entities described herein induce STING-dependent type I interferon production in a subject (e.g., a human).

Indications

In some embodiments, the condition, disease or disorder is cancer. Non-limiting examples of cancer include melanoma, carcinoma, lymphoma, blastoma, sarcoma, and leukemia or lymphoid malignancies. More particular examples of such cancers include breast cancer, colon cancer, rectal cancer, colorectal cancer, kidney or renal cancer, clear cell cancer lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, prostatic neoplasms, liver cancer, bladder cancer, cancer of the peritoneum, hepatocellular cancer, gastric or stomach cancer including gastrointestinal cancer, gastrointestinal stromal tumor, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma, myelodysplasia disorders, myeloproliferative disorders, chronic myelogenous leukemia, and acute hematologic malignancies, endometrial or uterine carcinoma, endometriosis, endometrial stromal sarcoma, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, mast cell sarcoma, ovarian sarcoma, uterine sarcoma, melanoma, malignant mesothelioma, skin carcinomas, Schwannoma, oligodendroglioma, neuroblastomas, neuroectodermal tumor, rhabdomyosarcoma, osteogenic sarcoma, leiomyosarcomas, Ewing Sarcoma, peripheral primitive neuroectodermal tumor, urinary tract carcinomas, thyroid carcinomas, Wilm's tumor, as well as abnormal vascular proliferation associated with phakomatoses, edema (such as that associated with brain tumors), and Meigs' syndrome. In some cases, the cancer is melanoma.

In some embodiments, the condition, disease or disorder is a neurological disorder, which includes disorders that involve the central nervous system (brain, brainstem and cerebellum), the peripheral nervous system (including cranial nerves), and the autonomic nervous system (parts of which are located in both central and peripheral nervous system). Non-limiting examples of cancer include acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjögren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

In some embodiments, the condition, disease or disorder is an autoimmune disease. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, modulation of the immune system by STING provides for the treatment of diseases, including diseases caused by foreign agents. Exemplary infections by foreign agents which may be treated and/or prevented by the method of the present invention include an infection by a bacterium (e.g., a Gram-positive or Gram-negative bacterium), an infection by a fungus, an infection by a parasite, and an infection by a virus. In one embodiment of the present invention, the infection is a bacterial infection (e.g., infection by *E. coli, Klebsiella pneumoniae, Pseudomonas aeruginosa, Salmonella* spp., *Staphylococcus aureus, Streptococcus* spp., or vancomycin-resistant *Enterococcus*). In another embodiment, the infection is a fungal infection (e.g. infection by a mould, a yeast, or a higher fungus). In still another embodiment, the infection is a parasitic infection (e.g., infection by a single-celled or multicellular parasite, including *Giardia duodenalis, Cryptosporidium parvum, Cyclospora cayetanensis*, and *Toxoplasma gondiz*). In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, and lower or upper respiratory tract infection (e.g., respiratory syncytial virus)).

In some embodiments, the condition, disease or disorder is hepatits B (see, e.g., WO 2015/061294).

In some embodiments, the condition, disease or disorder is mucositis, also known as stomatitits, which can occur as a result of chemotherapy or radiation therapy, either alone or in combination as well as damage caused by exposure to radiation outside of the context of radiation therapy.

In some embodiments, the condition, disease or disorder is uveitis, which is inflammation of the uvea (e.g., anterior uveitis, e.g., iridocyclitis or iritis; intermediate uveitis (also known as pars planitis); posterior uveitis; or chorioretinitis, e.g., pan-uveitis).

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional chemotherapeutic agent is an immunomodulatory moiety, e.g., an immune checkpoint inhibitor. In certain of these embodiments, the immune checkpoint inhibitor targets an immune checkpoint receptor selected from the group consisting of CTLA-4, PD-1, PD-L$^1$, PD-1-PD-L$^1$, PD-1-PD-L$^2$, interleukin-2 (IL-2), indoleamine 2,3-dioxygenase (IDO), IL-10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TLIA, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155; e.g., CTLA-4 or PD1 or PD-L$^1$). See, e.g., Postow, M. *J. Clin. Oncol.* 2015, 33, 1.

In certain of these embodiments, the immune checkpoint inhibitor is selected from the group consisting of: Urelumab, PF-05082566, MEDI6469, TRX518, Varlilumab, CP-870893, Pembrolizumab (PD1), Nivolumab (PDI), Atezolizumab (formerly MPDL3280A) (PDL1), MEDI4736 (PD-L$^1$), Avelumab (PD-L$^1$), PDR001 (PD1), BMS-986016, MGA271, Lirilumab, IPH2201, Emactuzumab, INCB024360, Galunisertib, Ulocuplumab, BKT140, Bavituximab, CC-90002, Bevacizumab, and MNRP1685A, and MGA271.

In certain embodiments, the additional chemotherapeutic agent is a STING agonist, e.g., a STING agonist other than a compound of formula (I) as described herein. For example, the STING agonist can comprise a flavonoid. Suitable flavonoids include, but are not limited to, 10-(carboxymethyl)-9(10H)acridone (CMA), 5,6-Dimethylxanthenone-4-acetic acid (DMXAA), methoxyvone, 6, 4'-dimethoxyflavone, 4'-methoxyflavone, 3', 6'-dihydroxyflavone, 7,2'-dihydroxyflavone, daidzein, formononetin, retusin 7-methyl ether, xanthone, or any combination thereof. In some aspects, the STING agonist can be 10-(carboxymethyl)-9(10H)acridone (CMA). In some aspects, the STING agonist can be 5,6-Dimethylxanthenone-4-acetic acid (DMXAA). In some aspects, the STING agonist can be methoxyvone. In some aspects, the STING agonist can be 6, 4'-dimethoxyflavone. In some aspects, the STING agonist can be 4'-methoxyflavone. In some aspects, the STING agonist can be 3', 6'-dihydroxyflavone. In some aspects, the STING agonist can be 7, 2'-dihydroxyflavone. In some aspects, the STING agonist can be daidzein. In some aspects, the STING agonist can be formononetin. In some aspects, the STING agonist can be retusin 7-methyl ether. In some aspects, the STING agonist can be xanthone. In some aspects, the STING agonist can be any combination of the above flavonoids. Thus, for example, in some embodiments the flavonoid comprises DMXAA.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semi-synthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an anti-metabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a vinca alkaloid, a podophyllotoxin and/or a taxane. Vinca alkaloids, in general, bind to specific sites on tubulin, inhibiting the assembly of tubulin into microtubules, generally during the M phase of the cell cycle. In an embodiment, a vinca alkaloid is derived, without limitation, from the Madagascar periwinkle, *Catharanthus roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited, to Taxol, Paclitaxel and/or Docetaxel. In a further embodiment a plant alkaloid or terpemoid is a synthetic, semisynthetic or derivative. In a further embodiment, a podophyllotoxin is, without limitation, an etoposide and/or teniposide. In an embodiment, a taxane is, without limitation, docetaxel and/or ortataxel.

In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613, which is incorporated herein by reference in its entirety.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the STING protein can serve as a biomarker for certain types of cancer, e.g., colon cancer and prostate cancer. In other embodiments, identifying a subject can include assaying the patient's tumor microenvironment for the absence of T-cells and/or presence of exhausted T-cells, e.g., patients having one or more cold tumors. Such patients can include those that are resistant to treatment with checkpoint inhibitors. In certain embodiments, such patients can be treated with a chemical entity herein, e.g., to recruit T-cells into the tumor, and in some cases, further treated with one or more checkpoint inhibitors, e.g., once the T-cells become exhausted.

In some embodiments, the chemical entities, methods, and compositions described herein can be administered to certain treatment-resistant patient populations (e.g., patients resistant to checkpoint inhibitors; e.g., patients having one or more cold tumors, e.g., tumors lacking T-cells or exhausted T-cells).

Compound Preparation

As can be appreciated by the skilled artisan, methods of synthesizing the compounds of the formulae herein will be evident to those of ordinary skill in the art. For example, the compounds described herein can be synthesized, e.g., using one or more of the methods described herein and/or using methods described in, e.g., US2015/0056224, the contents of each of which are hereby incorporated by reference in their entirety.

Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1$H NMR, heteronuclear NMR, mass spectrometry, liquid chromatography, and infrared spectroscopy. The foregoing list is a subset of characterization methods available to a skilled artisan and is not intended to be limiting.

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

The following abbreviations have the indicated meanings:
ACN=acetonitrile
BnNCO=(isocyanatomethyl)benzene
BSA=Amberlyst 15
BzCl=benzoyl chloride
$CCl_4$=carbon tetrachloride
CE=cyanoethyl
DCA=dichloroacetic acid
DCM=dichloromethane
DIAD=diisopropyl azodiformate
DIPEA=N,N-diethylisopropylamine
DMAP=4-(N,N-dimethylamino)pyridine
DMF=N,N-dimethylformamide
DMF-DMA=N,N-dimethylformamide dimethyl acetal
DMTrCl=1-[chloro(4-methoxyphenyl)benzyl]-4-methoxybenzene
$H_2O$=water
HF=hydrogen fluoride
$H_2S$=hydrogen sulfide
$I_2$=iodine
$MeNH_2$=methylamine
$NaN_3$=sodium azide
NMP=N-methylpyrrolidinone
Py or pyr=pyridine
Py-TFA=pyridinium trifluoroacetate
TBDPS=tert-butyldiphenylsilyl
TBDPSCl=tert-butyl(chloro)diphenylsilane
TEA=triethylamine
TEA.HF or TEA.3HF=triethylamine trihydrofluoride
TFA=trifluoroacetic acid
Tr or Trt=trityl
TrCl=trityl chloride or triphenylmethyl chloride
TMSCl=chlorotrimethylsilane Synthesis of Compounds of Formula I Including Amino Linkage at 3' Ribose Positions Scheme I depicts an example synthesis of cyclic dinucleotide phosphoramidates as disclosed herein that include an amino linkage bonded to the 3' position of each ribose moiety.

The sequence initiates with the treatment of compound 1 with trityl chloride in the presence of triethylamine to produce tritylated amine 2. Amine 2 is subjected to 3-((bis(diisopropylamino)phosphanyl)oxy)propanenitrile, pyridine, and trifluoroacetic acid to furnish phosphoramidite 3. Subsequent water or hydrogen sulfide treatment results in phosphonate 4a or phosphonothioate 4b, respectively. Compound 1 can then be combined with either of compounds 4a or 4b with triethylamine in carbon tetrachloride to generate either phosphoramidate 5a or phosphoramidothioate 5b, respectively. Subjection of compound 5a or compound 5b to 3-((bis(diisopropylamino)phosphanyl)oxy)propanenitrile, pyridine, and trifluoroacetic acid produces the corresponding phosphoramidite 6a or 6b. Sequential treatment of phosphoramidite 6a with water and dichloroacetic acid yields phosphonate 7a. Sequential treatment of phosphoramidite 6b with hydrogen sulfide and dichloroacetic acid yields phosphonothioate 7b. Compound 7a or 7b are then taken up in triethylamine and carbon tetrachloride to enable cyclization to produce cyclic phosphoramidates 8a and 8b. Lastly, treatment of compound 8a or 8b with methylamine and triethylamine-hydrogen fluoride complex, in turn, result in decyanoethylated cyclic dinucleotide phosphoramidates 9a or 9b, in which the adenine and/or guanine bases have also been deprotected.

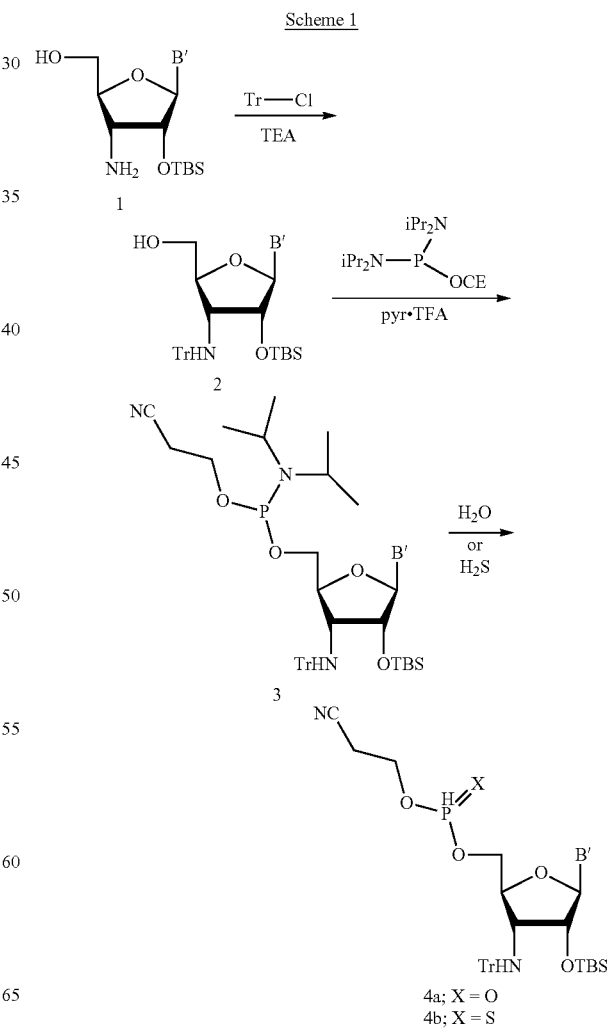

Scheme 1

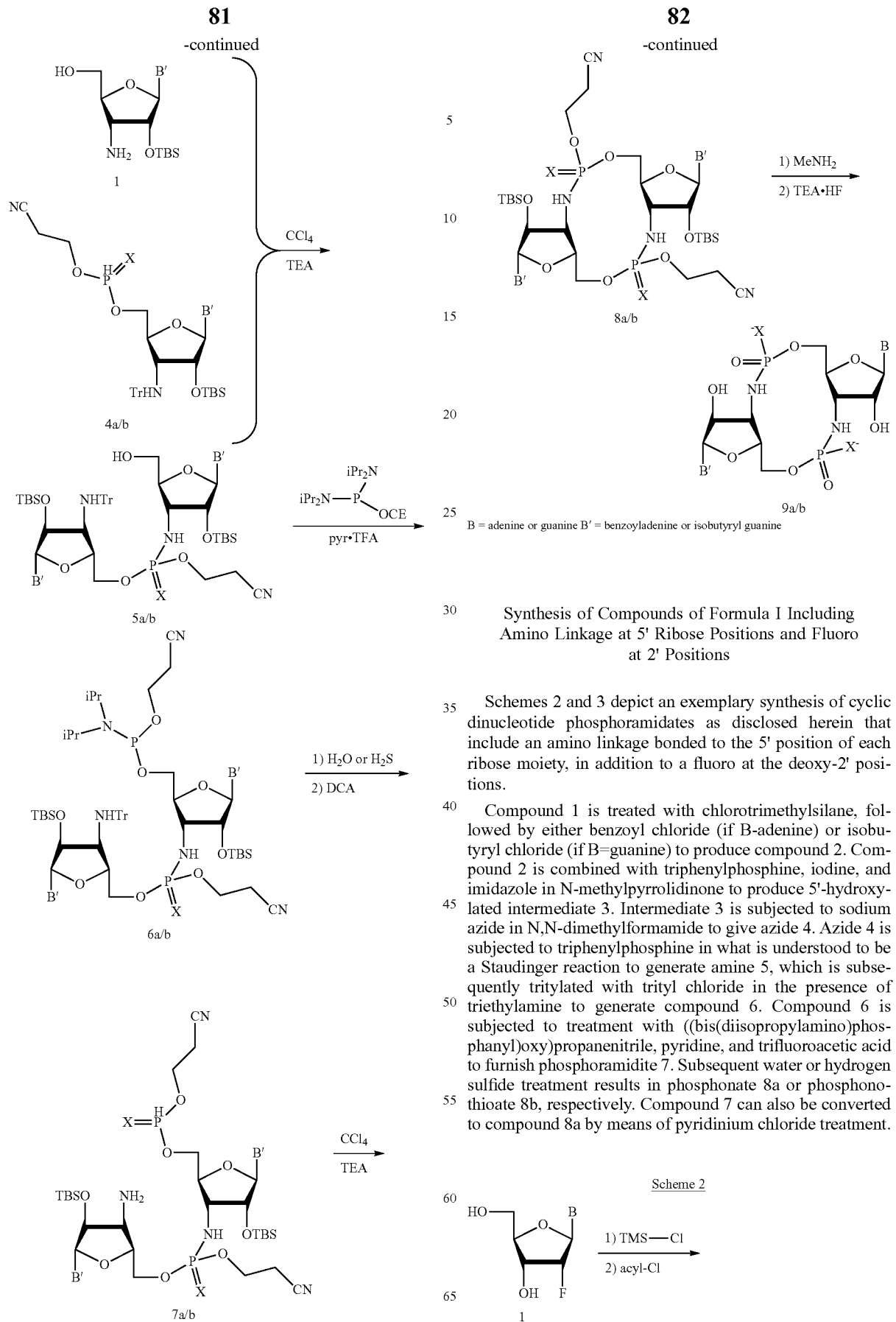

Synthesis of Compounds of Formula I Including Amino Linkage at 5' Ribose Positions and Fluoro at 2' Positions Schemes 2 and 3 depict an exemplary synthesis of cyclic dinucleotide phosphoramidates as disclosed herein that include an amino linkage bonded to the 5' position of each ribose moiety, in addition to a fluoro at the deoxy-2' positions.

Compound 1 is treated with chlorotrimethylsilane, followed by either benzoyl chloride (if B-adenine) or isobutyryl chloride (if B=guanine) to produce compound 2. Compound 2 is combined with triphenylphosphine, iodine, and imidazole in N-methylpyrrolidinone to produce 5'-hydroxylated intermediate 3. Intermediate 3 is subjected to sodium azide in N,N-dimethylformamide to give azide 4. Azide 4 is subjected to triphenylphosphine in what is understood to be a Staudinger reaction to generate amine 5, which is subsequently tritylated with trityl chloride in the presence of triethylamine to generate compound 6. Compound 6 is subjected to treatment with ((bis(diisopropylamino)phosphanyl)oxy)propanenitrile, pyridine, and trifluoroacetic acid to furnish phosphoramidite 7. Subsequent water or hydrogen sulfide treatment results in phosphonate 8a or phosphonothioate 8b, respectively. Compound 7 can also be converted to compound 8a by means of pyridinium chloride treatment.

Scheme 2 cyclic dinucleotide phosphoramidates 13a or 13b, in which the adenine and/or guanine bases have also been deprotected.

Scheme 3

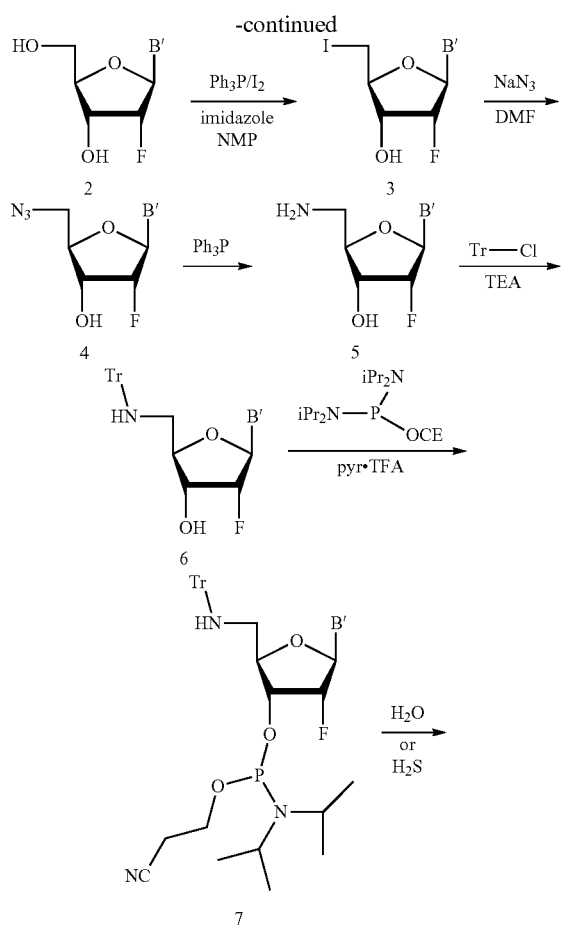

8a; X = O
8b; X = S

B = adenine or guanine  B' = benzoyladenine or isobutyryl guanine

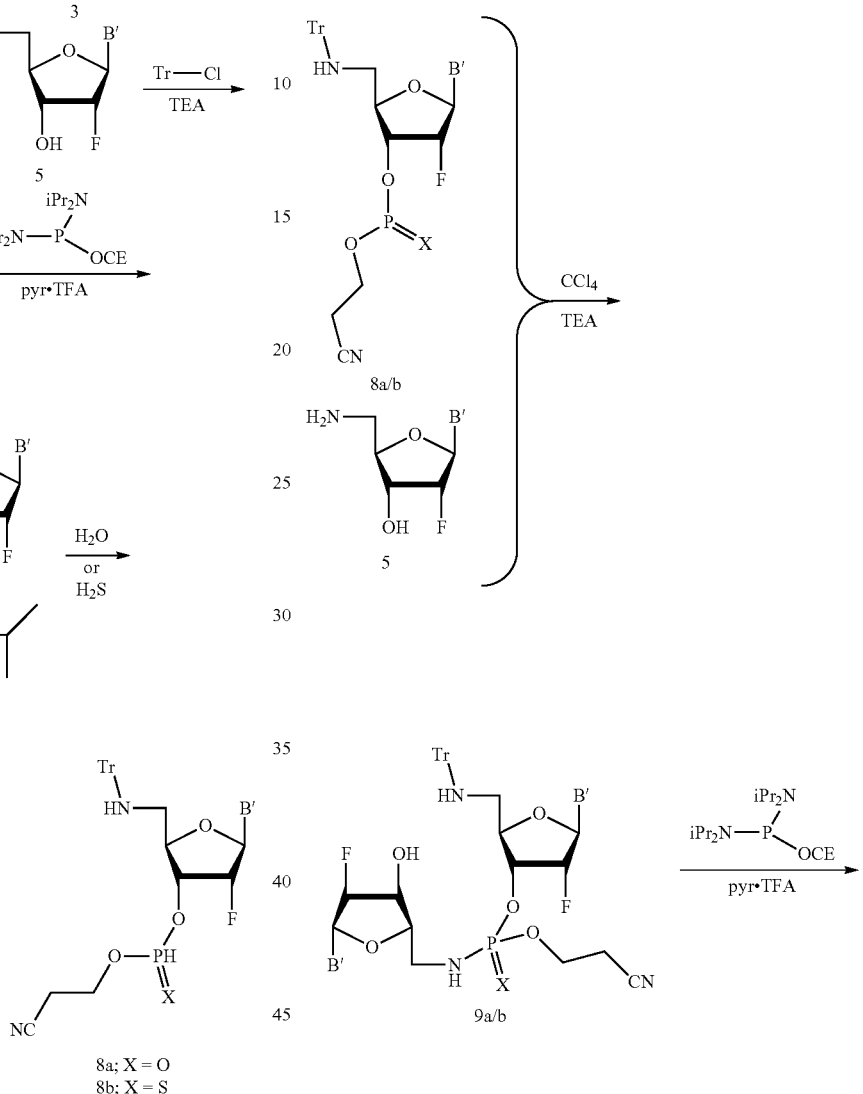

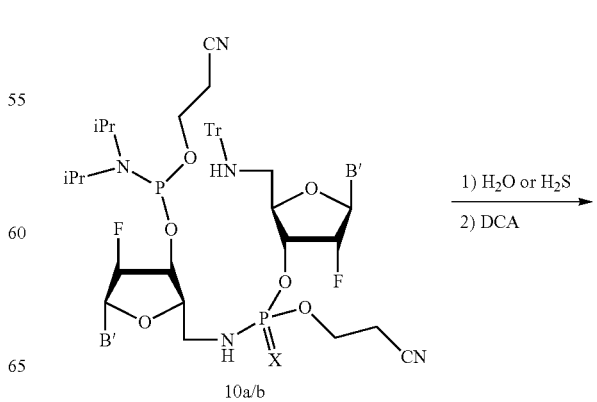

Compound 5 can then be combined with either of compounds 8a or 8b with triethylamine in carbon tetrachloride to generate either phosphoramidate 9a or phosphoramidothioate 9b, respectively. Subjection of compound 9a or compound 9b to 3-((bis(diisopropylamino)phosphanyl)oxy)propanenitrile, pyridine, and trifluoroacetic acid produces the corresponding phosphoramidite 10a or 10b. Sequential treatment of phosphoramidite 10a with water and dichloroacetic acid yields phosphonate 11a. Sequential treatment of phosphoramidite 10b with hydrogen sulfide and dichloroacetic acid yields phosphonothioate 11b. Compound 11a or 11b can be taken up in triethylamine and carbon tetrachloride to enable intramolecular cyclization to produce cyclic phosphoramidates 12a and 12b. Lastly, treatment of compound 12a or 12b with methylamine results in decyanoethylated

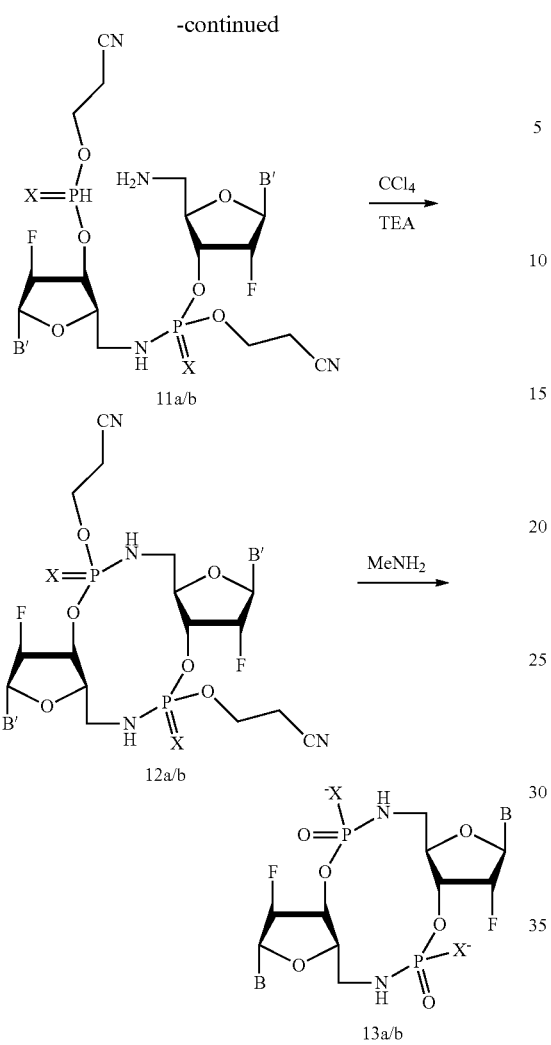

hydrogen sulfide and dichloroacetic acid yields phosphonothioate 7b. Compound 7a or 7b can be taken up in triethylamine and carbon tetrachloride to enable intramolecular cyclization to produce cyclic phosphoramidates 8a and 8b. Lastly, treatment of compound 8a or 8b with methylamine and trimethylamine trihydrofluoride, in turn, result in decyanoethylated cyclic dinucleotide phosphoramidates 9a or 9b, in which the adenine and/or guanine bases have also been deprotected.

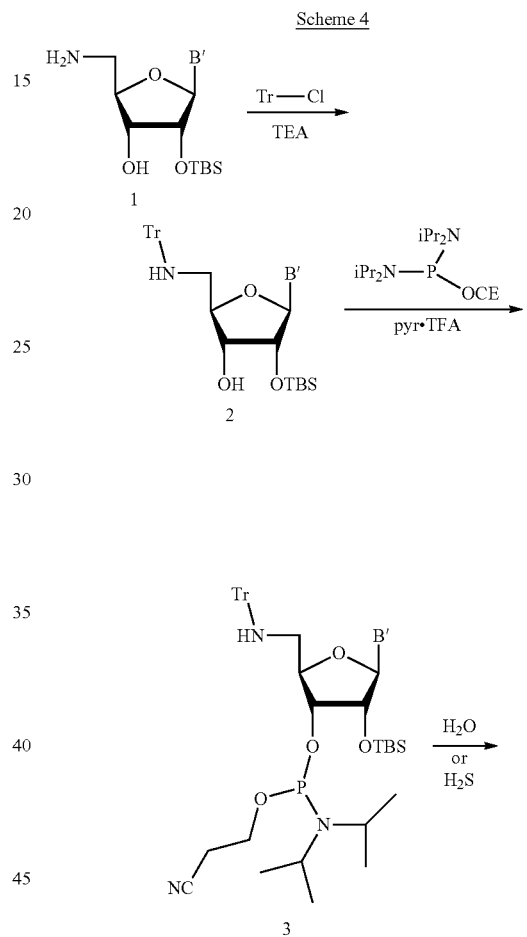

Synthesis of Compounds of Formula I Including Amino Linkage at 5' Ribose Positions Scheme 4 depicts an example synthesis of cyclic dinucleotide phosphoramidates as disclosed herein that include an amino linkage bonded to the 5' position of each ribose moiety.

The sequence initiates with the treatment of compound 1 with trityl chloride in the presence of triethylamine to produce tritylated amine 2. Amine 2 is subjected to 3-((bis(diisopropylamino)phosphanyl)oxy)propanenitrile, pyridine, and trifluoroacetic acid to furnish phosphoramidite 3. Subsequent water or hydrogen sulfide treatment results in phosphonate 4a or phosphonothioate 4b, respectively. Compound 1 can then be is combined with either of compounds 4a or 4b with triethylamine in carbon tetrachloride to generate either phosphoramidate 5a or phosphoramidothioate 5b, respectively. Subjection of compound 5a or compound 5b to 3-((bis(diisopropylamino)phosphanyl)oxy)propanenitrile, pyridine, and trifluoroacetic acid produces the corresponding phosphoramidite 6a or 6b. Sequential treatment of phosphoramidite 6a with water and dichloroacetic acid yields phosphonate 7a. Phosphoramidite 6a can also be converted to phosphonate 7a without a separate water treatment step. Sequential treatment of phosphoramidite 6b with

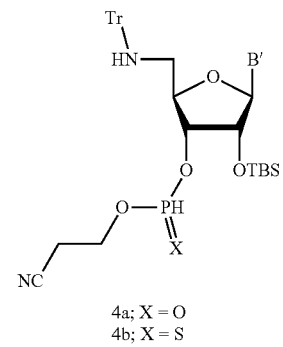

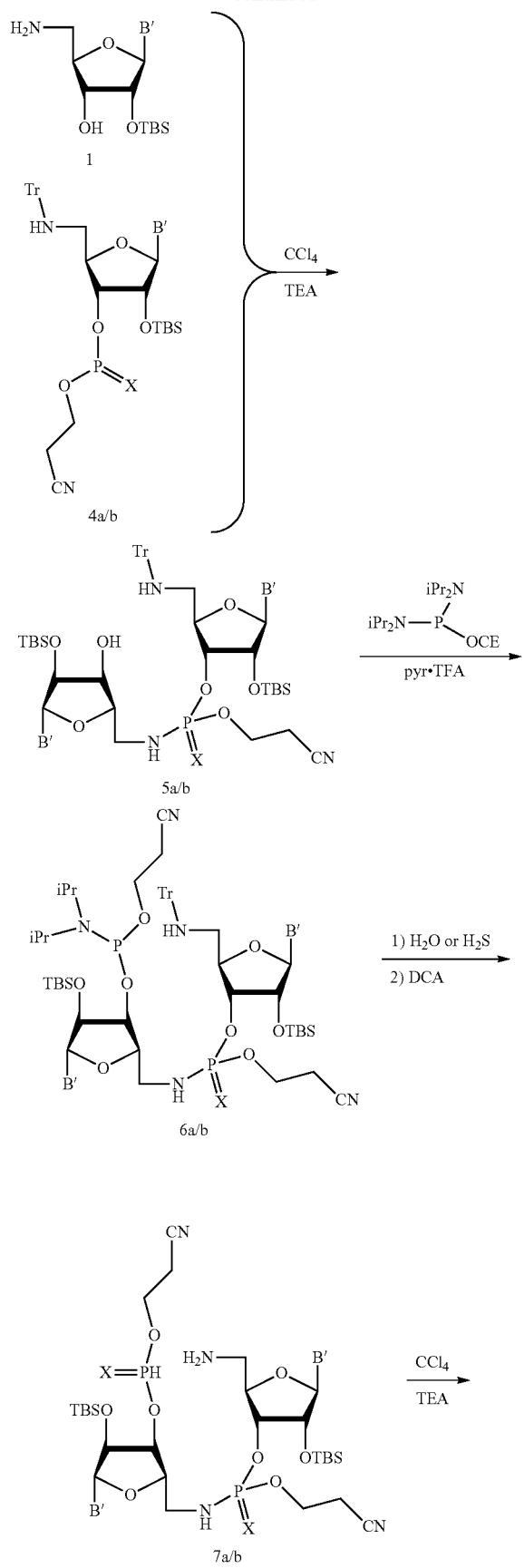
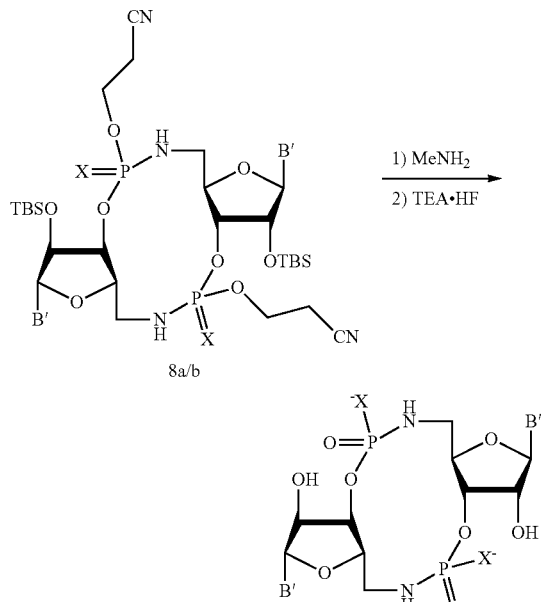
B = adenine or guanine   B' = benzoyladenine or isobutyryl guanine
EXAMPLES
Compound Preparation
Key Intermediates Preparation
N-(9-((2R,3R,4R,5S)-4-amino-3-(tert-butyldimethyl-silyloxy)-5-(hydroxymethyl)-tetrahydrofuran-2-yl)-9H-purin-6-yl)benzamide (INT-C)
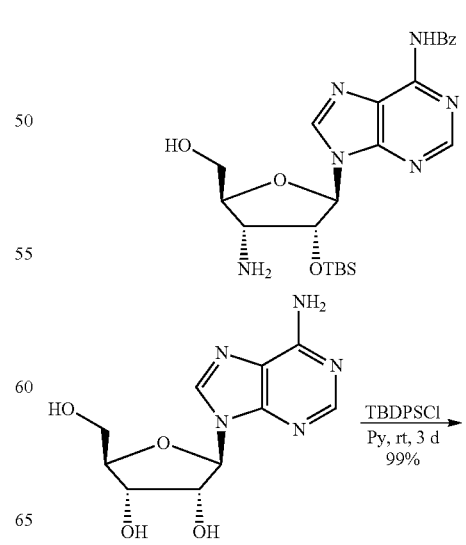

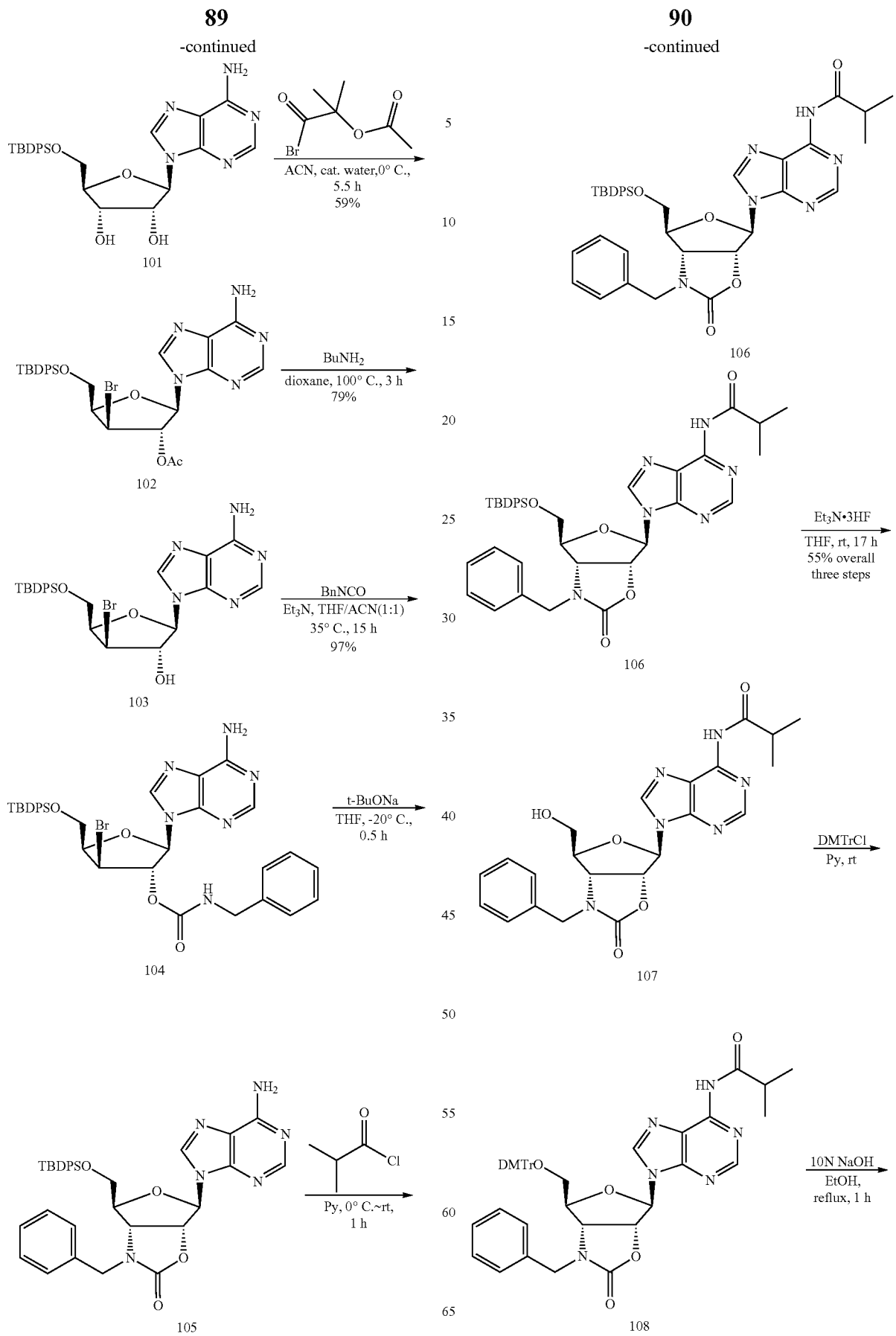

-continued

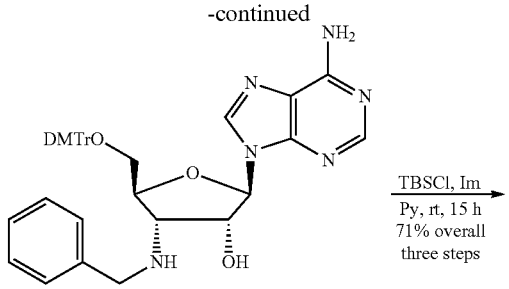

109

TBSCl, Im
Py, rt, 15 h
71% overall three steps

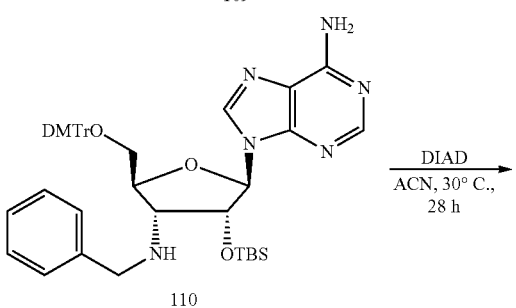

110

DIAD
ACN, 30° C.,
28 h

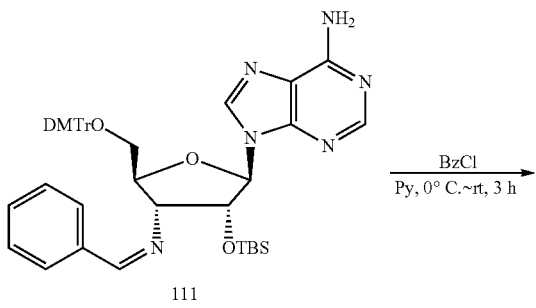

111

BzCl
Py, 0° C.~rt, 3 h

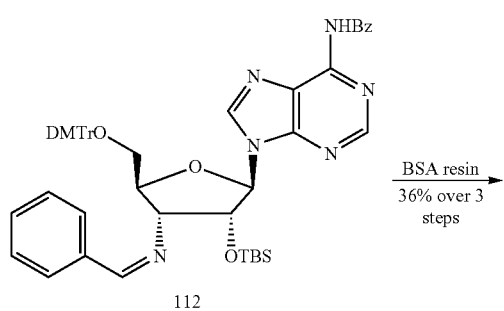

112

BSA resin
36% over 3 steps

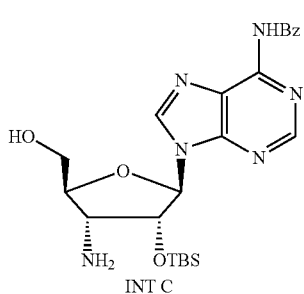

INT C

Step 1

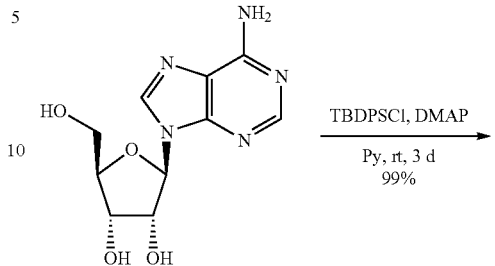

TBDPSCl, DMAP
Py, rt, 3 d
99%

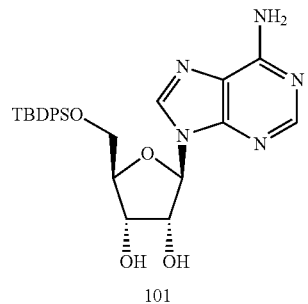

101

(2R,3R,4S,5R)-2-(6-amino-9H-purin-9-yl)-5-((tert-butyldiphenylsilyloxy)methyl)-tetrahydrofuran-3,4-diol (101)

To a suspension of (2R,3R,4S,5R)-2-(6-amino-9H-purin-9-yl)-5-(hydroxymethyl)-tetrahydrofuran-3,4-diol (500 g, 1.87 mol) in pyridine (3.5 L) were added 4,4-dimethylaminopyridine (22.9 g, 0.18 mol) and tert-butyl(chloro)diphenylsilane (616 g, 2.24 mol) under nitrogen atmosphere. After stirring for 1 day at ambient temperature, the reaction suspension changed to a clear solution. After total 3 days, the reaction solution was quenched by the addition of methanol (100 mL). The mixture was concentrated under reduced pressure. The residue was added to a mixture of chloroform (1.5 L) and diethyl ether (4 L) and vigorous stirring for 2 hours. The resulting precipitate was filtered and the filter cake was collected and dried in the air to give crude product. The crude product was added water (3 L) and vigorous stirring for 1 hour. The suspension was filtered, dried under infrared light to afford the title compound 101 as a colorless solid (937 g, 99%): $^1$H NMR (400 MHz, DMSO-$d_6$) δ 8.53 (s, 1H), 8.38 (s, 1H), 7.68-7.57 (m, 4H), 7.51-7.31 (m, 6H), 5.99 (d, J=4.5 Hz, 1H), 4.59 (t, J=4.8 Hz, 1H), 4.33 (t, J=5.0 Hz, 1H), 4.08 (q, J=4.5 Hz, 1H), 3.94 (dd, J=11.4, 3.7 Hz, 1H), 3.80 (dd, J=11.4, 4.8 Hz, 1H), 0.98 (s, 9H); LC/MS: [(M+1)]$^+$=506.2.

Step 2

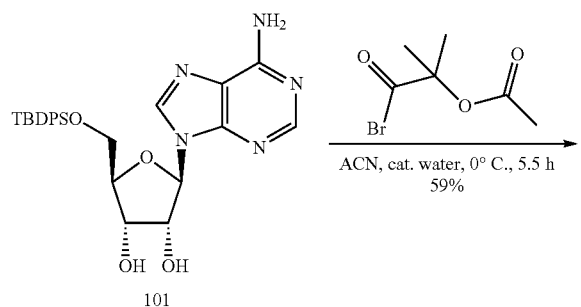

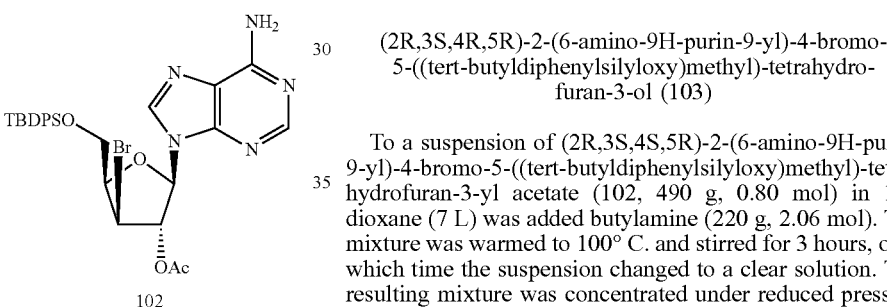

(2R,3S,4S,5R)-2-(6-amino-9H-purin-9-yl-4-bromo-5-((tert-butyldiphenylsilyloxy)methyl)-tetrahydrofuran-3-yl acetate (102)

To a suspension of (2R,3R,4S,5R)-2-(6-amino-9H-purin-9-yl)-5-((tert-butyldiphenylsilyloxy)methyl)-tetrahydrofuran-3,4-diol (101, 900 g, 1.78 mol) and H₂O (29.3 mL, 1.63 mol) in acetonitrile (13.5 L) was added dropwise a solution of 1-bromo-2-methyl-1-oxopropan-2-yl acetate (787 mL, 5.34 mol) in acetonitrile (4.5 L) over 2 hours under nitrogen atmosphere at 0° C. Upon complete addition, the suspension changed to a clear solution. After total 5.5 hours, the pH value of the reaction mixture was adjusted to 6 with sodium bicarbonate. The resulting mixture was concentrated under reduced pressure and the residue was triturated with dichloromethane (2 L), filtered and washed with water (1 L), dried under infrared light to give the title compound 102 as a white solid (597 g, 59%): ¹H NMR (400 MHz, DMSO-d₆) δ 8.38 (s, 1H), 8.28 (s, 1H), 7.73-7.63 (m, 4H), 7.55-7.36 (m, 6H), 6.24 (d, J=3.2 Hz, 1H), 5.91 (t, J=3.2 Hz, 1H), 4.94 (dd, J=5.0, 3.1 Hz, 1H), 4.57 (q, J=4.9 Hz, 1H), 4.06-3.95 (m, 2H), 2.13 (s, 3H), 1.02 (s, 9H); LC/MS: [(M+1)]⁺=610.2, 612.2.

Step 3

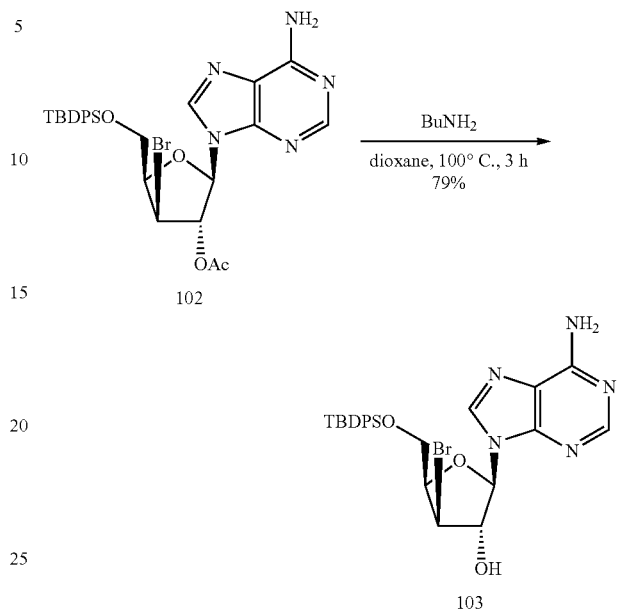

(2R,3S,4R,5R)-2-(6-amino-9H-purin-9-yl)-4-bromo-5-((tert-butyldiphenylsilyloxy)methyl)-tetrahydrofuran-3-ol (103)

To a suspension of (2R,3S,4S,5R)-2-(6-amino-9H-purin-9-yl)-4-bromo-5-((tert-butyldiphenylsilyloxy)methyl)-tetrahydrofuran-3-yl acetate (102, 490 g, 0.80 mol) in 1,4-dioxane (7 L) was added butylamine (220 g, 2.06 mol). The mixture was warmed to 100° C. and stirred for 3 hours, over which time the suspension changed to a clear solution. The resulting mixture was concentrated under reduced pressure and the residue was added to a mixture of petroleum, dichloromethane and methanol (3.1 L, 25/5/1, v/v/v) and stirred vigorously for 1 h. The suspension was filtered and the filter cake was washed with water (4 L) and dried under infrared light to afford the title compound 103 as a white solid (360 g, 79%): ¹H NMR (300 MHz, DMSO-d₆) δ 8.14 (s, 1H), 8.10 (s, 1H), 7.72-7.61 (m, 4H), 7.53-7.36 (m, 6H), 7.32 (s, 2H), 6.49 (d, J=5.2 Hz, 1H), 5.91 (d, J=3.8 Hz, 1H), 4.95 (q, J=4.3 Hz, 1H), 4.61 (dd, J=5.4, 4.0 Hz, 1H), 4.54 (q, J=4.9 Hz, 1H), 4.08-3.94 (m, 2H), 1.02 (s, 9H); LC/MS: [(M+1)]⁺=568.1, 570.1.

Step 4

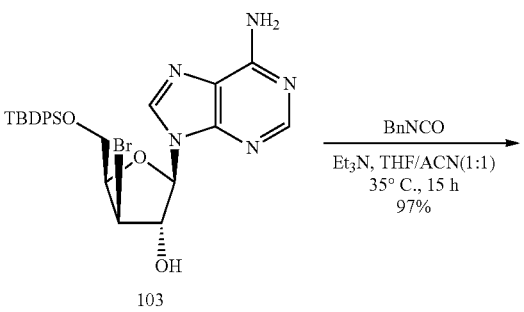

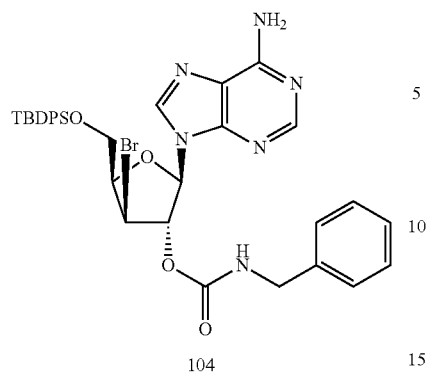

104

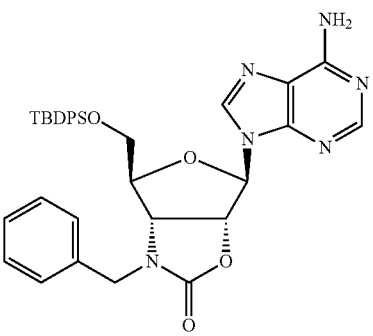

105

(2R,3S,4S,5R)-2-(6-amino-9H-purin-9-yl)-4-bromo-5-((tert-butyldiphenylsilyloxy)methyl)-tetrahydrofuran-3-yl benzylcarbamate (104)

To a suspension of (2R,3S,4R,5R)-2-(6-amino-9H-purin-9-yl)-4-bromo-5-((tert-butyldiphenylsilyloxy)methyl)-tetrahydrofuran-3-ol (103, 290 g, 0.51 mol) in a cosolvent of tetrahydrofuran and acetonitrile (5.8 L, 1/1, v/v) was added triethylamine (106 mL, 0.77 mol) and (isocyanatomethyl)benzene (102.7 g, 0.77 mol). The resulting suspension was stirred for 15 hours at 35° C. The reaction mixture was quenched by the addition of methanol (300 mL). The mixture was concentrated under reduced pressure and the residue was triturated by a mixture of petroleum ether, ethyl acetate and dichloromethane (2.2 L, 5/1/1.5, v/v/v). The suspension was filtered and the filter cake was collected, dried under infrared light to afford the title compound 104 as a white solid (348 g, 97%): $^1$H NMR (300 MHz, DMSO-d$_6$) δ 8.17-8.12 (m, 3H), 8.15 (s, 1H), 8.12 (s, 1H), 7.73-7.61 (m, 4H), 7.54-7.10 (m, 13H), 6.16 (d, J=4.0 Hz, 1H), 5.88 (t, J=4.1 Hz, 1H), 4.90 (dd, J=5.4, 4.2 Hz, 1H), 4.53 (q, J=4.8 Hz, 1H), 4.30-4.09 (m, 2H), 4.08-3.92 (m, 2H), 1.03 (s, 9H); LC/MS: [(M+1)]$^+$=701.2, 703.2.

(3aR,4S,6R,6aR)-6-(6-amino-9H-purin-9-yl)-3-benzyl-4-((tert-butyldiphenylsilyloxy)methyl)-tetrahydrofuro[3,4-d]oxazol-2(3H)-one (105)

A solution of (2R,3S,4S,5R)-2-(6-amino-9H-purin-9-yl)-4-bromo-5-((tert-butyldiphenylsilyloxy)methyl)-tetrahydrofuran-3-yl benzylcarbamate (104, 348 g, 0.50 mol) in tetrahydrofuran (10.5 L) was treated with sodium tert-butoxide (57.2 g, 0.60 mol) for 0.5 h at −20° C. The reaction was then quenched by the addition of saturated aqueous ammonium chloride (4 L). The organic phase was separated and the aqueous phase was extracted with ethyl acetate (2 L). The combined organic layers were dried over anhydrous sodium sulfate. After filtration, the filtrate was concentrated under reduced pressure to afford the title compound 105 which was used in the next step without further purification (315 g, white foam): LC/MS: [(M+1)]$^+$=621.2.

Step 6

Step 5

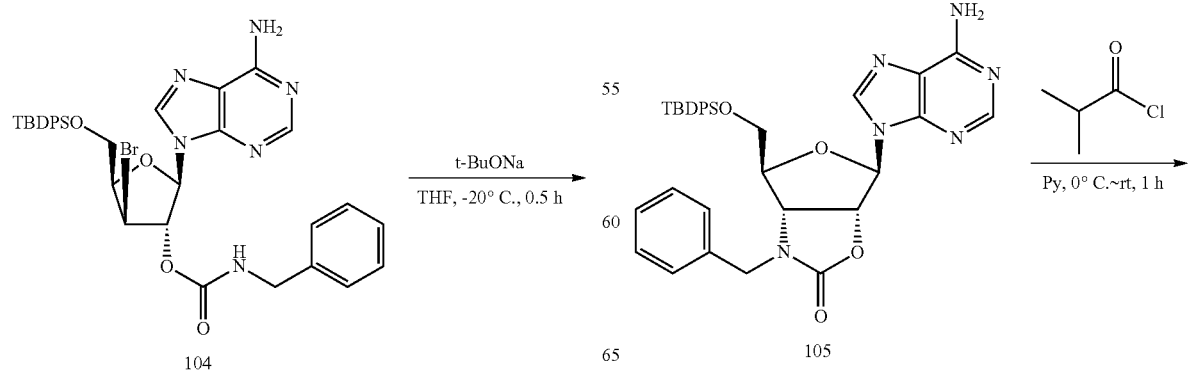

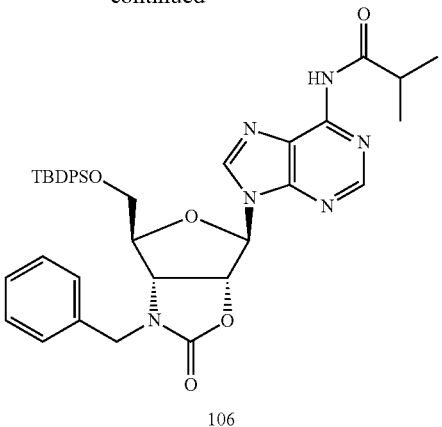

N-(9-((3aR,4S,6R,6aR)-3-benzyl-4-((tert-butyldiphenylsilyloxy)methyl)-2-oxo-hexahydrofuro[3,4-d]oxazol-6-yl)-9H-purin-6-yl)isobutyramide (106)

To the solution of To the above crude compound (105, 280 g) in distilled pyridine (2.8 L) was added isobutyryl chloride (71.7 g, 0.68 mol) at 0° C. Then the mixture was warmed to room temperature and stirred for 1 h, over which time the color of the reaction mixture changed to orange. The reaction mixture was quenched with methanol (250 mL) and concentrated under reduced pressure to afford the crude title compound 106 as a yellow oil (311 g): LC/MS: [(M+1)]+ =691.3.

N-(9-((3aR,4S,6R,6aR)-3-benzyl-4-(hydroxymethyl-2-oxo-hexahydrofuro[3,4-d]oxazol-6-yl)-9H-purin-6-yl)isobutyramide (107)

To a suspension of the above crude compound (106, 354 g) in tetrahydrofuran (3 L) was added triethylamine trihydrofluoride (590 g, 3.55 mol) and stirred for 17 hours at ambient temperature. Upon completion, the reaction mixture changed to a clear solution, which was quenched with saturated aqueous sodium bicarbonate (2 L). The organic layer was separated and the aqueous layer was extracted with dichloromethane (2×1 L). The organic layers were combined and dried over anhydrous sodium sulfate and filtered. The filtrate was concentrated under reduced pressure and the residue was triturated with petroleum ether and dichloromethane (2.5 L, 2:1, v/v). The resulting precipitate was filtered and dried under infrared light to afford the title compound 107 as a white solid. (124 g, 55% over 3 steps): $^1$H NMR (300 MHz, DMSO-$d_6$) δ 10.70 (s, 1H), 8.66 (s, 1H), 8.64 (s, 1H), 7.48-7.28 (m, 5H), 6.44 (d, J=3.2 Hz, 1H), 5.77 (dd, J=8.4, 3.3 Hz, 1H), 5.24-5.14 (m, 1H), 4.65 (d, J=15.4 Hz, 1H), 4.46-4.27 (m, 3H), 3.44 (t, J=5.3 Hz, 2H), 2.94 (h, J=6.9 Hz, 1H), 1.13 (d, J=6.8 Hz, 6H); LC/MS: [(M+1)]+=453.2.

Step 7

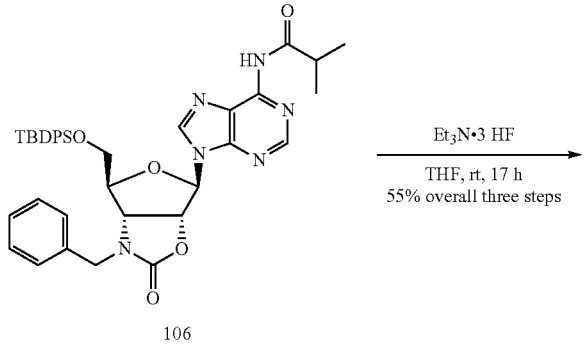

Step 8

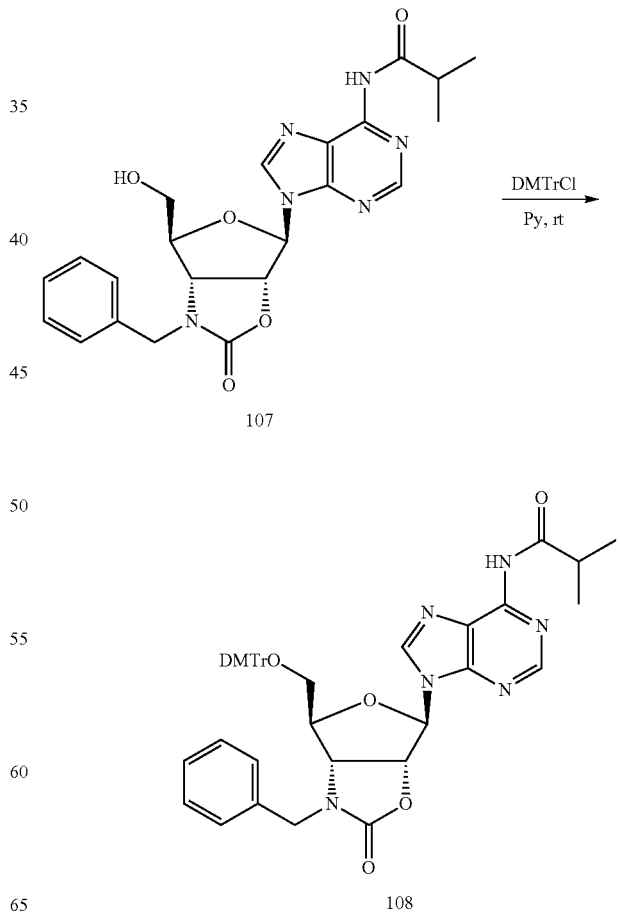

N-(9-((3aR,4S,6R,6aR)-3-benzyl-4-((bis(4-methoxyphenyl)(phenyl)methoxy)methyl)-2-oxo-hexahydrofuro[3,4-d]oxazol-6-yl)-9H-purin-6-yl)isobutyramide (108)

To a solution of N-(9-((3aR,4S,6R,6aR)-3-benzyl-4-(hydroxymethyl)-2-oxo-hexahydrofuro[3,4-d]oxazol-6-yl)-9H-purin-6-yl)isobutyramide (107, 94 g, 0.21 mol) in distilled pyridine (1 L) was added 1-[chloro(4-methoxyphenyl)benzyl]-4-methoxybenzene (98 g, 0.29 mol). The resulting solution was stirred for 7 h at ambient temperature. Upon completion, the reaction was quenched with methanol (50 mL). The reaction mixture was concentrated to afford the crude title compound 108 as an orange oil, which was used in the next step without further purification (157 g, crude oil): LC/MS: $[(M+1)]^+=755.3$.

Step 9

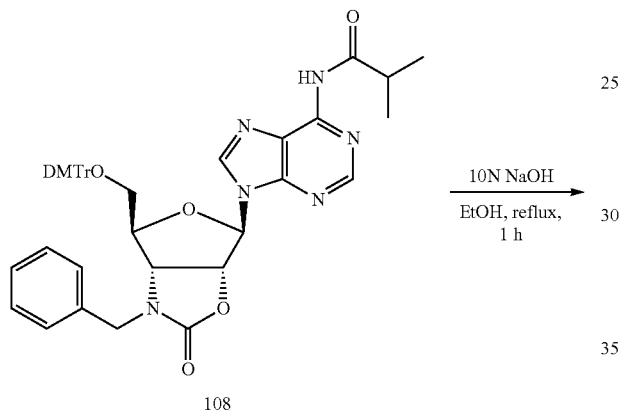

(2R,3R,4S,5S)-2-(6-amino-9H-purin-9-yl)-4-(benzylamino)-5-((bis(4-methoxyphenyl)(phenyl)methoxy)methyl)-tetrahydrofuran-3-ol (109)

A solution of the above crude product (108, 157 g) in ethanol (2 L) was treated with 10 N aqueous solution of sodium hydroxide (450 mL) at reflux for 1 h. After cooling down to ambient temperature, the resulting solution was concentrated to about one third volume then the pH value of the suspension was adjusted to 8 with saturated aqueous solution of ammonium chloride. The resulting mixture was extracted with dichloromethane (3×2 L). The organic layers were combined and dried over anhydrous sodium sulfate. After filtration, the filtrate was concentrated under reduced pressure to afford crude title compound 109 as a yellow solid, which was used in the next step reaction without further purification (137 g, crude yellow solid): LC/MS: $[(M+1)]^+=659.2$.

Step 10

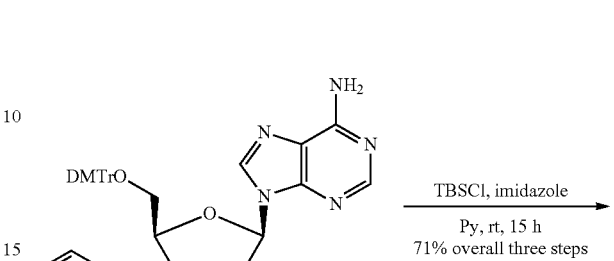

9-((2R,3R,4R,5S)-4-(benzylamino)-5-((bis(4-methoxyphenyl)(phenyl)methoxy)methyl)-3-(tert-butyldimethylsilyloxy)-tetrahydrofuran-2-yl)-9H-purin-6-amine (110)

To a solution of the above crude product (109, 137 g) in distilled pyridine (1.5 L) were added imidazole (71 g, 1.04 mol) and tert-butylchlorodimethylsilane (94 g, 0.62 mol). The resulting solution was stirred for 15 h at ambient temperature. The mixture was concentrated under reduced pressure and the residue was purified by silica gel column chromatography, eluting with 20%~40% petroleum ether in ethyl acetate (plus 0.1% TEA, v/v) to afford the title compound 110 as an orange oil (115 g, 71%): LC/MS: $[(M+1)]^+=773.3$.

Step 11

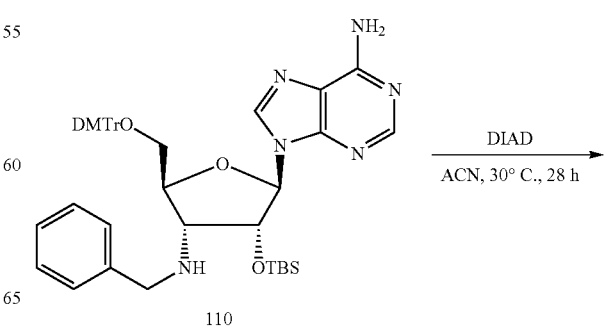

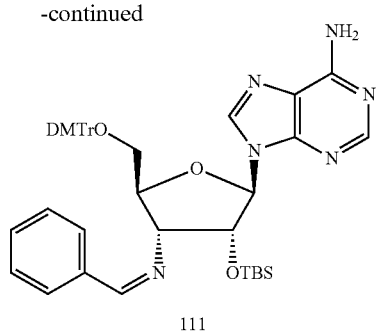

9-((2R,3R,4R,5S)-4-((Z)-benzylideneamino)-5-((bis(4-methoxyphenyl)(phenyl)methoxy)methyl)-3-(tert-butyldimethylsiloxy)-tetrahydrofuran-2-yl)-9H-purin-6-amine (111)

A solution of (E)-N'-(9-((2R,3R,4R,5S)-4-(benzylamino)-5-((bis(4-methoxyphenyl)(phenyl)methoxy)methyl)-3-((tert-butyldimethylsilyl)oxy)tetrahydrofuran-2-yl)-6-oxo-6,9-dihydro-1H-purin-2-yl)-N,N-dimethylformimidamide (110, 115 g, 148.8 mmol) in acetonitrile (1.5 L) was treated with diisopropyl azodiformate (300 g, 1.5 mol) for 28 hours at 30° C. The resulting mixture was concentrated under reduced pressure to afford compound 111, which was used in the next step without further purification (115 g, brown oil): LC/MS: $[(M+1)]^+=771.3$.

Step 12

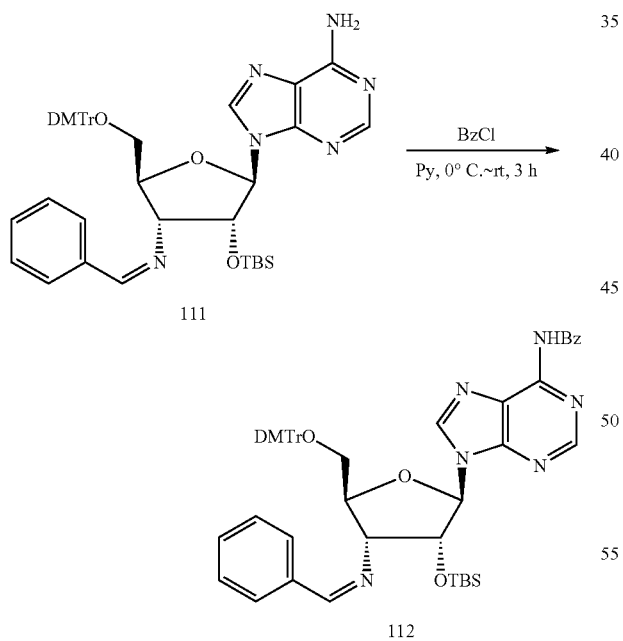

N-(9-((2R,3R,4R,5S)-4-((Z)-benzylideneamino)-5-((bis(4-methoxyphenyl)(phenylmethoxy)methyl)-3-(tert-butyldimethylsilyloxy)-tetrahydrofuran-2-yl)-9H-purin-6-yl)benzamide (112)

To a solution of the above crude product (111, 115 g) in distilled pyridine (1 L) was added benzoyl chloride (63 g) over 30 min at 0° C. The reaction mixture was then warmed to room temperature and stirred for 3 h. The reaction mixture was quenched by the addition of methanol (50 mL) and the resulting solution was concentrated under reduce pressure. The residue was dissolved in tetrahydrofuran (1 L), cooled to 0° C., followed by the addition of ammonium hydroxide (300 mL, 27% in water). The resulting precipitate was removed by filtration. The filtrate was concentrated under reduce pressure to afford crude title compound 112, which was used in the next step reaction without further purification: LC/MS: $[(M+1)]^+=875.3$.

Step 13

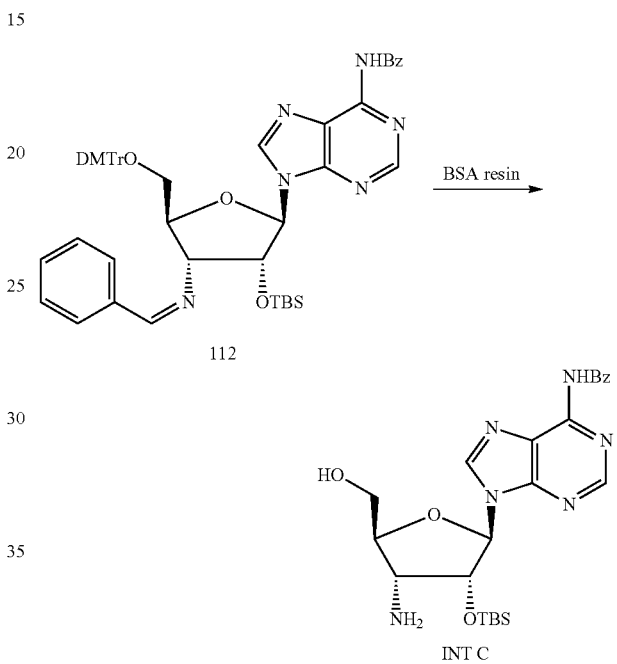

N-(9-((2R,3R,4R,5S)-4-amino-3-(tert-butyldimethylsilyloxy)-5-(hydroxymethyl)-tetrahydrofuran-2-yl)-9H-purin-6-yl)benzamide (INT-C)

The above crude solution of N-(9-((2R,3R,4R,5S)-4-((Z)-benzylideneamino)-5-((bis(4-methoxyphenyl)(phenyl)methoxy)methyl)-3-(tert-butyldimethylsilyloxy)-tetrahydrofuran-2-yl)-9H-purin-6-yl)benzamide (112, 115 g) in dichloromethane (1.2 L) and methanol (120 mL) were added Amberlyst-15 (300 g) and water (25 mL). After 2 hours at ambient temperature, the resulting mixture was filtered and washed with dichloromethane (2×200 mL). The solids were collected and washed with a mixture of dichloromethane, triethylamine and methanol (3×2 L, 7/2/1, v/v/v). The organic layers were combined and concentrated under reduced pressure and the residue was purified by silica gel column chromatography, eluting with 1%~3% methanol in dichloromethane (plus 0.1% TEA, v/v) to afford the title compound as a white solid (INT-C, 26 g, 36% over 3 steps). $^1$H NMR (400 MHz, DMSO-$d_6$) δ 8.81 (s, 1H), 8.76 (s, 1H), 8.10-8.02 (m, 2H), 7.70-7.51 (m, 3H), 6.12 (d, J=2.8 Hz, 1H), 5.77 (s, 1H), 5.21 (s, 1H), 4.60 (dd, J=5.1, 2.8 Hz, 1H), 3.88 (dt, J=6.8, 3.2 Hz, 1H), 3.81 (d, J=12.0 Hz, 1H), 3.71-3.58 (m, 2H), 3.00 (q, J=7.3 Hz, 10H), 1.18 (t, J=7.3 Hz, 15H), 0.86 (s, 9H), 0.07 (s, 3H), 0.02 (s, 3H); LC/MS: $[(M+1)]^+=485.2$.

N-(9-((2R,3R,4R,5S)-4-amino-3-((tert-butyldimethylsilyl)oxy)-5-(hydroxymethyl)tetrahydrofuran-2-yl)-6-oxo-6,9-dihydro-1H-purin-2-yl)isobutyramide (INT-D)
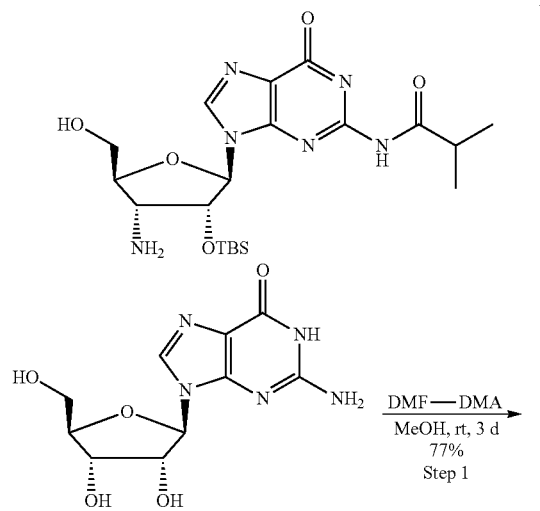
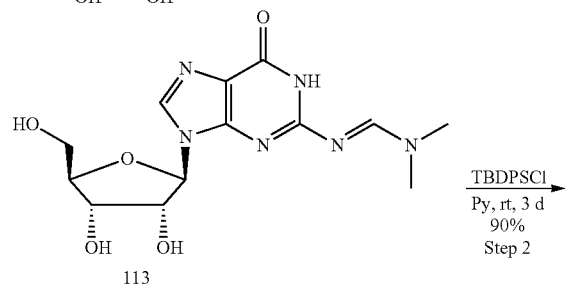
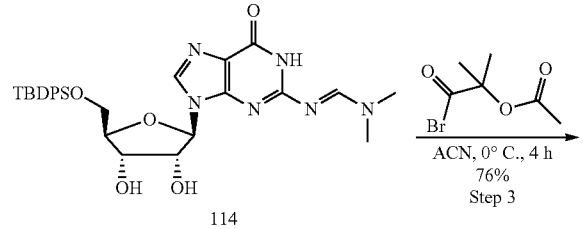
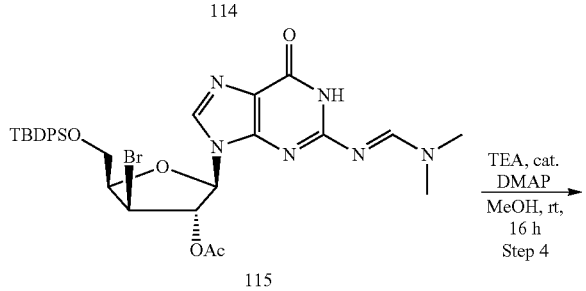
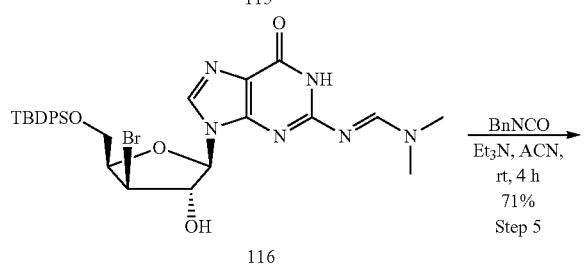
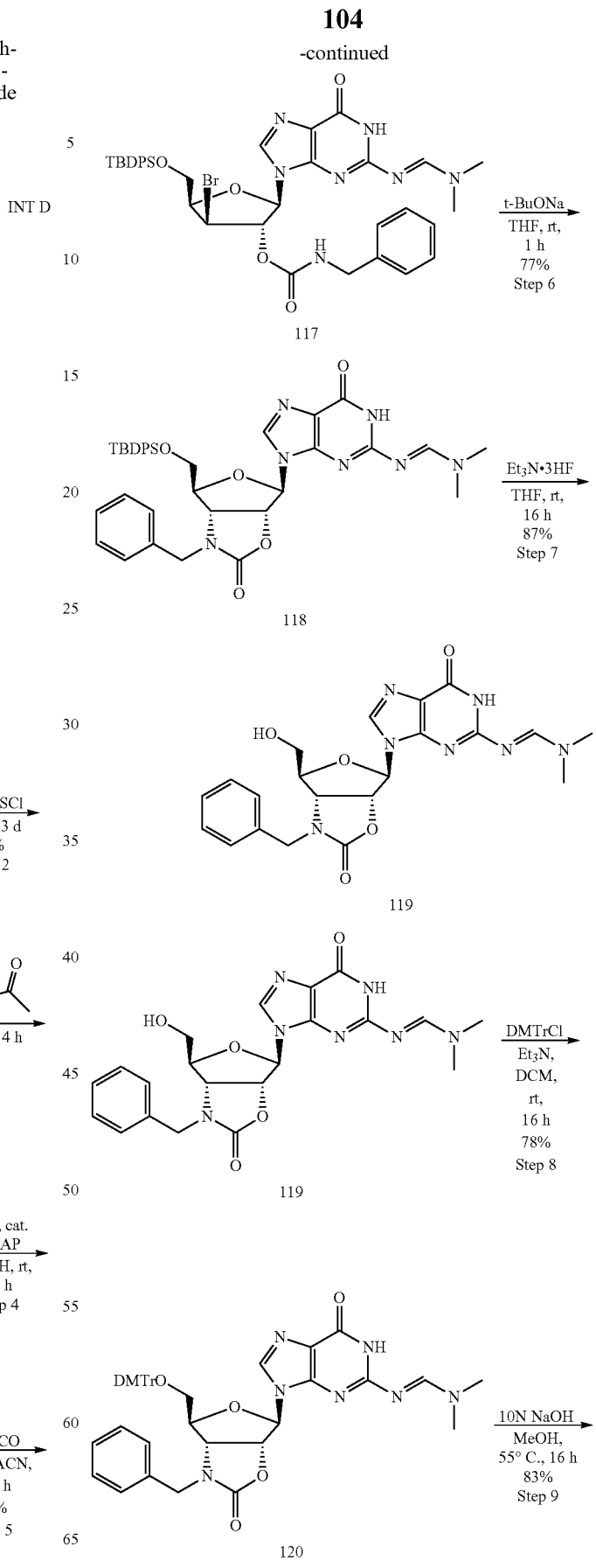

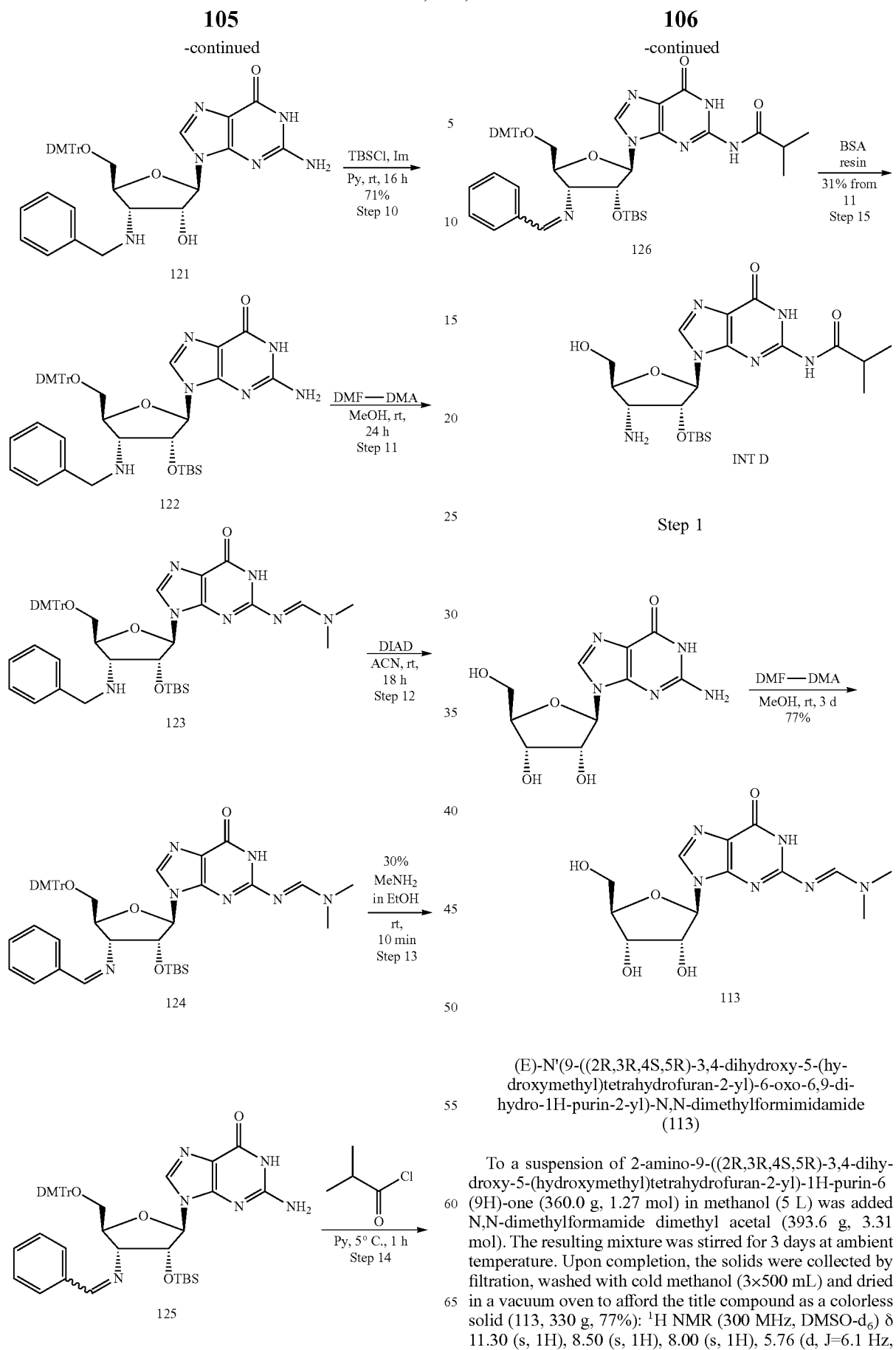

(E)-N'(9-((2R,3R,4S,5R)-3,4-dihydroxy-5-(hydroxymethyl)tetrahydrofuran-2-yl)-6-oxo-6,9-dihydro-1H-purin-2-yl)-N,N-dimethylformimidamide (113)

To a suspension of 2-amino-9-((2R,3R,4S,5R)-3,4-dihydroxy-5-(hydroxymethyl)tetrahydrofuran-2-yl)-1H-purin-6(9H)-one (360.0 g, 1.27 mol) in methanol (5 L) was added N,N-dimethylformamide dimethyl acetal (393.6 g, 3.31 mol). The resulting mixture was stirred for 3 days at ambient temperature. Upon completion, the solids were collected by filtration, washed with cold methanol (3×500 mL) and dried in a vacuum oven to afford the title compound as a colorless solid (113, 330 g, 77%): $^1$H NMR (300 MHz, DMSO-d$_6$) δ 11.30 (s, 1H), 8.50 (s, 1H), 8.00 (s, 1H), 5.76 (d, J=6.1 Hz, 1H), 5.37 (d, J=6.2 Hz, 1H), 5.13 (d, J=4.6 Hz, 1H), 4.98 (t, J=5.5 Hz, 1H), 4.45 (q, J=5.9 Hz, 1H), 4.08 (td, J=4.9, 3.2 Hz, 1H), 3.87 (q, J=3.8 Hz, 1H), 3.67-3.43 (m, 2H), 3.12 (s, 3H), 3.00 (s, 3H); LC/MS: [(M+1)]⁺=339.1.

Step 2

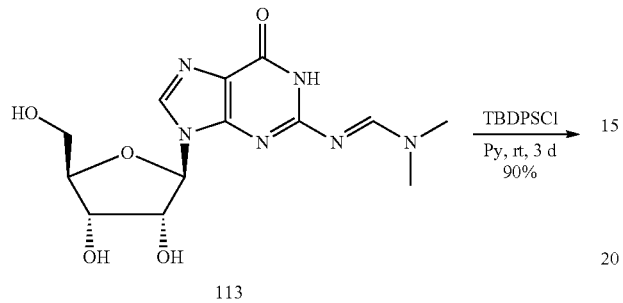

113

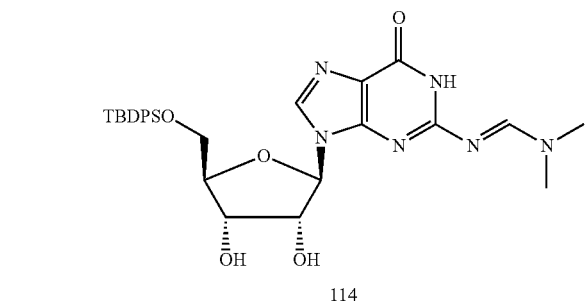

114

(E)-N'-(9-((2R,3R,4S,5R)-5-(((tert-butyldiphenylsilyl)oxy)methyl)-3,4-dihydroxytetrahydrofuran-2-yl)-6-oxo-6,9-dihydro-1H-purin-2-yl)-N,N-dimethylformimidamide (114)

To a suspension of (E)-N'-(9-((2R,3R,4S,5R)-3,4-dihydroxy-5-(hydroxymethyl)tetrahydrofuran-2-yl)-6-oxo-6,9-dihydro-1H-purin-2-yl)-N,N-dimethylformimidamide (113, 330 g, 0.97 mol) in pyridine (4 L) was added tert-butyl (chloro)diphenylsilane (294 g, 1.07 mol). The resulting solution was stirred for 3 days at ambient temperature to provide a clear solution. The solution was concentrated under reduced pressure and the residue was triturated with water (3 L) and filtered. The filter cake was washed with water (3×1 L), diethyl ether (3×1 L) and dried in a vacuum oven to afford the title compound 114 as a colorless solid (506 g, 90%): ¹H NMR (300 MHz, DMSO-d₆) δ 11.37 (s, 1H), 8.52 (s, 1H), 7.98 (s, 1H), 7.74-7.56 (m, 4H), 7.53-7.29 (m, 6H), 5.86 (d, J=5.0 Hz, 1H), 4.50 (t, J=5.1 Hz, 1H), 4.28 (t, J=4.9 Hz, 1H), 4.07-3.73 (m, 3H), 3.11 (s, 3H), 3.03 (s, 3H), 0.99 (s, 9H); LC/MS: [(M+1)]⁺=577.2.

Step 3

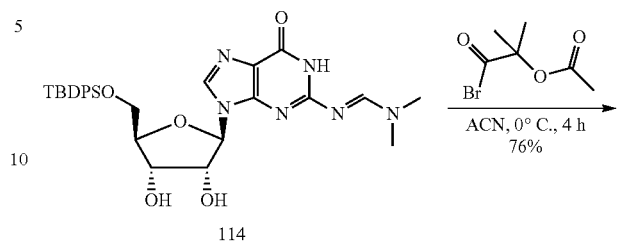

114

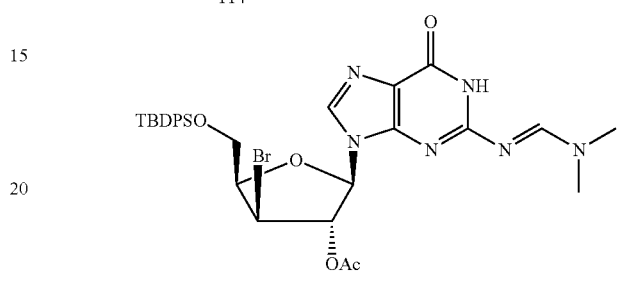

115

(2R,3S,4S,5R)-4-bromo-5-((((tert-butyldiphenylsilyl)oxy)methyl)-2-(2-((E)-((dimethylamino)methylene)amino)-6-oxo-1H-purin-9(6H)-yl)tetrahydrofuran-3-yl Acetate (115)

To a suspension of (E)-N'-(9-((2R,3R,4S,5R)-5-(((tert-butyldiphenylsilyl)oxy)methyl)-3,4-dihydroxytetrahydrofuran-2-yl)-6-oxo-6,9-dihydro-1H-purin-2-yl)-N,N-dimethylformimidamide (114, 300 g, 0.52 mol) in acetonitrile (4 L) was added water (4.7 g, 0.26 mol) followed by the addition of 1-bromo-2-methyl-1-oxopropan-2-yl acetate (419 g, 2.0 mol) at 0° C. The resulting solution was stirred for 4 hours at 0° C. then quenched by the addition of saturated aqueous sodium bicarbonate (3 L). The organic phase was collected and the aqueous phase was extracted with ethyl acetate (2×1 L). The organic layers were combined and dried with anhydrous sodium sulfate. After filtration, the filtrate was concentrated under reduced pressure and the residue was purified by silica gel column chromatography, eluting with 1% methanol in dichloromethane to afford the title compound 115 as a yellow solid (269 g, 76%): ¹H NMR (400 MHz, DMSO-d₆) δ 11.37 (s, 1H), 8.53 (s, 1H), 7.76 (s, 1H), 7.71-7.61 (m, 4H), 7.47-7.35 (m, 6H), 6.05 (t, J=2.8 Hz, 1H), 5.99 (d, J=3.1 Hz, 1H), 4.85 (dd, J=4.7, 2.4 Hz, 1H), 4.46 (q, J=5.0 Hz, 1H), 4.02-3.83 (m, 2H), 3.08 (s, 3H), 3.03-2.97 (m, 3H), 2.10 (s, 3H), 0.98 (s, 9H); LC/MS: [(M+1)]⁺=681.4, 683.4.

Step 4

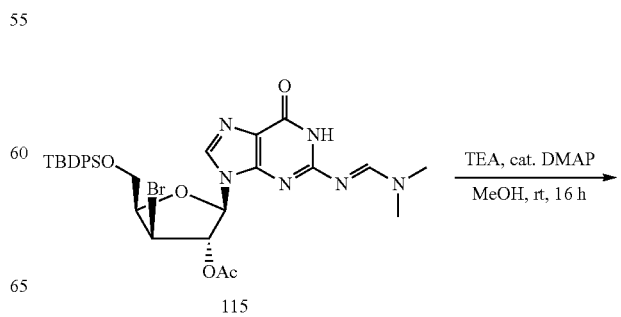

115

-continued

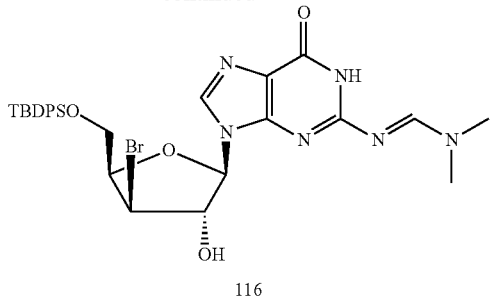

116

(E)-N'-(9-((2R,3S,4R,5R)-4-bromo-5-(((tert-butyldi-phenylsilyl)oxy)methyl)-3-hydroxytetrahydrofuran-2-yl)-6-oxo-6,9-dihydro-1H-purin-2-yl)-N,N-dimethylformimidamide (116)

To a solution of (2R,3S,4S,5R)-4-bromo-5-(((tert-butyldiphenylsilyl)oxy)methyl)-2-(2-((E)-((dimethylamino)methylene)amino)-6-oxo-1H-purin-9(6H)-yl)tetrahydrofuran-3-yl acetate (115, 390 g, 0.57 mol) in methanol (4 L) were added N,N-dimethylpyridin-4-amine (3.42 g, 0.03 mol) and triethylamine (230 mL, 1.71 mol). The resulting solution was stirred for 16 hours at ambient temperature. Upon completion, the resulting mixture was concentrated under reduced pressure to afford the title compound 116 as a colorless solid which was used in the next step without further purification (360 g): $^1$H NMR (400 MHz, DMSO-d$_6$) δ 11.40 (s, 1H), 8.56 (s, 1H), 7.86 (s, 1H), 7.65 (tt, J=6.2, 1.6 Hz, 4H), 7.53-7.35 (m, 6H), 6.49 (d, J=5.2 Hz, 1H), 5.82 (d, J=4.0 Hz, 1H), 4.94 (q, J=4.3 Hz, 1H), 4.60 (dd, J=5.4, 3.7 Hz, 1H), 4.48 (q, J=5.1 Hz, 1H), 4.04-3.91 (m, 2H), 3.12 (s, 3H), 3.03 (s, 3H), 1.02 (s, 9H); LC/MS: [(M+1)]$^+$=639.1, 641.1.

Step 5

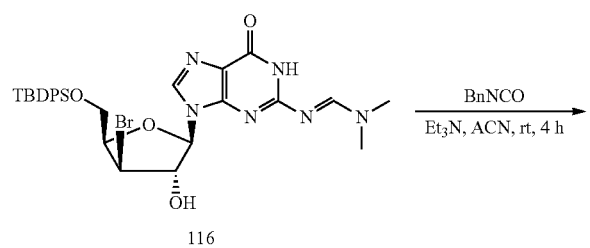

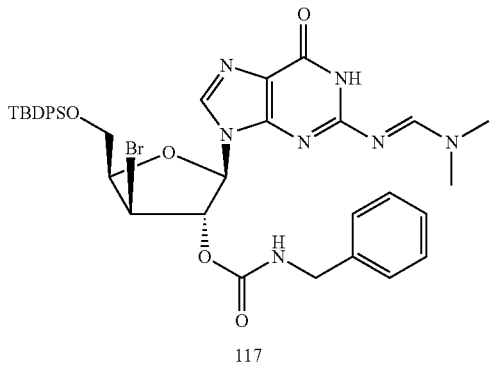

117

(2R,3S,4S,5R)-4-bromo-5-(((tert-butyldiphenylsilyl)oxy)methyl)-2-(2-((E)-((dimethylamino)methylene)amino)-6-oxo-1H-purin-9(6H)-yl)tetrahydrofuran-3-yl benzylcarbamate (117)

To a solution of (E)-N'-(9-((2R,3S,4R,5R)-4-bromo-5-(((tert-butyldiphenylsilyl)oxy)methyl)-3-hydroxytetrahydrofuran-2-yl)-6-oxo-6,9-dihydro-1H-purin-2-yl)-N,N-dimethylformimidamide (116, 370 g, 0.58 mol) in acetonitrile (4 L) were added triethylamine (14.6 g, 0.15 mol) and (isocyanatomethyl)benzene (92.6 g, 0.70 mol). The resulting solution was stirred for 4 hours at ambient temperature. Upon completion, the resulting mixture was concentrated under reduced pressure and the residue was purified by silica gel column chromatography, eluting with 1% methanol in dichloromethane to afford the title compound 117 as a colorless solid (317 g, 71%): $^1$H NMR (300 MHz, DMSO-d$_6$) δ 11.41 (s, 1H), 8.57 (s, 1H), 8.17 (s, 1H), 7.87-7.83 (s, 1H), 7.81-7.62 (m, 4H), 7.60-7.41 (m, 6H), 7.21-7.14 (m, 4H), 6.13 (s, 1H), 6.01 (s, 1H), 4.86 (dd, J=5.0, 3.1 Hz, 1H), 4.52 (q, J=5.0 Hz, 1H), 4.34-4.17 (m, 1H), 3.98-3.91 (m, 1H), 3.33 (s, 2H), 3.18 (d, J=4.9 Hz, 1H), 3.03 (d, J=4.7 Hz, 6H), 1.03 (s, 9H); LC/MS: [(M+1)]$^+$=772.1, 774.1.

Step 6

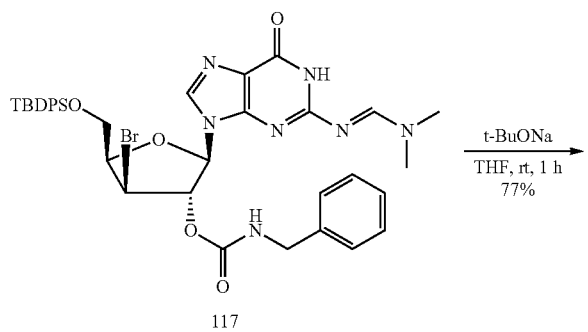

117

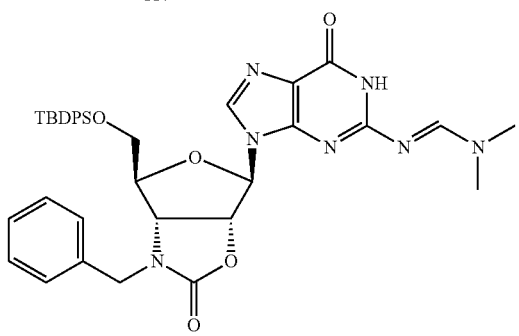

118

(E)-N'-(9-((3aR,4S,6R,6aR)-3-benzyl-4-(((tert-butyldiphenylsilyl)oxy)methyl)-2-oxohexahydrofuro[3,4-d]oxazol-6-yl)-6-oxo-6,9-dihydro-1H-purin-2-yl)-N,N-dimethylformimidamide (118)

A solution of (2R,3S,4S,5R)-4-bromo-5-(((tert-butyldiphenylsilyl)oxy)methyl)-2-(2-((E)-((dimethylamino)methylene)amino)-6-oxo-1H-purin-9(6H)-yl)tetrahydrofuran-3-yl benzylcarbamate (117, 214 g, 0.27 mol) in tetrahydrofuran (2.5 L) was treated with sodium tert-butoxide (79.84 g, 0.83 mol) for 1 hour at ambient temperature. The reaction was then quenched by the addition of saturated aqueous solution of ammonium chloride (5 L). The organic layer was separated and the aqueous layer was extracted with ethyl acetate (3×1 L). The organic layers were combined and dried over anhydrous sodium sulfate. After filtration, the filtrate was concentrated under reduced pressure and the residue was purified by silica gel column chromatography, eluting with 1% methanol in dichloromethane to afford the title compound 118 as a colorless solid (147 g, 77%): $^1$H NMR (400 MHz, DMSO-$d_6$) δ 11.44 (s, 1H), 8.51 (s, 1H), 7.95 (s, 1H), 7.49-7.27 (m, 15H), 6.31 (d, J=2.6 Hz, 1H), 6.03 (dd, J=8.4, 2.7 Hz, 1H), 4.69-4.53 (m, 2H), 4.46-4.35 (m, 2H), 3.56-3.43 (m, 2H), 2.98 (d, J=7.8 Hz, 6H), 0.83 (s, 9H); LC/MS: [(M+1)]$^+$=692.2.

Step 7

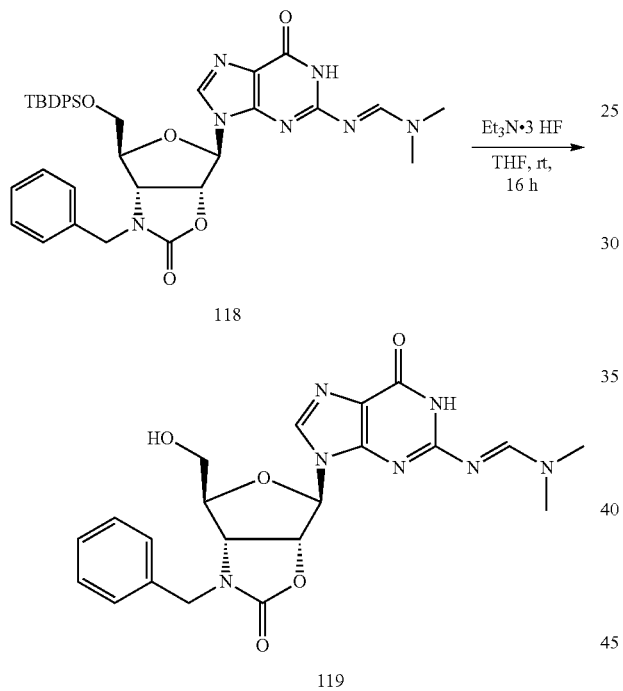

118

119

(E)-N'-(9-((3aR,4S,6R,6aR)-3-benzyl-4-(hydroxymethyl)-2-oxohexahydrofuro[3,4-d]oxazol-6-yl)-6-oxo-6,9-dihydro-1H-purin-2-yl)-N,N-dimethylformimidamide (119)

A solution of (E)-N'-(9-((3aR,4S,6R,6aR)-3-benzyl-4-(((tert-butyldiphenylsilyl)oxy)methyl)-2-oxohexahydrofuro[3,4-d]oxazol-6-yl)-6-oxo-6,9-dihydro-1H-purin-2-yl)-N,N-dimethylformimidamide (118, 146 g, 0.91 mol) in tetrahydrofuran (3 L) was treated with triethylamine trihydrofluoride (500 g, 3.5 mol) for 16 hours at ambient temperature. The reaction was quenched with a saturated aqueous solution of sodium bicarbonate (1 L). The organic layer was separated and the aqueous layer was extracted with ethyl acetate (2×1 L). The organic layers were combined and dried over anhydrous sodium sulfate. After filtration, the filtrate was concentrated under reduced pressure and the residue was purified by silica gel column chromatography, eluting with 1% methanol in dichloromethane to afford the title compound 119 as a colorless solid (119 g, 87%): $^1$H NMR (400 MHz, DMSO-$d_6$) δ 11.36 (s, 1H), 8.52 (s, 1H), 8.02 (s, 1H), 7.45-7.29 (m, 5H), 6.23 (d, J=3.2 Hz, 1H), 5.73 (dd, J=8.5, 3.2 Hz, 1H), 5.19-5.12 (m, 1H), 4.67 (d, J=15.4 Hz, 1H), 4.46-4.20 (m, 3H), 3.47-3.37 (m, 2H), 3.03 (d, J=7.7 Hz, 6H); LC/MS: [(M+1)]j=454.1.

Step 8

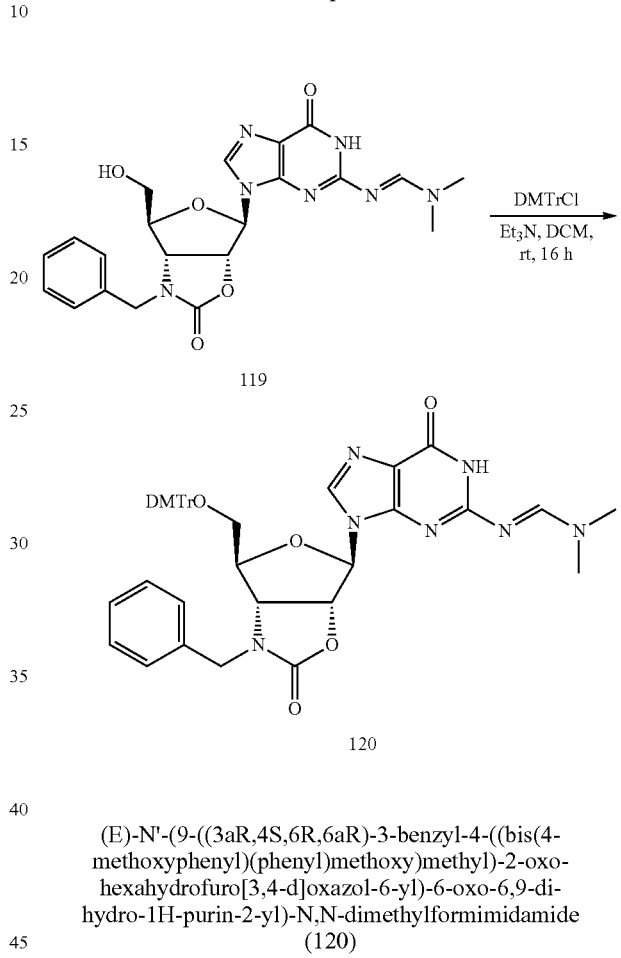

120

(E)-N'-(9-((3aR,4S,6R,6aR)-3-benzyl-4-((bis(4-methoxyphenyl)(phenyl)methoxy)methyl)-2-oxohexahydrofuro[3,4-d]oxazol-6-yl)-6-oxo-6,9-dihydro-1H-purin-2-yl)-N,N-dimethylformimidamide (120)

To a solution of (E)-N'-(9-((3aR,4S,6R,6aR)-3-benzyl-4-(hydroxymethyl)-2-oxohexahydrofuro[3,4-d]oxazol-6-yl)-6-oxo-6,9-dihydro-1H-purin-2-yl)-N,N-dimethylformimidamide (119, 55 g, 0.12 mol) in dichloromethane (500 mL) were added triethylamine (18 g, 0.18 mol) and 1-[chloro(4-methoxyphenyl)benzyl]-4-methoxybenzene (49 g, 0.14 mol). The resulting solution was stirred for 16 hours at ambient temperature. Upon completion, the reaction was quenched with a saturated aqueous solution of sodium bicarbonate (1 L). The organic layer was separated and the aqueous layer was extracted with dichloromethane (2×200 mL). The organic layers were combined and dried over anhydrous sodium sulfate. After filtration, the filtrate was concentrated under reduced pressure and the residue was purified by silica gel column chromatography, eluting with 1% methanol in dichloromethane (plus 0.1% TEA, v/v) to afford the title compound 120 as a red solid (71 g, 78%): $^1$H NMR (400 MHz, DMSO-$d_6$) δ 11.37 (s, 1H), 8.30 (s, 1H), 7.95 (s, 1H), 7.32 (q, J=3.6 Hz, 3H), 7.26-7.12 (m, 7H), 7.10-6.98 (m, 4H), 6.79-6.68 (m, 4H), 6.32 (d, J=2.4 Hz, 1H), 5.93 (dd, J=8.3, 2.4 Hz, 1H), 4.66 (d, J=15.8 Hz, 1H), 4.52-4.30 (m, 3H), 3.73 (d, J=2.3 Hz, 6H), 3.04 (td, J=10.2, 6.2 Hz, 1H), 2.95 (s, 3H), 2.86 (s, 3H), 2.76 (dd, J=9.9, 5.5 Hz, 1H); LC/MS: [(M+1)]$^+$=756.2.

Step 9

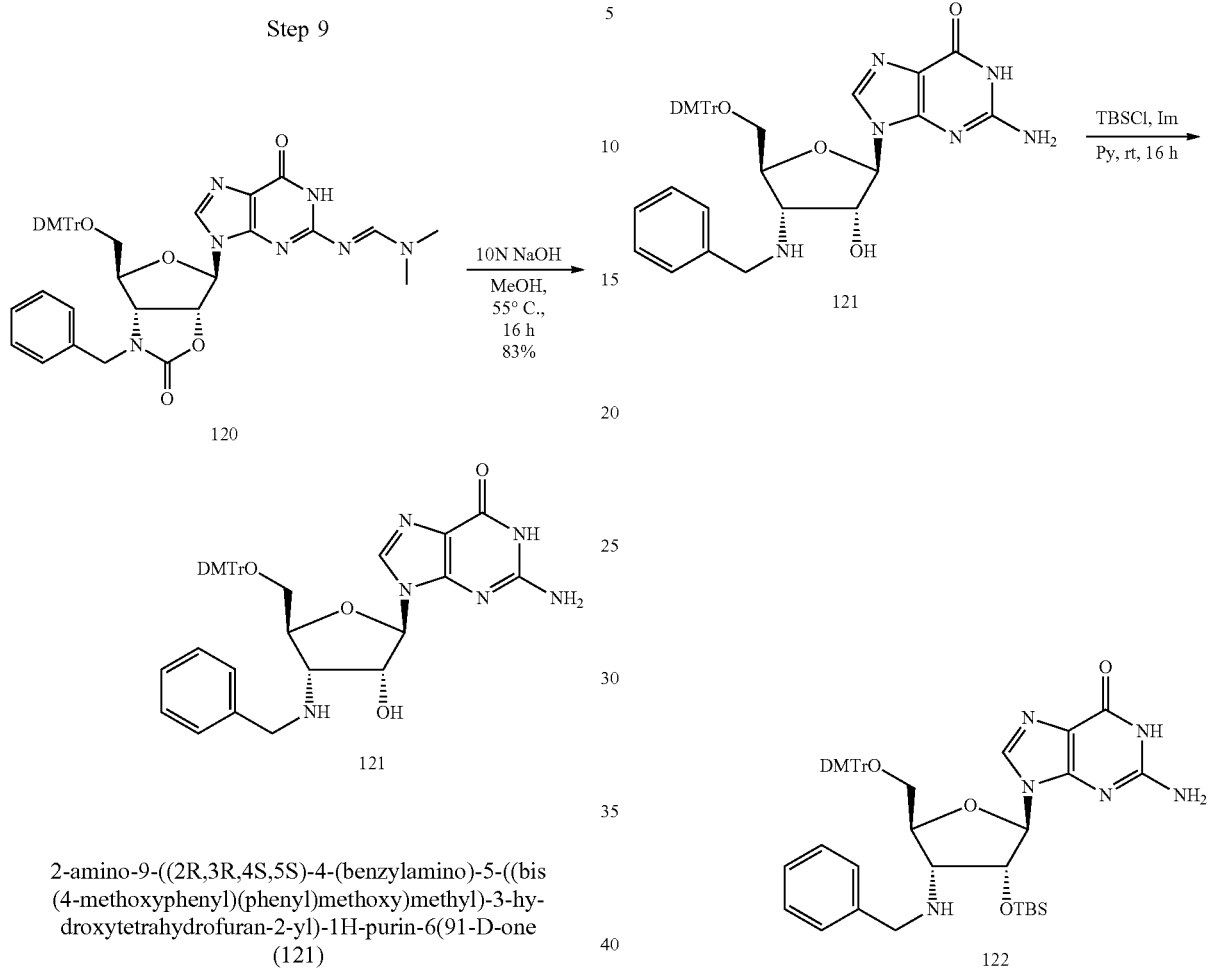

Step 10

2-amino-9-((2R,3R,4S,5S)-4-(benzylamino)-5-((bis(4-methoxyphenyl)(phenyl)methoxy)methyl)-3-hydroxytetrahydrofuran-2-yl)-1H-purin-6(9H)-one (121)

A solution of (E)-N'-(9-((3aR,4S,6R,6aR)-3-benzyl-4-((bis(4-methoxyphenyl)(phenyl)methoxy)methyl)-2-oxohexahydrofuro[3,4-d]oxazol-6-yl)-6-oxo-6,9-dihydro-1H-purin-2-yl)-N,N-dimethylformimidamide (120, 90 g, 0.12 mol) in methanol (1 L) was treated with a 10 N aqueous solution of sodium hydroxide (400 mL) for 16 hours at 55° C. After cooling down to ambient temperature, the resulting solution was concentrated to about one third volume then the pH value of the suspension was adjusted to 8-9 with 4 N hydrochloric acid (1 L). The resulting mixture was extracted with ethyl acetate (2×500 mL). The organic layers were combined and dried over anhydrous sodium sulfate. After filtration, the filtrate was concentrated under reduced pressure and the residue was purified by silica gel column chromatography, eluting with 1% to 2% methanol in dichloromethane (plus 0.1% TEA, v/v) to afford the title compound 121 as a red solid (66 g, 83%): $^1$H NMR (400 MHz, DMSO-d$_6$) δ 10.65 (s, 1H), 7.78 (s, 1H), 7.36-7.15 (m, 14H), 6.88-6.78 (m, 4H), 6.48 (s, 2H), 5.90 (d, J=4.9 Hz, 1H), 5.82 (d, J=2.5 Hz, 1H), 4.54 (td, J=4.8, 2.5 Hz, 1H), 3.91 (ddd, J=7.5, 4.7, 2.6 Hz, 1H), 3.80 (d, J=13.5 Hz, 1H), 3.71 (s, 6H), 3.70 (d, J=11.9 Hz, 1H), 3.48 (d, J=9.3 Hz, 1H), 3.24 (dd, J=10.6, 2.7 Hz, 1H), 3.16 (dd, J=10.4, 4.8 Hz, 1H), 2.25 (s, 1H); LC/MS: [(M+1)]$^+$=675.2.

2-amino-9-((2R,3R,4R,5S)-4-(benzylamino)-5-((bis(4-methoxyphenyl)(phenyl)methoxy)methyl)-3-((tert-butyldimethylsilyl)oxy)tetrahydrofuran-2-yl-1H-purin-6(9H)-one (122)

To a solution of 2-amino-9-((2R,3R,4S,5S)-4-(benzylamino)-5-((bis(4-methoxyphenyl)(phenyl)methoxy)methyl)-3-hydroxytetrahydrofuran-2-yl)-1H-purin-6(9H)-one (90 g, 0.13 mol) in pyridine (1 L) were added imidazole (121, 45 g, 0.67 mol) and tert-butylchlorodimethylsilane (50 g, 0.33 mol). The resulting solution was stirred for 16 hours at ambient temperature then quenched with methanol (10 mL). The resulting mixture was concentrated under reduced pressure and the residue was purified by silica gel column chromatography, eluting with 1% to 2% methanol in dichloromethane (plus 0.1% TEA, v/v) to afford the title compound 122 as a yellow solid (75 g, 71%): $^1$H NMR (400 MHz, DMSO-d$_6$) δ 10.50 (s, 1H), 7.82 (s, 1H), 7.45-7.11 (m, 14H), 6.86 (dd, J=8.8, 2.7 Hz, 4H), 6.43 (s, 2H), 5.83 (d, J=4.2 Hz, 1H), 4.75 (t, J=4.8 Hz, 1H), 3.98 (dd, J=6.1, 2.9 Hz, 1H), 3.77-3.73 (m, 8H), 3.47-3.14 (m, 3H), 2.05 (q, J=6.5 Hz, 1H), 0.80 (s, 9H), 0.00 (s, 3H), −0.08 (s, 3H); LC/MS: [(M+1)]$^+$=789.3.

Step 11

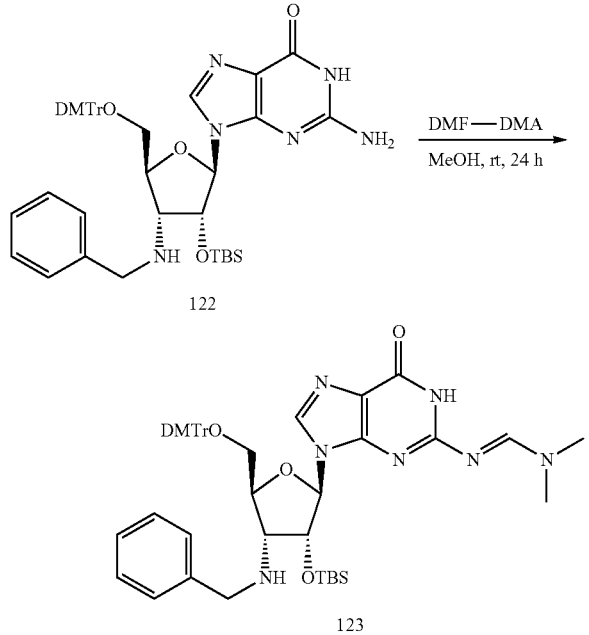

(E)-N'-(9-2R,3R,4R,5S)-4-(benzylamino)-5-((bis(4-methoxyphenyl(phenyl)methoxy)methyl)-3-((tert-butyldimethylsilyl)oxy)tetrahydrofuran-2-yl)-6-oxo-6,9-dihydro-1H-purin-2-yl)-N,N-dimethylformimidamide (123)

To a solution of 2-amino-9-((2R,3R,4R,5S)-4-(benzylamino)-5-((bis(4-methoxyphenyl)(phenyl)methoxy)methyl)-3-((tert-butyldimethylsilyl)oxy)tetrahydrofuran-2-yl)-1H-purin-6(9H)-one (122, 100 g, 0.13 mol) in methanol (1 L) was added N,N-dimethylformamide dimethyl acetal (52 g, 0.44 mol). The resulting solution was stirred for 24 hours at ambient temperature. Upon completion, the resulting mixture was concentrated under reduced pressure to afford the title compound 123 which was used in the next step without further purification (100 g, yellow solid): LC/MS: [(M+1)]$^+$=844.7.

Step 12

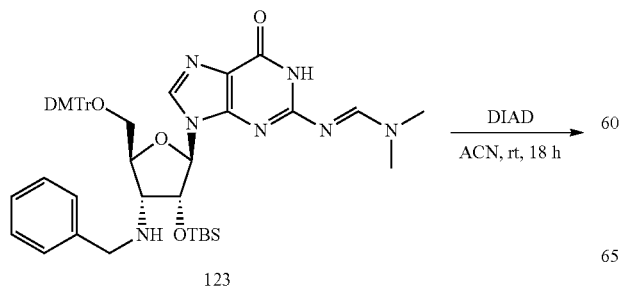

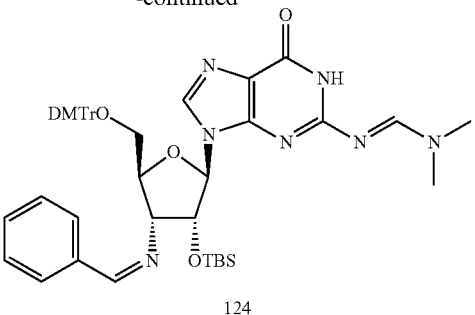

(1E)-N'-(9-((2R,3R,4R,5S)-4-(benzylideneamino)-5-((bis(4-methoxyphenyl)(phenyl)methoxy)methyl)-3-((tert-butyldimethylsilyl)oxy)tetrahydrofuran-2-yl)-6-oxo-6,9-dihydro-1H-purin-2-yl)-N,N-dimethylformimidamide (124)

A solution of (E)-N'-(9-((2R,3R,4R,5S)-4-(benzylamino)-5-((bis(4-methoxyphenyl)(phenyl)methoxy)methyl)-3-((tert-butyldimethylsilyl)oxy)tetrahydrofuran-2-yl)-6-oxo-6,9-dihydro-1H-purin-2-yl)-N,N-dimethylformimidamide (123, 59 g, 69.90 mmol) in acetonitrile (600 mL) was treated with diisopropyl azodiformate (141 g, 699 mmol) for 18 hours at ambient temperature. The resulting mixture was concentrated under reduced pressure and the residue was eluted through a short silica gel column to remove the excess of diisopropyl azodiformate (eluted with 10% ethyl acetate in petroleum ether plus 0.1% triethylamine, then 2% methanol in dichloromethane plus 0.1% TEA) to afford the crude title compound 124 which was used in the next step without further purification (89 g, brown oil): LC/MS: [(M+1)]$^+$=842.4.

Step 13

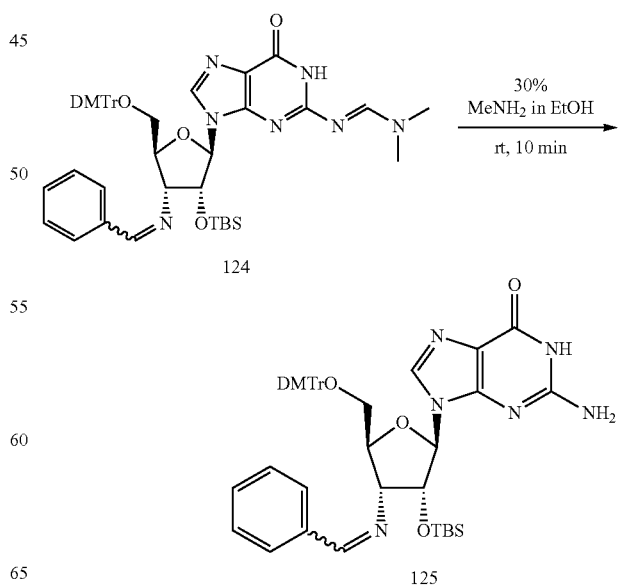

2-amino-9-((2R,3R,4R,5S)-4-(benzylideneamino)-5-((bis(4-methoxyphenyl)(phenyl)methoxy)methyl)-3-((tert-butyldimethylsilyl)oxy)tetrahydrofuran-2-yl)-1H-purin-6(9H)-one (125)

The above crude (1E)-N'-(9-((2R,3R,4R,5S)-4-(benzylideneamino)-5-((bis(4-methoxyphenyl)(phenyl)methoxy)methyl)-3-((tert-butyldimethylsilyl)oxy)tetrahydrofuran-2-yl)-6-oxo-6,9-dihydro-1H-purin-2-yl)-N,N-dimethylformimidamide (55 g) was treated with methylamine (124, 300 ml, 30% solution in ethanol) for 10 min at ambient temperature. Volatiles were distilled out under reduced pressure to give the crude title compound 125 which was used in the next step without further purification (45 g, yellow oil): LC/MS: [(M+1)]$^+$=699.3.

Step 14

Step 15

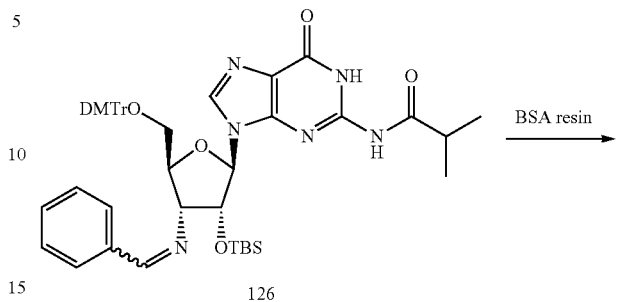

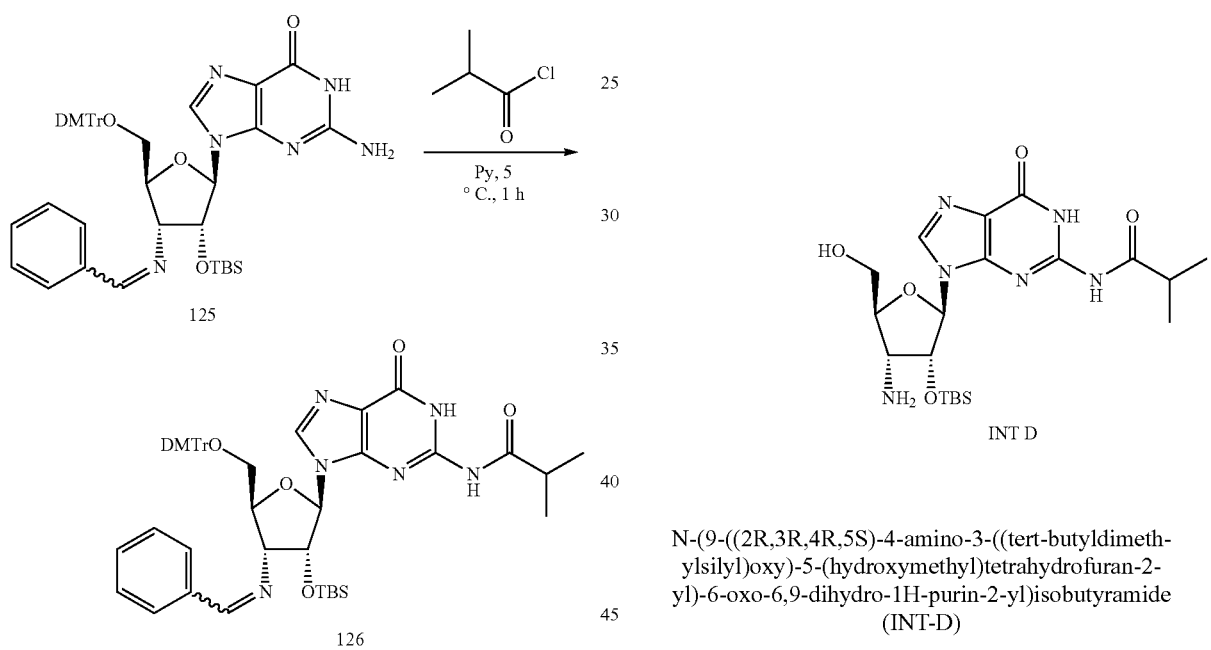

N-(9-((2R,3R,4R,5S)-4-(benzylideneamino)-5-((bis(4-methoxyphenyl)(phenyl)methoxy)methyl)-3-((tert-butyldimethylsilyl)oxy)tetrahydrofuran-2-yl)-6-oxo-6,9-dihydro-1H-purin-2-yl)isobutyramide (126)

The above crude 2-amino-9-((2R,3R,4R,5S)-4-(benzylideneamino)-5-((bis(4-methoxyphenyl)(phenyl)methoxy)methyl)-3-((tert-butyldimethylsilyl)oxy)tetrahydrofuran-2-yl)-1H-purin-6(9H)-one (125, 45 g) was dissolved in dry pyridine (500 mL), cooled to 0-5° C., then subjected to the addition of isobutyryl chloride (13.5 g, 0.13 mol). After 1 hour, the reaction was quenched with methanol (50 mL) and concentrated under reduced pressure to afford the crude title compound 126 as a brown oil (57 g): LC/MS: [(M+1)]$^+$=787.3.

N-(9-((2R,3R,4R,5S)-4-amino-3-((tert-butyldimethylsilyl)oxy)-5-(hydroxymethyl)tetrahydrofuran-2-yl)-6-oxo-6,9-dihydro-1H-purin-2-yl)isobutyramide (INT-D)

To the above crude solution of N-(9-((2R,3R,4R,5S)-4-(benzylideneamino)-5-((bis(4-methoxyphenyl)(phenyl)methoxy)methyl)-3-((tert-butyldimethylsilyl)oxy)tetrahydrofuran-2-yl)-6-oxo-6,9-dihydro-1H-purin-2-yl)isobutyramide (126, 57 g) in dichloromethane (600 mL) and methanol (60 mL) were added Amberlyst-15 (114 g) and water (14 mL). After 2 hours at ambient temperature, the resulting mixture was filtered and washed with 10% methanol in dichloromethane (300 mL). The solids were collected and washed with 20% trimethylamine in dichloromethane (3×500 mL). The combined organic layers were concentrated under reduced pressure and the residue was purified by silica gel column chromatography, eluting with 1%~4% methanol in dichloromethane to afford the title compound INT-D as a colorless solid (10 g, 31% over 4 steps): $^1$H NMR (400 MHz, DMSO-d$_6$) δ 11.59 (s, 1H), 8.28 (s, 1H), 5.88 (d, J=4.6 Hz, 1H), 5.01 (s, 1H), 4.50 (t, J=5.0 Hz, 1H), 3.78 (q, J=4.0 Hz, 1H), 3.69 (d, J=11.8 Hz, 1H), 3.62-3.48 (m, 2H), 2.79 (m, 1H), 1.13 (d, J=6.8 Hz, 6H), 0.81 (s, 9H), 0.01 (s, 3H), −0.12 (s, 3H); LC/MS: [(M+1)]$^{'0}$=467.2.

119

N-(9-((2R,3R,4R,5R)-3-fluoro-4-hydroxy-5-((tritylamino)methyl)tetrahydrofuran-2-yl)-9H-purin-6-yl)benzamide (INT-E)

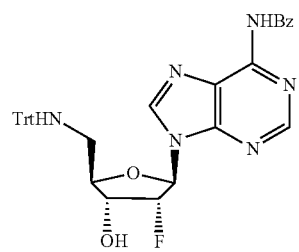

INT E

Scheme

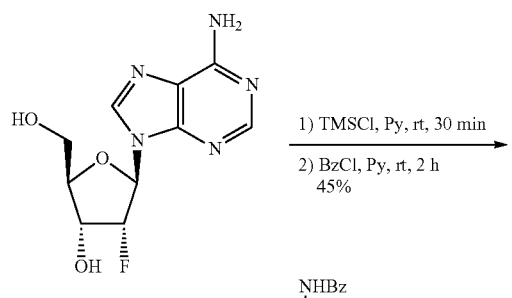

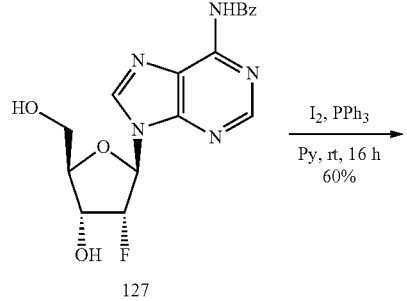

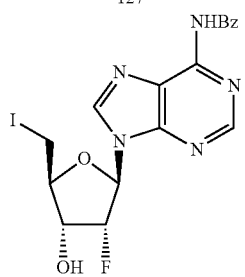

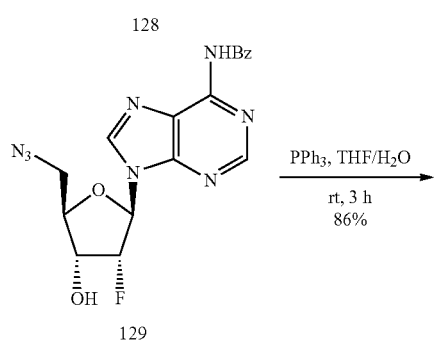

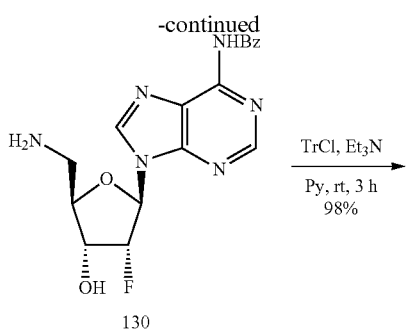

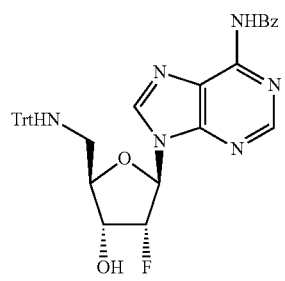

Step 1

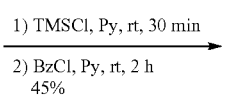

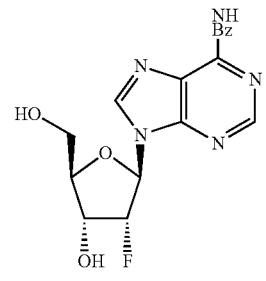

N-(9-((2R,3R,4R 5R)-3-fluoro-4-hydroxy-5-(hydroxymethyl)tetrahydrofuran-2-yl)-9H-purin-6-yl)benzamide (127)

To a suspension of (2R,3R,4R)-5-(6-amino-9H-purin-9-yl)-4-fluoro-2-(hydroxymethyl)oxolan-3-ol (20.0 g, 74.3 mmol) in pyridine (400 mL) was added trimethylsilyl chloride (40.2 g, 372.2 mmol) at 0° C. in 5 min. The suspension was stirred at ambient temperature for 30 min followed by the addition of benzoyl chloride (31.2 g, 233.1 mmol) at 0° C. in 5 min. The suspension was stirred at ambient temperature for 2 hours. Upon completion, the reaction was quenched with cold water (100 mL) and an aqueous solution of ammonia (240 mL, 25% w/w). The resulting mixture was stirred for 20 min at ambient temperature and was then concentrated under reduced pressure. The residue was purified by silica gel column chromatography, eluting with 10% methanol in dichloromethane to afford the title compound 127 as a colorless solid (25 g, 45%): $^1$H NMR (300 MHz, DMSO-$d_6$) δ 11.25 (s, 1H), 8.78 (s, 1H), 8.72 (s, 1H), 8.12-7.99 (m, 2H), 7.74-7.49 (m, 3H), 6.39 (dd, J=17.2, 2.4 Hz, 1H), 5.77 (d, J=6.2 Hz, 1H), 5.53 (ddd, J=52.8, 4.4, 2.4 Hz, 1H), 5.17 (t, J=5.4 Hz, 1H), 4.68-4.44 (m, 1H), 4.02 (dt, J=6.9, 3.4 Hz, 1H), 3.80 (d, J=12.4 Hz, 1H), 3.62 (dt, J=12.5, 4.5 Hz, 1H); $^{19}$F NMR (282 MHz, DMSO-$d_6$) δ −203.61; LC/MS (ESI, m/z): [(M+1)]$^+$=374.0.

Step 2

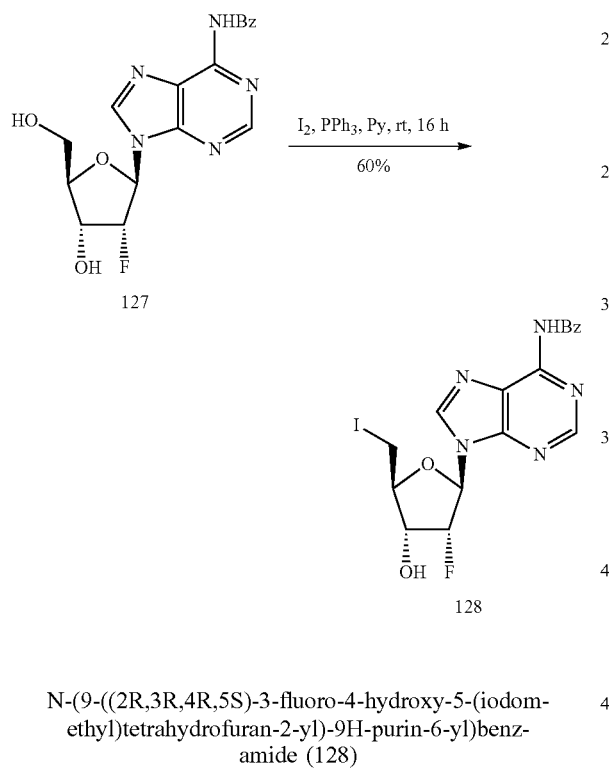

N-(9-((2R,3R,4R,5S)-3-fluoro-4-hydroxy-5-(iodomethyl)tetrahydrofuran-2-yl)-9H-purin-6-yl)benzamide (128)

To a mixture of N-(9-((2R,3R,4R,5R)-3-fluoro-4-hydroxy-5-(hydroxymethyl)tetrahydrofuran-2-yl)-9H-purin-6-yl)benzamide (127, 19.3 g, 51.6 mmol) and triphenylphosphine (33.8 g, 128.9 mmol) in pyridine (350 mL) was added a solution of iodine (28.8 g, 113.6 mmol) in pyridine (50 mL) below 20° C. over 10 min. The resulting dark solution was stirred for 16 hours at ambient temperature. Then it was quenched with saturated aqueous solution of sodium hyposulfite (800 mL) and extracted with ethyl acetate (3×500 mL). The combined organic layers was washed with brine (800 mL) and dried over anhydrous sodium sulfate. After filtration, the filtrate was concentrated under reduced pressure. The crude product was recrystallized from methanol to afford the pure title compound 128 as a brown solid (15 g, 60%): $^1$H NMR (300 MHz, DMSO-$d_6$) δ 11.27 (s, 1H), 8.79 (s, 1H), 8.67 (s, 1H), 8.12-8.00 (m, 2H), 7.73-7.49 (m, 3H), 6.42 (dd, J=19.7, 2.1 Hz, 1H), 6.04 (d, J=6.3 Hz, 1H), 5.74 (ddd, J=52.5, 4.7, 2.1 Hz, 1H), 4.58 (dq, J=18.7, 5.9 Hz, 1H), 3.96 (td, J=7.0, 3.9 Hz, 1H), 3.68 (dd, J=11.0, 3.9 Hz, 1H), 3.50 (dd, J=11.0, 6.6 Hz, 1H); $^{19}$F NMR (282 MHz, DMSO-$d_6$) δ −201.53; LC/MS (ESI, m/z): [(M+1)]$^+$=484.0.

Step 3

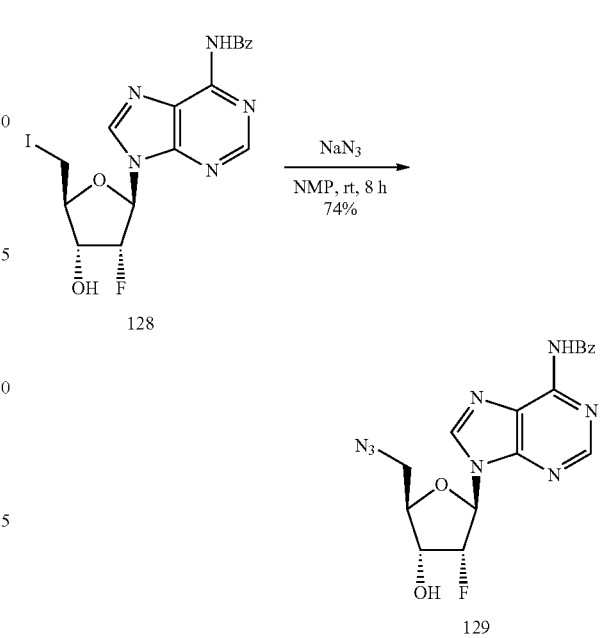

N-(9-((2R,3R,4R,5R)-5-(azidomethyl)-3-fluoro-4-hydroxytetrahydrofuran-2-yl)-9H-purin-6-yl)benzamide (129)

To a solution of N-(9-((2R,3R,4R,5S)-3-fluoro-4-hydroxy-5-(iodomethyl)tetrahydrofuran-2-yl)-9H-purin-6-yl)benzamide (128, 15 g, 31.1 mmol) in N-methyl pyrrolidone (220 mL) was added sodium azide (4.1 g, 62.2 mmol). The resulting mixture was stirred for 8 hours at ambient temperature. Upon completion, the resulting solution was poured into diethyl ether (4 L). Solids were precipitated and collected by filtration to afford the title compound 129 as a brown solid (9.2 g, 74%): $^1$H NMR (300 MHz, DMSO-$d_6$) δ 11.25 (s, 1H), 8.80 (s, 1H), 8.67 (s, 1H), 8.11-8.01 (m, 2H), 7.72-7.50 (m, 3H), 6.43 (dd, J=19.9, 2.0 Hz, 1H), 5.94 (d, J=6.4 Hz, 1H), 5.68 (ddd, J=52.5, 4.8, 2.0 Hz, 1H), 4.79 (dddd, J=21.2, 7.8, 6.6, 4.7 Hz, 1H), 4.14 (ddd, J=7.9, 5.4, 2.5 Hz, 1H), 3.77 (dd, J=13.7, 2.9 Hz, 1H), 3.59 (dd, J=13.6, 5.7 Hz, 1H); $^{19}$F NMR (282 MHz, DMSO-$d_6$) δ −201.66; LC/MS (ESI, m/z): [(M+1)]$^+$=399.0.

Step 4

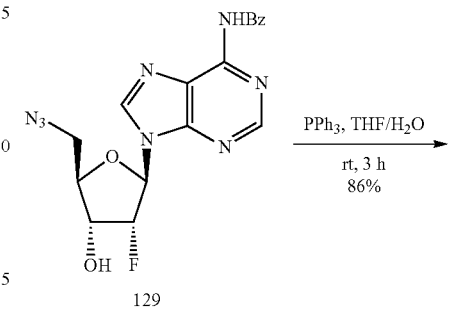

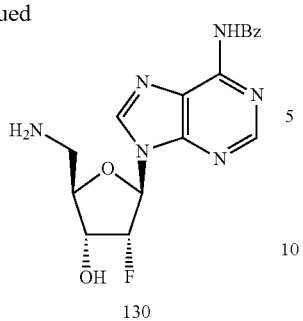

130

N-(9-((2R,3R,4R,5R)-5-(aminomethyl)-3-fluoro-4-hydroxytetrahydrofuran-2-yl)-9H-purin-6-yl)benzamide (130)

To a solution of N-(9-((2R,3R,4R,5R)-5-(azidomethyl)-3-fluoro-4-hydroxytetrahydrofuran-2-yl)-9H-purin-6-yl)benzamide (129, 16.1 g, 40.4 mmol) in tetrahydrofuran (160 mL) and water (32 mL) was added triphenylphosphine (31.7 g, 120.8 mmol). The resulting solution was stirred for 3 hours at ambient temperature. The resulting solution was diluted with methanol (200 mL) and filtered. The filter cake was collected to afford the title compound 130 as a colorless solid (13 g, 86%): $^1$H NMR (300 MHz, DMSO-$d_6$) δ 8.76 (s, 1H), 8.75 (s, 1H), 8.10-7.98 (m, 2H), 7.72-7.47 (m, 3H), 6.35 (dd, J=17.9, 2.7 Hz, 1H), 5.59 (ddd, J=52.9, 4.7, 2.8 Hz, 1H), 4.57 (ddd, J=18.8, 7.0, 4.8 Hz, 1H), 3.95 (dd, J=7.3, 3.8 Hz, 1H), 2.94 (dd, J=13.8, 3.8 Hz, 1H), 2.80 (dd, J=13.8, 5.2 Hz, 1H); $^{19}$F NMR (282 MHz, DMSO-$d_6$) δ −203.45; LC/MS (ESI, m/z): [(M+1)]$^+$=373.0.

Step 5

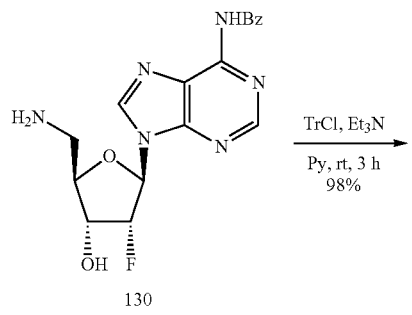

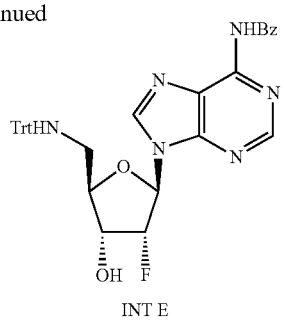

INT E

N-(9-((2R,3R,4R,5R)-3-fluoro-4-hydroxy-5-((tritylamino)methyltetrahydrofuran-2-yl)-9H-purin-6-yl)benzamide (INT-E)

To a solution of N-(9-((2R,3R,4R,5R)-5-(aminomethyl)-3-fluoro-4-hydroxytetrahydrofuran-2-yl)-9H-purin-6-yl)benzamide (130, 3.0 g, 8.1 mmol) in pyridine (30 mL) was added triethylamine (1.2 g, 12.1 mmol) and triphenylmethyl chloride (2.4 g, 8.6 mmol). The resulting solution was stirred for 3 hours at ambient temperature. The reaction was then quenched by the addition of methanol (0.2 mL) and concentrated under reduced pressure. The residue was purified by silica gel column chromatography, eluting with 20%~40% ethyl acetate in petroleum ether to afford the title compound INT-E as a colorless solid (4.8 g, 98%): $^1$H NMR (400 MHz, DMSO-$d_6$) δ 11.22 (s, 1H), 8.63 (s, 1H), 8.39 (s, 1H), 8.09-7.98 (m, 2H), 7.71-7.61 (m, 1H), 7.55 (dd, J=8.3, 7.0 Hz, 2H), 7.44-7.34 (m, 6H), 7.32-7.10 (m, 9H), 6.36 (dd, J=18.3, 2.9 Hz, 1H), 5.85-5.60 (m, 2H), 4.87 (dq, J=17.7, 5.9 Hz, 1H), 4.19-4.09 (m, 1H), 2.88 (dd, J=9.8, 6.1 Hz, 1H), 2.43 (ddd, J=15.1, 9.9, 5.4 Hz, 1H), 2.32 (ddd, J=12.6, 6.1, 3.2 Hz, 1H); $^{19}$F NMR (376 MHz, DMSO-$d_6$) δ −203.14; LC/MS (ESI, m/z): [(M+1)]$^+$=615.0.

Analog Preparation

Diammonium (1S,6S,8R,9R,10S,15S,17R,18R)-8-(2-amino-6-oxo-6,9-dihydro-1H-purin-9-yl)-17-(6-amino-9H-purin-9-yl)-9,18-dihydroxy-3,12-dioxo-4,7,13,16-tetraoxa-2,11-diaza-3λ$^s$,12λ$^s$-diphosphatricyclo[13.3.0.0$^{6,10}$]octadecane-3,12-bis(olate)

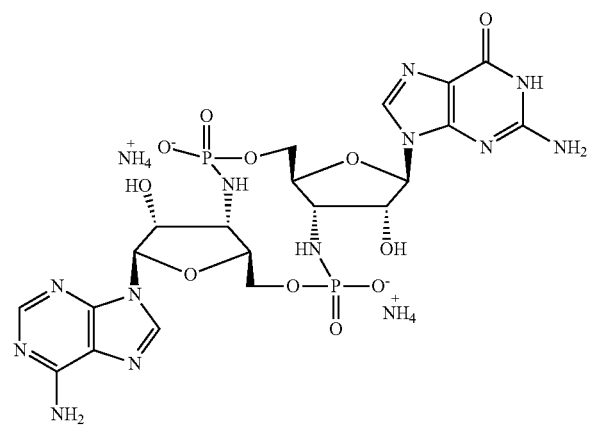

-continued
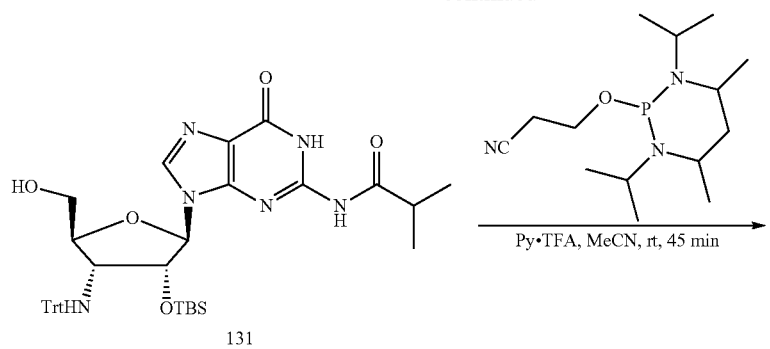
131
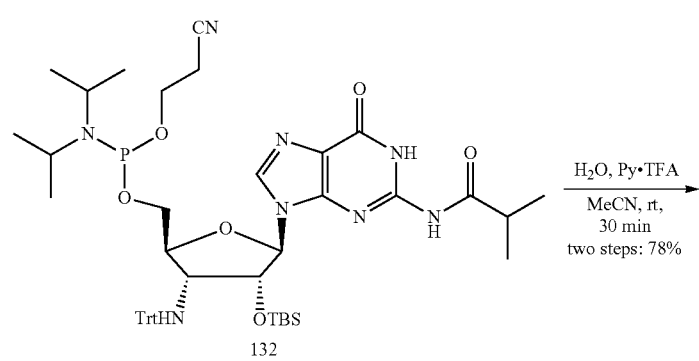
132
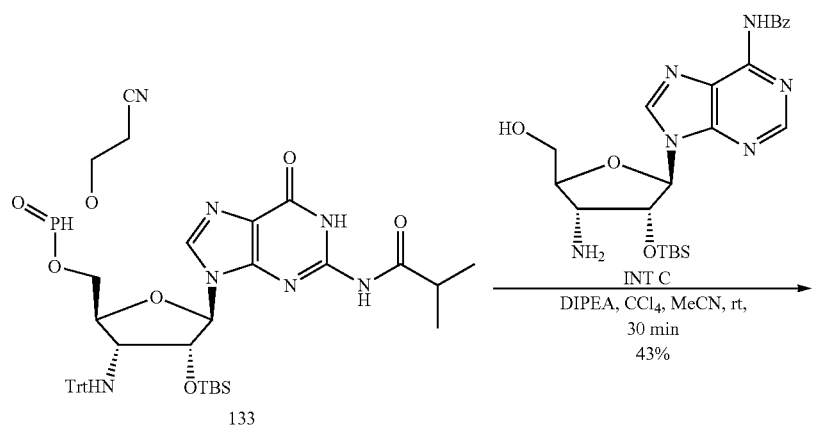
133
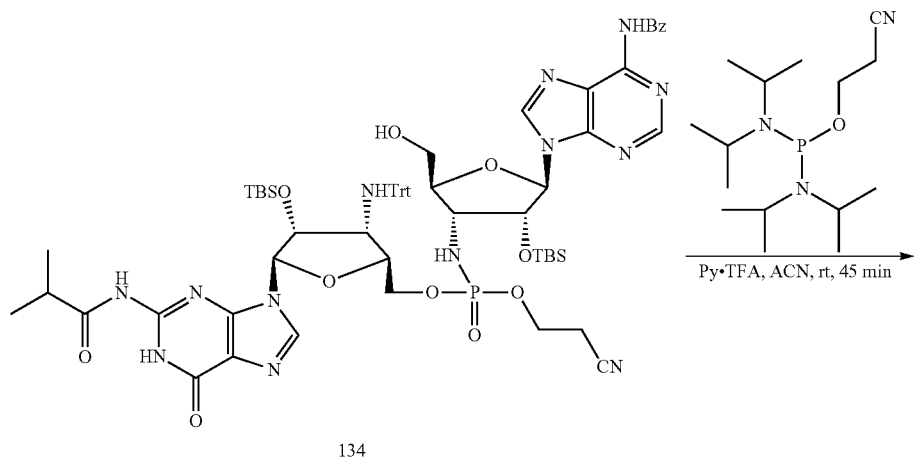
134

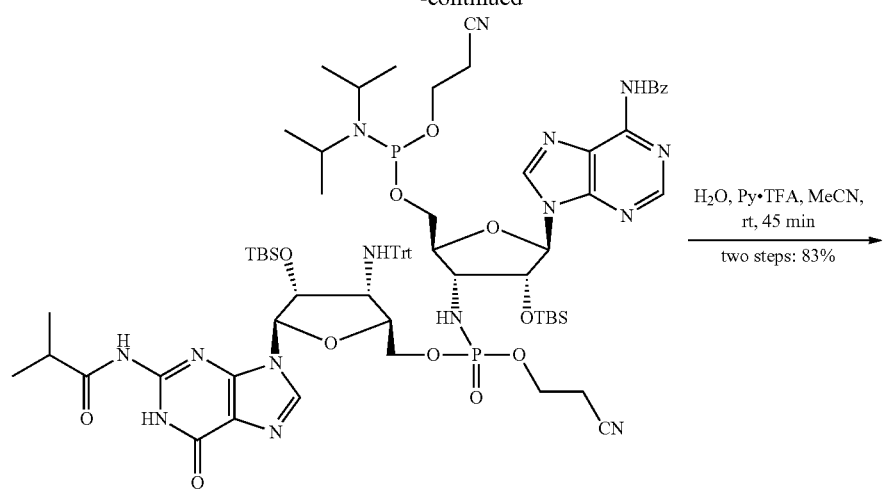
135
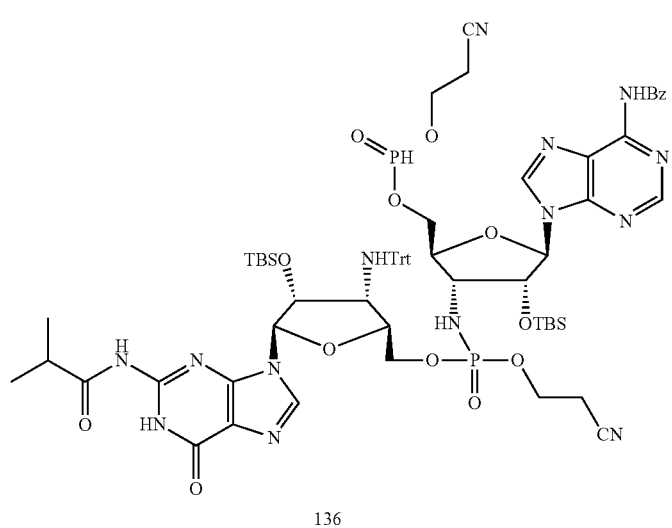
136
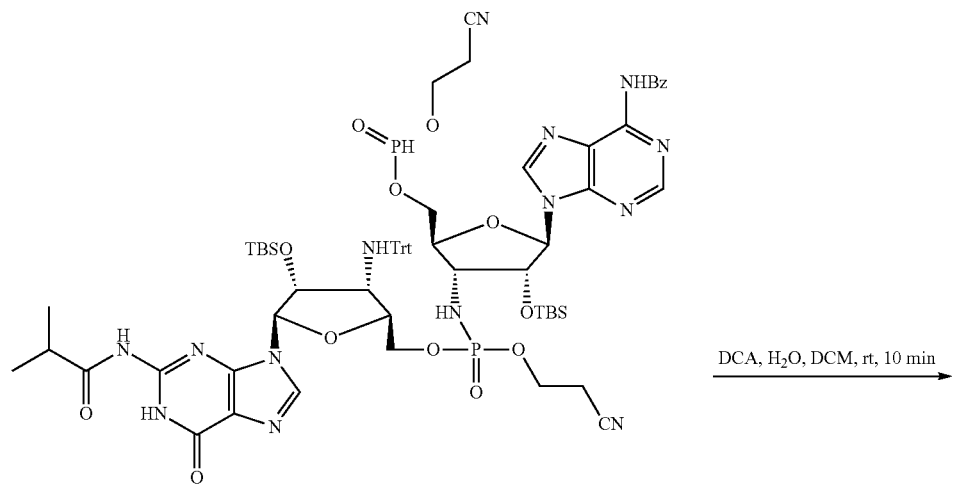
136

-continued
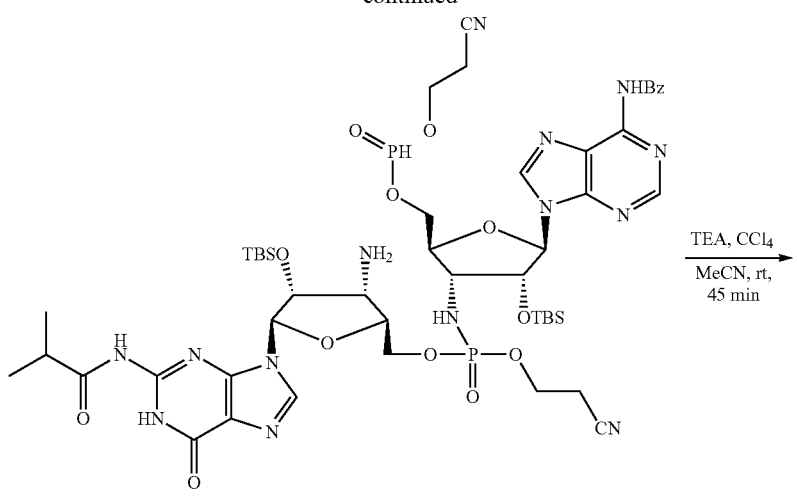
137
TEA, CCl₄
MeCN, rt,
45 min
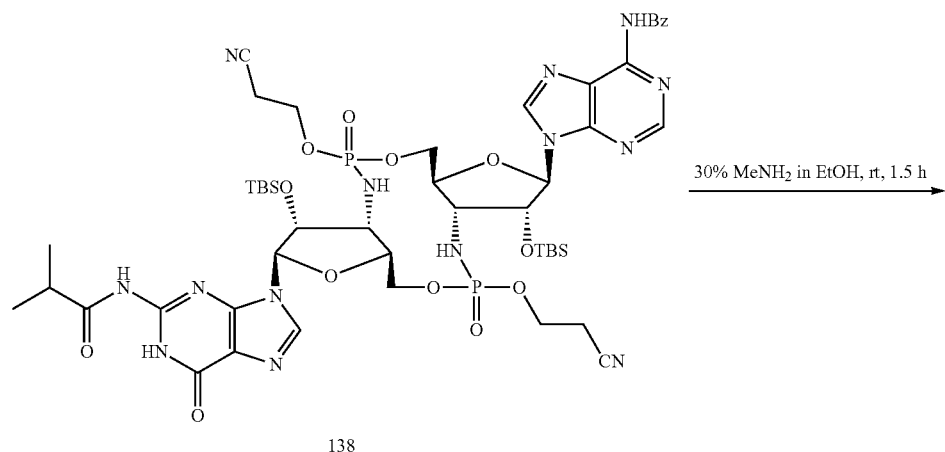
138
30% MeNH₂ in EtOH, rt, 1.5 h
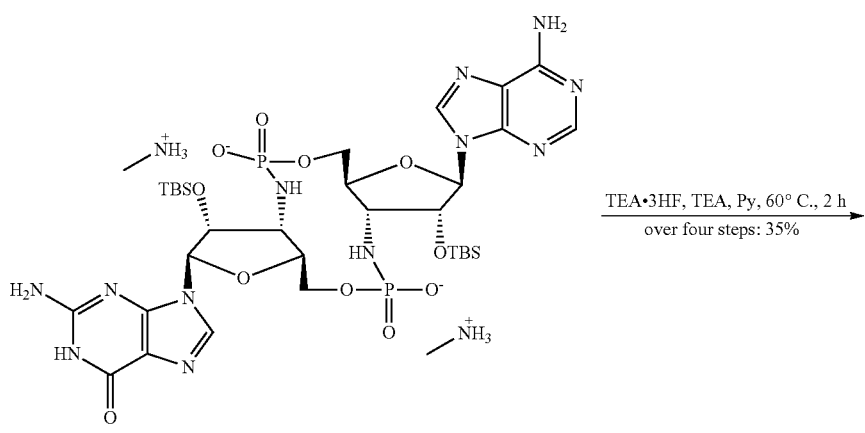
139
TEA·3HF, TEA, Py, 60° C., 2 h
over four steps: 35%

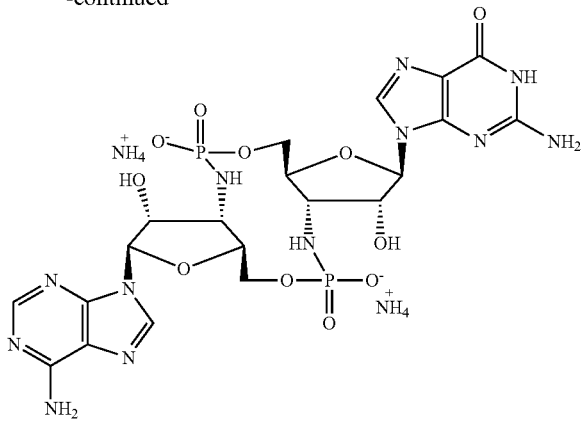

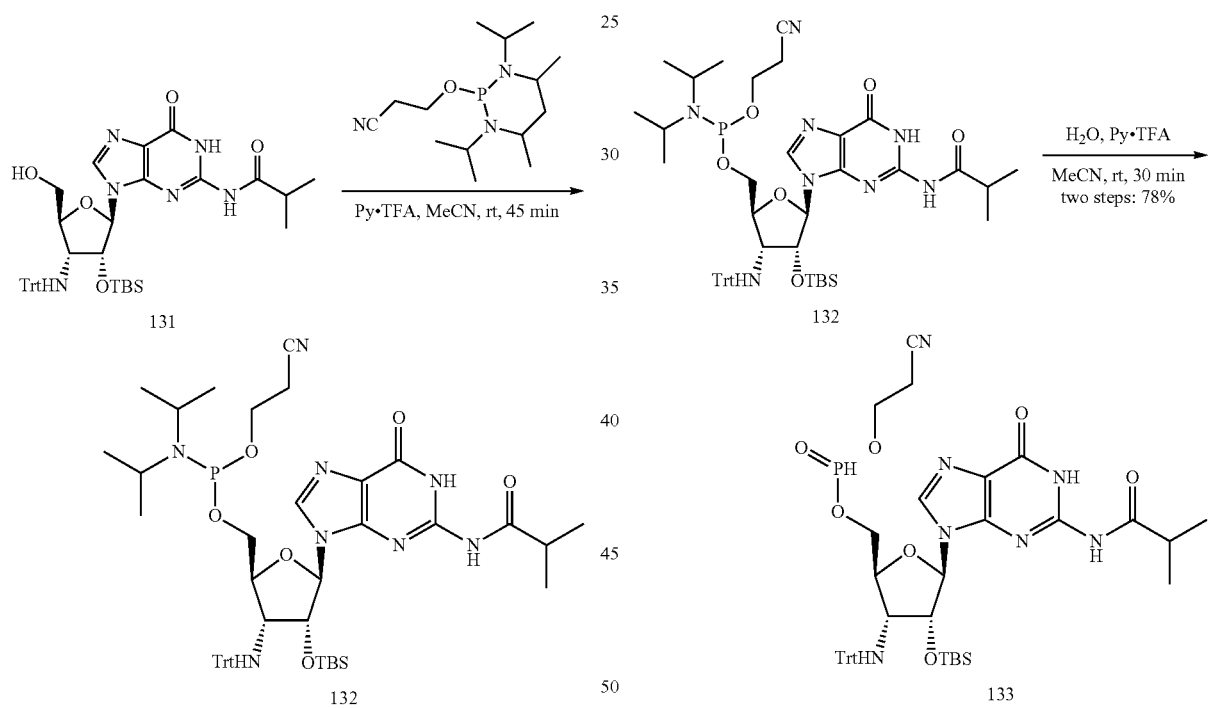

((2S,2R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl (2-cyanoethyl) diisopropylphosphoramidite (132)

To a solution of N-(9-((2R,3R,4R,5S)-3-((tert-butyldimethylsilyl)oxy)-5-(hydroxymethyl)-4-(tritylamino)tetrahydrofuran-2-yl)-6-oxo-6,9-dihydro-1H-purin-2-yl)isobutyramide (131, 700 mg, 0.98 mmol) in acetonitrile (5 mL) were added 3-(bis[bis(propan-2-yl)amino]phosphanyloxy)propanenitrile (595 mg, 1.97 mmol) and pyridinium trifluoroacetate (285 mg, 1.48 mmol) The resulting solution was stirred for 45 min at ambient temperature. The resulting solution of compound 132 was used in the next step without work up: LC/MS (ESI, m/z): [(M+1)]⁺=909.4.

((2S,3R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl (2-cyanoethyl) phosphonate (133)

To the above solution of compound 132 were added water (0.18 g, 10 mmol) and pyridinium trifluoroacetate (0.28 g, 1.48 mmol). The resulting solution was stirred for 30 min at ambient temperature. Upon completion, the resulting solution was applied onto a reversed phase C18 column, eluting with 70%~95% (25 min) acetonitrile in water to afford the title compound 133 as a colorless solid (0.64 g, over two steps 78%): ¹H NMR (400 MHz, DMSO-d₆) δ 12.12 (s, 1H), 11.40 (d, J=5.9 Hz, 1H), 8.16 (d, J=12.5 Hz, 1H), 7.57-7.45 (m, 6H), 7.37 (t, J=7.6 Hz, 6H), 7.32-7.22 (m, 3H), 6.18 (dd, J=6.5, 4.4 Hz, 1H), 4.60 (dt, J=19.0, 6.0 Hz, 1H), 4.20-4.07 (m, 1H), 4.02 (ddt, J=11.6, 8.5, 5.8 Hz, 2H), 3.79-3.64 (m, 2H), 2.95 (dt, J=4.8, 2.1 Hz, 1H), 2.89-2.73 (m, 3H), 1.15 (dd, J=6.9, 3.0 Hz, 6H), 0.77 (s, 9H), −0.11 (d, J=3.3 Hz, 3H), −0.40 (d, J=9.8 Hz, 3H); $^{31}$P NMR (162 MHz, DMSO-$d_6$) δ 9.92, 9.09; LC/MS (ESI, m/z): [(M+1)]$^+$=826.3.

Step 3

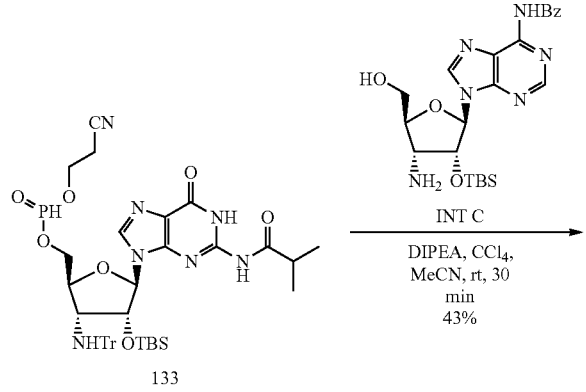

((2S,3R,4R,5R)-4-((tert-butyldimethylsilyl)oxy-5-(2-isobutyramido-6-oxo-1H-purin-9(6H)-yl)-3-(tritylamino)tetrahydrofuran-2-yl)methyl (2-cyanoethyl) ((2S,3R,4R,5R)-5-(6-benzamido-9H-purin-9-yl)-4-((tert-butyldimethylsilyl)oxy)-2-(hydroxymethyl) tetrahydrofuran-3-yl)phosphoramidate (134)

To a mixture of [(2S,3R,4R,5R)-4-[(tert-butyldimethylsilyl)oxy]-5-[2-(2-methylpropanamido)-6-oxo-6,9-dihydro-1H-purin-9-yl]-3-[(triphenylmethyl)amino]oxolan-2-yl] methyl 2-cyanoethyl phosphonate (133, 640 mg, 0.71 mmol) and N-(9-((2R,3R,4R,5S)-4-amino-3-((tert-butyldimethylsilyl)oxy)-5-(hydroxymethyl)tetrahydrofuran-2-yl)-9H-purin-6-yl)benzamide (INT-C, 375 mg, 0.71 mmol) in acetonitrile (8 mL) were added N,N-diisopropylethylamine (200 mg, 1.55 mmol) and carbon tetrachloride (477 mg, 3.10 mmol). The resulting mixture was stirred for 30 min at ambient temperature. Upon completion, the resulting mixture was applied onto a reversed phase C18 column, eluting with 70%~95% (25 min) acetonitrile in water to afford the title compound 134 as a colorless solid (440 mg, 43%): $^1$H NMR (400 MHz, DMSO-$d_6$) δ 12.07 (d, J=8.7 Hz, 1H), 11.45 (d, J=10.8 Hz, 1H), 11.17 (d, J=5.0 Hz, 1H), 8.77-8.68 (m, 1H), 8.17 (d, J=5.4 Hz, 1H), 8.04 (dd, J=13.6, 7.7 Hz, 2H), 7.68-7.59 (m, 1H), 7.59-7.40 (m, 9H), 7.30 (td, J=8.1, 3.1 Hz, 6H), 7.20 (q, J=7.5 Hz, 4H), 6.30-5.95 (m, 2H), 5.24-4.97 (m, 2H), 4.64-4.53 (m, 1H), 4.52-4.37 (m, 1H), 4.07 (d, J=16.0 Hz, 1H), 4.02-3.70 (m, 5H), 3.56 (q, J=16.1, 12.7 Hz, 2H), 3.23 (s, 1H), 2.85-2.65 (m, 4H), 1.07 (dt, J=9.8, 5.8 Hz, 6H), 0.91-0.59 (m, 18H), 0.02--0.25 (m, 9H), −0.50 (d, J=26.5 Hz, 3H); $^{31}$P NMR (162 MHz, DMSO-$d_6$) δ 8.72, 8.62; LC/MS (ESI, m/z): [(M+1)]$^+$=1308.5.

Step 4

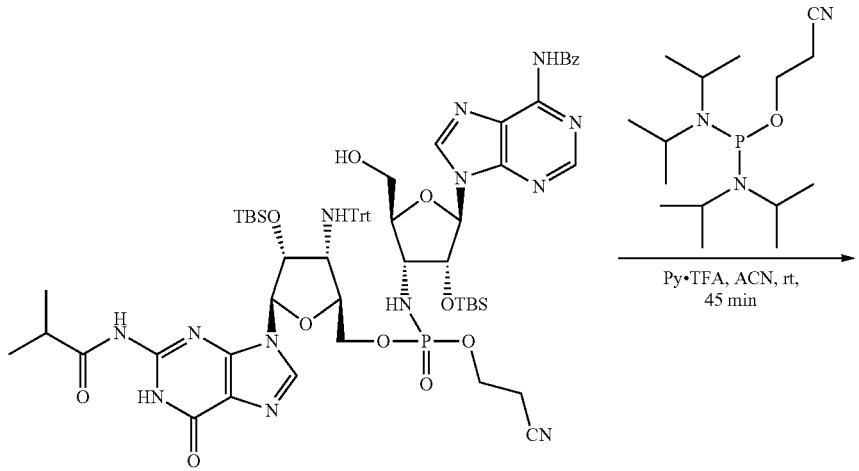

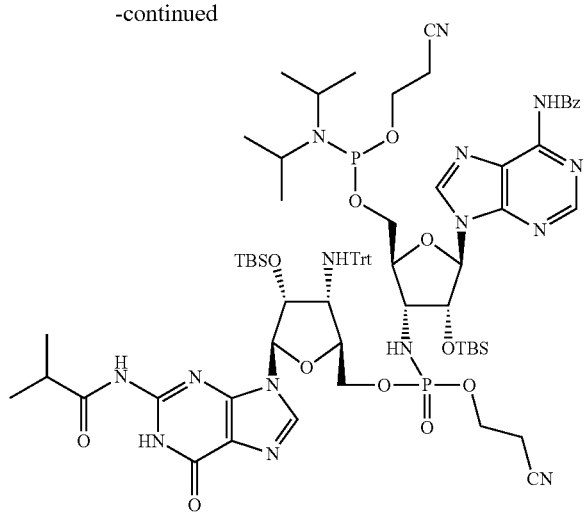

135

((2S,3R,4R,5R)-4-((tert-butyldimethylsilyl)oxy)-5-(2-isobutyramido-6-oxo-1-purin-9(61f-yl))-3-(tritylamino tetrahydrofuran-2-Ylmethyl (2-cyanoethyl) ((2S,3R,4R,5R)-5-(6-benzamido-9H-purin-9-yl-4-((tert-butyldimethylsilyl)oxy)-2-((((2-cyanoethoxy)(diisopropylamino)phosphino)oxy)methyl)tetrahydrofuran-3-yl)phosphoramidate (135)

To a solution of ((2S,3R,4R,5R)-4-(tert-butyldimethylsilyloxy)-5-(2-isobutyramido-6-oxo-1,6-dihydropurin-9-yl)-3-(tritylamino)-tetrahydrofuran-2-yl)methyl 2-cyanoethyl (2S,3R,4R,5R)-5-(6-benzamido-9H-purin-9-yl)-4-(tert-butyldimethylsilyloxy)-2-(hydroxymethyl)-tetrahydrofuran-3-yl)phosphoramidate (134, 440 mg, 0.34 mmol) in acetonitrile (2 mL) were added 3-(bis[bis(propan-2-yl)amino] phosphanyloxy)propanenitrile (203 mg, 0.67 mmol) and pyridinium trifluoroacetate (97 mg, 0.50 mmol). The resulting mixture was stirred for 45 min at ambient temperature and was used in the next step directly.

Step 5

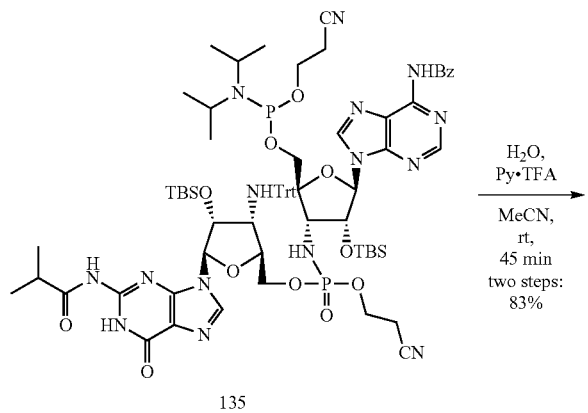

135

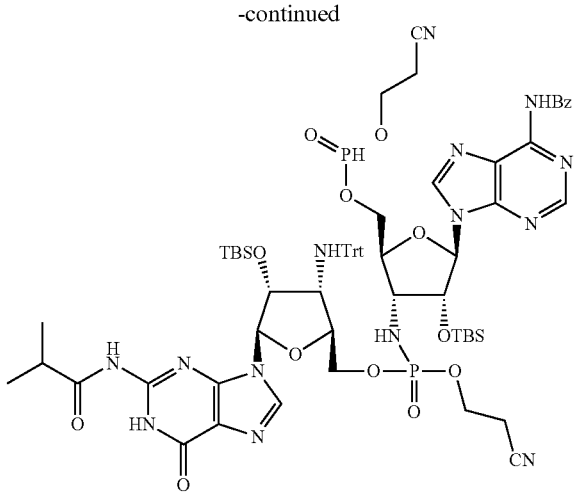

136

((2S,3R,4R,5R)-4-(tert-butyldimethylsilyloxy)-5-(2-isobutyramido-6-oxo-1,6-dihydropurin-9-yl)-3-(tritylamino)-tetrahydrofuran-2-yl)methyl 2-cyanoethyl (2S,3R 4R,5R)-5-(6-benzamido-9H-purin-9-yl)-4-(tert-butyldimethylsilyloxy)-2-(((2-cyanoethoxy)hydrophosphoryloxy)methyl-tetrahydrofuran-3-yl)phosphoramidate (136)

To the solution from the previous step were added water (0.06 g, 3.36 mmol) and pyridinium trifluoroacetate (0.10 g, 0.51 mmol). The resulting solution was stirred for 45 min at ambient temperature. Upon completion, the resulting solution was applied onto a reversed phase C18 column, eluting with 70%~95% (25 min) acetonitrile in water to afford the title compound 136 as a colorless solid (400 mg, 83%): $^1$H NMR (400 MHz, DMSO-$d_6$) δ 12.09 (d, J=9.1 Hz, 1H), 11.48-11.38 (m, 1), 11.20 (d, J=3.2 Hz, 1H), 8.79-8.51 (m, 2H), 8.24-8.14 (m, 1H), 8.08-7.99 (m, 2H), 7.84-7.12 (m, 20H), 6.28-5.88 (m, 2H), 5.09 (q, J=9.7, 8.5 Hz, 1H), 4.77-4.58 (m, 1H), 4.46-3.72 (m, 10H), 3.60 (t, J=11.7 Hz, 1H), 3.25 (d, J=15.0 Hz, 1H), 2.91-2.67 (m, 6H), 1.25-1.05

(m, 6H), 0.86-0.66 (m, 18H), 0.01--0.18 (in, 10H), -0.48 (d, J=24.4 Hz, 2H); $^{31}$P NMR (162 MHz, DMSO-$d_6$) δ 9.75, 9.71, 9.23, 9.14, 8.49, 8.34; LC/MS (ESI, m/z): [(M+1)]$^+$ =1425.5.

combined and dried over anhydrous sodium sulfate. After filtration, the filtrate was concentrated under reduced pressure to afford the title compound 137, which was used in the next step without further purification.

Step 6

Step 7

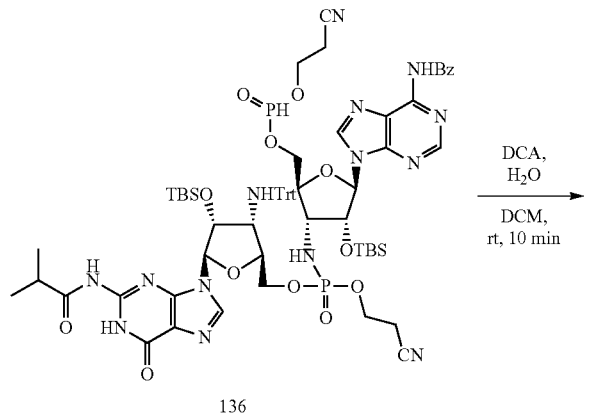

136

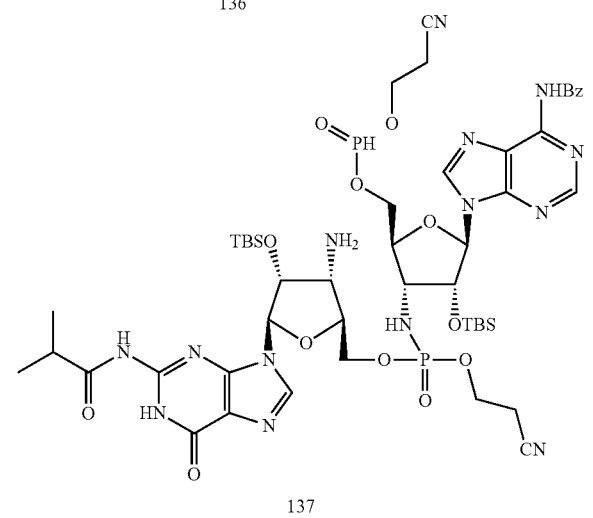

137

((2S,3R,4R,5R)-3-amino-4-(tert-butyldimethylsilyloxy)-5-(2-isobutyramido-6-oxo-1,6-dihydropurin-9-yl)-tetrahydrofuran-2-yl)methyl 2-cyanoethyl (2S, 3R,4R,5R)-5-(6-benzamido-9H-purin-9-yl)-4-tert-butyldimethylsilyloxy)-2-(((2-cyanoethoxy) hydrophosphoryloxy)methyl-tetrahydrofuran-3-yl) phosphoramidate (137)

To a solution of ((2S,3R,4R,5R)-4-(tert-butyldimethylsilyloxy)-5-(2-isobutyramido-6-oxo-1,6-dihydropurin-9-yl)-3-(tritylamino)-tetrahydrofuran-2-yl)methyl 2-cyanoethyl (2S,3R,4R,5R)-5-(6-benzamido-9H-purin-9-yl)-4-(tert-butyldimethylsilyloxy)-2-(((2-cyanoethoxy)hydrophosphoryloxy)methyl)-tetrahydrofuran-3-ylphosphoramidate (136, 400 mg, 0.28 mmol) in dichloromethane (8 mL) were added water (25 mg, 1.40 mmol) and dichloroacetic acid (640 mg, 2.81 mmol). The resulting solution was stirred for 10 min at ambient temperature. Upon completion, the reaction was quenched by the addition of saturated aqueous sodium bicarbonate (30 mL). The resulting mixture was extracted with dichloromethane (3×30 mL). The organic layers were

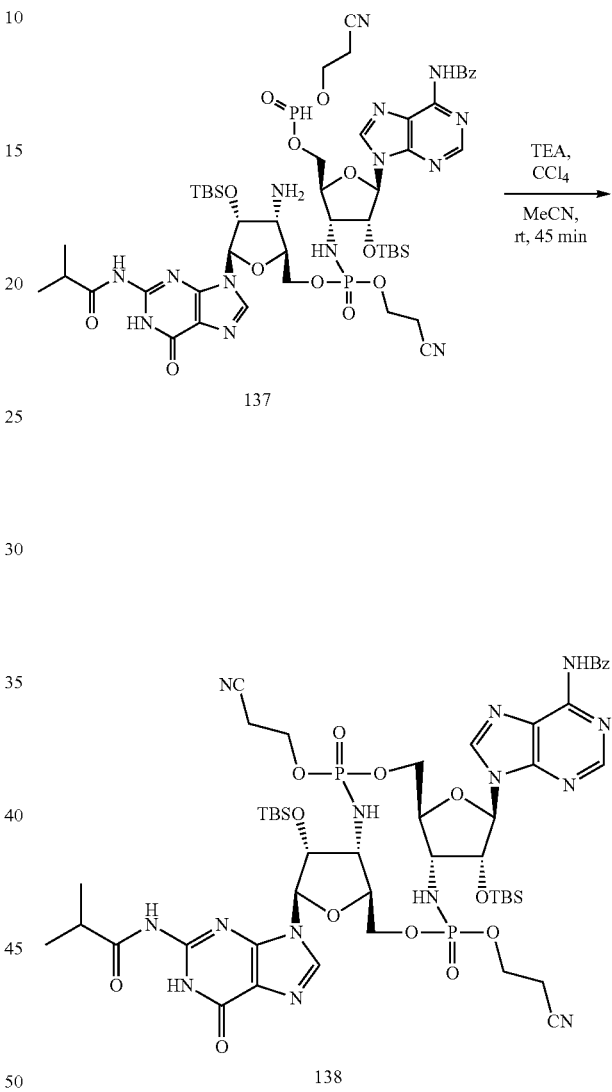

138

N-{9-[(1R,6S,8R,9R,10R,15S,17R,18R)-9,18-bis [(tert-butyldimethylsilyl)oxy]-3,12-bis(2-cyanoethoxy)-17-[2-(2-methylpropanamido)-6-oxo-6,9-dihydro-1H-purin-9-yl]-3,12-dioxo-4,7,13,16-tetraoxa-2,11-diaza-3λ$^s$,12λ$^s$-diphosphatricyclo[13.3.0.0$^{6,10}$] octadecan-8-yl]-9H-purin-6-yl}benzamide (138)

To a solution of the above crude compound (137, 332 mg) in acetonitrile (56 mL) were added triethylamine (1.1 mL) and carbon tetrachloride (1.1 mL). The resulting solution was stirred for 10 min at ambient temperature. Upon completion, the resulting solution was concentrated under reduced pressure to afford the crude title compound 138, which was used in the next step without further purification.

Step 8

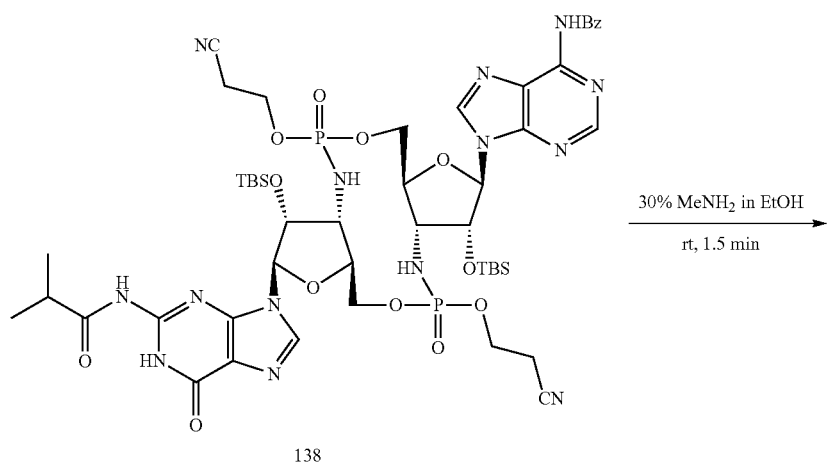

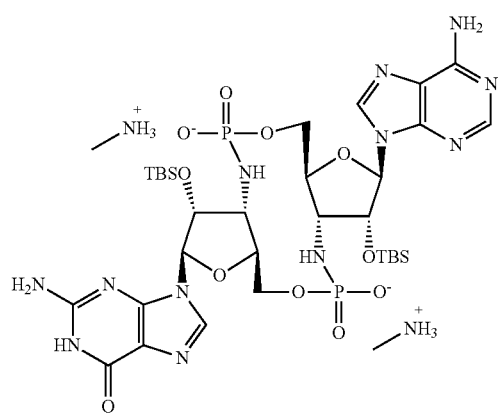

(1R,6S,8R,9R,10R,15S,17R,18R)-8-(2-amino-6-oxo-6,9-dihydro-1H-purin-9-yl)-17-(6-amino-9H-purin-9-yl)-9,18-bis[(tert-butyldimethylsilyl)oxy]-3,12-dioxo-4,7,13,16-tetraoxa-2,11-diaza-3λ$^5$,12λ$^5$-diphosphatricyclo[13.3.0.0$^{6,10}$]octadecane-3,12-bis(olate); bis(methanaminium) (139)

The above crude compound 138 was treated with a solution of methylamine in ethanol (14 mL, 30%, w/w) for 30 min at ambient temperature. Upon completion, the resulting solution was concentrated under reduced pressure to afford the title compound 139 as a colorless solid, which was used in the next step without further purification: LC/MS (ESI, m/z): [(M−2MeNH$_2$+1)]$^+$=901.4.

Step 9

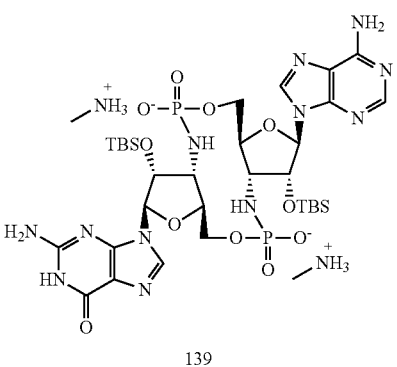

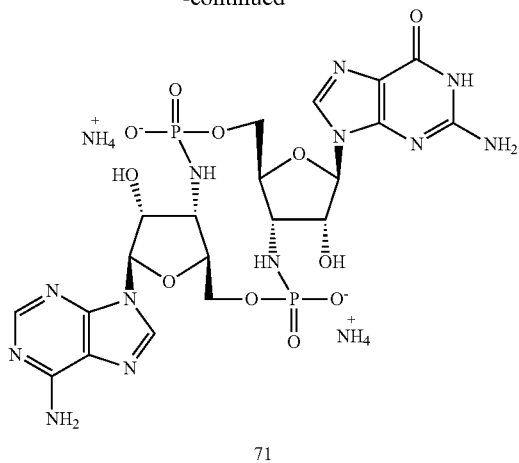

71

Diammonium (1S,6S,8R,9R,10S,15S,17R,18R)-8-(2-amino-6-oxo-6,9-dihydro-1H-purin-9-yl)-17-(6-amino-9H-purin-9-yl)-9,18-dihydroxy-3,12-dioxo-4,7,13,16-tetraoxa-2,11-diaza-3λ$^s$,12λ$^s$-diphosphatricyclo[13.3.0.0$^{6,10}$]octadeane-3,12-bis(olate) (71)

To a solution of the above crude compound 139 in pyridine (3 mL) were added triethylamine (1 mL) and triethylamine trihydrofluoride (2.26 g, 14.00 mmol). The resulting solution was stirred for 2 hours at 60° C. After cooling down to ambient temperature, acetone (56 mL) was added to precipitate the crude product which was purified by Prep-HPLC under the following conditions: Column: XBridge Prep OBD C18 Column, 19*250 mm, 5 um; Mobile phase A: Water (plus 50 mmol/L of NH$_4$HCO$_3$); Mobile phase B: ACN. Detector: 254/220 nm; Gradient: 0% B 7 min, 0%~20% B in 30 min; Flow rate: 20 mL/min. Retention time: 17.83 min. to afford the title compound 71 as a colorless solid (66.9 mg, 35%): $^1$H NMR (400 MHz, D$_2$O) δ 8.43 (s, 1H), 8.17 (d, J=48.1 Hz, 2H), 5.98 (s, 1H), 5.81 (s, 1H), 4.54 (s, 1H), 4.33 (s, 1H), 4.20 (t, J=14.8 Hz, 2H), 4.14-3.98 (m, 4H), 3.87 (s, 2H); $^{31}$P NMR (162 MHz, D$_2$O) δ 6.58; LC/MS (ESI, m/z): [(M−2NH$_3$−1)]$^+$=671.0.

Diammonium [(1S,6S,8R,9R,10S,15S,17R,18R)-8-(2-amino-6-oxo-6,9-dihydro-1H-purin-9-yl)-17-(6-amino-9H-purin-9-yl)-9,18-dihydroxy-3,12-dioxo-12-sulfanidyl-4,7,13,16-tetraoxa-2,11-diaza-3λ$^s$,12λ$^s$-diphosphatricyclo[13.3.0.0$^{6,10}$]octadecan-3-yl] sulfanide

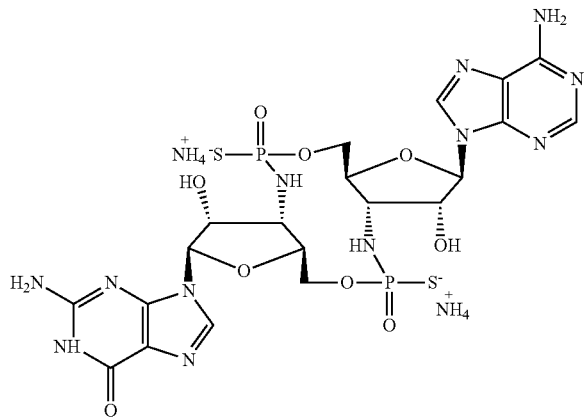

72

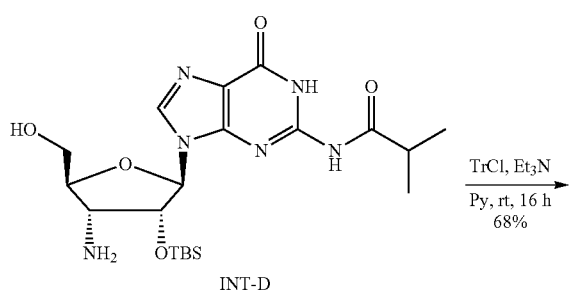

INT-D

-continued
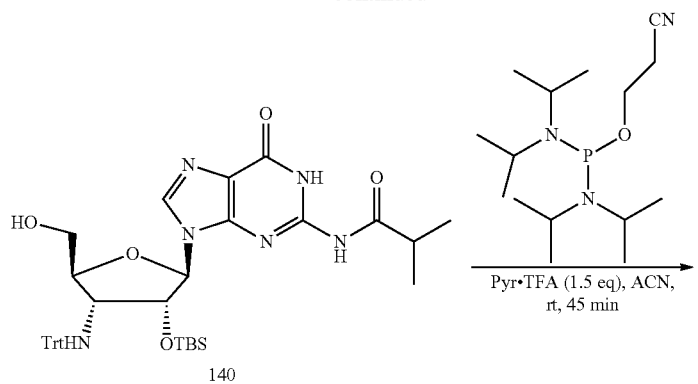
140
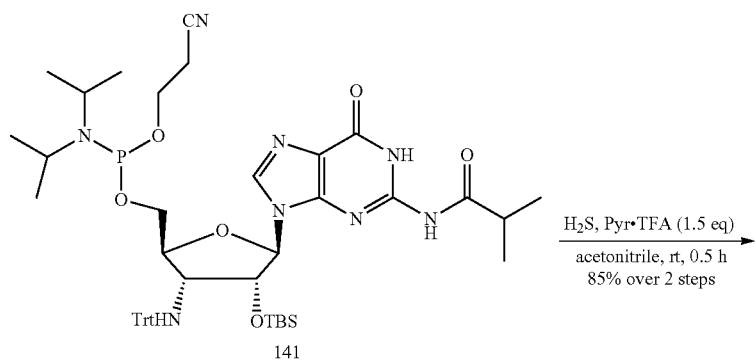
141
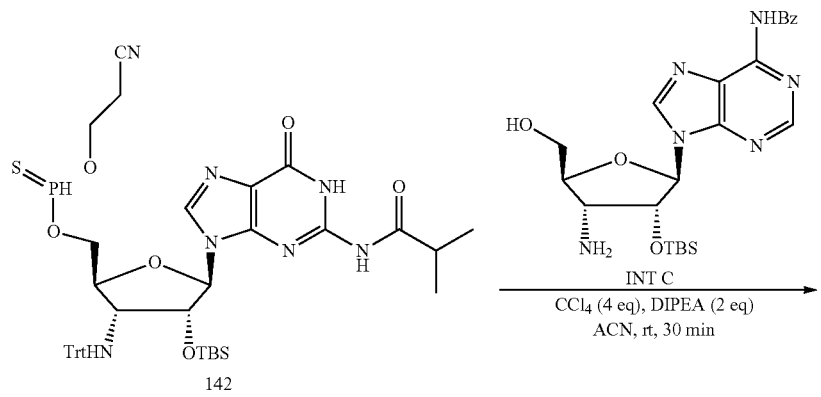
142
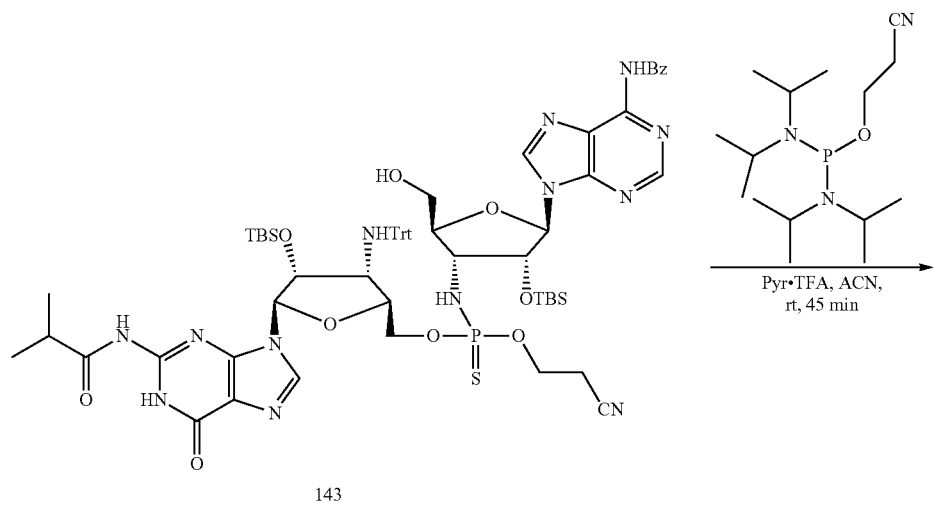
143

-continued
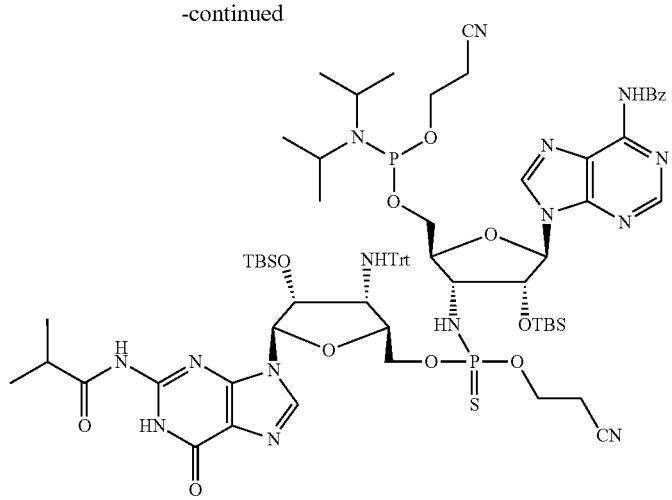
144
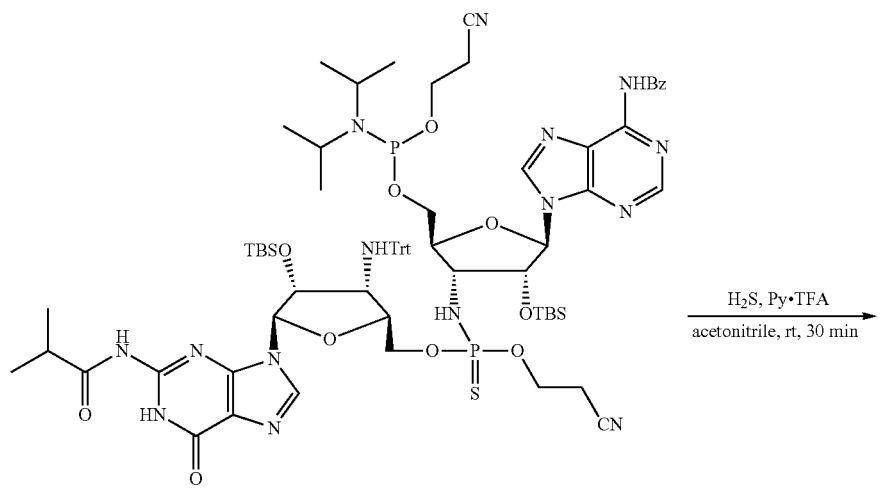
H₂S, Py·TFA
acetonitrile, rt, 30 min
144
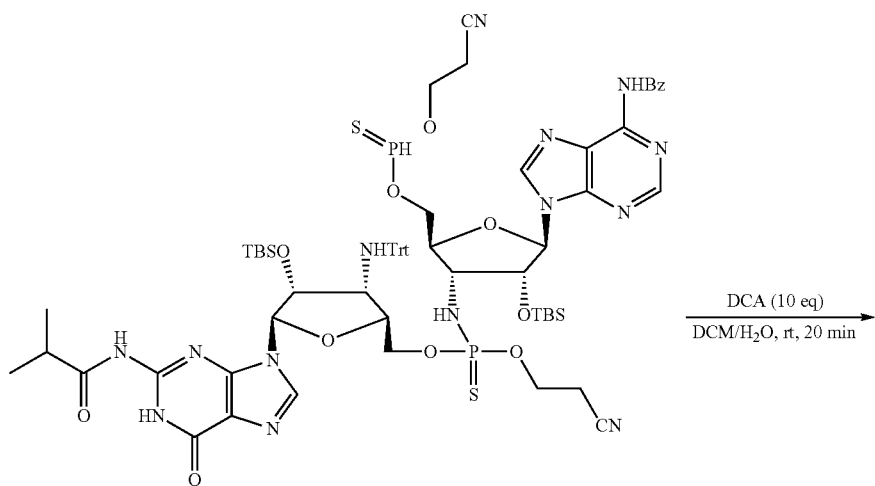
DCA (10 eq)
DCM/H₂O, rt, 20 min
145

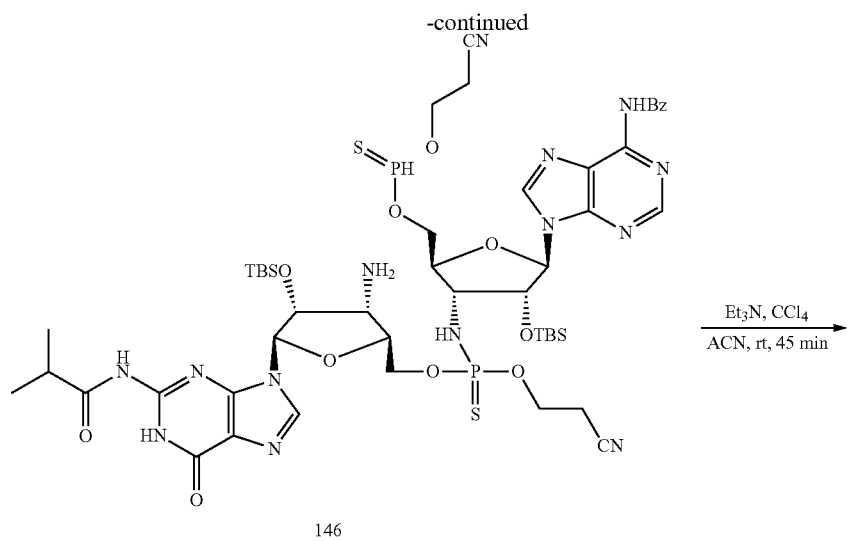
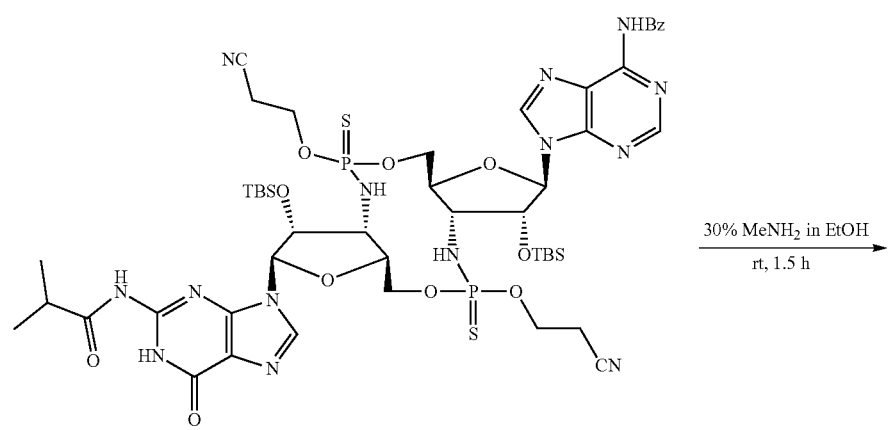
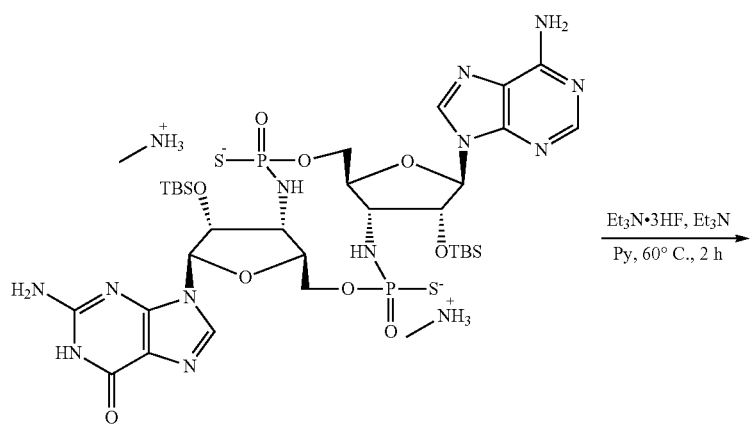

-continued

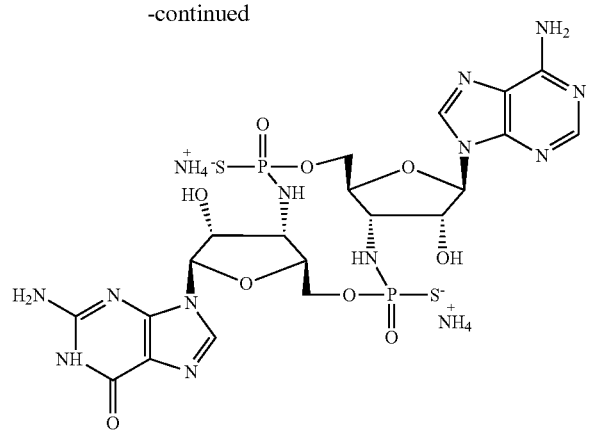

72

Step 1

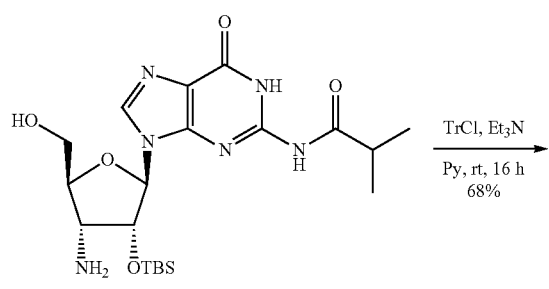

as a colorless solid (5.2 g, 68%): $^1$H NMR (400 MHz, DMSO-$d_6$) δ 12.09 (s, 1H), 11.56 (s, 1H), 8.27 (s, 1H), 7.54-7.42 (m, 5H), 7.44-7.17 (m, 10H), 6.17 (d, J=6.3 Hz, 1H), 5.02 (t, J=4.7 Hz, 1H), 4.43 (t, J=5.8 Hz, 1H), 3.62 (q, J=2.5 Hz, 1H), 3.36-3.24 (m, 1H), 3.23-3.13 (m, 1H), 2.98 (dt, J=4.5, 2.0 Hz, 1H), 2.84 (p, J=6.8 Hz, 1H), 1.23-1.09 (m, 6H), 0.75 (s, 9H), −0.15 (s, 3H), −0.39 (s, 3H). LC/MS (ESI, m/z): [(M+1)]$^+$=709.4.

Step 2

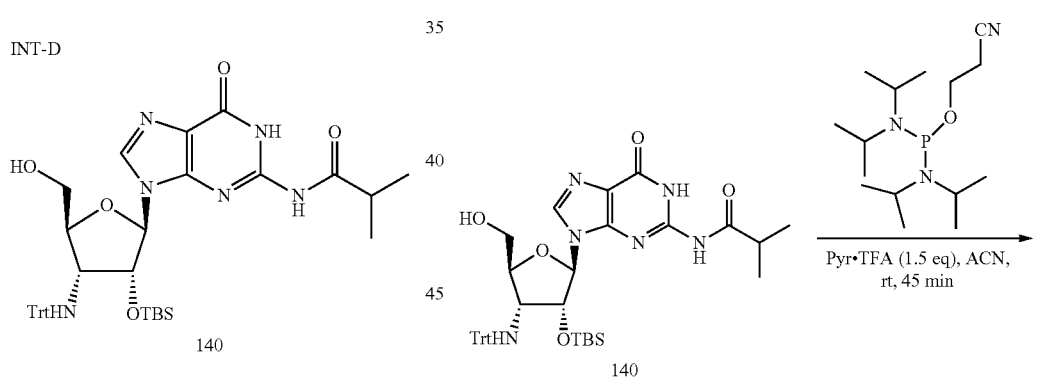

N-(9-((2R,3R,4R,5S)-3-((tert-butyldimethylsilyl)oxy)-5-(hydroxymethyl)-4-(tritylamino)tetrahydrofuran-2-yl)-6-oxo-6,9-dihydro-1H-purin-2-yl)isobutyramide (140)

To a solution of N-[9-[(2R,3R,4R,5S)-4-amino-3-[(tert-butyldimethylsilyl)oxy]-5-(hydroxymethyl)oxolan-2-yl]-6-oxo-6,9-dihydro-1H-purin-2-yl]-2-methylpropanamide (INT-D, 5.0 g, 10.72 mmol) in pyridine (96 mL) were added triethylamine (3 mL, 21.44 mmol) and (chlorodiphenylmethyl)benzene (4.6 g, 16.50 mmol). The resulting solution was stirred for 16 hours at ambient temperature, and then quenched by the addition of methanol (10 mL) and saturated aqueous sodium bicarbonate (2 mL). The resulting mixture was concentrated under reduced pressure and the residue was applied onto a silica gel column, eluting with 60% ethyl acetate in petroleum ether to afford the title compound 140

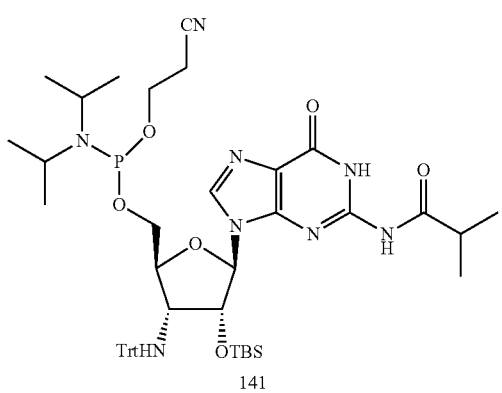

((2S,3R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl (2-cyanoethyl) diisopropylphosphoramidite (141)

To a solution of N-[9-[(2R,3R,4R,5S)-3-[(tert-butyldimethylsilyl)oxy]-5-(hydroxymethyl)-4-[(triphenylmethyl)amino]oxolan-2-yl]-6-oxo-6,9-dihydro-1H-purin-2-yl]-2-methylpropanamide (140, 1.50 g, 2.12 mmol) and 3-(bis[bis(propan-2-yl)amino]phosphanyloxy)propanenitrile (1.70 g, 5.64 mmol) in acetonitrile (6 mL) was added pyridinium trifluoroacetate (0.82 g, 4.25 mmol). The resulting solution was stirred for 45 min at ambient temperature and was used in the next step directly without any workup: MS (ESI, m/z): [(M+1)]=909.4.

Step 3

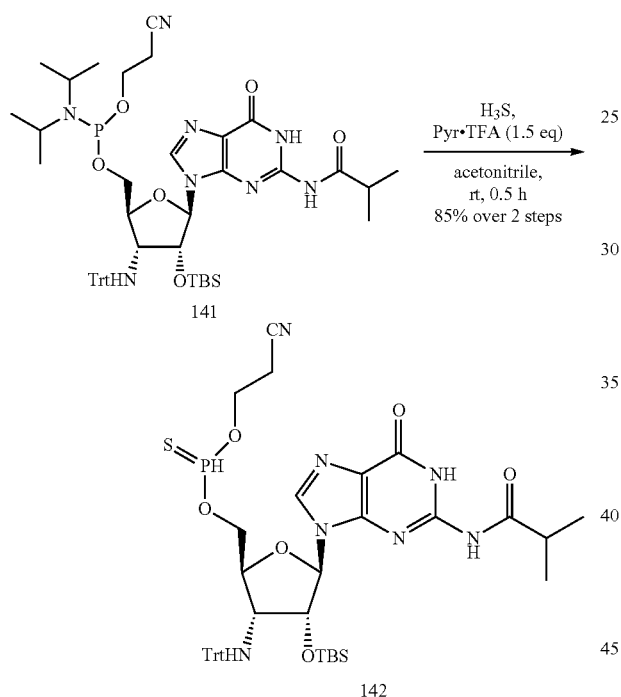

O-(((2S,3R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl)O-(2-cyanoethyl) phosphonothioate (142)

In the above reaction solution was bubbled hydrogen sulfide for 1 min followed by the addition of pyridinium trifluoroacetate (820 mg, 4.25 mmol). The resulting solution was stirred for 30 min at ambient temperature and applied onto a reversed phase C18 column, eluting with 70%~95% acetonitrile (25 min) in water to afford the title compound 142 as a colorless solid (1.0 g, two steps 85%): $^1$H NMR (400 MHz, DMSO-$d_6$) δ 12.12 (d, J=5.0 Hz, 1H), 11.46 (s, 1H), 8.13 (d, J=3.8 Hz, 1H), 7.53-7.42 (m, 6H), 7.41-7.19 (m, 10H), 6.26-6.13 (m, 1H), 4.60 (dt, J=21.3, 6.0 Hz, 1H), 4.13-3.94 (m, 3H), 3.82-3.75 (m, 0.4H), 3.59 (t, J=6.0 Hz, 0.4H), 3.30 (d, J=2.5 Hz, 1H), 2.85 (dddd, J=30.2, 18.9, 9.2, 4.7 Hz, 4H), 1.29-1.08 (m, 6H), 0.76 (d, J=3.2 Hz, 9H), −0.09--0.19 (m, 3H), −0.34--0.51 (m, 3H); $^{31}$P NMR (162 MHz, DMSO) δ 72.81, 72.40; LC/MS (ESI, m/z): [(M+1)]$^+$= 842.3.

Step 4

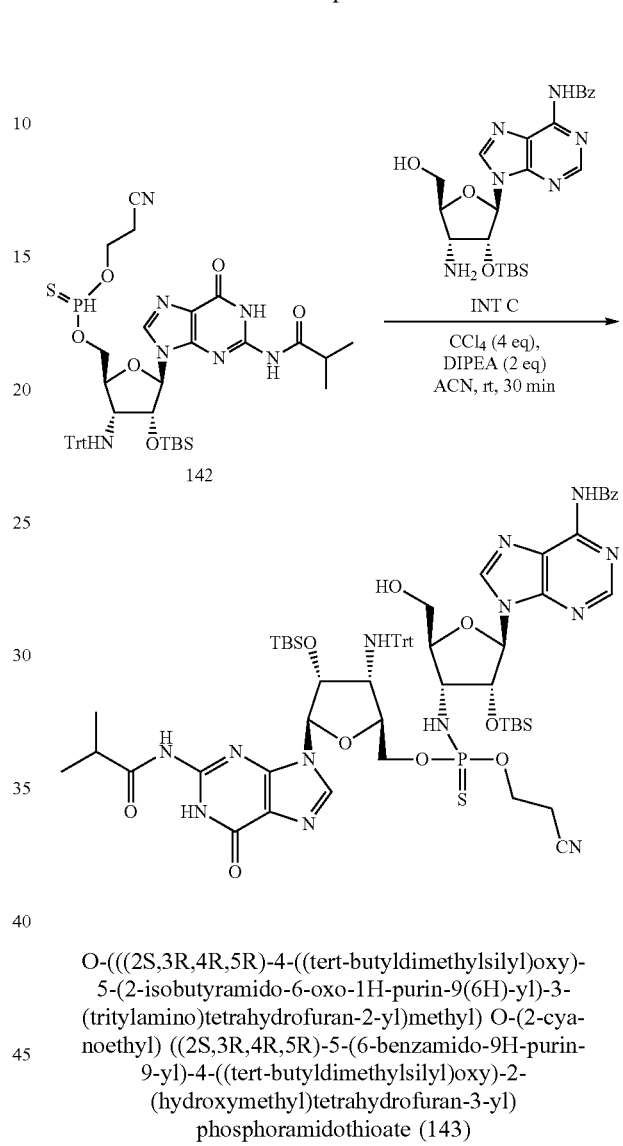

O-(((2S,3R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl) O-(2-cyanoethyl) ((2S,3R,4R,5R)-5-(6-benzamido-9H-purin-9-yl)-4-((tert-butyldimethylsilyl)oxy)-2-(hydroxymethyl)tetrahydrofuran-3-yl) phosphoramidothioate (143)

To a mixture of [(3S,5R)-4-[(tert-butyldimethylsilyl)oxy]-5-[2-(2-methylpropanamido)-6-oxo-6,9-dihydro-1H-purin-9-yl]-3-[(triphenylmethyl)amino]oxolan-2-yl]methyl 2-cyanoethyl sulfanylidenephosphonite (142, 0.60 g, 0.71 mmol) and N-(9-[(2R,4S)-4-amino-3-[(tert-butyldimethylsilyl)oxy]-5-(hydroxymethyl)oxolan-2-yl]-9H-purin-6-yl)benzamide (INT-C, 0.35 g, 0.71 mmol) in acetonitrile (8 mL) were added N,N-diisopropylethylamine (0.24 mL, 1.42 mmol) and carbon tetrachloride (0.27 mL, 2.84 mmol). The resulting solution was stirred for 30 min at ambient temperature and applied onto a reversed phase C18 column, eluted with 70%~99% acetonitrile (25 min) in water to afford two isomers of the title compound as a colorless foam: isomer A (0.33 g, 35%, eluted out with 95% acetonitrile): $^1$H NMR (300 MHz, DMSO-$d_6$) δ 12.06 (s, 1H), 11.40 (s, 1H), 11.16 (s, 1H), 8.68 (d, J=6.6 Hz, 2H), 8.14 (s, 1H), 8.01 (d, J=7.6 Hz, 2H), 7.69-7.15 (m, 20H), 6.18 (d, J=6.4 Hz, 1H), 6.06 (d, J=3.6 Hz, 1H), 5.49 (t, J=10.4 Hz, 1H), 5.06 (t, J=5.4

Hz, 1H), 4.71 (d, J=6.6 Hz, 1H), 4.55 (t, J=4.6 Hz, 1H), 3.74 (dt, J=28.9, 9.0 Hz, 2H), 3.58 (d, J=11.7 Hz, 1H), 3.41 (d, J=14.1 Hz, 1H), 3.29 (s, 4H), 2.74 (p, J=7.4, 6.6 Hz, 4H), 1.28-1.16 (m, 1H), 1.08 (dd, J=6.8, 2.4 Hz, 6H), 0.69 (d, J=11.4 Hz, 18H), −0.17 (d, J=3.0 Hz, 9H), −0.44 (s, 3H); $^{31}$P NMR (121 MHz, DMSO-$d_6$) δ 73.08; LC/MS (ESI, m/z): [(M+1)]$^+$=1324.5. And isomer B (0.35 g, 37%, eluted out with 99% acetonitrile): $^1$H NMR (300 MHz, DMSO-$d_6$) δ 12.09 (s, 1H), 11.40 (s, 1H), 11.13 (s, 1H), 8.69 (d, J=1.4 Hz, 2H), 8.10-7.96 (m, 3H), 7.67-7.38 (m, 9H), 7.22 (dt, J=33.9, 7.3 Hz, 10H), 6.10 (t, J=5.3 Hz, 2H), 5.61 (t, J=10.5 Hz, 1H), 5.17 (t, J=5.2 Hz, 1H), 4.56 (t, J=4.6 Hz, 1H), 4.24 (t, J=5.5 Hz, 1H), 3.96 (ddt, J=24.1, 20.9, 6.8 Hz, 6H), 3.71 (dd, J=14.9, 8.7 Hz, 2H), 3.49 (dt, J=12.4, 4.4 Hz, 1H), 3.17 (d, J=2.8 Hz, 1H), 2.78 (h, J=7.9, 7.3 Hz, 4H), 1.09 (dd, J=6.9, 1.5 Hz, 6H), 0.73 (d, J=16.6 Hz, 18H), −0.09 (d, J=15.8 Hz, 6H), −0.18 (s, 3H), −0.41 (s, 3H); $^{31}$P NMR (121 MHz, DMSO-$d_6$) δ 72.91; LC/MS (ESI, m/z): [(M+1)]$^+$=1324.5. Isomer A and isomer B were independently carried through the remainder of the synthesis (Step 5 through Step 10).

Step 5

O-(((2S,3R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl O-(2-cyanoethyl) ((2S,3R,4R,5R)-5-(6-benzamido-9H-purin-9-yl)-4-((tert-butyldimethylsilyl)oxy)-2-((((2-cyanoethoxy)(diisopropylamino)phosphino)oxy)methyltetrahydrofuran-3-yl)phosphoramidothioate (144)

To a solution of O-(((2S,3R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl) O-(2-cyanoethyl) ((2S,3R,4R,5R)-5-(6-benzamido-9H-purin-9-yl)-4-((tert-butyldimethylsilyl)oxy)-2-(hydroxymethyl)tetrahydrofuran-3-yl)phosphoramidothioate (143, 330 mg, 0.25 mmol, isomer A) in acetonitrile (2 mL) were added 3-(bis[bis(propan-2-yl)amino]phosphanyloxy)propanenitrile (150 mg, 0.50 mmol) and pyridinium trifluoroacetate (66 mg, 0.34 mmol). The resulting solution was stirred for 45 min at ambient temperature and was used in the next step directly without workup: LC/MS (ESI, m/z): [(M+1)]$^+$=1523.9.

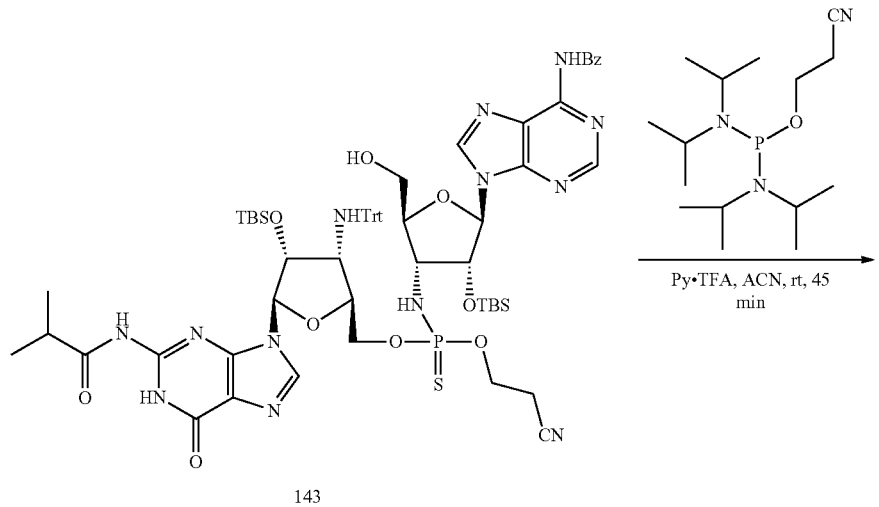

143

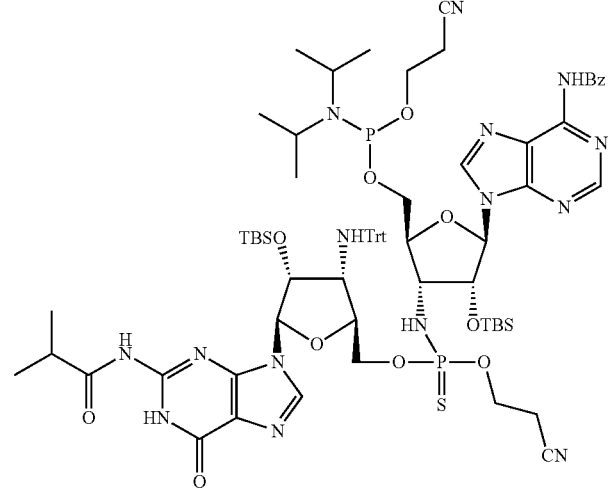

144

Step 6

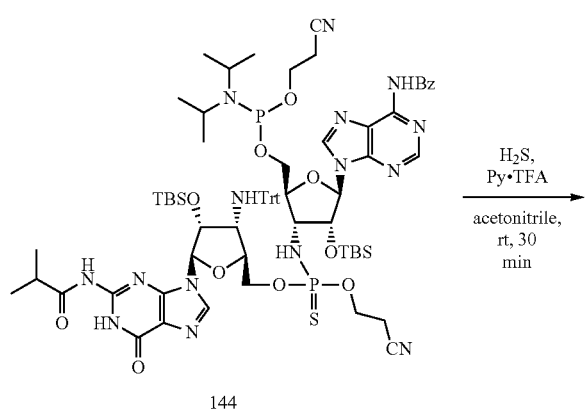

O-[(2S,3R,4R,5R)-5-(6-benzamido-9H-purin-9-yl)-4-[(tert-butyldimethylsilyl)oxy]-3-[({[(2S,3R,4R,5R)-4-[(tert-butyldimethylsilyl)oxy]-5-[2-(2-methyl-propanamido)-6-oxo-6,9-dihydro-1H-purin-9-yl]-3-[(triphenylmethyl)amino]oxolan-2-yl]methoxy}(2-cyanoethoxy)sulfanylidene-λ⁵-phosphanyl)amino]oxolan-2-yl]methyl O-2-cyanoethyl phosphonothioate (145)

The above solution was sparged with hydrogen sulfide for 2 min followed by the addition of pyridinium trifluoroacetate (66 mg, 0.34 mmol). The resulting solution was stirred for 30 min at ambient temperature and concentrated under reduced pressure. The residue was applied onto a reversed phase C18 column, eluting with 70%~99% acetonitrile (25 min) in water to afford the title compound 145 as a colorless solid (150 mg, 40%, contains 5% 1H-phosphate byproduct): $^1$H NMR (400 MHz, DMSO-$d_6$) δ 12.10 (s, 1H), 11.46-11.41 (m, 1H), 11.20 (d, J=8.7 Hz, 1H), 8.72 (d, J=9.2 Hz, 1H), 8.68-8.57 (m, 1H), 8.21-8.14 (m, 1H), 8.05 (d, J=7.7 Hz, 2H), 7.74-7.61 (m, 2H), 7.54 (dd, J=26.6, 7.7 Hz, 9H), 7.37 (t, J=7.6 Hz, 7H), 7.26 (t, J=7.2 Hz, 3H), 6.25-6.18 (m, 1H), 6.09 (dd, J=6.0, 3.4 Hz, 1H), 5.53 (d, J=10.8 Hz, 0.7H), 4.74 (s, 1.4H), 4.04 (q, J=7.1 Hz, 2H), 3.73 (s, 2H), 3.28 (s, 2H), 2.93-2.73 (m, 6H), 2.54 (s, 2H), 1.27-1.09 (m, 6H), 0.78-0.61 (m, 18H), −0.07--0.19 (m, 9H), −0.36--0.42 (m, 3H); $^{31}$P NMR (162 MHz, DMSO-$d_6$) δ 73.27, 73.15, 73.09, 72.82; LC/MS (ESI, m/z): [(M+1)]⁺=1458.5. The same procedure was used on isomer B to generate the other isomer as a colorless solid (190 mg, 45%): $^1$H NMR (400 MHz, DMSO-$d_6$) δ 12.17-12.11 (m, 1H), 11.44 (d, J=3.5 Hz, 1H), 11.19 (s, 1H), 8.80-8.63 (m, 2H), 8.67-8.57 (m, 1H), 8.14-8.02 (m, 3H), 7.70-7.61 (m, 1H), 7.56 (dd, J=8.4, 7.0 Hz, 2H), 7.51-7.44 (m, 7H), 7.32 (td, J=7.9, 1.9 Hz, 7H), 7.26-7.17 (m, 3H), 6.14 (ddd, J=5.7, 3.8, 2.1 Hz, 2H), 5.65 (s, 1H), 4.74 (q, J=7.4, 5.7 Hz, 1H), 4.18 (d, J=9.7 Hz, 1H), 4.09-3.90 (m, 6H), 3.85-3.76 (m, 1H), 3.21 (s, 1H), 2.94-2.75 (m, 6H), 2.53 (m, 2H), 1.27-1.10 (m, 6H), 0.91-0.69 (m, 18H), 0.00--0.09 (m, 3H), −0.03--0.11 (m, 3H), −0.14 (s, 3H), −0.36 (d, J=4.2 Hz, 3H); $^{31}$P NMR (162 MHz, DMSO-$d_6$) δ 73.31, 72.94, 72.70, is 72.64; LC/MS (ESI, m/z): [(M+1)]⁺=1458.5.

Step 7

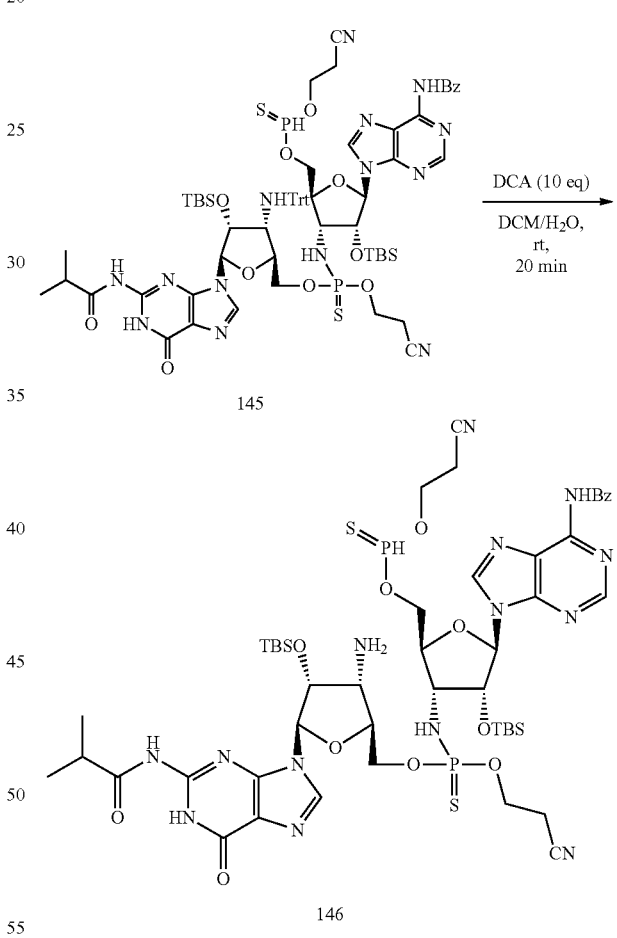

O-(2S,3R,4R,5R)-3-[({[(2S,3R 4R,5R)-3-amino-4-[(tert-butyldimethylsilyl)oxy]-5-[2-(2-methylpropanamido)-6-oxo-6,9-dihydro-1H-purin-9-yl]oxolan-2-yl]methoxy}(2-cyanoethoxy)sulfanylidene-λ⁵-phosphanyl)aminol-5-(6-benzamido-9H-purin-9-yl)-4-[(tert-butyldimethylsilyl)oxy]oxolan-2-yl]methyl O-2-cyanoethyl Phosphonothioate (146)

To a solution of O-[(2S,3R,4R,5R)-5-(6-benzamido-9H-purin-9-yl)-4-[(tert-butyldimethylsilyl)oxy]-3-[({[(2S,3R, 4R,5R)-4-[(tert-butyldimethylsilyl)oxy]-5-[2-(2-methylpropanamido)-6-oxo-6,9-dihydro-1H-purin-9-yl]-3-[(triphenylmethyl)amino]oxolan-2-yl]methoxy}(2-cyanoethoxy)sulfanylidene-λ$^s$-phosphanyl)amino]oxolan-2-yl]methyl O-2-cyanoethyl phosphonothioate (145, 150 mg, 0.11 mmol) in dichloromethane (3 mL) and water (10 mg, 0.5 mmol) was added dichloroacetic acid (150 mg, 0.62 mmol). The resulting solution was stirred for 20 min at ambient temperature and then quenched by the addition of saturated aqueous solution of sodium bicarbonate (1.1 mL). The resulting mixture was extracted with dichloromethane (3×10 mL) and the organic layers were combined and dried over anhydrous sodium sulfate. After filtration, the filtrate was concentrated under reduced pressure and the residue was used in the next step without further purification (146, 0.2 g, brown solid): LC/MS (ESI, m/z): [(M+1)]$^+$=1215.4.

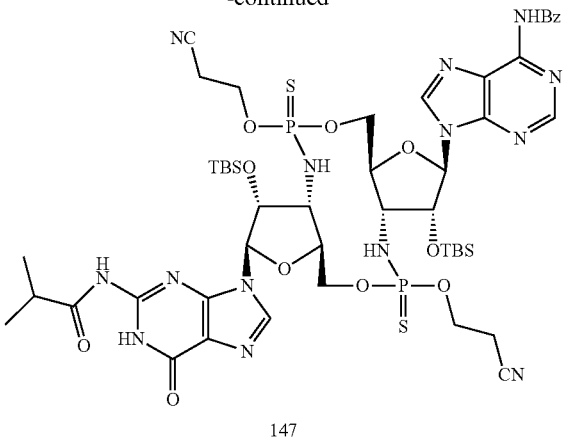

147

N-{9-[(1R,6S,8R,9R,10R,15S,17R,18R)-9,18-bis[(tert-butyldimethylsilyl)oxy]-3,12-bis(2-cyanoethoxy)-17-[2-(2-methylpropanamido)-6-oxo-6,9-dihydro-1H-purin-9-yl]-3,12-disulfanylidene-4,7,13,16-tetraoxa-2,11-diaza-3λ$^s$,12λ$^s$-diphosphatricyclo[13.3.0.0$^{6,10}$]octadecan-8-yl]-9H-purin-6-yl}benzamide (147)

To a solution of the above O-[(2S,3R,4R,5R)-3-[({[(2S,3R,4R,5R)-3-amino-4-[(tert-butyldimethylsilyl)oxy]-5-[2-(2-methylpropanamido)-6-oxo-6,9-dihydro-1H-purin-9-yl]oxolan-2-yl]methoxy}(2-cyanoethoxy)sulfanylidene-λ$^s$-phosphanyl)amino]-5-(6-benzamido-9H-purin-9-yl)-4-[(tert-butyldimethylsilyl)oxy]oxolan-2-yl]methyl O-2-cyanoethyl phosphonothioate (146, 200 mg) in acetonitrile (30 mL) were added triethylamine (0.7 mL) and carbon tetrachloride (0.7 mL). The resulting solution was stirred for 45 min at ambient temperature and concentrated under reduced pressure to afford the crude title compound 147 as a brown solid (200 mg) which was used in the next step directly without further purification: LC/MS (ESI, m/z): [(M+1)]$^+$=1213.4.

Step 8

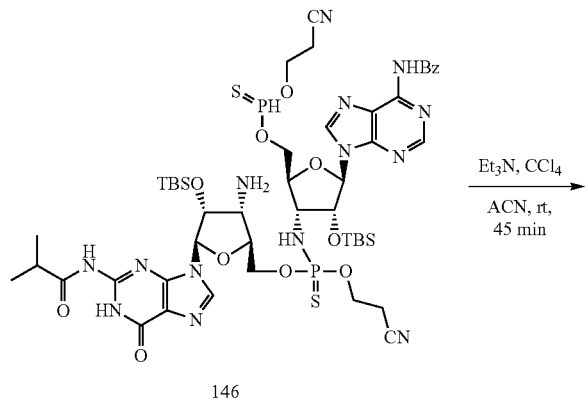

146

Et$_3$N, CCl$_4$

ACN, rt,
45 min

Step 9

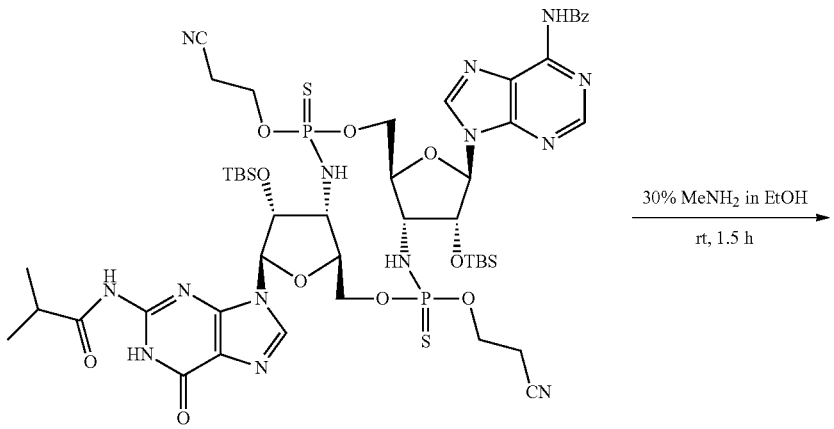

147

30% MeNH$_2$ in EtOH rt, 1.5 h

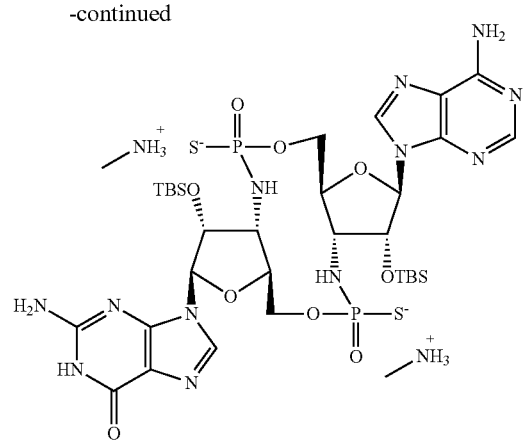

148

[(1R,6S,8R,9R,10R,15S,17R,18R)-8-(2-amino-6-oxo-6,9-dihydro-1H-purin-9-yl)-7-(6-amino-9H-purin-9-yl)-9,18-bis[(tert-butyldimethylsilyl)oxy]-3,12-dioxo-12-sulfanidyl-4,7,13,16-tetraoxa-2,11-diaza-3$\lambda^s$,12$\lambda^s$-diphosphatricyclo[13.3.0.0$^{6,10}$]octadecan-3-yl]sulfanide; bis(methanaminium) (148)

The above crude product (147, 200 mg) was treated with methylamine (6 mL, 30% ethanol solution, w/w) for 1.5 hour at ambient temperature. Upon completion, the resulting solution was concentrated under reduced pressure and the residue was used in the next step directly without further purification (200 mg): LC/MS (ESI, m/z): [(M−2MeNH$_2$+1)]$^+$=933.6.

Step 10

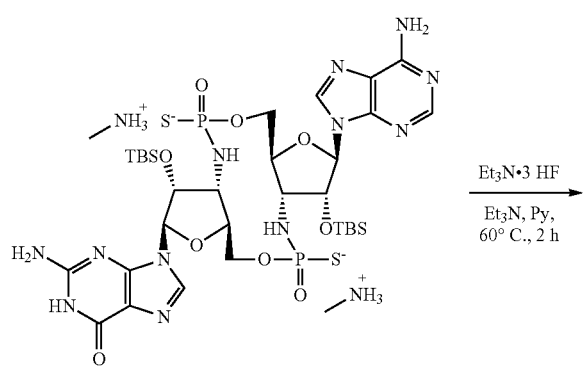

148

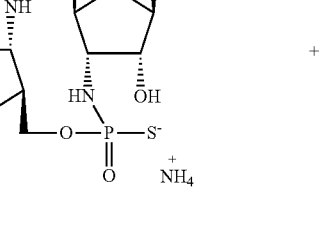

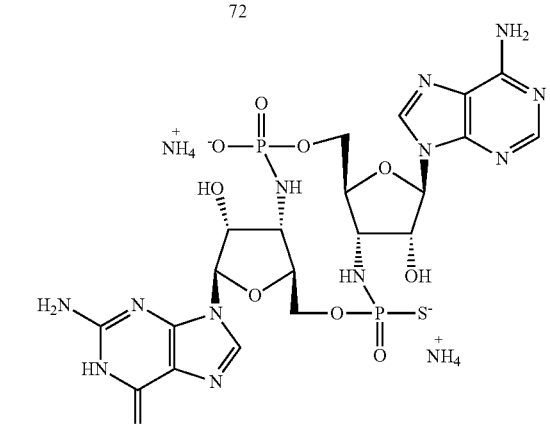

72

72-0A1

Diammonium [(1S,6S,8R,19R,10S,15S,17R,18R)-8-(2-amino-6-oxo-6,9-dihydro-1H-purin-9-yl)-17-(6-amino-9H-purin-9-yl)-9,18-dihydroxy-3,12-dioxo-12-sulfanidyl-4,7,13,16-tetraoxa-2,11-diaza-3$\lambda^s$,12$\lambda^s$-diphosphatricyclo[13.3.0.0$^{6,10}$]octadecan-3-yl]sulfanide (72)

To a solution of the above crude compound 148 in pyridine (1.5 mL) was added triethylamine trihydrofluoride (1.2 mL) and triethylamine (0.4 mL). The resulting solution was stirred for 2 hours at 60° C. After cooling down to ambient temperature, acetone (32 mL) was added to precipitate the crude product which was purified using the following conditions: column: Atlantis Prep T$_3$ OBD column, 19×250 mm, 10 um; Mobile Phase A: water (plus 20 mmol/L of NH$_4$HCO$_3$), Mobile Phase B: ACN; Flow rate: 20 mL/min; Gradient: 1% B to 14% B in 26 min; Detector: 254/220 nm; to afford the mixed phosphate/thiophosphate 72-0A1 as a colorless solid (single isomer) (6.6 mg, retention time is 17.12 min): $^1$H NMR (400 MHz, D$_2$O+DMSO-d$_6$) δ 8.48 (br s, 0.6H), 8.24 (br s, 1.4H), 8.12 (br s, 0.6H), 8.03 (br s, 0.4H), 5.95 (s, 1H), 5.76 (s, 1H), 4.39-3.70 (m, 10H); $^{31}$P NMR (162 MHz, D$_2$O+DMSO-d$_6$) δ 56.24, 3.46, 2.01; LC/MS (ESI, m/z): [(M−2NH$_3$−1)]$^−$=687.0. One isomer herein referred to 72-0A2 as a colorless solid (6.3 mg, 9% over 4 steps, retention time is 17.83 min): $^1$H NMR (400 MHz, D$_2$O) δ 8.63 (s, 1H), 8.08 (s, 1H), 8.03 (s, 11), 6.07 (s, 1H), 5.88 (s, 1H), 4.36 (d, J=4.4 Hz, 1H), 4.29 (d, J=12.1 Hz, 1H), 4.21 (d, J=11.9 Hz, 1H), 4.09 (d, J=11.2 Hz, 3H), 3.94 (ddt, J=26.6, 10.5, 5.1 Hz, 3H); $^{31}$P NMR (162 MHz, D$_2$O) δ 57.85, 54.61; LC/MS (ESI, m/z): [(M−2NH$_3$−1)]$^−$=703.0. And the other isomer herein referred to as 72-0A3 as a colorless solid (6.8 mg, 10% over 4 steps, retention time is 25.18 min): $^1$H NMR (400 MHz, D$_2$O+DMSO-d$_6$) δ 8.39 (s, 1H), 8.21 (s, 1H), 8.07 (s, 1H), 5.95 (s, 1H), 5.72 (s, 1H), 4.19-3.99 (m, 6H), 3.91-3.78 (m, 4H); $^{31}$P NMR (162 MHz, D$_2$O+DMSO-d$_6$) δ 54.36; LC/MS (ESI, m/z): [(M−2NH$_3$−1)]$^+$=703.0. FIG. 2A depicts a representation of compound 72-0A3.

Steps 5-10 above were performed on the isomer B obtained in Step 4 to generate the other two isomers, which were purified by Prep-HPLC with the following conditions: Column: Atlantis Prep T$_3$ OBD column, 19×250 mm, 10 urn; Mobile Phase A: water (plus 20 mmol/L of NH$_4$HCO$_3$), Mobile Phase B: ACN; Flow rate: 20 mL/min; Gradient: 0% B to 13% B in 21 min; Detector: 254/220 nm; One isomer herein referred to as 72-0B1 as a colorless solid (5.6 mg, 6% over 4 steps, retention time is 14.52 min): $^1$H NMR (400 MHz, 1D$_2$O) δ 8.65 (s, 1H), 8.20 (s, 1H), 8.09 (s, 1H), 6.09 (s, 11H), 5.88 (s, 1H), 4.68 (m, 2H), 4.17-4.02 (m, 6H), 3.99-3.88 (m, 1H), 3.87-3.68 (m, 1H); $^{31}$P NMR (162 MHz, D$_2$O) δ 57.91; LC/MS (ESI, m/z): [(M−2NH$_3$−1)]$^−$=703.0. And the other isomer herein referred to as 72-0B2 as a colorless solid (9.2 mg, 10% over 4 steps, retention time is 18.50 min): $^1$H NMR (400 MHz, D$_2$O) δ 8.41 (s, 1H), 8.21 (s, 1H), 8.09 (s, 1H), 6.07 (s, 1H), 5.85 (s, 1H), 4.72 (d, J=4.8 Hz, 1H), 4.37-4.29 (m, 2H), 4.20-3.81 (m, 7H); $^{31}$P NMR (162 MHz, D$_2$O) δ 57.94, 57.46, 54.46, 50.95; LC/MS (ESI, m/z): [(M−2NH$_3$−1)]$^−$=703.0. The isomers 72-0A2, 72-0A3, 72-0B1, and 72-0B2 are believed to vary in stereochemical configuration at the phosphorus atoms.

Diammonium (1S,6S,8R,9R,10S,15S,17R,18R)-8,17-bis(6-amino-9H-purin-9-yl)-9,18-dihydroxy-3,12-dioxo-4,7,13,16-tetraoxa-2,11-diaza-3λ$^s$,12λ$^s$-diphosphatricyclo[13.3.0.0$^{6,10}$]octadecane-3,12-bis(olate)

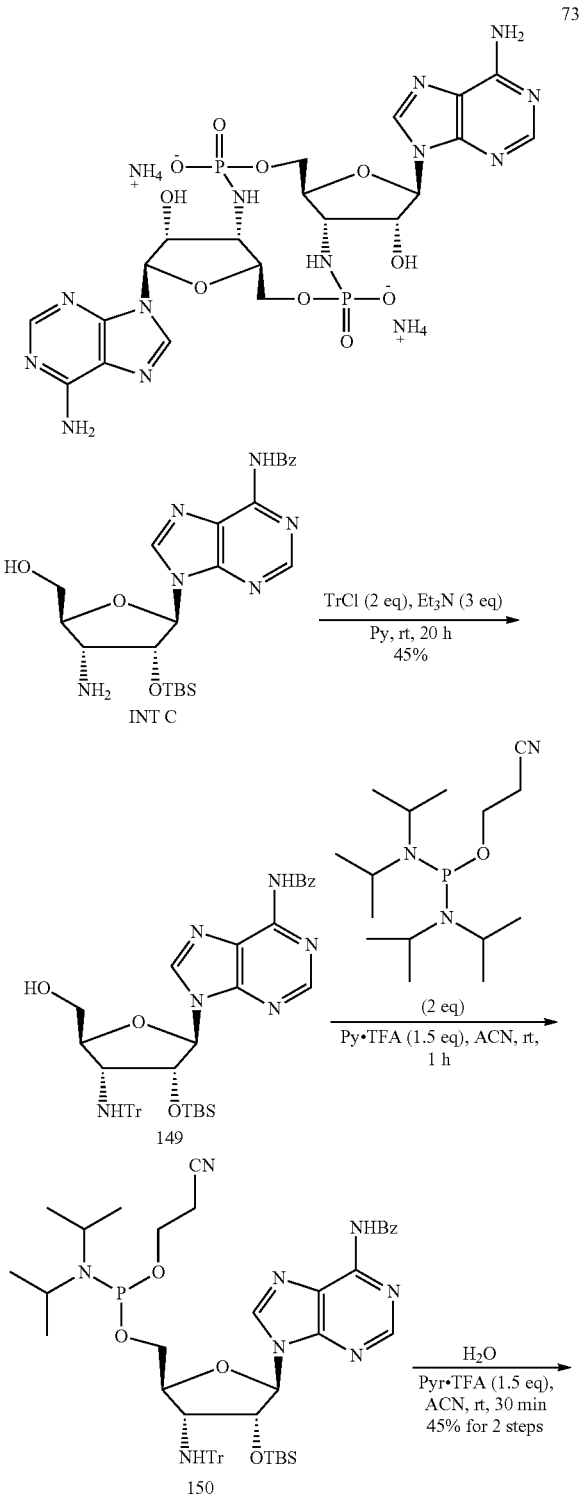

163
-continued
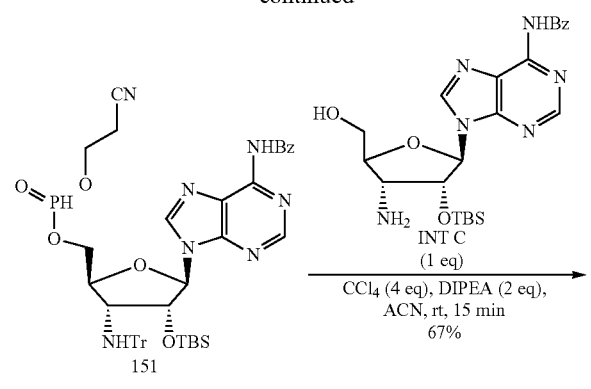
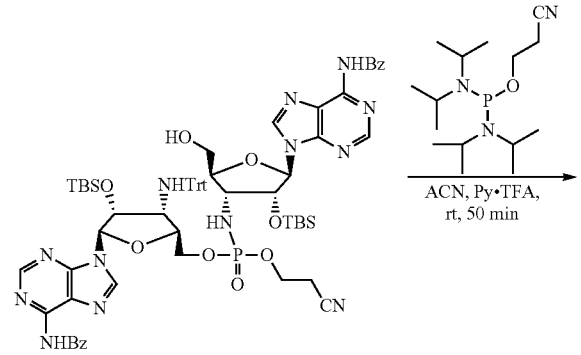
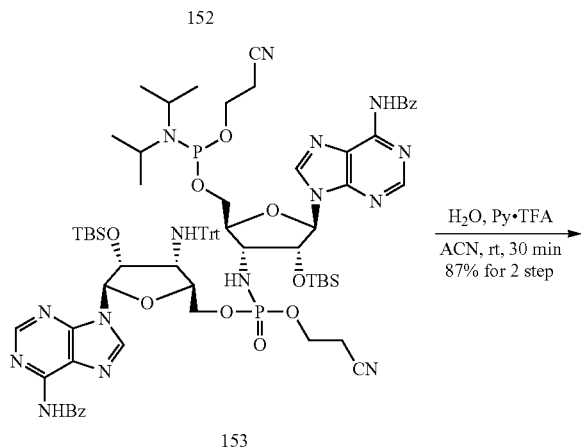
164
-continued
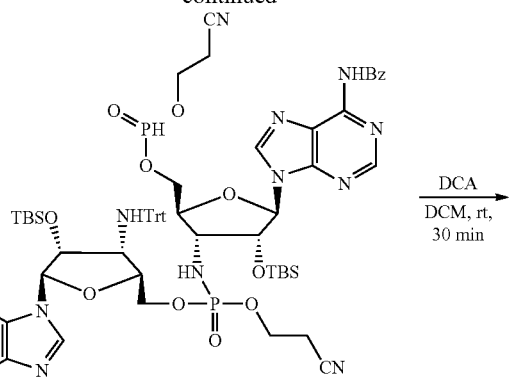
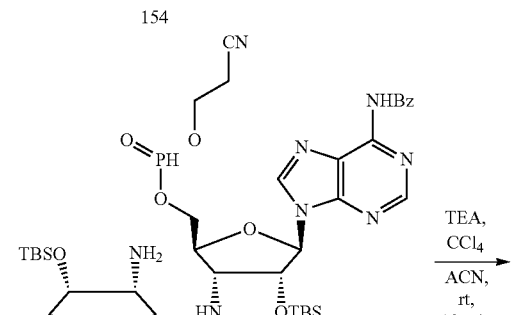

-continued

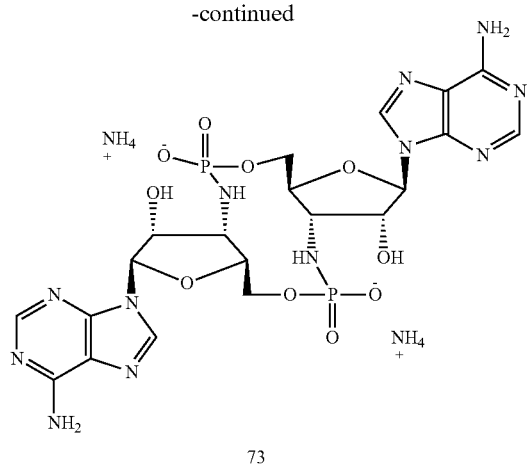

73

Step 1

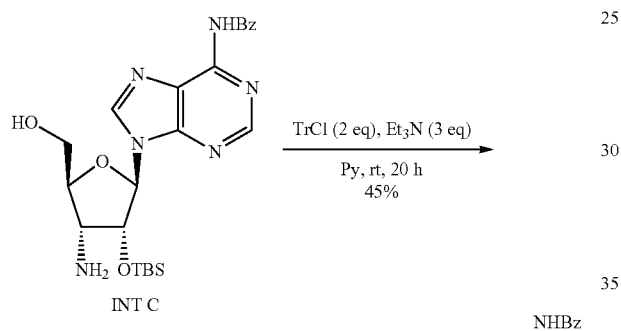

N-(9-((2R,3R,4R,5S)-3-((tert-butyldimethylsilyl)oxy)-5-(hydroxymethyl)-4-(tritylamino)tetrahydrofuran-2-yl-9H-purin-6-yl)benzamide (149)

To a solution of N-[9-[(2R,5S)-4-amino-3-[(tert-butyldimethylsilyl)oxy]-5-(hydroxymethyl)oxolan-2-yl]-9H-purin-6-yl]benzamide (INT-C, 1.20 g, 2.47 mmol) in pyridine (24 mL) were added triethylamine (0.69 mL, 4.95 mmol) and triphenylmethyl chloride (1.04 g, 3.70 mmol). The resulting mixture was stirred for 20 hours at ambient temperature. Upon completion, the reaction was quenched with methanol (10 mL). The resulting solution was concentrated under reduced pressure and the residue was purified by flash column chromatography, eluting with 1% methanol in dichloromethane to afford the title compound 149 as a colorless solid (0.80 g, 45%): $^1$H NMR (300 MHz, DMSO-$d_6$) δ 11.26-11.06 (m, 1H), 8.69 (s, 1H), 8.68 (s, 1H), 8.02 (dd, J=7.1, 1.9 Hz, 2H), 7.60-7.12 (m, 18H), 6.13 (d, J=3.3 Hz, 1H), 5.20-5.00 (m, 1H), 3.90-3.73 (m, 1H), 3.64 (d, J=18.5 Hz, 2H), 3.34 (t, J=3.9 Hz, 1H), 3.16-3.03 (m, 1H), 2.96 (d, J=6.3 Hz, 1H), 0.76 (s, 9H), −0.11 (s, 3H), −0.22 (s, 3H); LC/MS (ESI, m/z): [(M+1)]$^+$=727.3.

Step 2

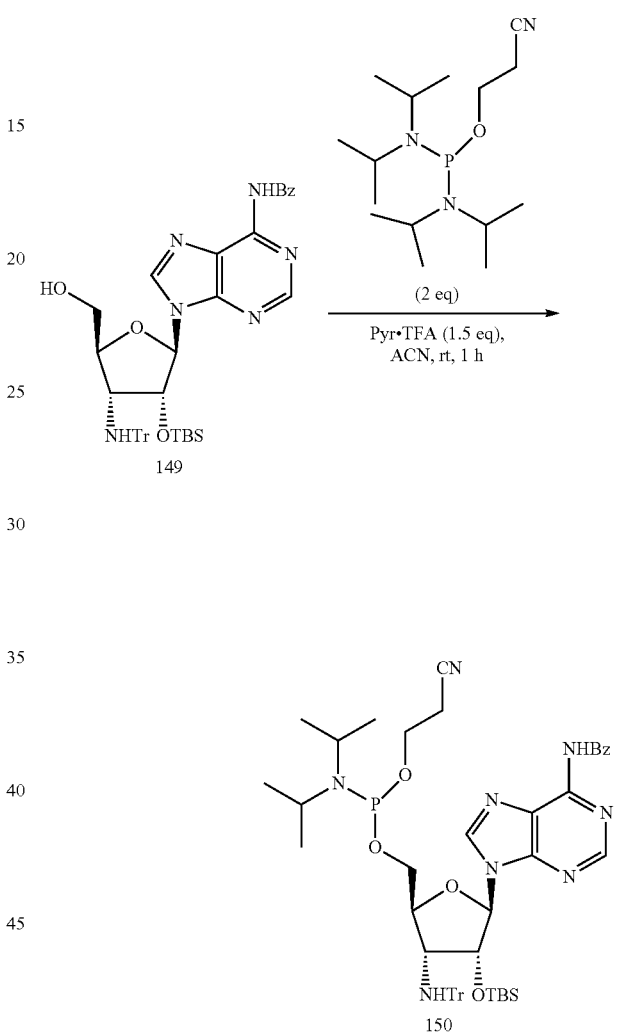

((2S,3R,4R,5R)-5-(6-benzamido-9H-purin-9-yl)-4-((tert-butyldimethylsilyl)oxy)-3-(tritylamino)tetrahydrofuran-2-yl)methyl (2-cyanoethyl) diisopropylphosphoramidite 150)

To a solution of N-(9-((2R,3R,4R,5S)-3-((tert-butyldimethylsilyl)oxy)-5-(hydroxymethyl)-4-(tritylamino)tetrahydrofuran-2-yl)-9H-purin-6-yl)benzamide (149, 0.80 g, 1.10 mmol) in acetonitrile (20 mL) were added 3-({bis[bis(propan-2-yl)amino]phosphanyl}oxy)propanenitrile (0.32 g, 1.06 mmol) and pyridinium trifluoroacetate (0.66 g, 1.65 mmol). The resulting solution was stirred for 1 hour at ambient temperature. The resulting solution was used in the next step without work up: LC/MS (ESI, m/z): [(M+1)]$^+$=927.4.

Step 3

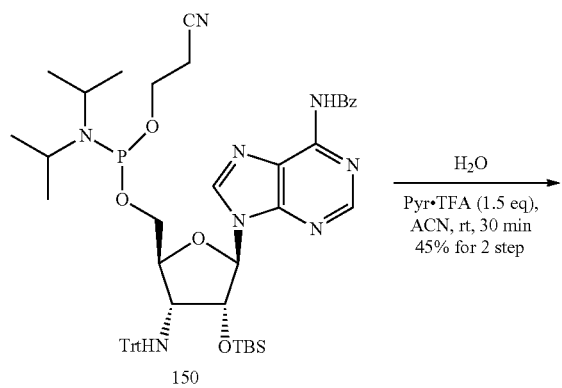

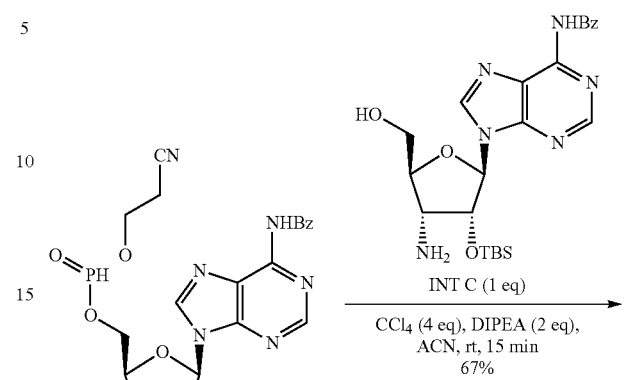

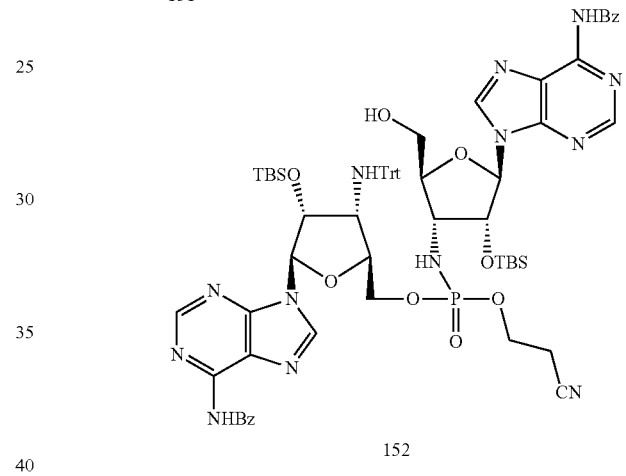

((2S,3R,4R,5R)-5-(6-benzamido-9H-purin-9-yl)-4-((tert-butyldimethylsilyl)oxy)-3-(tritylamino)tetrahydrofuran-2-yl)methyl (2-cyanoethyl) phosphonate (151)

To the above solution were added water (150, 0.20 g, 10.60 mmol) and pyridinium trifluoroacetate (0.50 g, 1.65 mmol). The resulting solution was stirred for 30 min at ambient temperature. Upon completion of the reaction, the resulting solution was applied onto a reversed phase C18 column, eluting with 70%~95% (25 min) acetonitrile in water to afford the title compound 151 as a colorless solid (0.50 g, 54% for two steps): $^1$H NMR (300 MHz, DMSO-$d_6$) δ 11.18 (s, 1H), 8.68 (s, 1H), 8.46 (s, 1H), 8.14-8.00 (m, 2H), 7.67-6.97 (m, 18H), 6.15 (d, J=3.4 Hz, 1H), 5.55 (s, 1H), 4.41-4.20 (m, 1H), 4.20-4.10 (m, 1H), 4.08-3.89 (m, 3H), 3.77-3.55 (m, 1H), 3.19-3.01 (m, 2H), 2.83 (dt, J=7.8, 5.8 Hz, 2H), 0.79 (s, 9H), −0.10 (d, J=5.1 Hz, 3H), −0.22 (s, 3H); $^{31}$P NMR (121 MHz, DMSO-$d_6$) δ 9.62, 8.87; LC/MS (ESI, m/z): [(M+1)]$^+$=844.3.

Step 4

((2S,3R,4R,5R)-5-(6-benzamido-9H-purin-9-yl)-4-((tert-butyldimethylsilyl)oxy)-3-(tritylamino)tetrahydrofuran-2-yl)methyl (2-cyanoethyl) ((2S,3R,4R,5R)-5-(6-benzamido-9H-purin-9-yl)-4-((tert-butyldimethylsilyl)oxy)-2-(hydroxymethyl)tetrahydrofuran-3-yl)phosphoramidate (152)

To a mixture of ((2S,3R,4R,5R)-5-(6-benzamido-9H-purin-9-yl)-4-((tert-butyldimethylsilyl)oxy)-3-(tritylamino)tetrahydrofuran-2-yl)methyl (2-cyanoethyl) phosphonate (151, 0.51 g, 0.60 mmol) and N-(9-((2R,3R,4R,5S)-4-amino-3-((tert-butyldimethylsilyl)oxy)-5-(hydroxymethyl)tetrahydrofuran-2-yl)-9H-purin-6-yl)benzamidein (INT-C, 0.29 g, 0.60 mmol) in acetonitrile (6 mL) were added N,N-diisopropylethylamine (0.15 g, 1.20 mmol) and carbon tetrachloride (0.36 g, 2.40 mmol). The resulting mixture was stirred for 15 min at ambient temperature. Upon completion, the resulting mixture was loaded on a reversed phase C18 column, eluting with 70%~95% (25 min) acetonitrile in water to is afford the title compound 152 as a colorless solid (0.53 g, 67%): $^1$H NMR (300 MHz, DMSO-$d_6$) δ 11.27-11.06 (m, 2H), 8.79-8.68 (m, 2H), 8.68-8.56 (m, 2H), 8.08-7.86 (m, 4H), 7.62-7.04 (m, 21H), 6.19-5.93 (m, 2H), 5.27-5.09 (m, 1H), 5.09-4.82 (m, 1H), 4.67-4.47 (m, 1H), 4.29-4.10 (m, 2H), 4.06-3.96 (m, 2H), 3.90-3.80 (m, 2H), 3.75-3.62 (m, 1H), 3.61-3.52 (m, 1H), 3.16-2.94 (m, 2H), 2.80-2.68 (m, 2H), 0.87-0.69 (m, 18H), 0.00 (d, J=8.4 Hz, 3H), −0.06 (d, J=3.7 Hz, 3H), −0.12 (d, J=4.8 Hz, 3H), −0.21 (d, J=13.6 Hz, 3H); $^{31}$P NMR (121 MHz, DMSO-d$_6$) δ 8.80, 8.31; LC/MS (ESI, m/z): [(M+1)]$^+$=1326.9.

Step 5

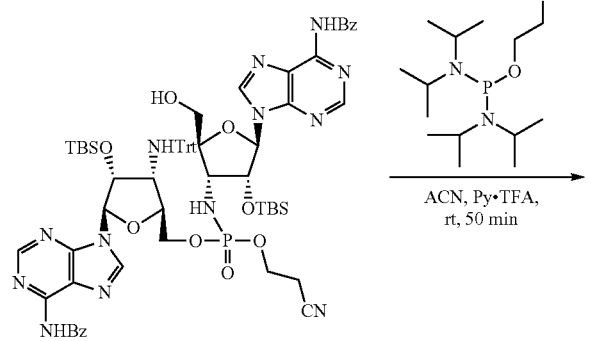

153

((2S,3R,4R,5R)-5-(6-benzamido-9H-purin-9-yl-4-((tert-butyldimethylsilyl)oxy)-3-(tritylamino)tetrahydrofuran-2-yl)methyl (2-cyanoethyl) ((2S,3R,4R,5R)-5-(6-benzamido-9H-purin-9-yl)-4-((tert-butyldimethylsilyl)oxy)-2-((((2-cyanoethoxy)(diisopropylamino)phosphino)oxy)methyl)tetrahydrofuran-3-yl)phosphoramidate (153)

To a solution of ((2S,3R,4R,5R)-5-(6-benzamido-9H-purin-9-yl)-4-((tert-butyldimethylsilyl)oxy)-3-(tritylamino)tetrahydrofuran-2-yl)methyl (2-cyanoethyl) ((2S,3R,4R,5R)-5-(6-benzamido-9H-purin-9-yl)-4-((tert-butyldimethylsilyl)oxy)-2-(hydroxymethyl)tetrahydrofuran-3-yl)phosphoramidate (152, 0.53 g, 0.40 mmol) in acetonitrile (5 mL) were added 3-([bis[bis(propan-2-yl)amino]phosphanyl]oxy)propanenitrile (0.24 g, 0.80 mmol) and pyridinium trifluoroacetate (0.12 g, 0.60 mmol). The resulting mixture was stirred for 50 min at ambient temperature and was used in the next step directly.

Step 6

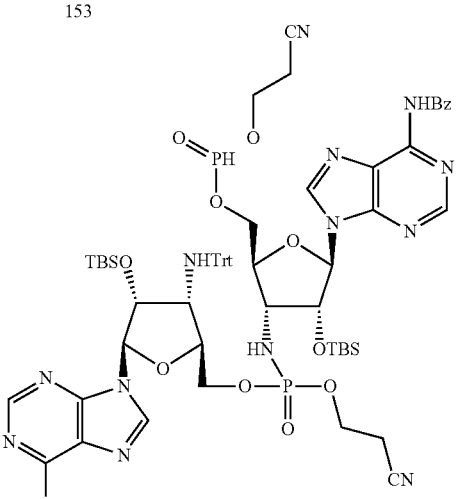

154

[(2S,3R,4R,5R)-5-(6-benzamido-9H-purin-9-yl-3-[({[(2S,3R,4R,5R)-5-(6-benzamido-9H-purin-9-yl)-4-[(tert-butyldimethylsilyl)oxy]-3-[(triphenylmethyl)amino]oxolan-2-yl]methoxy}(2-cyano ethoxy)phosphoryl)amino]-4-[(tert-butyldimethylsilyl)oxy]oxolan-2-yl]methyl-2-cyanoethyl Phosphorate (154)

To the above solution were added water (0.07 g, 4.0 mmol) and pyridinium trifluoroacetate (0.12 g, 0.60 mmol). The resulting solution was stirred for 30 mins at ambient temperature. Upon completion, the resulting solution was applied onto a reversed phase C18 column, eluting with 70%~95% (25 min) acetonitrile in water to afford the title compound 154 as a colorless solid (0.50 g, 87% for two steps): $^1$H NMR (300 MHz, DMSO-d$_6$) δ 11.24-11.08 (m, 2H), 8.76-8.45 (m, 4H), 8.05-7.97 (m, 4H), 7.63-7.07 (m, 21H), 6.20-5.97 (m, 2H), 5.24-4.88 (m, 1H), 4.83-4.62 (m, 1H), 4.43-3.91 (m, 10H), 3.94-3.81 (m, 1H), 3.15-2.97 (m, 2H), 2.92-2.72 (m, 4H), 0.84-0.69 (m, 18H), 0.05-−0.04 (m, 4H), −0.07-−0.25 (m, 8H); $^{31}$P NMR (121 MHz, DMSO-d$_6$) δ 9.90, 9.81, 9.28, 9.23, 8.77, 8.73, 8.10, 8.07. LC/MS (ESI, m/z): [(M+1)]$^+$=1444.5

Step 7

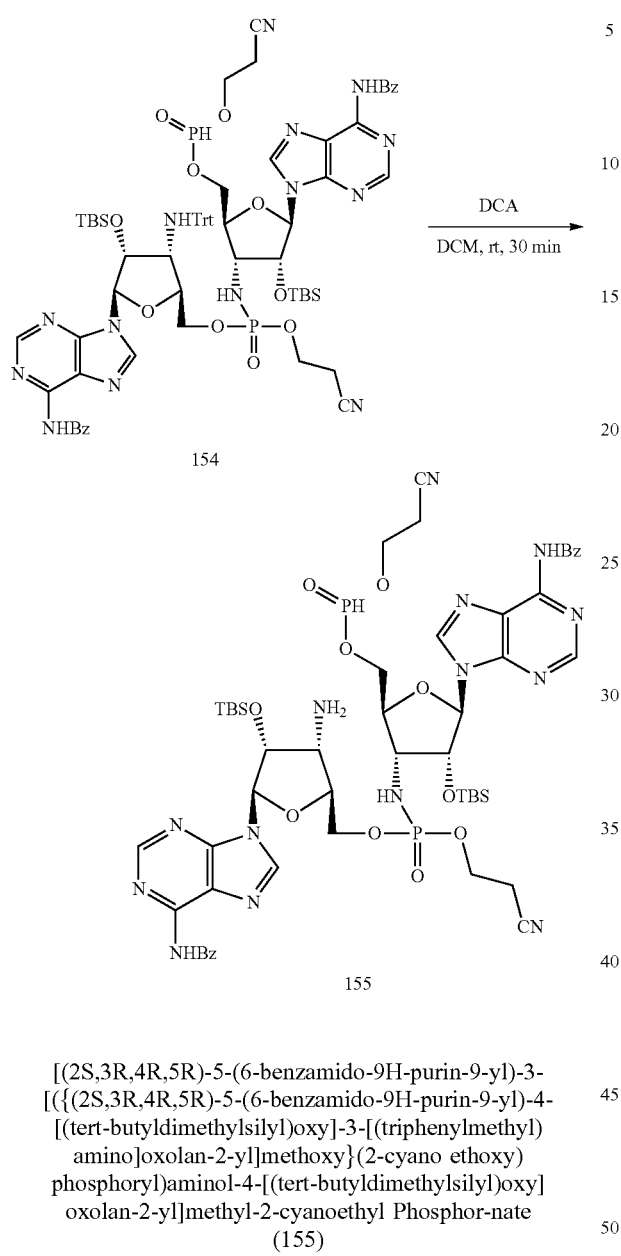

[(2S,3R,4R,5R)-5-(6-benzamido-9H-purin-9-yl)-3-
[({(2S,3R,4R,5R)-5-(6-benzamido-9H-purin-9-yl)-4-
[(tert-butyldimethylsilyl)oxy]-3-[(triphenylmethyl)
amino]oxolan-2-yl]methoxy}(2-cyano ethoxy)
phosphoryl)amino]-4-[(tert-butyldimethylsilyl)oxy]
oxolan-2-yl]methyl-2-cyanoethyl Phosphor-nate
(155)

To a solution of [(2S,3R,4R,5R)-5-(6-benzamido-9H-purin-9-yl)-3-[({[(2S,3R,4R,5R)-5-(6-benzamido-9H-purin-9-yl)-4-[(tert-butyldimethylsilyl)oxy]-3-[(triphenylmethyl)amino]oxolan-2-yl]methoxy}(2 cyanoethoxy)phosphoryl)amino]-4-[(tert-butyldimethylsilyl)oxy]oxolan-2-yl]methyl 2-cyanoethyl phosphonate (154, 504 mg, 0.35 mmol) in dichloromethane (7 mL) were added water (31.4 mg, 0.98 mmol) and dichloroacetic acid (447 mg, 1.96 mmol). The resulting solution was stirred for 30 min at ambient temperature. Upon completion, the reaction was quenched by the addition of saturated aqueous solution of sodium bicarbonate (30 mL). The resulting mixture was extracted with dichloromethane (3×30 mL). The organic layers were combined and dried over anhydrous sodium sulfate. After filtration, the filtrate was concentrated under reduced pressure to afford the title compound 155, which was used in the next step without further purification: LC/MS (ESI, m/z): [(M+1)]$^+$=1201.4.

Step 8

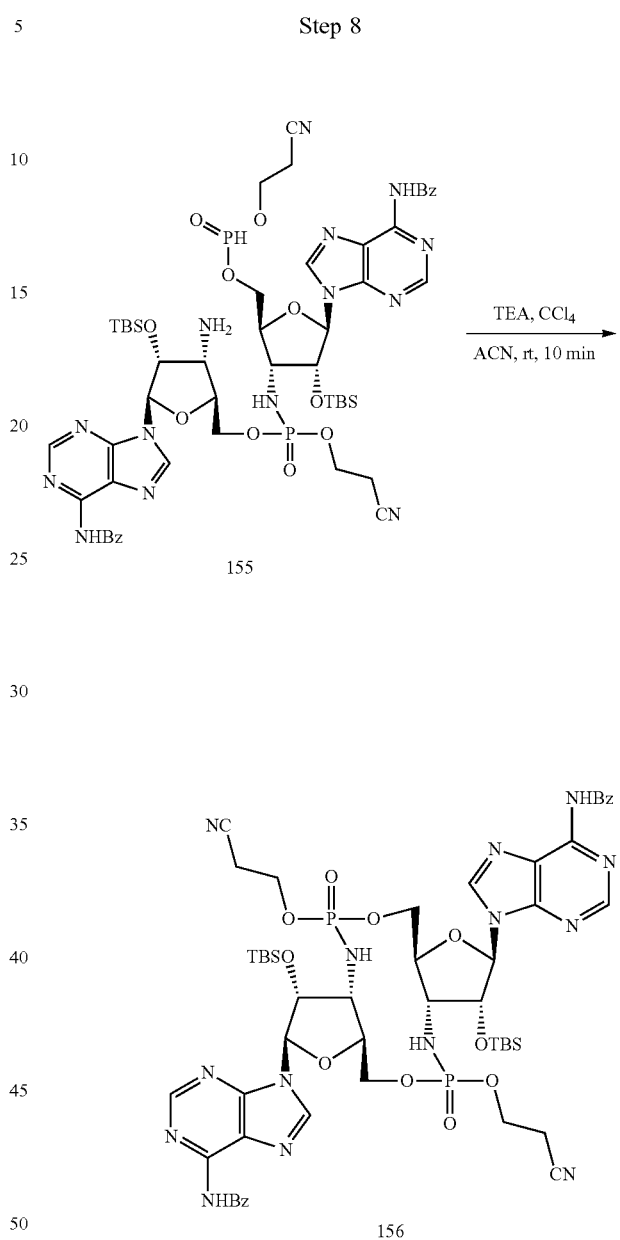

N-{9-[(1R,6S,8R,9R,10R,15S,17R,18R)-17-(6-benzamido-9H-purin-9-yl)-9,18-bis[(tert-butyldimethylsilyl)oxy]-3,12-bis(2-cyanoethoxy)-3,12-dioxo-4,7,13,16-tetraoxa-2,11-diaza-3$\lambda^s$,12$\lambda^s$-diphosphatricyclo[13.3.0.0$^{6,10}$]octadecan-8-yl]-9H-purin-6-yl}benzamide (156)

To a solution of the above crude compound 155 in acetonitrile (70 mL) were added triethylamine (1.4 mL) and carbon tetrachloride (1.4 mL). The resulting solution was stirred for 10 min at ambient temperature. Upon completion, the resulting solution was concentrated under reduced pressure to afford the crude title compound 156, which was used in the next step without further purification.

Step 9

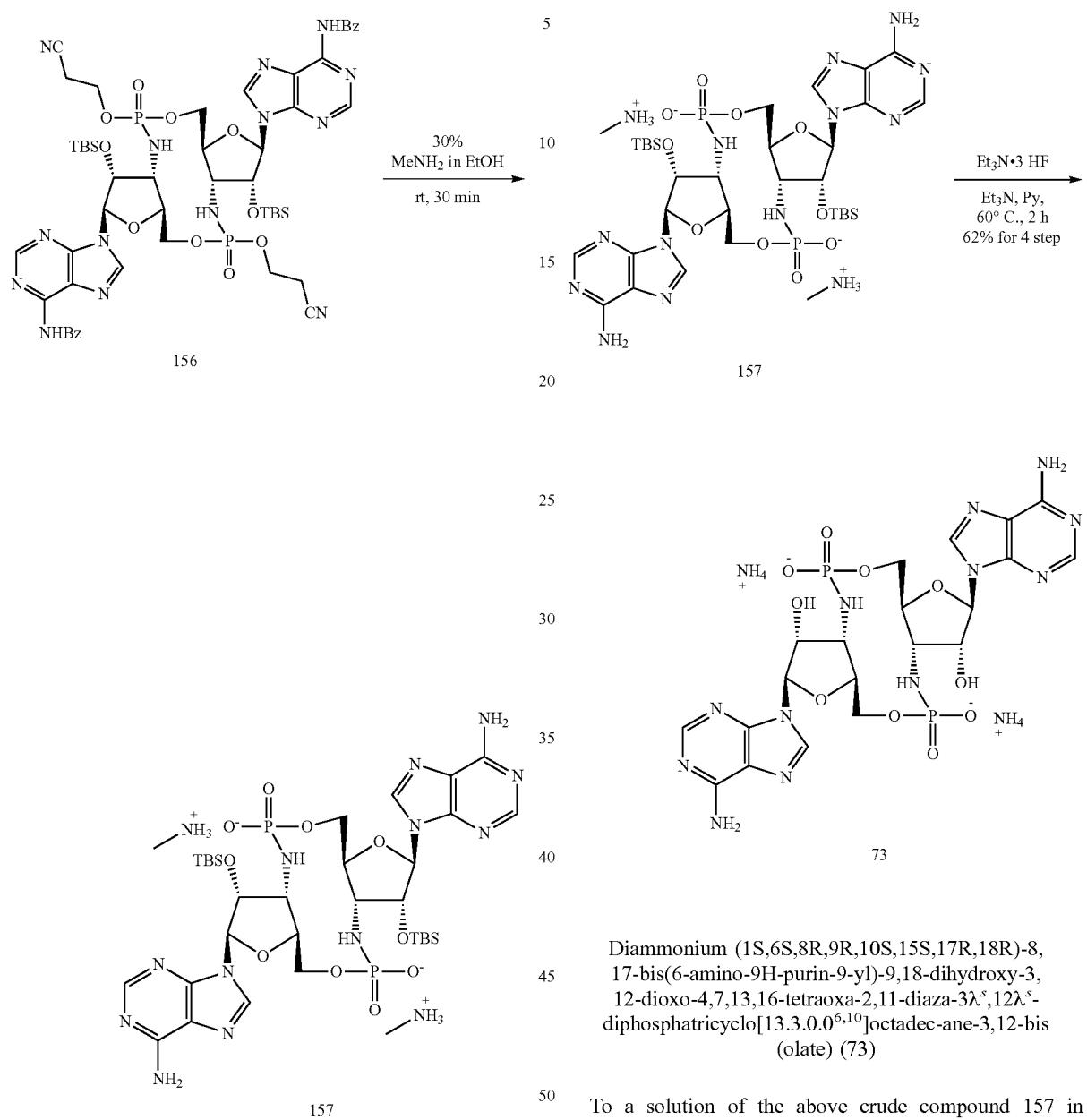

(1R,6S,8R,9R,10R 15S,17R,18R)-8,17-bis(6-amino-9H-purin-9-yl)-9,18-bis[(tert-butyldimethylsilyl)oxy]-3,12-dioxo-4,7,13,16-tetraoxa-2,11-diaza-3λ$^s$,12λ$^s$-diphosphatricyclo[13.3.0.0$^{6,10}$]octadecane-3,12-bis(olate): bis(methanaminium) (157)

The above crude compound 156 was treated with a solution of methylamine in ethanol (14 mL, 30%, w/w) for 30 min at ambient temperature. Upon completion, the resulting solution was concentrated under reduced pressure to afford the title compound 157 as a colorless solid, which was used in the next step without further purification.

Step 10

Diammonium (1S,6S,8R,9R,10S,15S,17R,18R)-8,17-bis(6-amino-9H-purin-9-yl)-9,18-dihydroxy-3,12-dioxo-4,7,13,16-tetraoxa-2,11-diaza-3λ$^s$,12λ$^s$-diphosphatricyclo[13.3.0.0$^{6,10}$]octadec-ane-3,12-bis(olate) (73)

To a solution of the above crude compound 157 in pyridine (3.48 mL) were added triethylamine (1 mL) and triethylamine trihydrofluoride (2.8 g, 17.4 mmol). The resulting solution was stirred for 2 hours at 60° C. After cooling down to ambient temperature, acetone (200 ml) was added to precipitate the crude product which was purified by Prep-HPLC with the following conditions: Column: Atlantis Prep T3 OBD Column, 19*250 mm, 10 um; Mobile Phase A: Water (plus 20 mmol/L of NH$_4$HCO$_3$); Mobile Phase B: ACN; Flow rate: 20 mL/min; Gradient: 0% B to 15% B in 1 min; Detector: 254/220 nm; to afford the title compound 73 as a colorless solid. (0.15 g, 62% for 4 steps, retention time is 10.18 min): $^1$H NMR (300 MHz, D$_2$O) δ 8.59-8.40 (m, 2H), 8.04-7.79 (m, 2H), 6.08 (d, J=1.0 Hz, 2H), 4.40 (d, J=3.9 Hz, 2H), 4.30-4.17 (m, 2H), 4.17-3.89 (m, 4H), 3.78-3.52 (m, 2H); $^{31}$P NMR (121 MHz, D$_2$O) δ 6.23; LC/MS (ESI, m/z): [(M−2NH$_3$−1)]$^-$=655.05.

Diammonium [(1S,6S,8R,9R,10S,15S,17R,18R)-8,17-bis(6-amino-9H-purin-9-yl)-9,18-dihydroxy-3,12-dioxo-12-sulfanidyl-4,7,13,16-tetraoxa-2,11-diaza-3λ$^s$,12λ$^s$-diphosphatricyclo[13.3.0.0$^{6,10}$]octadecan-3-yl]sulfanide
74
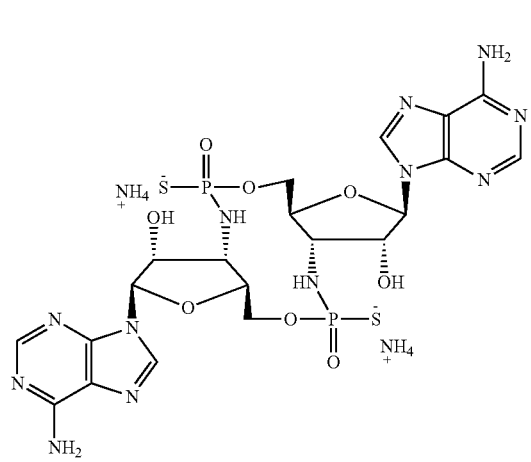
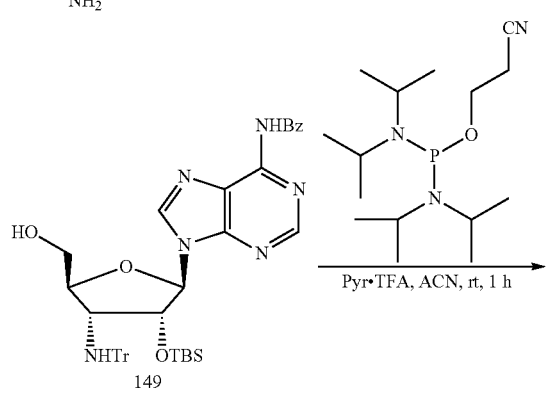
149
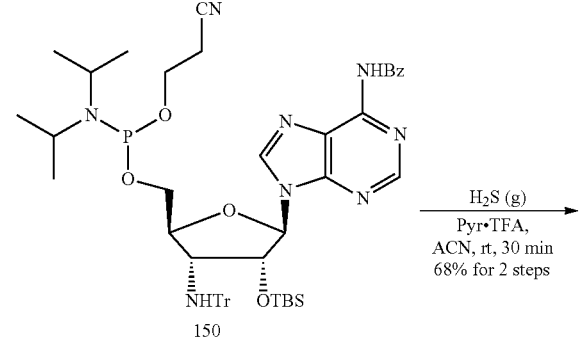
150
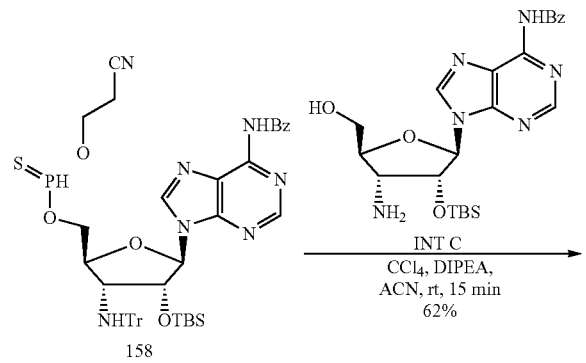
158
-continued
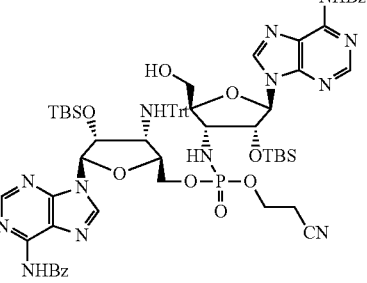
159
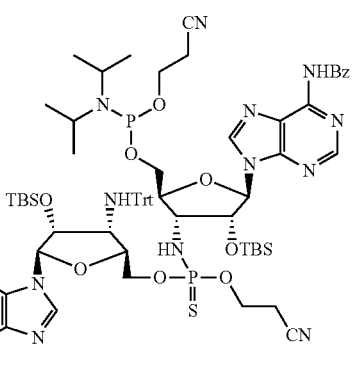
160
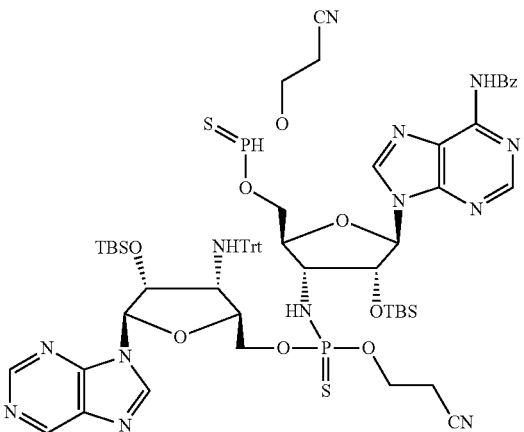
161

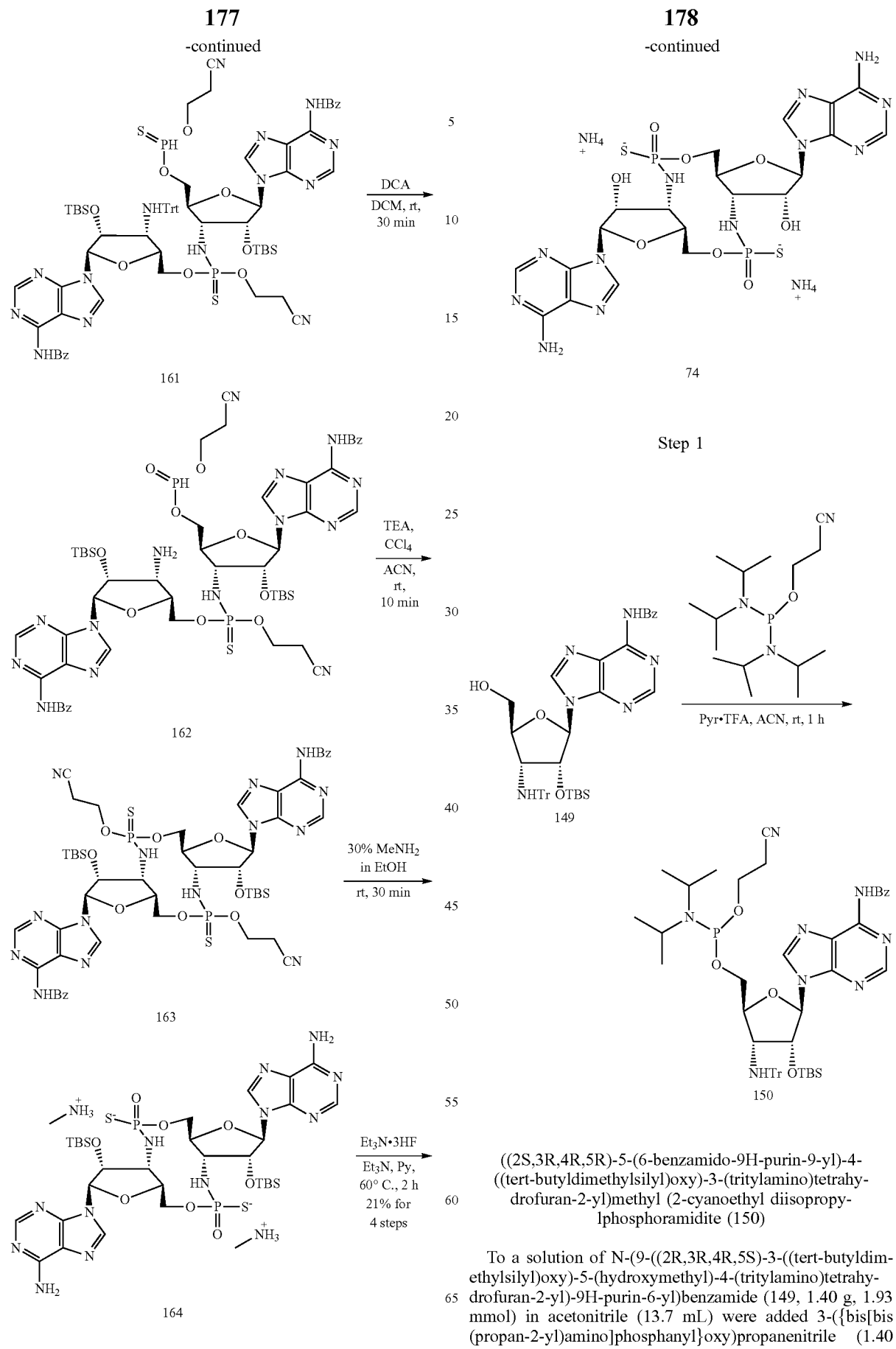
((2S,3R,4R,5R)-5-(6-benzamido-9H-purin-9-yl)-4-((tert-butyldimethylsilyl)oxy)-3-(tritylamino)tetrahydrofuran-2-yl)methyl (2-cyanoethyl diisopropylphosphoramidite (150)
To a solution of N-(9-((2R,3R,4R,5S)-3-((tert-butyldimethylsilyl)oxy)-5-(hydroxymethyl)-4-(tritylamino)tetrahydrofuran-2-yl)-9H-purin-6-yl)benzamide (149, 1.40 g, 1.93 mmol) in acetonitrile (13.7 mL) were added 3-({bis[bis(propan-2-yl)amino]phosphanyl}oxy)propanenitrile (1.40 ml, 3.86 mmol) and pyridinium trifluoroacetate (0.56 g, 2.80 mmol). The resulting solution was stirred for 1 hour at ambient temperature. The resulting solution was used in the next step without work up: LC/MS (ESI, m/z): [(M+1)]⁺ =927.4.

Step 2

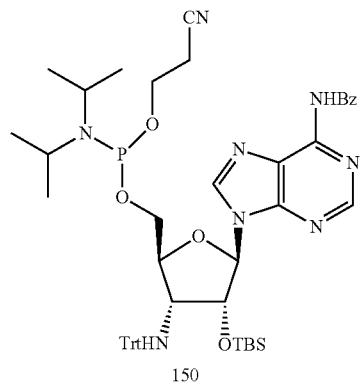

150

H₂S (g)
Pyr·TFA, ACN,
rt, 30 min
68% for 2 steps

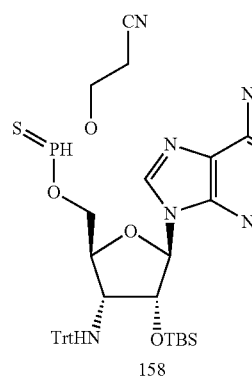

158

O-[(2S,3R,4R,5R)-5-(6-benzamido-9H-purin-9-yl)-4 [(tert-butyldimethylsilyl)oxy]-3-[(triphenylmethyl) amino]oxolan-2-yl]methyl O-2-cyanoethyl Phosphonothioate (158)

To the above solution was bubbled hydrogen sulfide gas for 1 min followed by the addition of pyridinium trifluoroacetate (0.56 g, 2.8 mmol). The resulting solution was stirred for 30 min at ambient temperature. Upon completion, the resulting solution was applied onto a reversed phase C18 column, eluting with 75%~99% (25 min) acetonitrile in water to afford the title compound 158 as a colorless solid (1.12 g, 68% for two steps): ¹H NMR (300 MHz, DMSO-d₆) δ 11.20 (s, 1H), 8.71 (d, J=3.5 Hz, 1H), 8.48 (d, J=8.6 Hz, 1H), 8.05 (d, J=7.6 Hz, 2H), 7.66-7.08 (m, 18H), 6.19 (t, J=3.1 Hz, 1H), 4.42-4.19 (m, 2H), 4.05-3.97 (m, 1H), 3.78-3.66 (m, 1H), 3.36-3.21 (m, 2H), 3.23-3.03 (m, 2H), 2.95-2.75 (m, 2H), 0.80 (s, 9H), −0.08 (d, J=5.5 Hz, 3H), −0.19 (d, J=2.2 Hz, 3H); ³¹P NMR (121 MHz, DMSO) δ 73.01, 72.43; LC/MS (ESI, m/z): [(M+1)]=860.0

Step 3

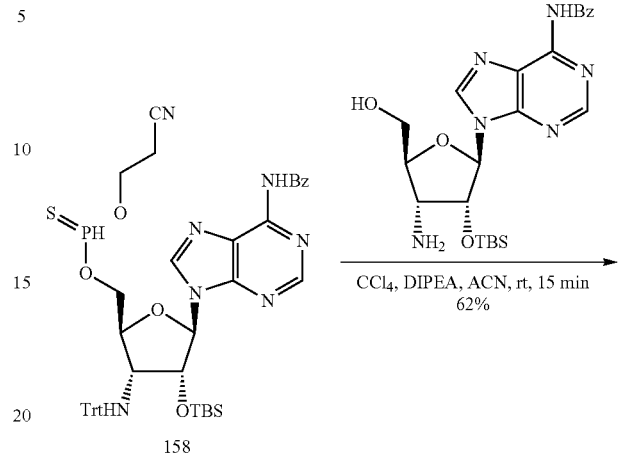

158

CCl₄, DIPEA, ACN, rt, 15 min
62%

159

N-{9-[(2R,3R,4R,5S)-5-{([({[(2S,3R,4R,5R)-5-(6-benzamido-9H-purin-9-yl)-4-[(tert-butyl dimethylsilyl)oxy]-2-(hydroxymethyl)oxolan-3-yl]amino}(2-cyanoethoxy)sulfanylidene-λ⁵-phosphanyl) oxy] methyl}-3-[(tert-butyldimethylsilyl)oxy]-4-[(triphenylmethyl)amino]oxolan-2-yl]-9H-purin-6-yl} Benzamide (159)

To a mixture of [(2S,3R,4R,5R)-5-(6-benzamido-9H-purin-9-yl)-4-[(tert-butyldimethylsilyl)oxy]-3-[(triphenylmethyl)amino]oxolan-2-yl]methyl-2-cyanoethylphosphonate (158, 1.12 g, 1.33 mmol) and N-9-[(2R,5S)-4-amino-3-[(tert-butyldimethylsilyl)oxy]-5-(hydroxyl methyl)oxolan-2-yl]-9H-purin-6-ylbenzamide (0.29 g, 1.33 mmol) in acetonitrile (13 mL) were added N,N-diisopropylethylamine (0.34 g, 2.66 mmol) and carbon tetrachloride (0.79 g, 5.32 mmol). The resulting solution was stirred for 15 min at ambient temperature. Upon completion, the resulting mixture was applied onto a reversed phase C18 column, eluting with 75%~99% (25 min) acetonitrile in water to afford the title compound 159 as a colorless solid (1.1 g, 62%): ¹H NMR (300 MHz, DMSO-d₆) δ 11.22-11.01 (m, 2H), 8.73-8.34 (m, 4H), 8.05-7.94 (m, 4H), 7.63-7.05 (m, 21H), 6.21-5.96 (m, 2H), 5.69-5.45 (m, 1H), 5.13 (dt, J=25.9, 5.1 Hz, 1H), 4.61-4.51 (m, 1H), 4.40-4.20 (m, 1H), 4.18-3.94 (m, 5H), 3.79-3.70 (m, 1H), 3.66-3.46 (m, 1H), 3.16-2.94

(m, 2H), 2.88-2.75 (m, 2H), 0.83-0.64 (m, 18H), 0.07--0.04 (m, 3H), −0.07--0.28 (m, 9H); $^{31}$P NMR (121 MHz, DMSO) δ 73.32, 72.28; LC/MS (ESI, m/z): [(M+1)]$^+$ =1342.5.

Step 4

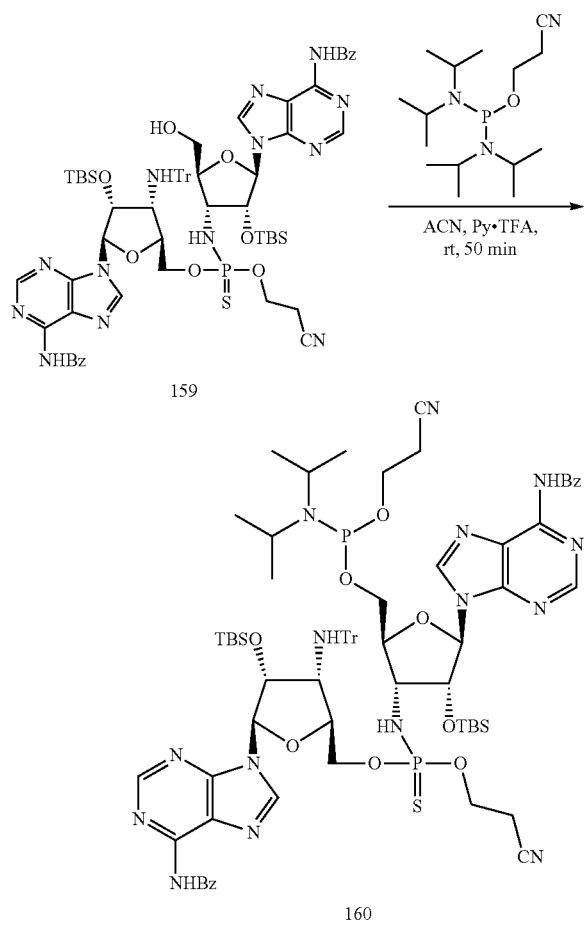

N-{9-[(2R,3R,4R,5S)-5-({[(R)-{[(2S,3R,4R,5R)-5-(6-benzamido-9H-purin-9-yl)-2-[({[bis (propan-2-yl)amino](2-cyanoethoxy)phosphanyl}oxy)methyl]-4-[(tert-butyldimethylsilyl)oxy]oxolan-3-yl]amino} (2-cyanoethoxy)sulfanylidene-λ$^s$-phosphanyl] oxy}methyl)-3-[(tert-butyldimethylsilyl)oxy]-4-[(triphenylmethyl)amino]oxolan-2-yl]-9H-purin-6-yl}benzamide (160)

To a solution is of N-{9-[(2R,3R,4R,5S)-5-{[({[(2S,3R,4R,5R)-5-(6-benzamido-9H-purin-9-yl)-4-[(tert-butyldimethylsilyl)oxy]-2-(hydroxymethyl)oxolan-3-yl]amino}(2-cyanoethoxy)sulfanylidene-λ$^s$-phosphanyl)oxy]methyl}-3-[(tert-butyldimethylsilyl)oxy]-4-[(triphenylmethyl)amino] oxolan-2-yl]-9H-purin-6-yl}benzamide (159, 1.1 g, 0.82 mmol) in acetonitrile (3.3 mL) were added 3-(bis[bis(propan-2-yl)amino]phosphanyloxy)propanenitrile (0.49 g, 1.64 mol) and pyridinium trifluoroacetate (0.24 g, 1.23 mmol). The resulting mixture was stirred for 50 min at ambient temperature and was used in the next step directly.

O-[(2S,3R,4R,5R)-5-(6-benzamido-9H-purin-9-yl)-3-[({[(2S,3R,4R,5R)-5-(6-benzamido-9H-purin-9-yl)-4-[(tert-butyldimethylsilyl)oxy]-3-[(triphenylmethyl)amino]oxolan-2-yl]methoxy}(2-cyanoethoxy) sulfanylidene-λ$^s$-phosphanyl)amino]-4-[(tert-butyldimethylsilyl)oxy]oxolan-2-yl]methyl O-2-cyanoethyl Phosphonothioate (161)

To the above solution was bubbled with hydrogen sulfide for 1 min followed by the addition of pyridinium trifluoroacetate (0.24 g, 1.23 mmol). After stirring for 30 min at ambient temperature, the resulting solution was applied onto a reversed phase C18 column, eluting with 75%~99% (25 min) acetonitrile in water to afford two isomers of the title compound as a colorless solid: isomer A (faster eluting part, eluted with 95% acetonitrile) (530 mg, 44% for two steps, contains 10% phosphate byproduct): $^1$H NMR (300 MHz, DMSO-d$_6$) δ 11.32-10.99 (m, 2H), 8.78-8.43 (m, 4H), 8.10-7.95 (m, 4H), 7.77-6.95 (m, 21H), 6.25-5.98 (m, 2H), 5.64-5.30 (m, 1H), 4.82-4.42 (m, 1H), 4.46-3.85 (m, 10H), 3.85-3.61 (m, 1H), 3.61-3.37 (m, 1H), 3.23-2.97 (m, 2H), 2.92-2.66 (m, 4H), 0.89-0.56 (n, 18H), −0.07--0.27 (m, 12H); $^{31}$P NMR (121 MHz, DMSO) δ 74.19, 74.06, 73.96, 73.46, 73.37, 73.31, 73.27, 72.79, 9.69, 9.15, 5.34, 4.70, 1.38, −1.11, −1.22, −1.67, −1.92; LC/MS (ESI, m/z): [(M+1)]$^+$=1475.4. And isomer B (slower eluting part, eluted with 99% acetonitrile) (560 mg, 46% for two steps, contains 10% phosphate byproduct): $^1$H NMR (300 MHz, DMSO-d$_6$) δ 11.26-10.97 (m, 2H), 8.72-8.38 (m, 4H), 8.12-7.90 (m, 4H), 7.67-7.00 (m, 21H), 6.20-5.87 (m, 2H), 4.80-4.55 (m, 1H), 4.36-3.75 (m, 10H), 3.62-3.44 (m, 1H), 3.31-3.13 (m, 1H), 3.13-2.91 (m, 2H), 2.89-2.62 (m, 4H), 0.97-0.57 (m, 18H), 0.10--0.01 (m, 3H), −0.04--0.24 (m, 9H); $^{31}$P NMR (121 MHz, DMSO) δ 114.61, 73.39, 73.00, 72.66, 72.26, 72.22, 72.07, 71.94, 9.83, 9.24, 5.35, 4.70, 1.37, −1.12, −1.18; LC/MS (ESI, m/z): [(M+1)]$^+$=1475.4. Isomer A and isomer B were independently carried through the remainder of the synthesis (Step 6 through Step 9).

Step 6

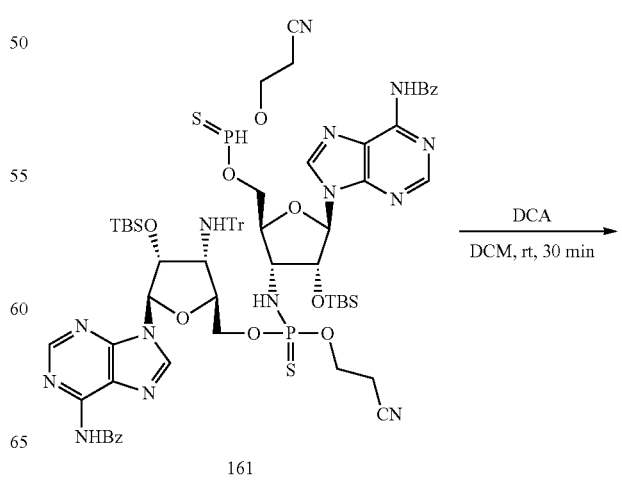

Step 7

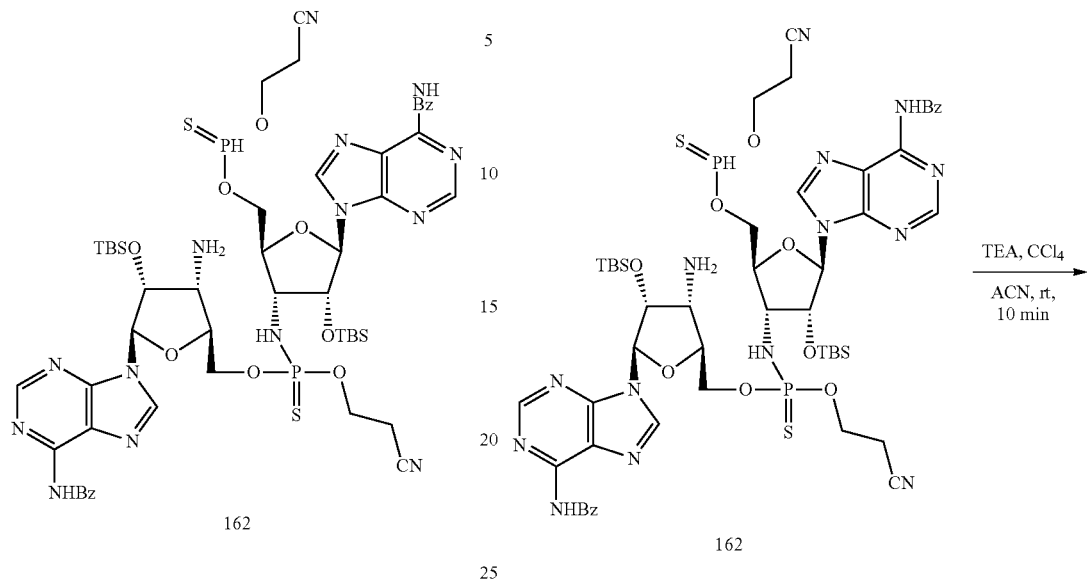

O-[(2S,3R,4R 5R)-3-[({[(2S,3R,4R,5R)-3-amino-5-(6-benzamido-9H-purin-9-yl)-4-[(tert-butyldimethyl-silyl)oxy]oxolan-2-yl]methoxy}(2-cyanoethoxy)sulfanylidene-$\lambda^s$-phosphanyl)amino]-5-(6-benzamido-9H-purin-9-yl)-4-[(tert-butyldimethylsilyl)oxy]oxolan-2-yl]methyl O-2-cyanoethyl Phosphonothioate (162)

To a solution of O-[(2S,3R,4R,5R)-5-(6-benzamido-9H-purin-9-yl)-3-[({[(2S,3R,4R,5R)-5-(6-benzamido-9H-purin-9-yl)-4-[(tert-butyldimethylsilyl)oxy]-3-[(triphenylmethyl)amino]oxolan-2-yl]methoxy}(2-cyanoethoxy)sulfanylidene-$\lambda^s$-phosphanyl)amino]-4-[(tert-butyldimethylsilyl)oxy]oxolan-2-yl]methyl O-2-cyanoethyl phosphonothioate (161, 530 mg, 0.36 mmol, isomer A from previous step) in dichloromethane (7.2 mL) were added dichloroacetic acid (460 mg, 3.59 mmol) and water (32 mg, 1.80 mmol). The resulting solution was stirred for 30 min at ambient temperature. Upon completion, the reaction was quenched by the addition of saturated aqueous sodium bicarbonate (30 mL). The resulting mixture was extracted with dichloromethane (3×30 mL). The organic layers were combined and dried over anhydrous sodium sulfate. After filtration, the filtrate was concentrated under reduced pressure to afford the title compound 162, which was used in the next step without further purification.

N-{9-(1R,6S,8R,9R,10R,15S,17R,18R)-17-(6-benzamido-9H-purin-9-yl)-9,18-bis[(tert-butyldimethylsilyl)oxy-3,12-bis(2-cyanoethoxy)-3,12-disulfanylidene-4,7,13,16-tetraoxa-2,11-diaza-3$\lambda^s$,12$\lambda^s$-diphosphatricyclo[13.3.0.0$^{6,10}$]octadecan-8-yl]-9H-purin-6-yl}benzamide (163)

To a solution of the above crude compound 162 in acetonitrile (72 mL) were added triethylamine (1.44 mL) and carbon tetrachloride (1.44 mL). The resulting solution was stirred for 10 min at ambient temperature. Upon completion, the resulting solution was concentrated under reduced pressure to afford the crude title compound 163, which was used in the next step without further purification.

Step 8

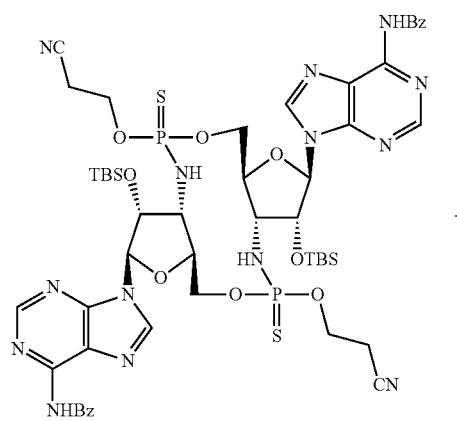

163

30% MeNH₂ in EtOH rt, 30 min

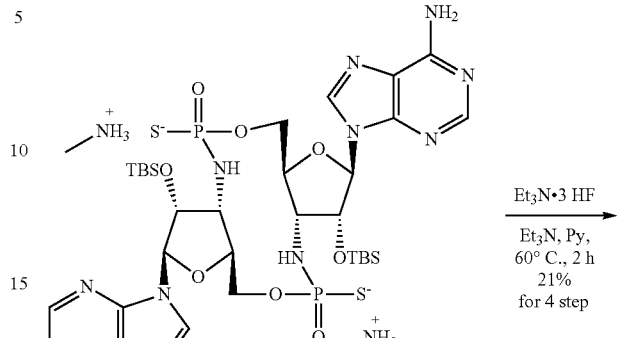

164

Et₃N·3 HF

Et₃N, Py,
60° C., 2 h
21%
for 4 step

Step 9

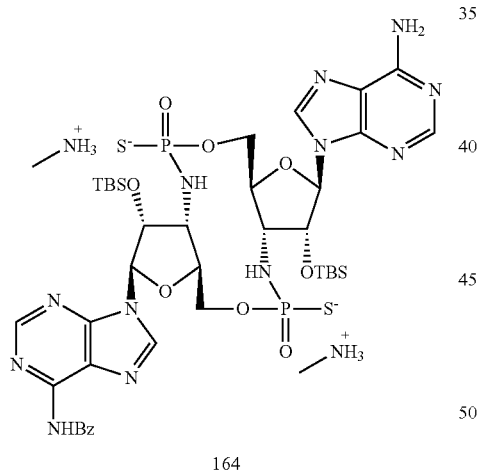

164

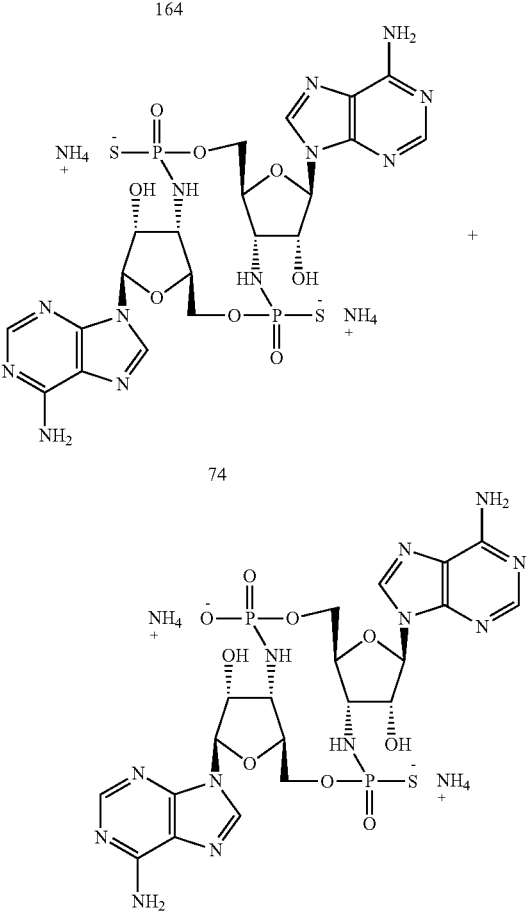

74

74-OBO

[(1R,6S,8R,9R,10R,15S,17R,18R)-8,17-bis(6-amino-9H-purin-9-yl)-9,18-bis[(tert-butyldimethylsilyl)oxy]-3,12-dioxo-2-sulfanidyl-4,7,13,16-tetraoxa-2,11-diaza-3λ$^s$,12λ$^s$-diphosphatricyclo[13.3.0.0$^{6,10}$]octadecan-3-yl]sulfanide; bis(methanaminium) (164)

The above crude compound was treated with a solution of methylamine in ethanol (163, 14.4 mL, 30%, w/w) for 30 min at ambient temperature. Upon completion, the resulting solution was concentrated under reduced pressure to afford the title compound 164 as a colorless solid, which was used in the next step without further purification.

Diammonium [(1S,6S,8R,9R,10S,15S,17R,18R)-8,17-bis(6-amino-9H-purin-9-yl)-9,18-dihydroxy-3,12-dioxo-12-sulfanidyl-4,7,13,16-tetraoxa-2,11-diaza-3λ$^s$,12λ$^s$-diphosphatricyclo[13.3.0.0$^{6,10}$]octadecan-3-yl]sulfanide (74)

To a solution of the above crude compound 164 in pyridine (3.6 mL) were added triethylamine (1 mL) and triethylamine trihydrofluoride (2.89 g, 17.95 mmol). The resulting solution was stirred for 2 hours at 60° C. After cooling down to ambient temperature, acetone (200 mL) was is added to precipitate the crude product which was purified by Prep-HPLC with the following conditions: Column: XBridge Prep C18 OBD Column 19*150 mm, 5 um; Mobile Phase A: Water (plus 20 mmol/L of NH₄HCO₃); Mobile Phase B: ACN; Flow rate: 20 mL/min; Gradient: 1% B to 15% B in 11 min; Detector: 254/220 nm; to afford one isomer (faster eluting peak, retention time is 7.52 min, herein referred to 74-0A1) as a colorless solid (40.2 mg, 16.3% for 4 step): $^1$H NMR (300 MHz, D$_2$O) δ 8.49 (s, 1H), 8.41 (s, 1H), 8.14-8.02 (m, 1H), 7.96-7.86 (m, 1H), 6.08 (s, 1H), 6.05 (s, 1H), 4.82 (d, J=4.1 Hz, 1H), 4.40-4.28 (m, 2H), 4.26-3.93 (m, 5H), 3.75 (d, J=10.6 Hz, 2H); $^{31}$P NMR (121 MHz, D$_2$O) δ 57.74, 54.73; LC/MS (ESI, m/z): [(M−2NH$_3$−1)]$^−$=686.9. And the other isomer (slower eluting peak, retention time is 9.77 min, here referred to 74-0A2) as a colorless solid: $^1$H NMR (300 MHz, D$_2$O+DMSO-d$_6$) δ 8.50 (s, 2H), 8.02 (s, 2H), 6.09 (s, 2H), 4.50-4.27 (m, 4H), 4.13 (d, J=10.5 Hz, 2H), 3.98 (dd, J=11.9, 5.4 Hz, 2H), 3.85 (s, 2H); $^{31}$P NMR (121 MHz, D$_2$O+DMSO-d$_6$) δ 52.39; LC/MS (ESI, m/z): [(M−2NH$_3$−1)]$^−$=686.9.

Steps 6-9 above were performed on the isomer B obtained in Step 5 to generate the other two isomers and a mixed phosphate/thiophosphate: They were purified by Prep-HPLC with the following conditions: XBridge Prep C18 OBD Column 19*150 mm, 5 um; Mobile Phase A: water (plus 20 mmol/L of NH₄HCO₃); Mobile Phase B: ACN; Flow rate: 20 mL/min; Gradient: 1% B to 40% B in 10 min; Detector: 254/220 nm; to afford the mixed phosphate thiophosphate diammonium salt 74-0B0 (single isomer) [(1S,6S,8R,9R,10S,15S,17R,18R)-8,17-bis(6-amino-9H-purin-9-yl)-9,18-dihydroxy-12-oxido-3,12-dioxo-4,7,13,16-tetraoxa-2,11-diaza-3λ$^s$,12λ$^s$-diphosphatricyclo[13.3.0.0$^{6,10}$]octadecan-3-yl]sulfanide as a colorless solid (5.6 mg, retention time is 4.57 min): $^1$H NMR (400 MHz, D$_2$O) δ 8.72-8.49 (m, 2H), 8.16-7.95 (m, 2H), 6.24-6.09 (m, 2H), 4.84 (q, J=5.8, 5.0 Hz, 1H), 4.48-4.38 (m, 1H), 4.33-4.21 (m, 2H), 4.21-4.02 (m, 4H), 3.94-3.72 (m, 2H); $^{31}$P NMR (162 MHz, D$_2$O) δ 57.80, 6.25; LC/MS (ESI, m/z): [(M−2NH$_3$−1)]$^−$=670.9. And one isomer here referred to 74-0B1 as a colorless solid (16.4 mg, 6% over 4 steps, retention time is 5.23 min): $^1$H NMR (300 MHz, DMSO-d$_6$) δ 8.64 (s, 2H), 8.13 (s, 2H), 5.97 (s, 2H), 4.37-4.29 (m, 2H), 4.11-4.00 (m, 2H), 4.02-3.88 (m, 4H); $^{31}$P NMR (121 MHz, DMSO) δ 57.54. LC/MS (ESI, m/z): [(M−2NH$_3$−1)]$^−$=686.9. The other isomer here referred to as 74-0B2 as a colorless solid (35 mg, 13% over 4 steps, retention time is 8.80 min), which has the same characteristics as 74-0A1. The isomers 74-0A1, 74-0A2, 74-0B1, and 74-0B2 are believed to vary in stereochemical configuration at the phosphorus atoms.

Diammonium (1S,6S,8R,9R,10S,15S,17R,18R)-8,17-bis(2-amino-6-oxo-6,9-dihydro-1H-purin-9-yl)-9,18-dihydroxy-3,12-dioxo-4,7,13,16-tetraoxa-2,11-diaza-3λ$^s$,12λ$^s$-diphosphatricyclo[13.3.0.0$^{6,10}$]octadecane-3,12-bis(olate)

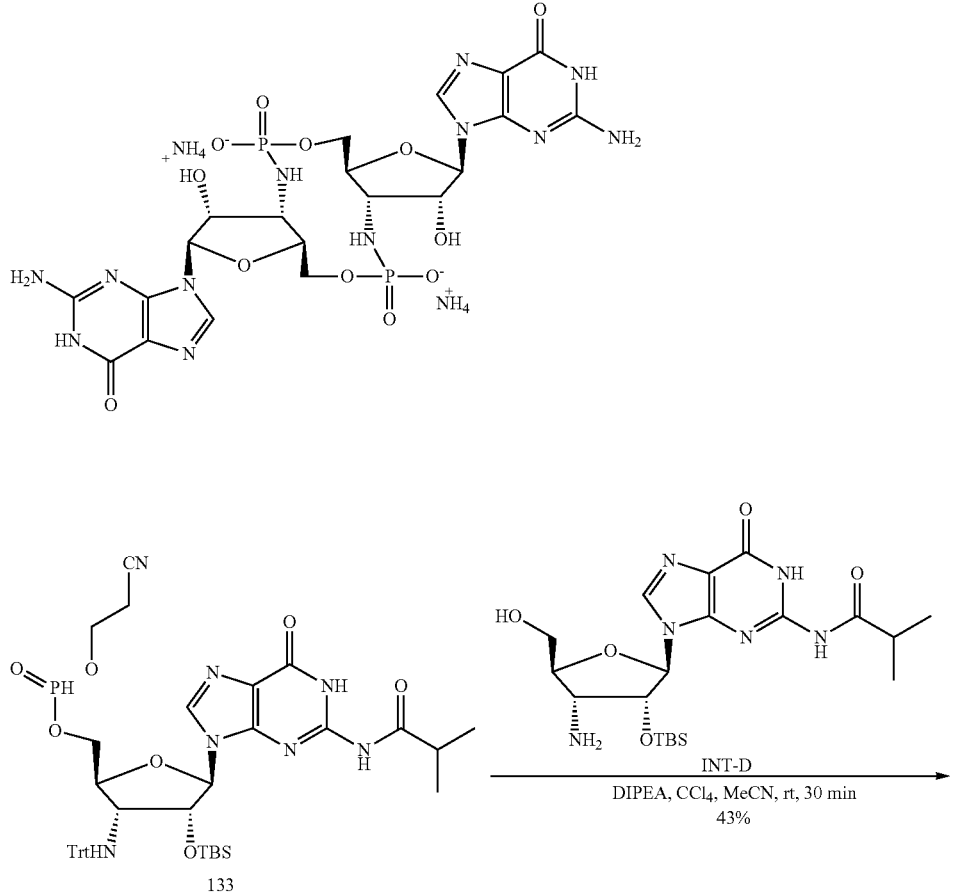

-continued
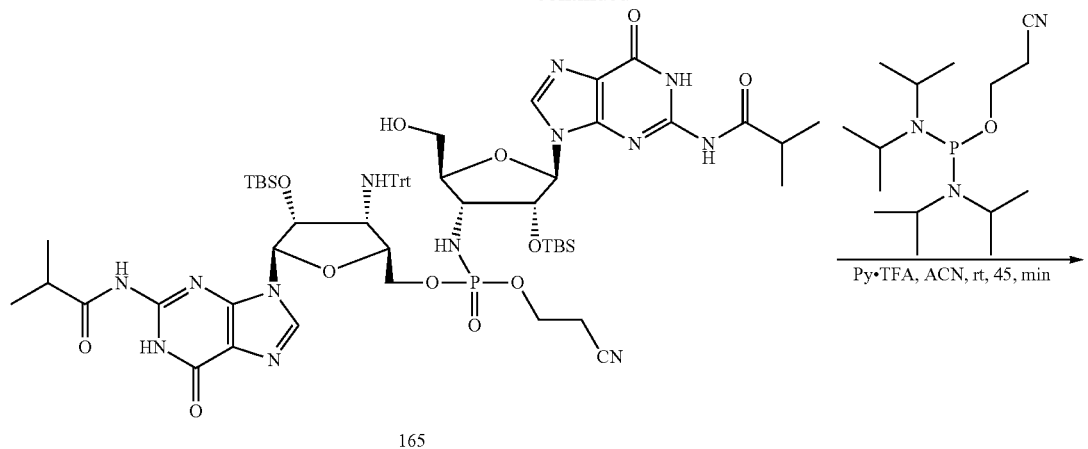
165
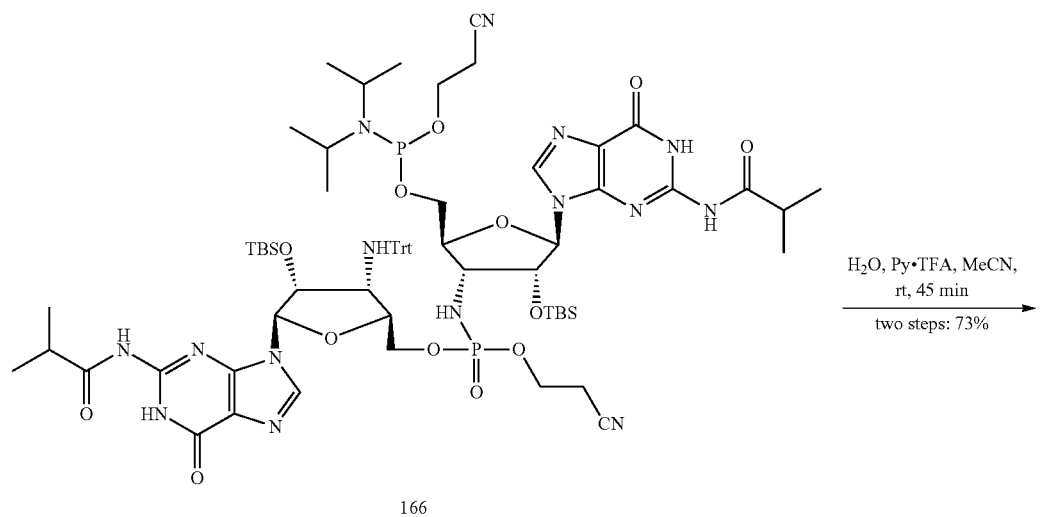
166
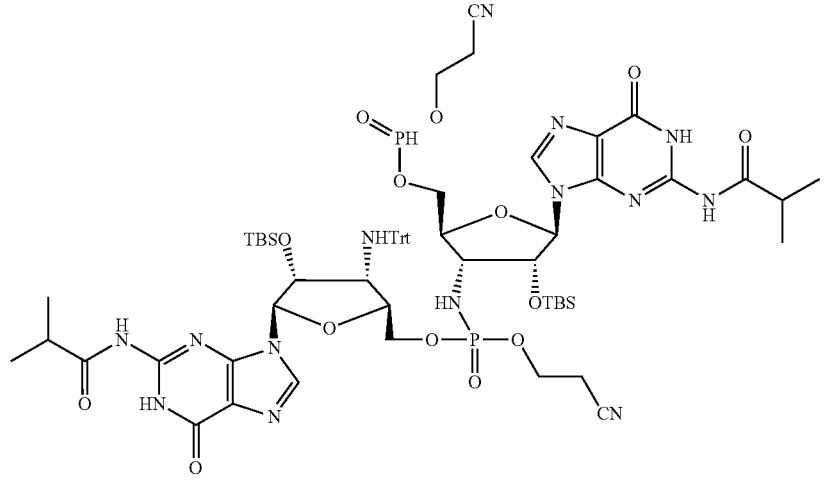
167

-continued
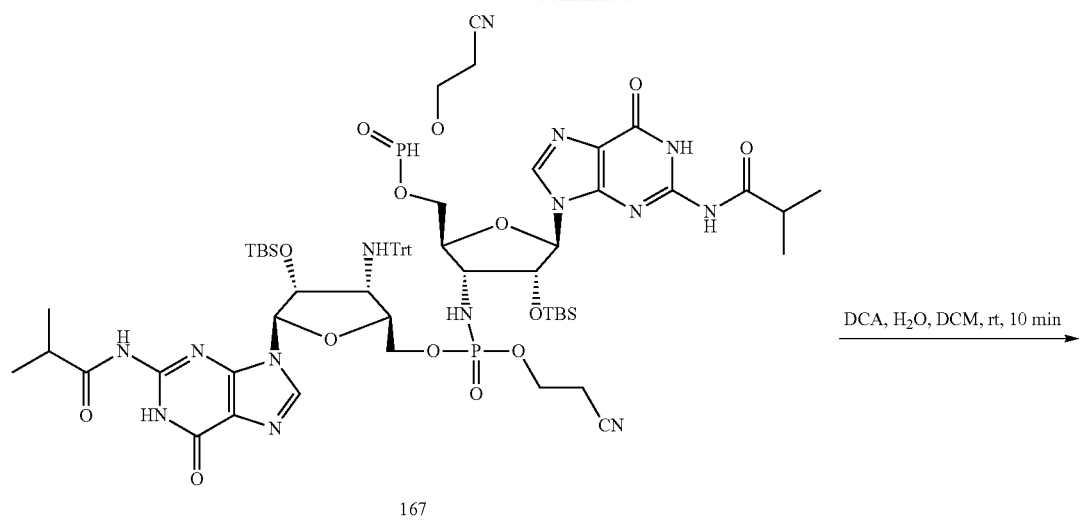
167
DCA, H₂O, DCM, rt, 10 min
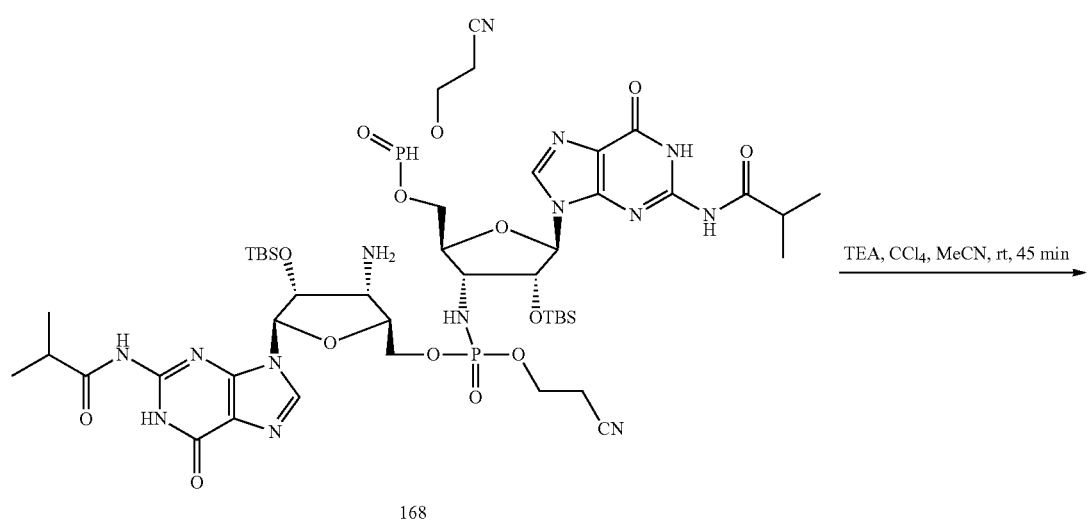
168
TEA, CCl₄, MeCN, rt, 45 min
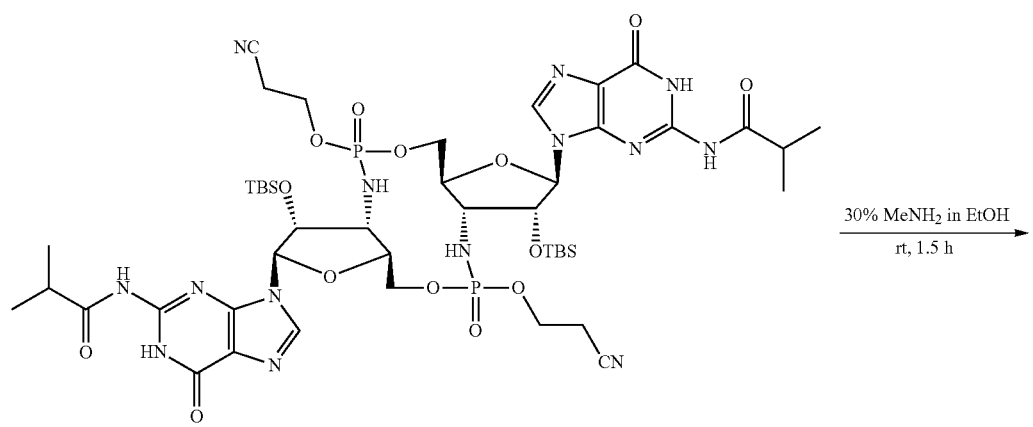
169
30% MeNH₂ in EtOH
rt, 1.5 h -continued
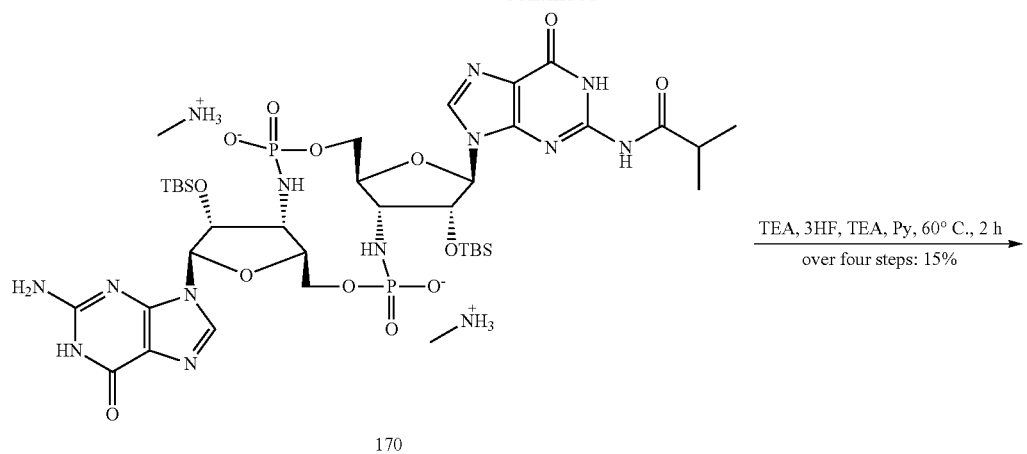
170
TEA, 3HF, TEA, Py, 60° C., 2 h
over four steps: 15%
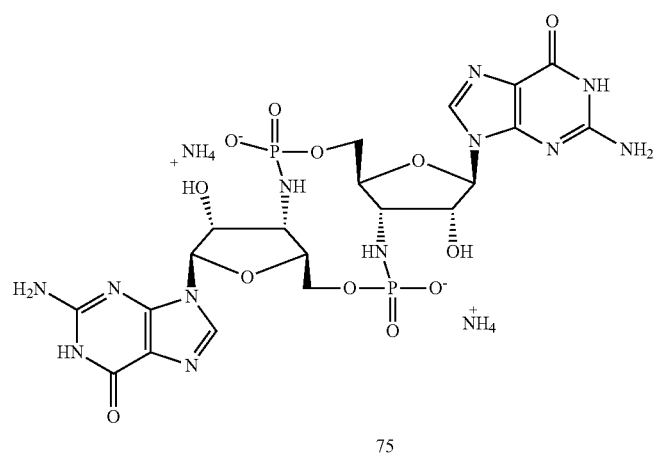
75
Step 1
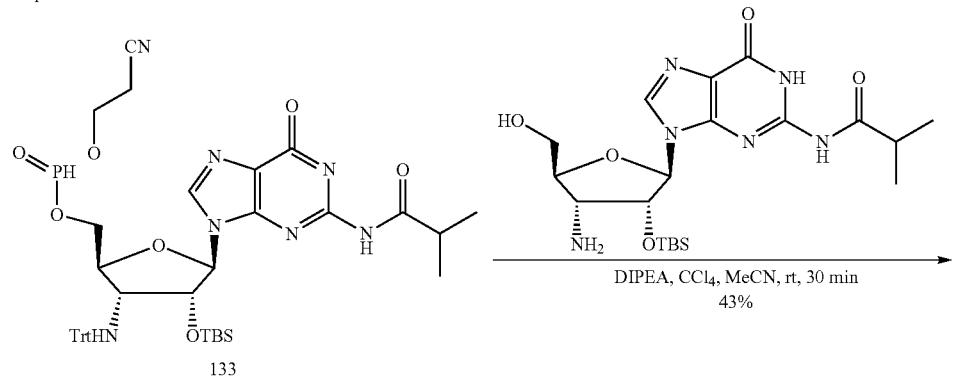
133
DIPEA, CCl₄, MeCN, rt, 30 min
43%

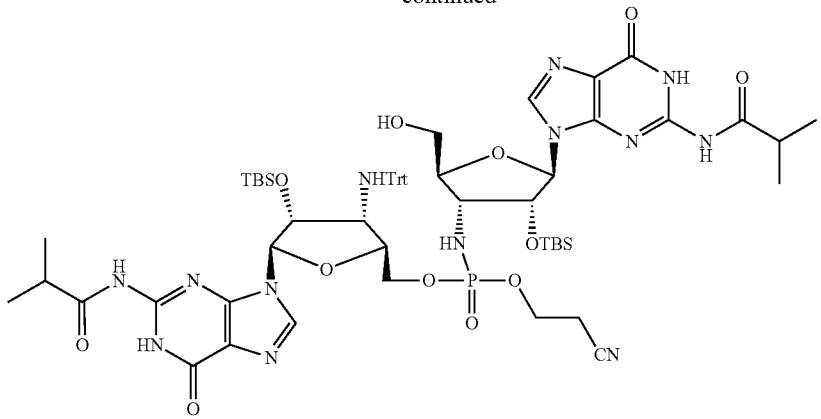

165

((2S,3R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl (2-cyanoethyl) ((2S,3R,4R,5R)-4-((tert-butyldimethylsilyl)oxy)-2-(hydroxymethyl)-5-(2-isobutyramido-6-oxo-1H-purin-9(H)-yl)tetrahydrofuran-3-yl)phosphoramidate (165)

To a mixture of [(2S,3R,4R,5R)-4-[(tert-butyldimethylsilyl)oxy]-5-[2-(2-methylpropanamido)-6-oxo-6,9-dihydro-1H-purin-9-yl]-3-[(triphenylmethyl)amino]oxolan-2-yl]methyl 2-cyanoethyl phosphonate (1.0 g, 1.21 mmol) and N-(9-((2R,3R,4R,5S)-4-amino-3-(tert-butyldimethylsilyloxy)-5-(hydroxymethyl)-tetrahydrofuran-2-yl)-6-oxo-6,9-dihydro-1H-purin-2-yl)isobutyramide (133, 0.56 g, 1.21 mmol) in acetonitrile (12 mL) were added N,N-diisopropylethylamine (0.38 mL, 2.42 mmol) and carbon tetrachloride (0.47 mL, 4.84 mmol). The resulting mixture was stirred for 30 min at ambient temperature. Upon completion, the resulting mixture was applied onto a reversed phase C18 column, eluting with 70%~95% (25 min) acetonitrile in water to afford the title compound 165 as a colorless solid (440 mg, 43%): $^1$H NMR (400 MHz, DMSO-$d_6$) δ 12.12 (s, 2H), 11.46 (t, J=11.1 Hz, 2H), 8.23 (s, 1H), 8.18 (s, 1H), 7.48 (dd, J=6.3, 2.9 Hz, 6H), 7.40-7.31 (m, 6H), 7.25 (dt, J=9.4, 7.5 Hz, 3H), 6.22 (dd, J=17.5, 6.5 Hz, 1H), 5.77 (dd, J=26.0, 4.5 Hz, 1H), 5.19-4.88 (m, 2H), 4.57-4.45 (m, 1H), 4.35 (d, J=6.9 Hz, 1H), 4.19-3.39 (m, 6H), 3.27 (dd, J=17.9, 2.3 Hz, 1H), 2.89-2.70 (m, 5H), 1.13 (dt, J=6.6, 3.2 Hz, 12H), 0.72 (d, J=32.6 Hz, 18H), 0.05--0.22 (m, 9H), -0.43 (d, J=19.3 Hz, 3H); $^{31}$P NMR (162 MHz, DMSO-$d_6$) δ 8.98, 8.82; LC/MS (ESI, m/z): [(M+1)]$^+$=1308.5.

Step 2

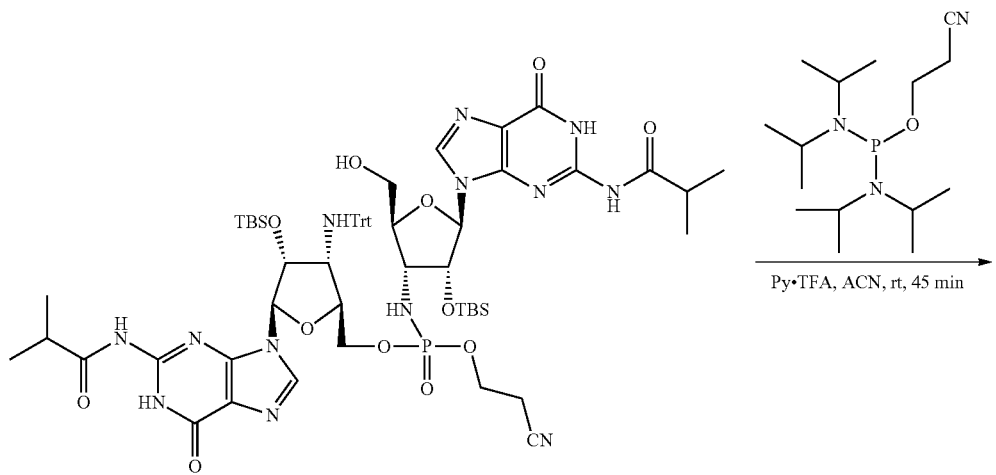

165

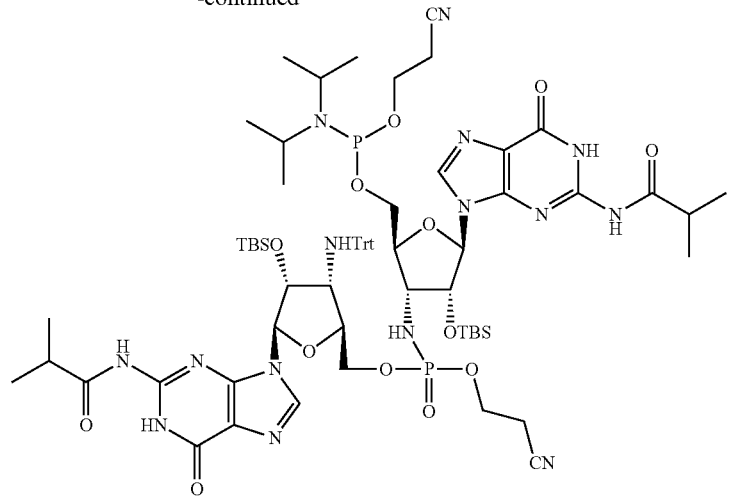

166

((2S,3R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl (2-cyanoethyl) ((2S,3R,4R,5R)-4-((tert-butyldimethylsilyl)oxy)-2-((((2-cyanoethoxy)(diisopropylamino)phosphino)oxy)methyl)-5-(2-isobutyramido-6-oxo-1H-purin-9(6H)-yl)tetrahydrofuran-3-yl)phosphoramidate (166)

To a solution of ((2S,3R,4R,5R)-4-(tert-butyldimethylsilyloxy)-5-(2-isobutyramido-6-oxo-1,6-dihydropurin-9-yl)-3-(tritylamino)-tetrahydrofuran-2-yl)methyl 2-cyanoethyl (2S,3R,4R,5R)-4-(tert-butyldimethylsilyloxy)-2-(hydroxymethyl)-5-(2-isobutyramido-6-oxo-1,6-dihydropurin-9-yl)-tetrahydrofuran-3-ylphosphoramidate (165, 1.0 g, 0.77 mmol) were added 3-(bis[bis(propan-2-yl)amino]phosphanyloxy)propanenitrile (224 mg, 0.74 mmol) and pyridinium trifluoroacetate (224 mg, 1.16 mmol). The resulting mixture was stirred for 45 min at ambient temperature and was used in the next step directly without further purification.

Step 3

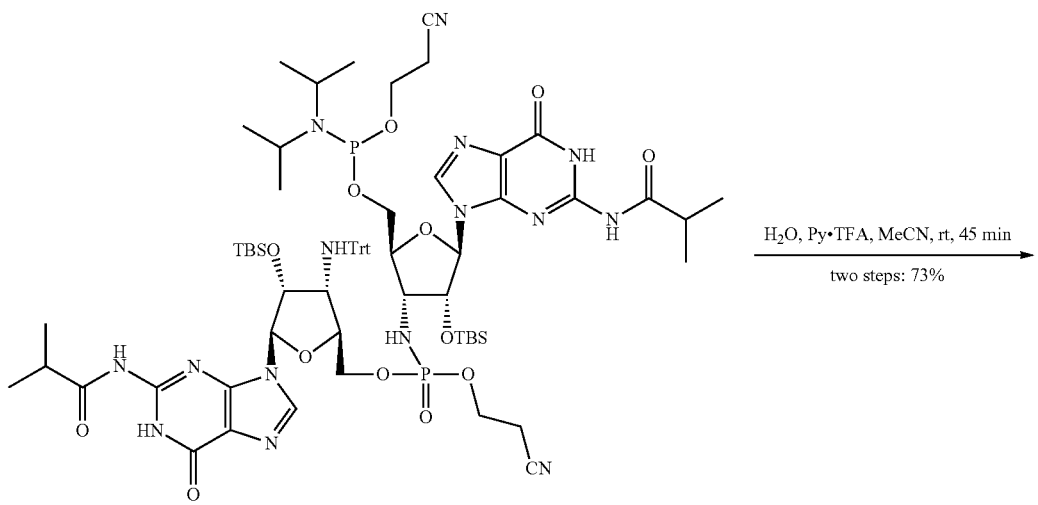

166

H₂O, Py·TFA, MeCN, rt, 45 min
two steps: 73%

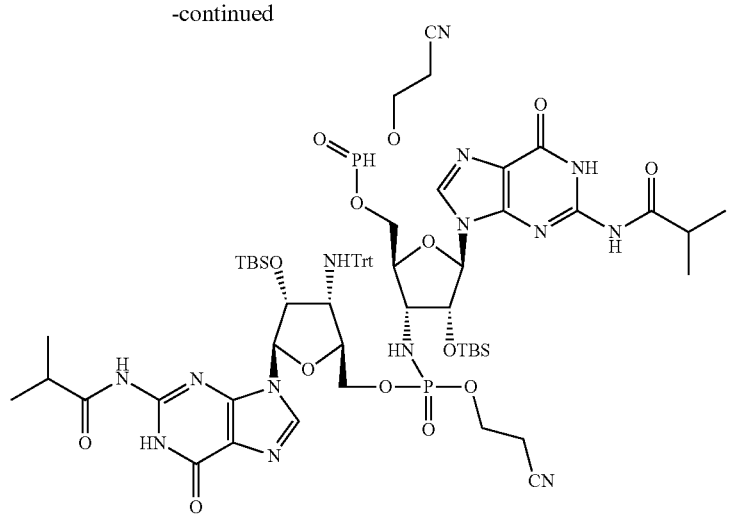

167

((2S,3R,4R,5R)-4-(tert-butyldimethylsilyloxy)-5-(2-isobutyramido-6-oxo-1,6-dihydropurin-9-yl)-3-(tritylamino)-tetrahydrofuran-2-yl)methyl 2-cyanoethyl (2S,3R,4R,5R)-4-(tert-butyldimethylsilyloxy)-2-(((2-cyanoethoxy)hydrophoshosoryloxy)methyl)-5-(2-isobutyramido-6-oxo-1,6-dihydropurin-9-yl)-tetrahydrofuran-3-ylphosphoramidate (167)

To the above solution were added water (144 mg, 7.99 mmol) and pyridinium trifluoroacetate (224 mg, 1.16 mmol). The resulting solution was stirred for 45 min at ambient temperature. Upon completion, the resulting solution was applied onto a reversed phase C18 column, eluting with 70%~95% (25 min) acetonitrile in water to afford the title compound 167 as a colorless solid (800 mg, 73%): $^1$H NMR (400 MHz, DMSO-d$_6$) δ 12.07 (t, J=8.4 Hz, 2H), 11.40 (s, 2H), 8.23-8.03 (m, 2H), 7.51-7.15 (m, 15H), 6.17 (dd, J=12.4, 6.4 Hz, 1H), 5.80-5.65 (m, 2H), 4.66-4.55 (m, 1H), 4.25 (d, J=7.0 Hz, 1H), 4.19-3.94 (m, 5H), 3.96-3.76 (m, 3H), 3.60 (s, 1H), 3.41 (dq, J=18.4, 6.9 Hz, 1H), 3.22 (d, J=16.2 Hz, 1H), 2.84 (q, J=6.0 Hz, 5H), 1.09 (dt, J=6.8, 3.4 Hz, 12H), 0.73 (d, J=2.3 Hz, 15H), 0.63 (d, J=1.9 Hz, 3H), −0.08 (d, J=2.3 Hz, 2H), −0.12--0.27 (m, 7H), −0.40--0.51 (m, 3H); $^{31}$P NMR (162 MHz, DMSO-d$_6$) δ 9.75, 9.71, 9.23, 9.14, 8.49, 8.34; LC/MS (ESI, m/z): [(M+1)]$^+$=1407.5.

Step 4

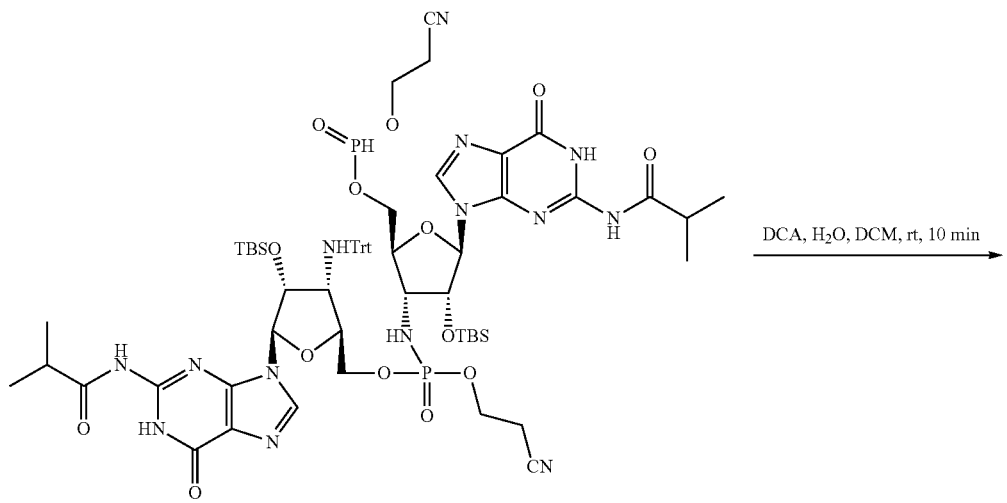

167

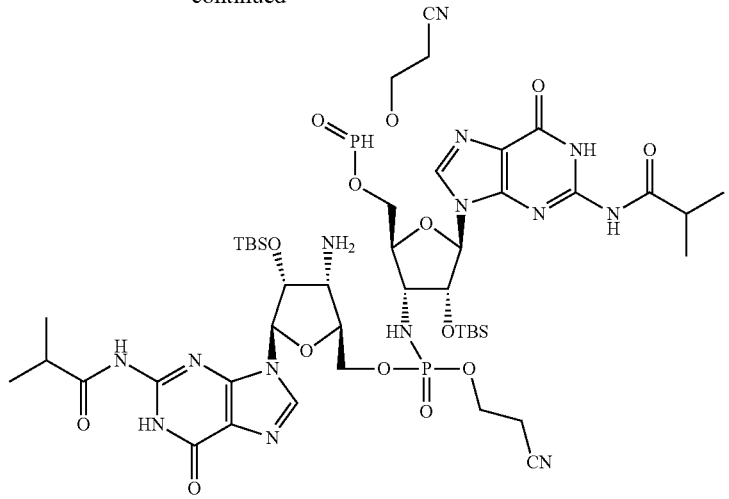

168

(((2S,3R,4R,5R)-3-amino-4-(tert-butyldimethylsilyloxy)-5-(2-isobutyramido-6-oxo-1,6-dihydropurin-9-yl)-tetrahydrofuran-2-yl)methyl 2-cyanoethyl (2S,3R,4R,5R)-4-(tert-butyldimethylsilyloxy)-2-(((2-cyanoethoxy)hydrophosphoryloxy)methyl)-5-(2-isobutyramido-6-oxo-1,6-dihydropurin-9-yl)-tetrahydrofuran-3-ylphosphoramidate (168)

To a solution of ((2S,3R,4R,5R)-4-(tert-butyldimethylsilyloxy)-5-(2-isobutyramido-6-oxo-1,6-dihydropurin-9-yl)-3-(tritylamino)-tetrahydrofuran-2-yl)methyl 2-cyanoethyl (2S,3R,4R,5R)-4-(tert-butyldimethylsilyloxy)-2-(((2-cyanoethoxy)hydrophosphoryloxy)methyl)-5-(2-isobutyramido-6-oxo-1,6-dihydropurin-9-yl)-tetrahydrofuran-3-ylphosphoramidate (167, 800 mg, 0.57 mmol) in dichloromethane (15 mL) were added water (0.51 mL) and dichloroacetic acid (0.47 mL, 5.7 mmol). The resulting solution was stirred for 10 min at ambient temperature, Upon completion, the is reaction was quenched by the addition of saturated aqueous solution of sodium bicarbonate (30 mL). The resulting mixture was extracted with dichloromethane (3×30 mL). The organic layers were combined and dried over anhydrous sodium sulfate. After filtration, the filtrate was concentrated under reduced pressure to afford the title compound 168, which was used in the next step without further purification: LC/MS (ESI, m/z): [(M+1)]$^+$=1165.4.

Step 5

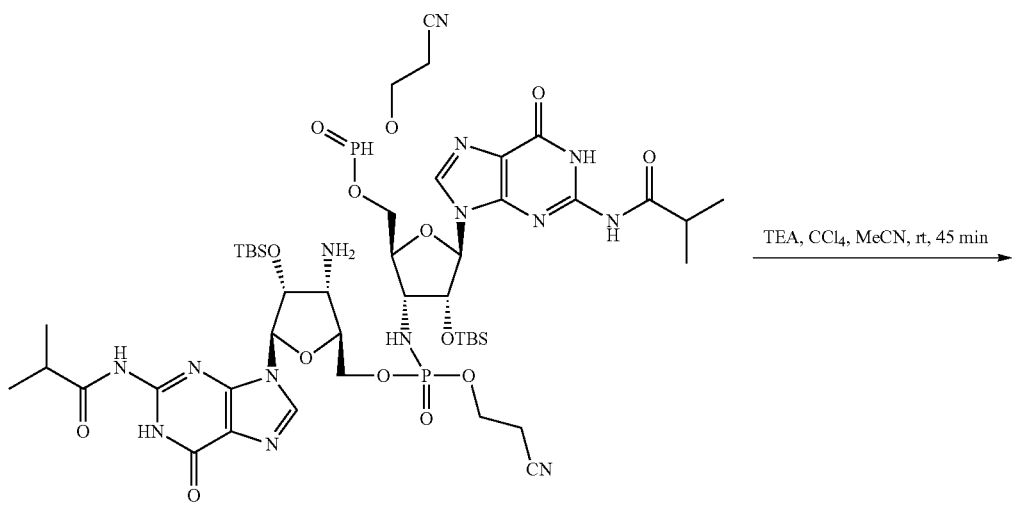

168

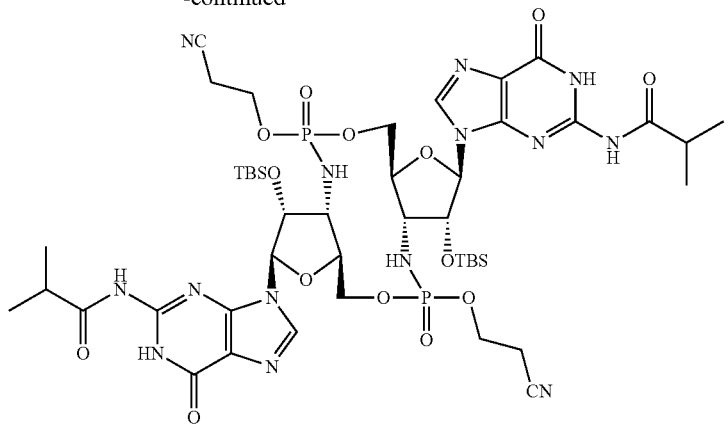

169

N-{9-[(1R,6S,8R,9R,10R,15S,17R,18R)-9,18-bis[(tert-butyldimethylsilyl)oxy]-3,12-bis(2-cyanoethoxy)-17-[2-(2-methylpropanamido)-6-oxo-6,9-dihydro-1H-purin-9-yl]-3,12-dioxo-4,7,13,16-tetraoxa-2,11-diaza-3$\lambda^s$,12$\lambda^s$-diphosphatricyclo[13.3.0.0$^{6,10}$]octadecan-8-yl]6-oxo-6,9-dihydro-1H-purin-2-yl}-2-methylpropanamide (169)

To a solution of the above crude compound 168 in acetonitrile (80 mL) were added triethylamine (1.4 mL) and carbon tetrachloride (1.4 mL). The resulting solution was stirred for 10 min at ambient temperature. Upon completion, the resulting solution was concentrated under reduced pressure to afford the crude title compound 169, which was used in the next step without further purification: LC/MS (ESI, m/z): [(M+1)]$^+$=1163.5.

Step 6

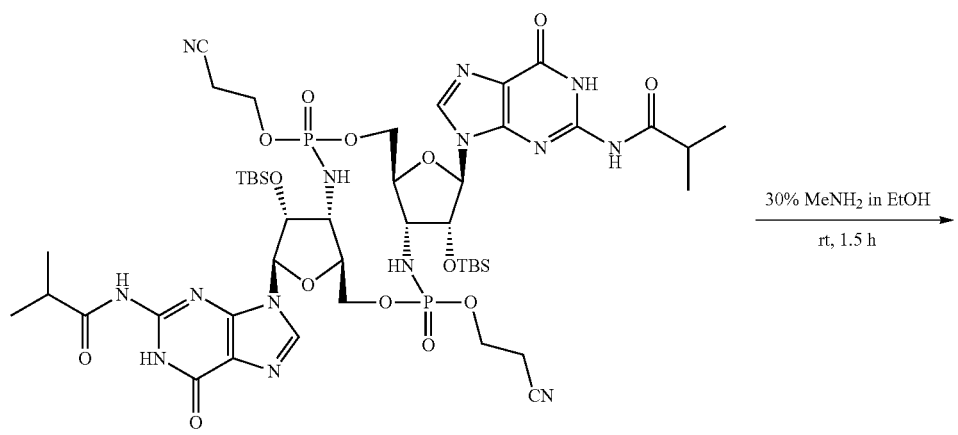

169

30% MeNH$_2$ in EtOH
rt, 1.5 h

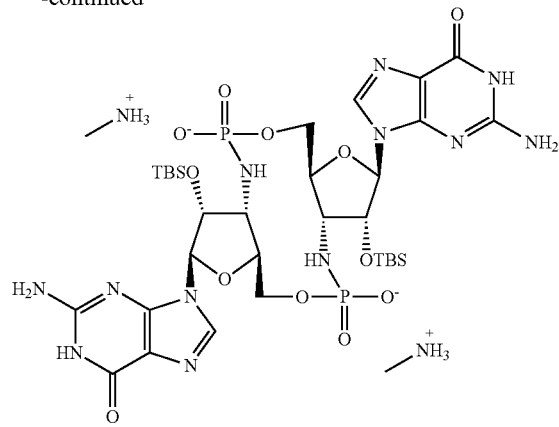

170

(1R,6S,8R,9R,10R,15S,17R,18R)-8,17-bis(2-amino-6-oxo-6,9-dihydro-1H-purin-9-yl)-9,18-bis[(tert-butyldimethylsilyl)oxy]-3,12-dihydroxy-4,7,13,16-tetraoxa-2,11-diaza-3λ$^s$,12λ$^s$-diphosphatricyclo[13.3.0.0$^{6,10}$]octadecane-3,12-dione (170)

The above crude compound was treated with a solution of methylamine in ethanol (14 mL, 30%, w/w) for 30 min at ambient temperature. Upon completion, the resulting solution was concentrated under reduced pressure to afford the title compound 170 as a colorless solid, which was used in the next step without further purification: LC/MS (ESI, m/z): [(M−2MeNH$_2$+1)]$^+$=917.7.

Step 7

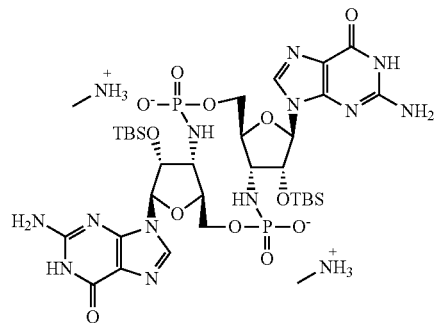

170

TEA·3 HF,
TEA,
Py, 60° C.,
2 h
—————→
over four steps: 15%

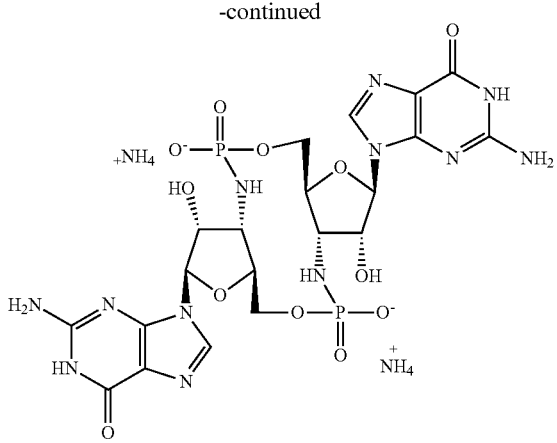

75 diammonium (1S,6S,8R,9R,10S,15S,17R,18R)-8,17-bis(2-amino-6-oxo-6,9-dihydro-1H-purin-9-yl)-9,18-dihydroxy-3,12-dioxo-4,7,13,16-tetraoxa-2,11-diaza-3λ$^s$,12λ$^s$-diphosphatricyclo[13.3.0.0$^{6,10}$]octadecane-3,12-bis(olate) (75)

To a solution of the above crude compound in pyridine (3 mL) were added triethylamine (0.42 mL) and triethylamine trihydrofluoride (1.18 g, 14.00 mmol). The resulting solution was stirred for 2 hours at 60° C. After cooling down to ambient temperature, acetone (30 mL) was added to precipitate the crude product which was purified by Prep-HPLC with the following conditions: Column: Atlantis Prep T3 OBD Column, 19*250 mm, 10 um; Mobile Phase A: water (plus 20 mmol/L of NH$_4$HCO$_3$), Mobile Phase B: ACN; Flow rate: 20 mL/min; Gradient: 0% B to 12% B in 10 min; Detector: 254/220 nm; Retention time: 9.35 min; to afford the title compound 75 as a colorless solid (50.7 mg, 15%): $^1$H NMR (400 MHz, D$_2$O) δ 8.06 (s, 2H), 5.74 (s, 2H), 4.47 (s, 2H), 4.19 (d, J=11.8 Hz, 2.3H), 4.09-3.98 (m, 6.5H); $^{31}$P NMR (162 MHz, D$_2$O) δ 6.97; LC/MS (ESI, m/z): [(M−2NH$_3$−1)]$^−$=687.1.

Diammonium [(1S,6S,8R,9R,10S,15S,17R,18R)-8,17-bis(2-amino-6-oxo-6,9-dihydro-1H-purin-9-yl)-9,18-dihydroxy-3,12-dioxo-12-sulfanidyl-4,7,13,16-tetraoxa-2,11-diaza-3λ$^s$,12λ$^s$-diphosphatricyclo[13.3.0.0$^{6,10}$]octadecan-3-yl]sulfanide
76
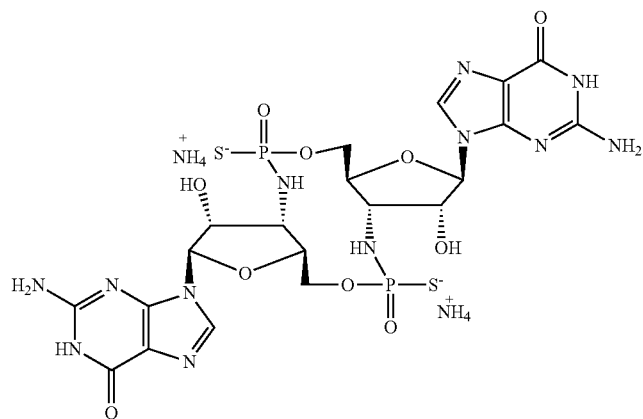
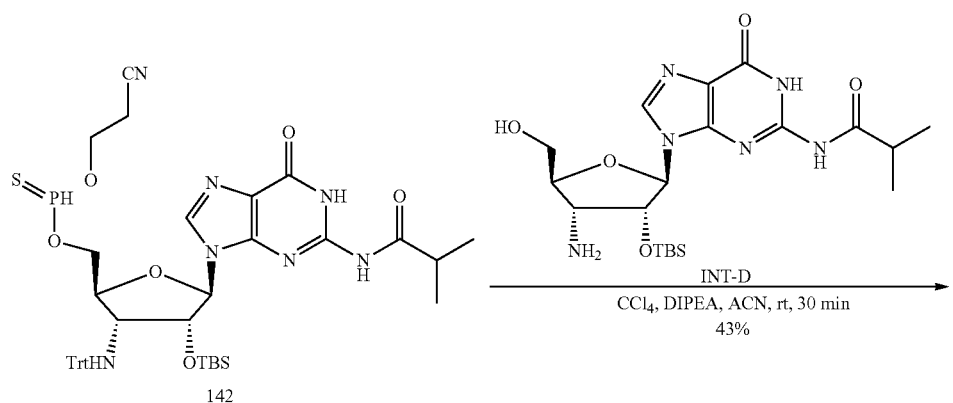
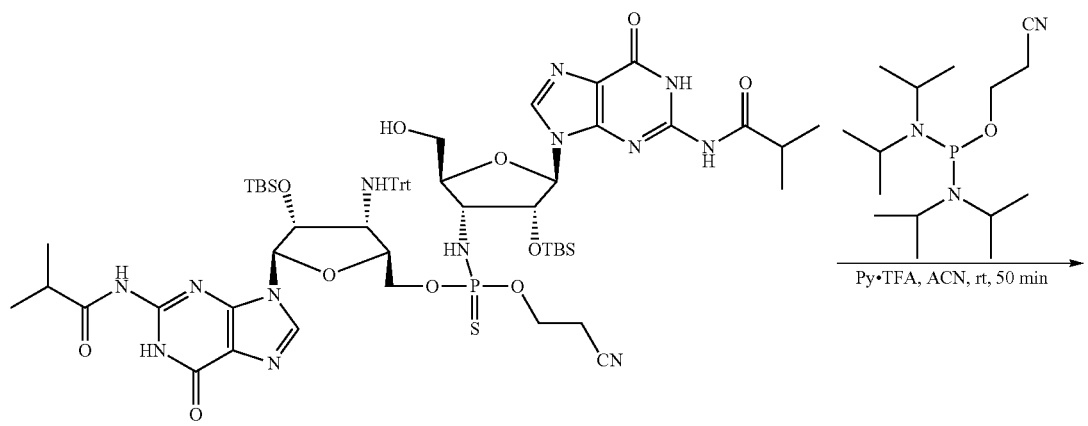

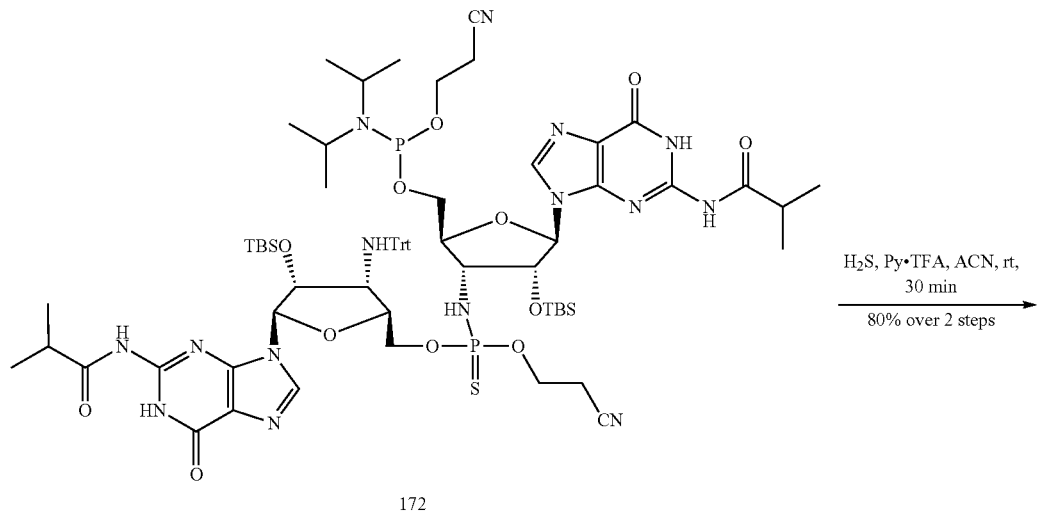
172
H₂S, Py·TFA, ACN, rt, 30 min
80% over 2 steps
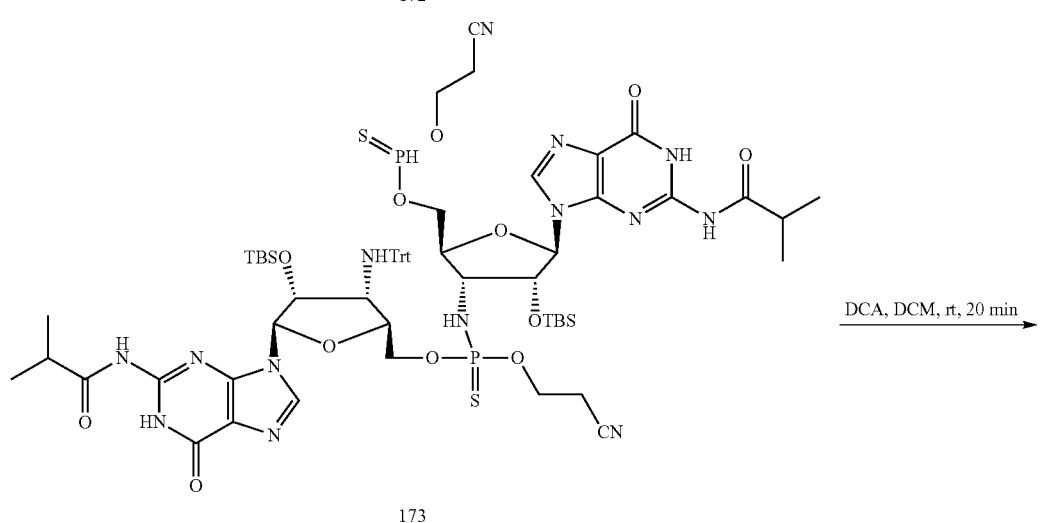
173
DCA, DCM, rt, 20 min
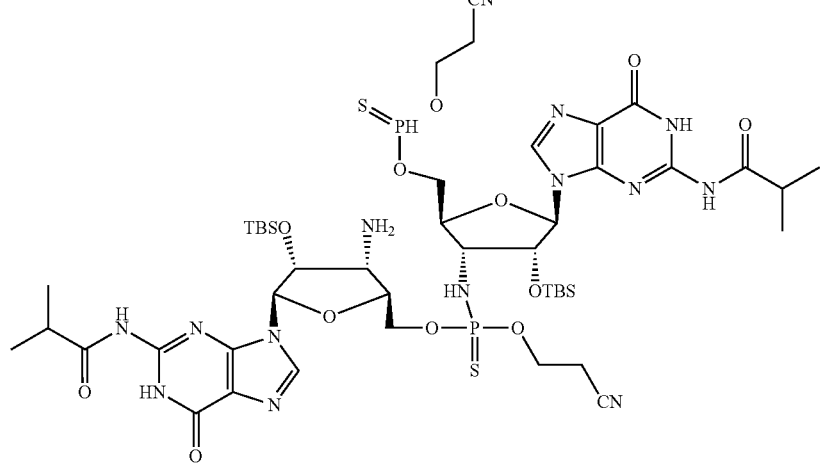
174

-continued
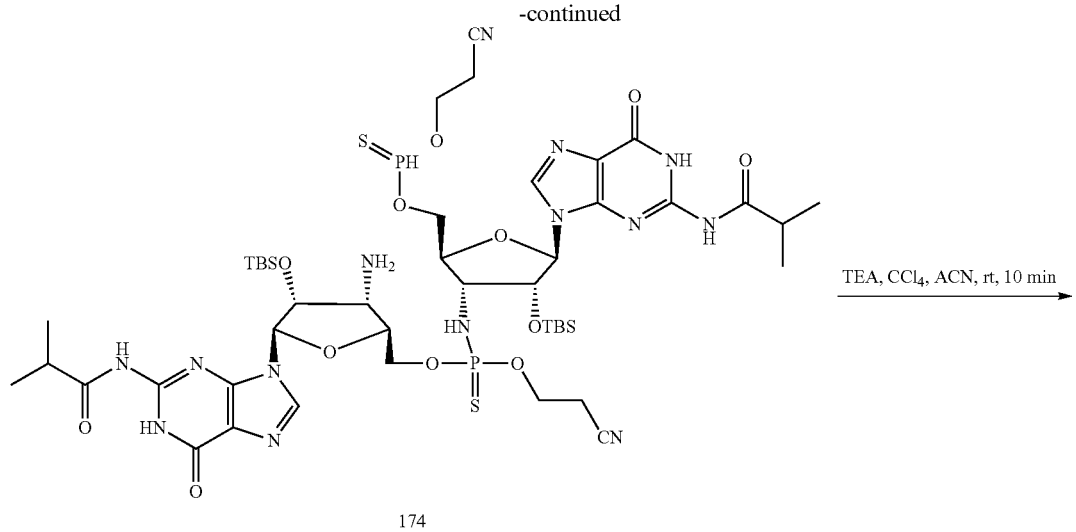
174
TEA, CCl₄, ACN, rt, 10 min
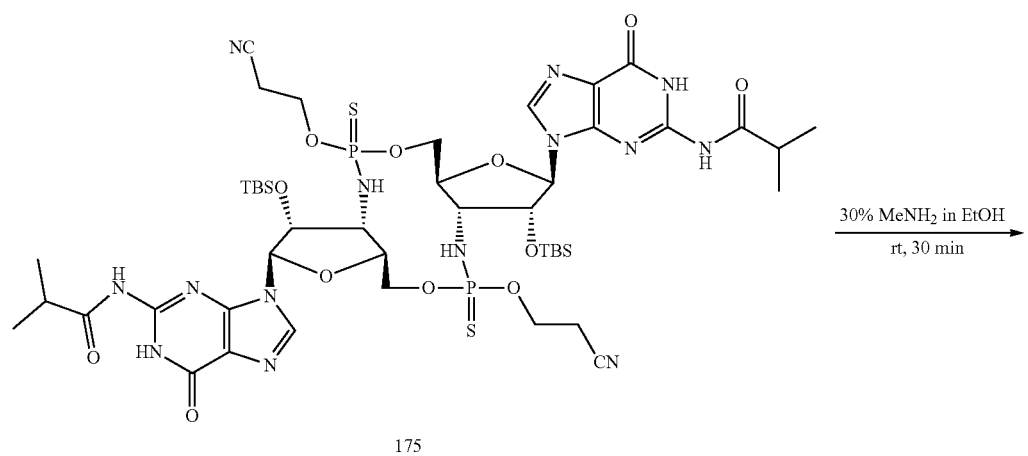
175
30% MeNH₂ in EtOH
rt, 30 min
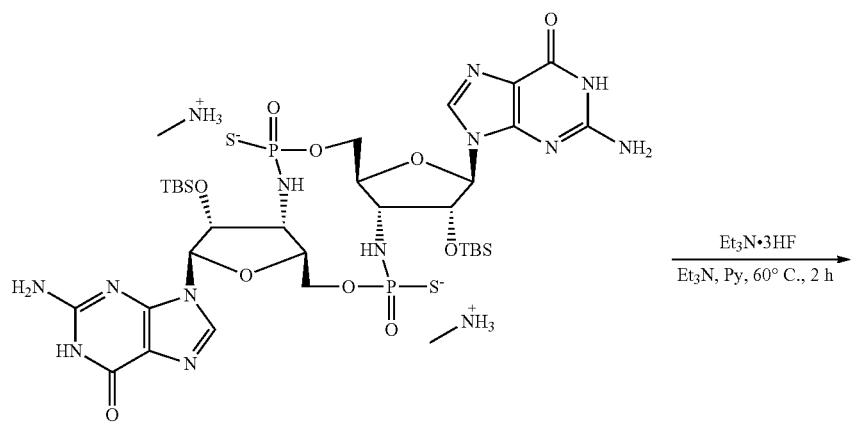
176
Et₃N·3HF
Et₃N, Py, 60° C., 2 h

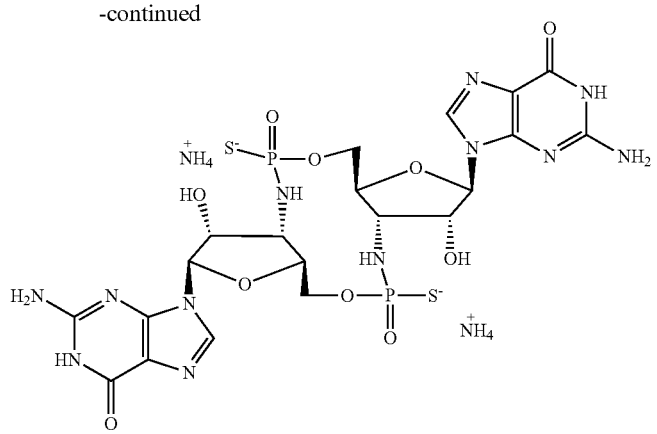
76
Step 1
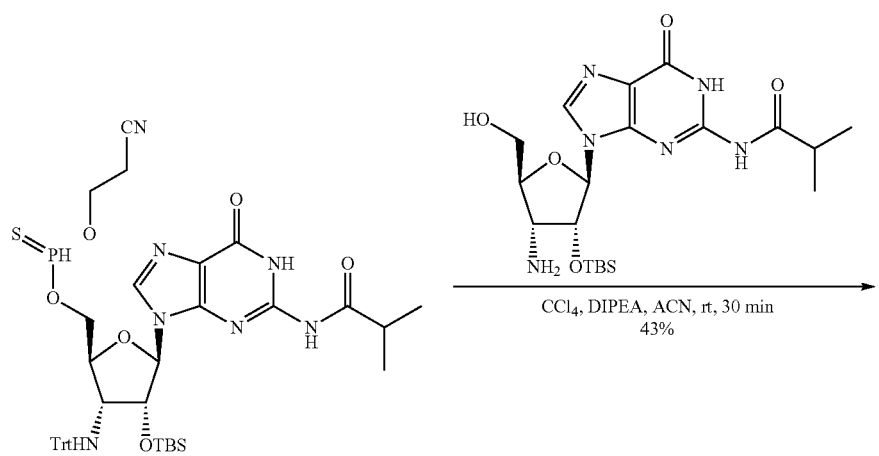
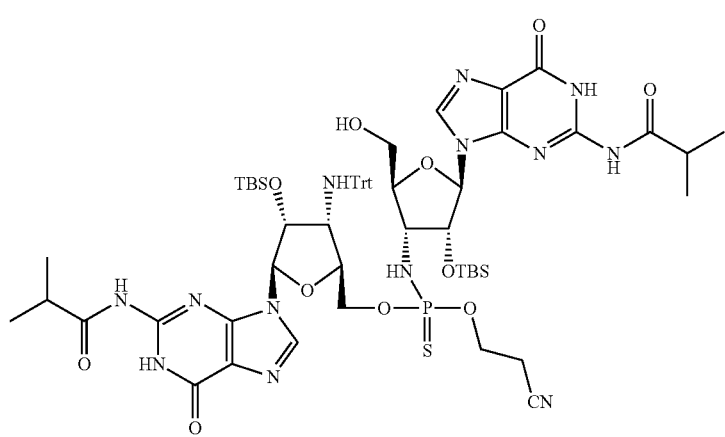

O-(((2S,3R,4R,5R)-4-((tert-butyldimethylsilyl)oxy)-5-(2-isobutyramido-6-oxo-1H-purin-9(6)-yl)₃-(tritylamino)tetrahydrofuran-2-yl)methyl) O-(2-cyanoethyl) ((2S,3R,4R,5R)-4-(tert-butyldimethylsilyl)oxy)-2-(hydroxymethyl)-5-(2-isobutyramido-6-oxo-1H-purin-9(6H-yl)tetrahydrofuran-3-yl) phosphoramidothioate (171)

To a mixture of [(3S,5R)-4-[(tert-butyldimethylsilyl)oxy]-5-[2-(2-methylpropanamido)-6-oxo-6,9-dihydro-1H-purin-9-yl]-3-[(triphenylmethyl)amino]oxolan-2-yl]methyl 2-cyanoethyl sulfanylidenephosphonite (142, 1.20 g, 1.42 mmol) and N-9-[(2R,4S)-4-amino-3-[(tert-butyldimethylsilyl)oxy]-5-(hydroxymethyl)oxolan-2-yl]-6-oxo-6,9-dihydro-1H-purin-2-yl-2-methylpropanamide (0.67 g, 1.42 mmol) in acetonitrile (15 mL) were added N,N-diisopropylethylamine (0.48 mL, 2.84 mmol) and carbon tetrachloride (0.60 mL, 5.68 mmol). The resulting solution was stirred for 30 min at ambient temperature. Upon completion, the resulting mixture was applied onto a reversed phase C18 column, eluting with 75%~99% (25 min) acetonitrile in water to afford the title compound 171 (two isomers: isomer A and isomer B) as a colorless solid: Isomer A (faster eluting part, eluted with 95% acetonitrile) (325 mg, 18%): ¹H NMR (400 MHz, DMSO-d₆) δ 12.10 (s, 2H), 11.45 (d, J=15.3 Hz, 2H), 8.19 (d, J=2.6 Hz, 2H), 7.54-7.47 (m, 6H), 7.37 (t, J=7.7 Hz, 6H), 7.31-7.22 (m, 3H), 6.23 (d, J=6.6 Hz, 1H), 5.75 (d, J=4.9 Hz, 1H), 5.33 (dd, J=11.2, 7.3 Hz, 1H), 5.00 (t, J=5.3 Hz, 1H), 4.82 (s, 1H), 4.52 (t, J=5.3 Hz, 1H), 4.05 (q, J=9.8 Hz, 1H), 3.98-3.80 (m, 5H), 3.69 (t, J=9.3 Hz, 1H), 3.55 (dd, J=11.5, 5.0 Hz, 1H), 3.46-3.33 (m, 1H), 3.27 (d, J=2.2 Hz, 1H), 2.79 (dtd, J=19.7, 6.3, 4.4 Hz, 5H), 1.25 (d, J=3.1 Hz, 2H), 1.17-1.09 (m, 10H), 0.75 (s, 9H), 0.67 (s, 9H), −0.09--0.24 (m, 9H), −0.39 (s, 3H); ³¹P NMR (162 MHz, DMSO-d₆) δ 73.63; LC/MS (ESI, m/z): [(M+1)]⁺=1306.5. And isomer B (slower eluting part, eluted with 99% acetonitrile) (452 mg, 25%): ¹H NMR (400 MHz, DMSO-d₆) δ 12.14 (d, J=7.5 Hz, 2H), 11.48 (d, J=18.3 Hz, 2H), 8.18 (s, 1H), 8.11 (s, 1H), 7.51-7.44 (m, 6H), 7.33 (t, J=7.7 Hz, 6H), 7.23 (dd, J=8.2, 6.4 Hz, 3H), 6.14 (d, J=5.7 Hz, 1H), 5.82 (d, J=4.7 Hz, 1H), 5.56 (d, J=9.9 Hz, 1H), 5.11 (t, J=5.2 Hz, 1H), 4.50 (t, J=5.2 Hz, 1H), 4.22 (s, 1H), 3.95 (dd, J=13.6, 7.2 Hz, 6H), 3.79 (d, J=9.4 Hz, 1H), 3.64 (s, 1H), 3.48 (s, 1H), 3.21 (s, 1H), 2.90-2.75 (m, 4H), 1.14 (ddd, J=10.0, 6.8, 1.6 Hz, 12H), 0.75 (d, J=5.0 Hz, 18H), −0.05 (s, 3H), −0.14 (d, J=2.6 Hz, 6H), −0.35 (s, 3H); ³¹P NMR (162 MHz, DMSO-d₆) δ 73.21; LC/MS (ESI, m/z): [(M+1)]⁺=1306.5. Isomer A and isomer B were independently carried through the remainder of the steps (Step 2 through Step 7).

Step 2

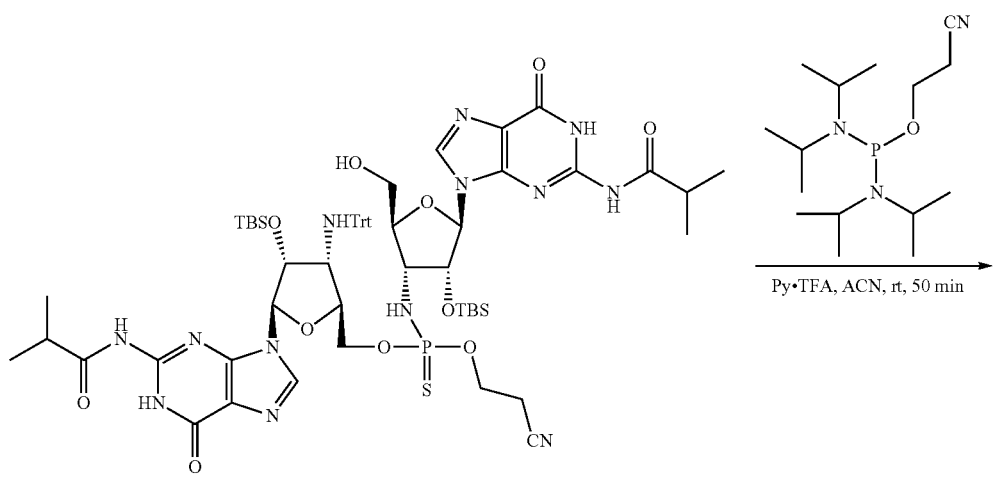

171

-continued

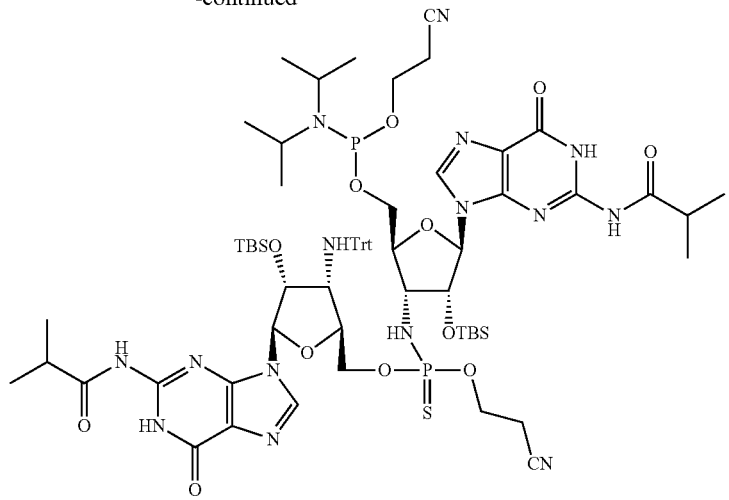

172

O-(((2S,3R,4R,5R)-4-((tert-butyldimethylsiloxy)-5-(2-isobutyramido-6-oxo-1H-purin-9(6H)-yl)-3-(tritylamino)tetrahydrofuran-2-yl)methyl) O-(2-cyanoethyl) ((2S,3R,4R,5R)-4-((tert-butyldimethylsilyl)oxy)-2-((((2-cyanoethoxy)(diisopropylamino)phosphino)oxy)methyl)-5-(2-isobutyramido-6-oxo-1H-purin-9(6H)-yl)tetrahydrofuran-3-yl) phosphoramidothioate (172)

To a solution of O-(((2S,3R,4R,5R)-4-((tert-butyldimethylsilyl)oxy)-5-(2-isobutyramido-6-oxo-1H-purin-9(6H)-yl)-3-(tritylamino)tetrahydrofuran-2-yl)methyl) O-(2-cyanoethyl) ((2S,3R,4R,5R)-4-((tert-butyldimethylsilyl)oxy)-2-(hydroxymethyl)-5-(2-isobutyramido-6-oxo-1H-purin-9(6H)-yl)tetrahydrofuran-3-yl)phosphoramidothioate (171 isomer A, 325 mg, 0.25 mmol) in acetonitrile (2 mL) were added 3-(bis[bis(propan-2-yl)amino]phosphanyloxy)propanenitrile (150 mg, 0.50 mol) and pyridinium trifluoroacetate (72 mg, 0.37 mmol). The resulting mixture was stirred for 50 min at ambient temperature and was used in the next step directly.

Step 3

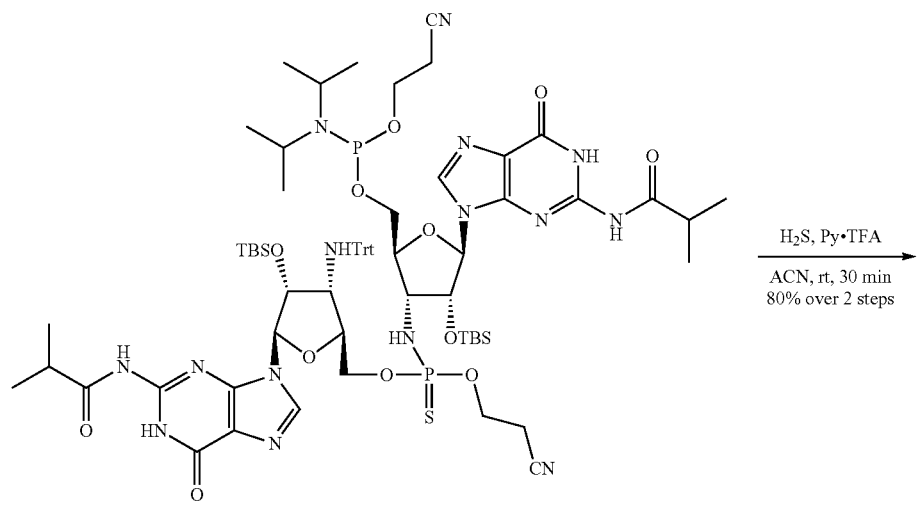

172

-continued

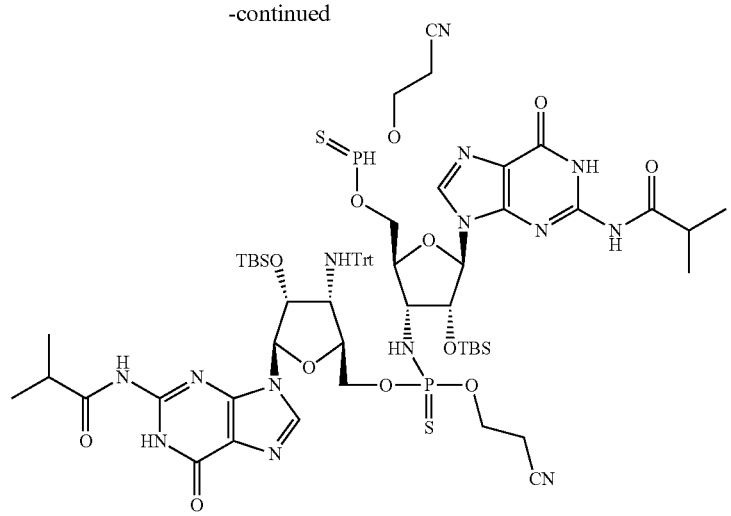

173

O-[(2S,3R 4R,5R)-4-[(tert-butyldimethylsilyl)oxy]-3-[({[(2S,3R,4R,5R)-4-[(tert-butyldimethylsilyl)oxy]-5-[2-(2-methylpropanamido)-6-oxo-6,9-dihydro-1H-purin-9-yl]-3-[(triphenylmethyl)amino]oxolan-2-yl]methoxy}(2-cyanoethoxy)sulfanylidene-$\lambda^s$-phosphanyl)amino]-5-[2-(2-methylpropanamido)-6-oxo-6,9-dihydro-1H-purin-9-yl]oxolan-2-yl]methyl O-2-cyanoethyl Phosphonothioate (173)

To the above solution was bubbled with hydrogen sulfide for 1 min followed by the addition of pyridinium trifluoroacetate (72 mg, 0.37 mmol). After stirring for 30 min at ambient temperature, the resulting solution was applied onto a reversed phase C18 column, eluting with 75%~99% (25 min) acetonitrile in water to afford the desired compound as a colorless solid (278 mg, 80% for two steps): LC/MS (ESI, m/z): [(M+1)]$^+$=1439.9.

Step 4

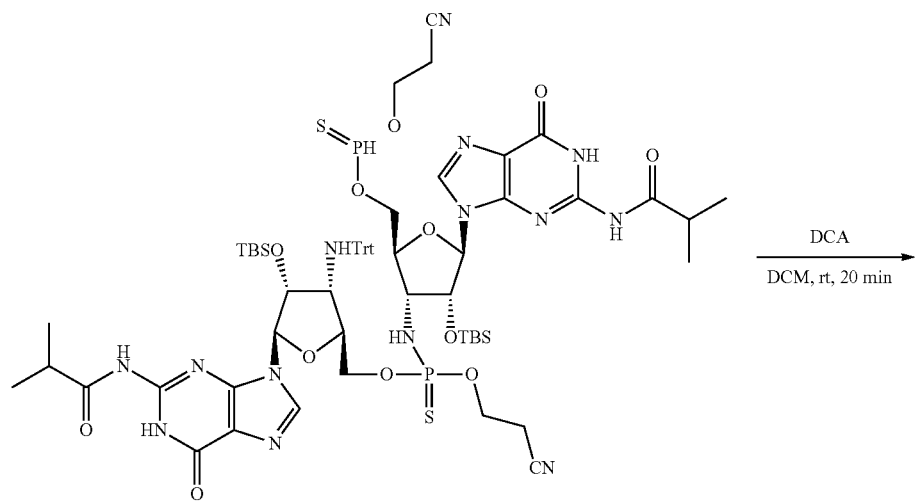

173

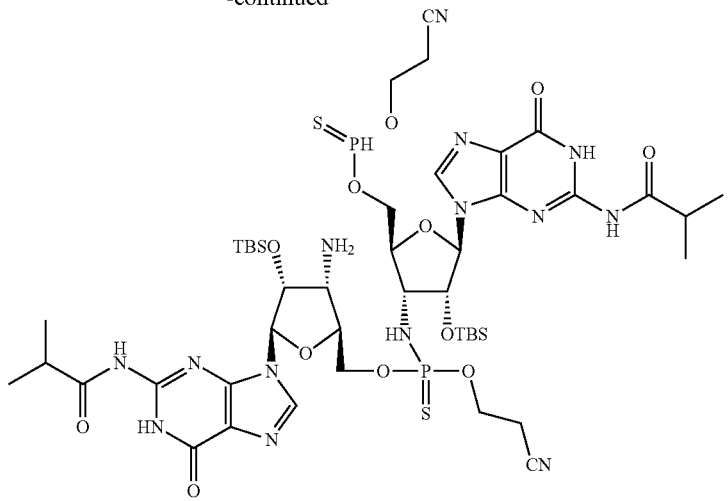

174

O-[(2S,3R,4R,5R)-3-[({[(2S,3R,4R,5R)-3-amino-4-[(tert-butyldimethylsilyl)oxy]-5-[2-(2-methylpropanamido)-6-oxo-6,9-dihydro-1H-purin-9-yl]oxolan-2-yl]methoxy}(2-cyanoethoxy)sulfanylidene-λ⁵-phosphanyl)amino]-4-[(tert-butyldimethylsilyl)oxy]-5-[(2-(2-methylpropanamido)-6-oxo-6,9-dihydro-1H-purin-9-yl]oxolan-2-yl]methyl O-2-cyanoethyl Phosphonothioate (174)

To a solution of O-[(2S,3R,4R,5R)-4-[(tert-butyldimethylsilyl)oxy]-3-[({[(2S,3R,4R,5R)-4-[(tert-butyldimethylsilyl)oxy]-5-[2-(2-methylpropanamido)-6-oxo-6,9-dihydro-1H-purin-9-yl]-3-[(triphenylmethyl)amino]oxolan-2-yl]methoxy}(2-cyanoethoxy)sulfanylidene-s-phosphanyl)amino]-5-[2-(2-methylpropanamido)-6-oxo-6,9-dihydro-1H-purin-9-yl]oxolan-2-yl]methyl O-2-cyanoethyl phosphonothioate (173, 278 mg, 0.19 mmol) in dichloromethane (4 mL) were added dichloroacetic acid (247 mg, 1.10 mmol) and water (17.4 mg, 0.97 mmol). The resulting solution was stirred for 20 min at ambient temperature. Upon completion, the reaction was quenched by the addition of saturated aqueous solution of sodium bicarbonate (30 mL). The resulting mixture was extracted with dichloromethane (3×30 mL). The organic layers were combined and dried over anhydrous sodium sulfate. After filtration, the filtrate was concentrated under reduced pressure to afford the title compound 174, which was used in the next step without further purification.

Step 5

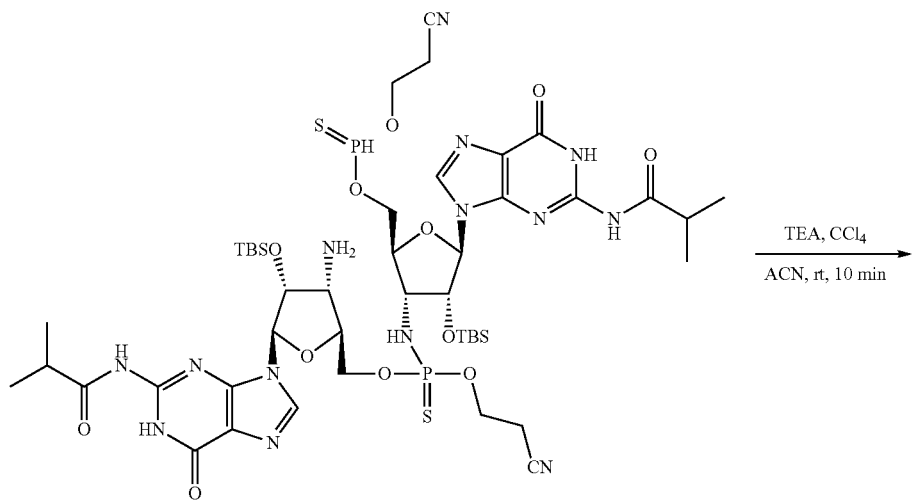

174

-continued

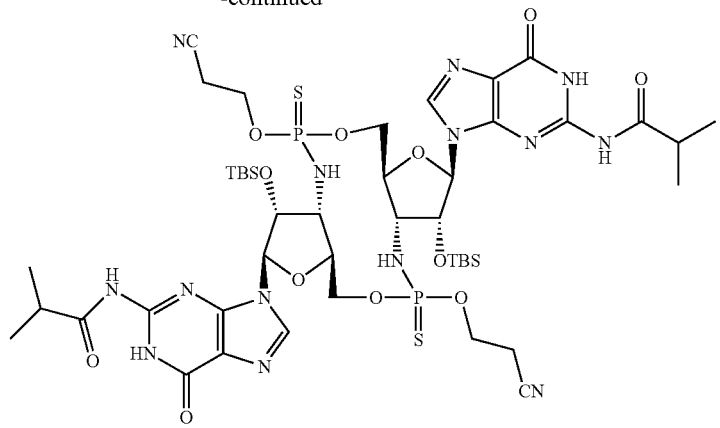

175

N-{9-[(1R,6S,8R,9R,10R,15S,17R,18R)-9,18-bis[(tert-butyldimethylsilyl)oxy]-3,12-bis(2-cyanoethoxy)-17-[2-(2-methylpropanamido)-6-oxo-6,9-dihydro-1H-purin-9-yl]-3,12-disulfanylidene-4,7,13,16-tetraoxa-2,11-diaza-3λ$^s$,12λ$^s$-diphosphatricyclo[13.3.0.0$^{6,10}$]octadecan-8-yl]-6-oxo-6,9-dihydro-1H-purin-2-yl}-2-methylpropanamide (175)

To a solution of the above crude compound 174 in acetonitrile (38.6 mL) were added triethylamine (0.77 mL) and carbon tetrachloride (0.77 mL). The resulting solution was stirred for 10 min at ambient temperature. Upon completion, the resulting solution was concentrated under reduced pressure to afford the crude title compound 175, which was used in the next step without further purification.

Step 6

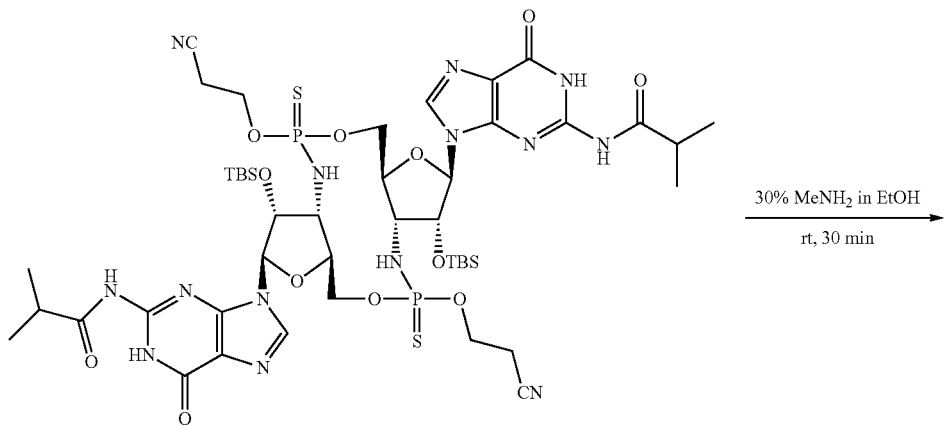

175

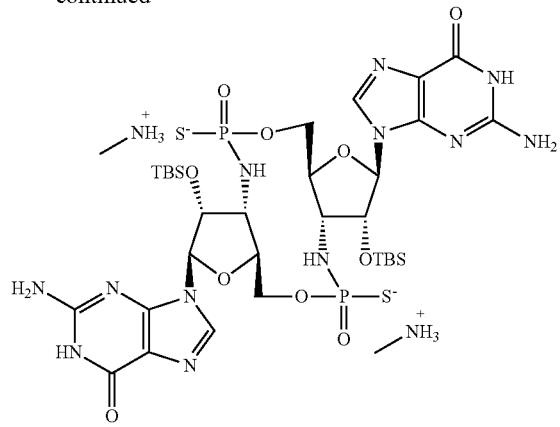

176

[(1R,6S,8R,9R,10R,15S,17R,18R)-8,17-bis(2-amino-6-oxo-6,9-dihydro-1H-purin-9-yl)-9,18-bis[(tert-butyldimethylsilyl)oxy]-3,12-dioxo-12-sulfanidyl-4,7,13,16-tetraoxa-2,11-diaza-3$\lambda^s$,12$\lambda^s$-diphosphatricyclo[13.3.0.0$^{6,10}$]octadecan-3-yl] sulfanide; bis(methanaminium) (176)

The above crude compound 175 was treated with a solution of methylamine in ethanol (14.4 mL, 30%, w/w) for 30 min at ambient temperature. Upon completion, the resulting solution was concentrated under reduced pressure to afford the title compound 176 as a colorless solid, which was used in the next step without further purification.

Step 7

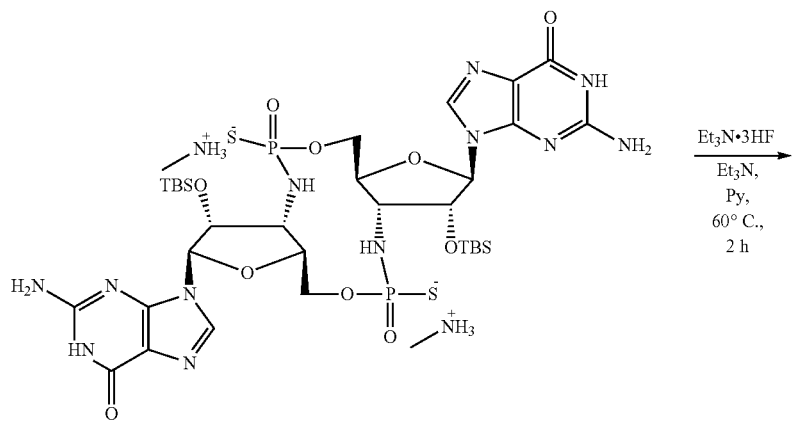

176

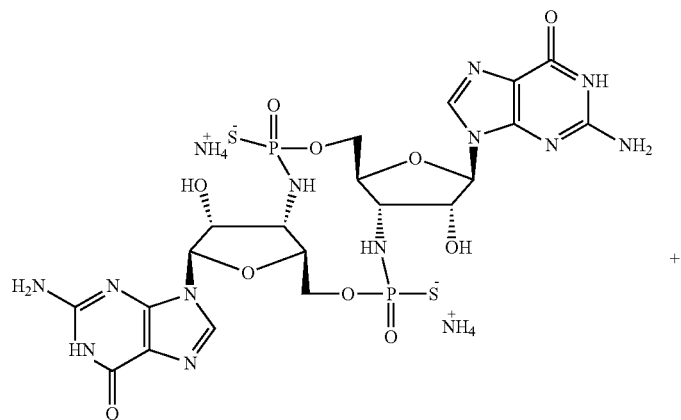

76

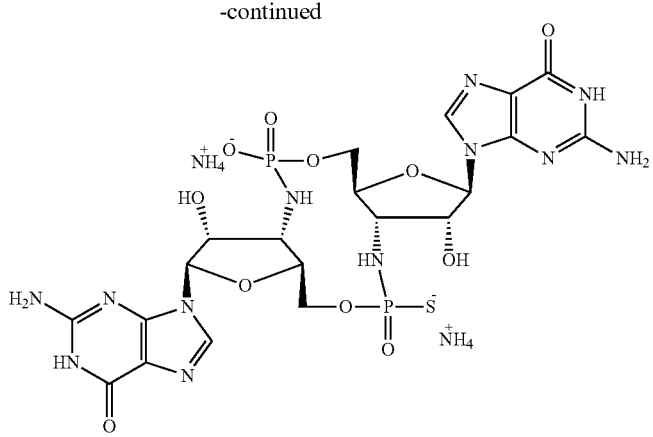

76-0A1

Diammonium [(1S,6S,8R,9R,10S,15S,17R,18R)-9,18-dihydroxy-8,17-bis[2-(2-methylpropanamido)-6-oxo-6,9-dihydro-1H-purin-9-yl]-3,12-dioxo-12-sulfanidyl-4,7,13,16-tetraoxa-2,11-diaza-3$\lambda^s$,12$\lambda^s$-diphosphatricyclo[13.3.0.0$^{6,10}$]octadecan-3-yl] sulfanide (76)

To a solution of the above crude compound 176 in pyridine (2.76 mL) were added triethylamine (0.41 mL) and triethylamine trihydrofluoride (2.2 mL). The resulting solution was stirred for 2 hours at 60° C. After cooling down to ambient temperature, acetone (55 mL) was added to precipitate the crude product which was purified by Prep-HPLC with the following conditions: column: Atlantis Prep T3 OBD column, 19×250 mm, 10 um; Mobile Phase A: water (plus 10 mmol/L of NH$_4$HCO$_3$); Mobile Phase B: ACN; Flow rate: 20 m/min; Gradient: 1% B to 12% B in 26 min; Detector: 254/220 nm; to afford the mixed phosphate/thiophosphate diammonium salt [(1S,6S,8R,9R,10S,15S,17R,18R)-8,17-bis(2-amino-6-oxo-6,9-dihydro-8.17H-purin-9-yl)-9,18-dihydroxy-12-oxido-3,12-dioxo-4,7,13,16-tetraoxa-2,11-diaza-3$\lambda^s$,12$\lambda^s$-diphosphatricyclo[13.3.0.0$^{6,10}$]octadecan-3-yl]sulfanide (the first eluting peak, retention time is 14.65 min, herein referred to 76-0A1) as a colorless solid (3.6 mg, 1.4%): $^1$H NMR (400 MHz, D$_2$O) δ 7.97 (d, J=11.2 Hz, 2H), 5.79 (d, J=5.1 Hz, 2H), 4.51 (s, 1H), 4.44 (s, 1H), 4.36 (d, J=12.0 Hz, 1H), 4.29-3.98 (m, 711); $^{31}$P NMR (162 MHz, D$_2$O) δ 57.92, 56.01, 54.65, 7.09; LC/MS (ESI, m/z): [(M−1)]$^-$=703.0. One isomer (the second eluting peak, retention time is 14.97 min, herein referred to 76-0A2) as a colorless solid (14.6 mg, 5.7%): $^1$H NMR (400 MHz, D$_2$O) δ 8.28 (s, 1H), 8.10 (s, 1H), 5.94 (s, 2H), 4.41-4.28 (m, 2H), 4.23-3.91 (m, 8H); $^{31}$P NMR (162 MHz, D$_2$O) δ 58.10, 54.47; LC/MS (ESI, m/z): [(M−1)]$^-$=718.95. And the other isomer (the third eluting peak, retention time is 22.75 min, herein referred to 76-0A3) as a colorless solid (22.8 mg, 8.9%): $^1$H NMR (400 MHz, D$_2$O) δ 10.33 (s, 2H), 7.96 (s, 2H), 6.36 (m, 4H), 6.24 (m, 2H), 6.03 (m, 3H); $^{31}$P NMR (162 MHz, D$_2$O) δ 56.81; LC/MS (ESI, m/z): [(M−1)]$^-$=718.9.

Steps 2-7 were performed on the isomer B obtained in step 1 to generate the last desired product, herein referred to as 76-0B1, which was purified by Prep-HPLC with the following conditions: column: XBridge Prep C18 OBD column 19×150 mm, 5 um; Mobile Phase A: water (plus 20 mmol/L of NH$_4$HCO$_3$); Mobile Phase B: ACN; Flow rate: 20 mL/min; Gradient: 1% B to 9% B in 8 min; Detector: 254/220 nm; retention time is 6.85 min (7.3 mg, yield for 5 steps is 3.8%): $^1$H NMR (300 MHz, D$_2$O) δ 8.24 (s, 1H), 8.04 (s, 1H), 5.88 (s, 2H), 4.37-4.21 (m, 2H), 4.20-3.86 (m, 8H); $^{31}$P NMR (121 MHz, D$_2$O) δ 58.03, 54.44; LC/MS (ESI, m/z): [(M−1)]$^-$=719.0. The isomers 76-0A2, 76-0A3, and 76-0B1 are believed to vary in stereochemical configuration at the phosphorus atoms.

Diammonium [(1R,6R,8R,9R,10R,15R,17R,18R)-8,17-bis(6-amino-9H-purin-9-yl)-9,18-difluoro-3,12-dioxo-12-sulfanidyl-2,7,11,16-tetraoxa-4,13-diaza-3$\lambda^s$,12$\lambda^s$-diphosphatricyclo[13.3.0.0$^{6,10}$]octadecan-3-yl]sulfanide

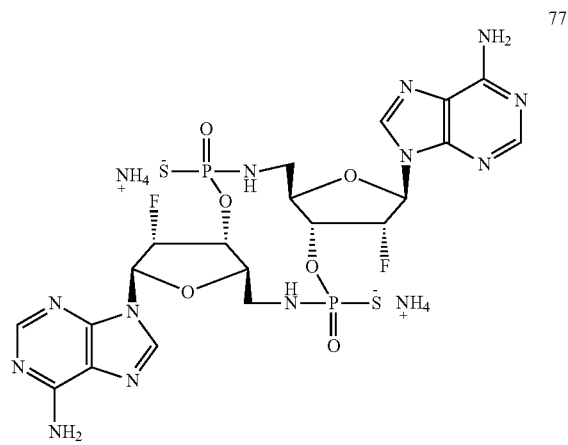

77

229
-continued
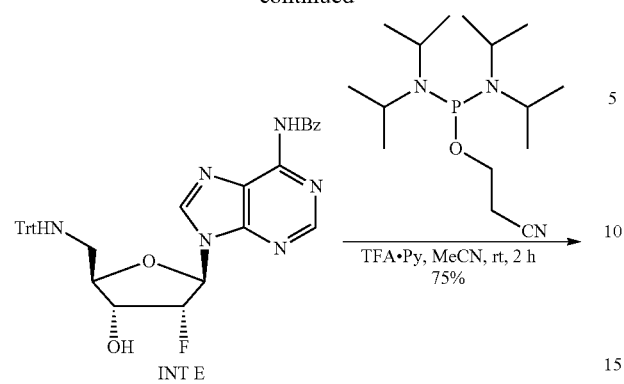
INT E
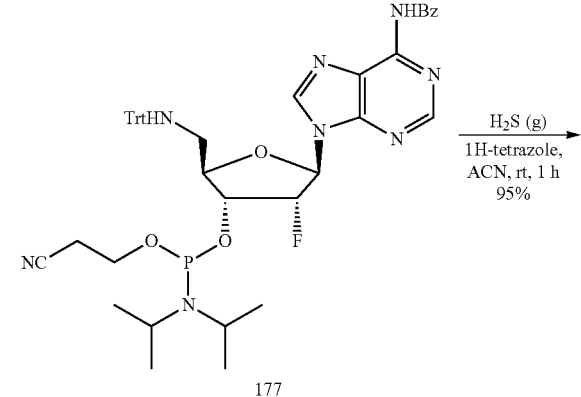
177
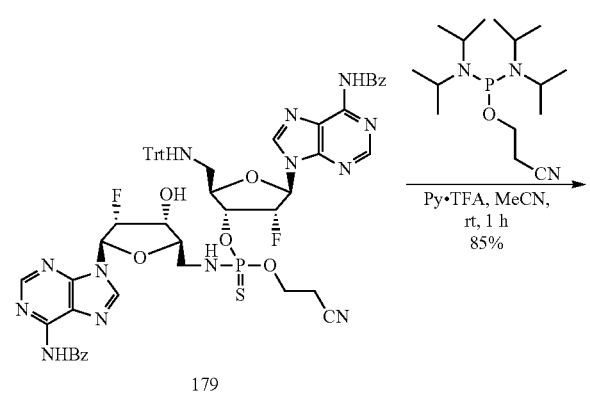
178
179
230
-continued
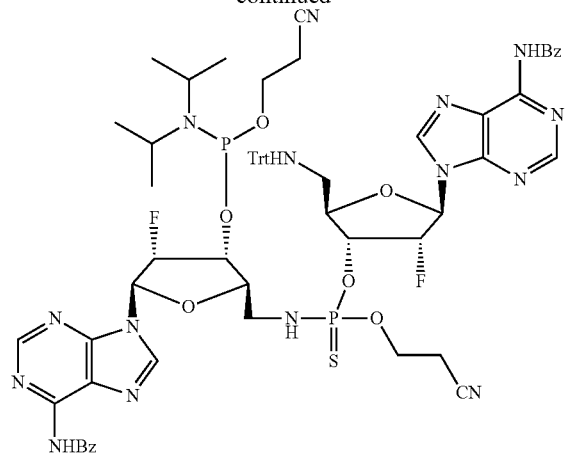
180
180
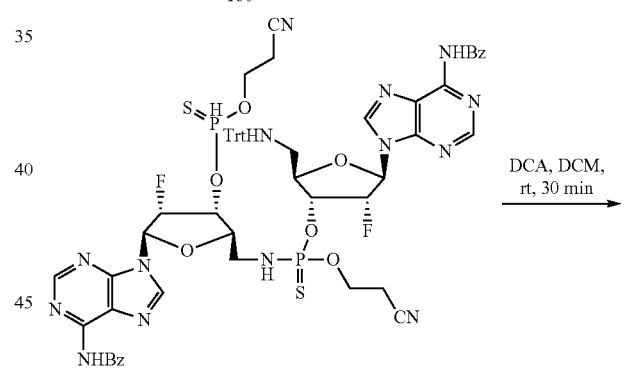
181
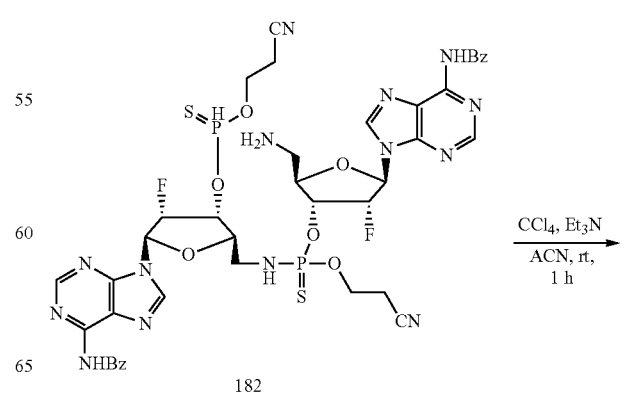
182

-continued

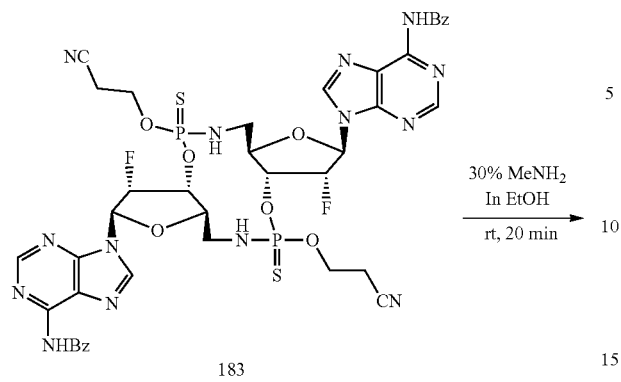
183

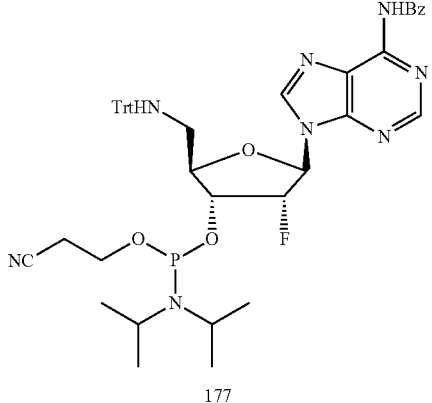
177

-continued (2R,3R,4R,5S)-5-(6-benzamido-9H-purin-9-yl)-4-fluoro-2-((tritylamino)methyl)tetrahydrofuran-3-yl (2-cyanoethyl) diisopropylphosphoramidite (177)

To a solution of N-(9-((2S,3R,4R,5R)-3-fluoro-4-hydroxy-5-((tritylamino)methyl)tetrahydrofuran-2-yl)-9H-purin-6-yl)benzamide (INT-E, 0.80 g, 1.31 mmol) in acetonitrile (5 mL) were added pyridinium trifluoroacetate (0.38 g, 1.91 mmol) and 3-(bis[bis(propan-2-yl)amino]phosphanyloxy)propanenitrile (0.78 g, 2.60 mmol). The resulting solution was stirred for 2 hours at ambient temperature. Upon completion, the resulting solution was applied onto a reversed phase C18 column, eluting with 70%~95% (25 min) acetonitrile in water to afford the title compound 177 as a colorless solid (0.8 g, 75%): $^1$H NMR (300 MHz, DMSO-$d_6$) δ 11.25 (s, 1H), 8.67 (d, J=2.5 Hz, 1H), 8.40-8.32 (m, 1H), 8.07 (d, J=7.5 Hz, 2H), 7.74-7.08 (m, 18H), 6.44 (ddd, J=19.5, 11.7, 2.9 Hz, 1H), 5.89 (dq, J=52.9, 3.8 Hz, 1H), 5.38-5.09 (m, 1H), 4.36-4.20 (m, 1H), 3.97-3.78 (m, 1H), 3.78-3.48 (m, 3H), 3.09-2.63 (m, 3H), 2.43 (d, J=5.3 Hz, 1H), 1.31-0.96 (m, 12H); $^{19}$F NMR (282 MHz, DMSO-$d_6$) δ −200.77, −200.79, −201.31, −201.36; $^{31}$P NMR (121 MHz, DMSO-$d_6$) δ 149.59, 149.50, 149.45; LC/MS (ESI, m/z): [(M+1)]$^+$=787.0.

77

Step 1

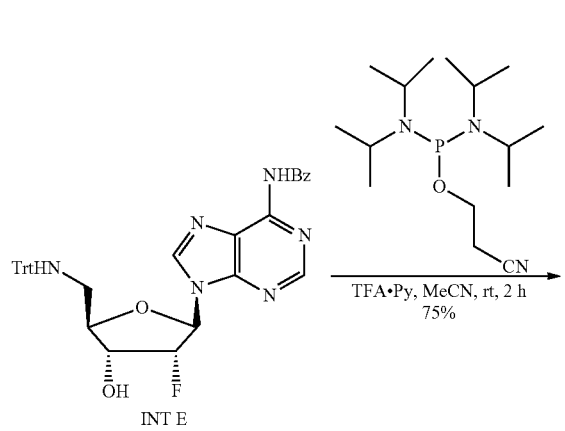

Step 2

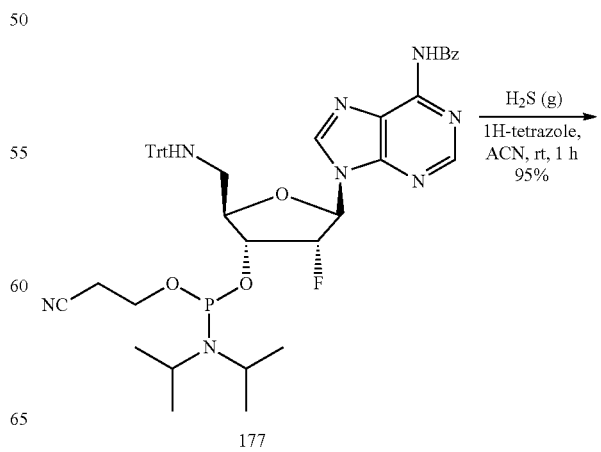
177

-continued

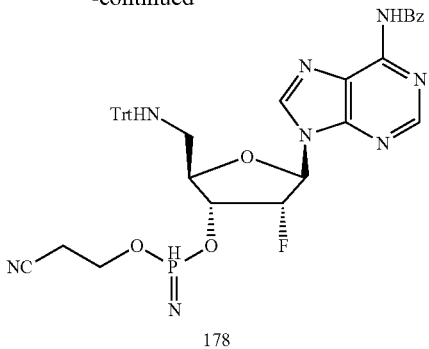

178

O-((2R,3R,4R,5S)-5-(6-benzamido-9H-purin-9-yl)-4-fluoro-2-((tritylamino)methyl)tetrahydrofuran-3-yl) O-(2-cyanoethyl) Phosphonothioate (178)

To a mixture of (2R,3R,4R,5S)-5-(6-benzamido-9H-purin-9-yl)-4-fluoro-2-((tritylamino)methyl)tetrahydrofuran-3-yl (2-cyanoethyl) diisopropylphosphoramidite (177, 0.80 g, 0.98 mmol) and 1H-1,2,3,4-tetrazole (69 mg, 0.98 mmol) in dry acetonitrile (5 mL) was bubbled hydrogen sulfide for 1 min at ambient temperature. The resulting solution was sealed and stirred for another 1 hour at ambient temperature. Upon completion, the resulting solution was applied onto a reversed phase C18 column, eluting with 70%~95% (25 min) acetonitrile in water to afford the title compound 178 as a colorless solid (0.70 g, 95%): $^1$H NMR (400 MHz, DMSO-$d_6$) δ 11.26 (s, 1H), 8.66-8.65 (m, 1H), 8.41 (s, 1H), 8.08-8.04 (m, 2H), 7.70-7.20 (m, 18H), 6.46 (dd, J=18.2, 2.6 Hz, 1H), 6.16-5.24 (m, 2H), 4.65-4.50 (m, 1H), 4.37-3.83 (m, 4H), 3.11-2.93 (m, 1H), 2.93-2.72 (m, 3H); $^{19}$F NMR (376 MHz, DMSO-$d_6$) δ −201.20, −203.22; $^{31}$P NMR (162 MHz, DMSO-$d_6$) δ −2.64; LC/MS (ESI, m/z): [(M+1)]$^+$= 748.0.

Step 3

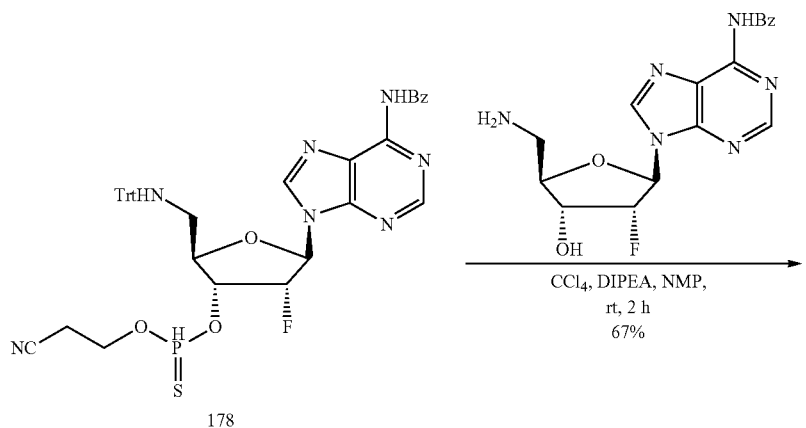

178

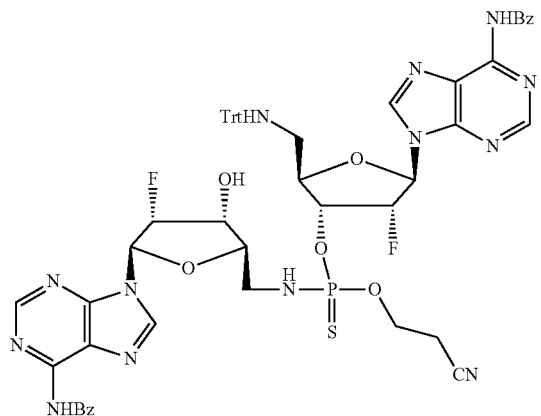

179

O-((2R,3R,4R,5R)-5-(6-benzamido-9H-purin-9-yl)-4-fluoro-2-((tritylamino)methyl)tetrahydrofuran-3-yl)O-(2-cyanoethyl) (((2R,3R,4R,5R)-5-(6-benzamido-9H-purin-9-yl)-4-fluoro-3-hydroxytetrahydrofuran-2-yl)methyl) phosphoramidothioate (179)

To a solution of O-((2R,3R,4R,5S)-5-(6-benzamido-9H-purin-9-yl)-4-fluoro-2-((tritylamino)methyl)tetrahydrofuran-3-yl)O-(2-cyanoethyl) phosphonothioate (178, 0.70 g, 0.94 mmol) in N-methyl pyrrolidone (5 mL) were added N,N-diisopropylethylamine (0.48 g, 3.76 mmol), N-(9-((2S,3R,4R,5R)-5-(aminomethyl)-3-fluoro-4-hydroxytetrahydrofuran-2-yl)-9H-purin-6-yl)benzamide (349 mg, 0.94 mmol) and carbon tetrachloride (0.58 mg, 3.76 mmol) at ambient temperature. The resulting solution was stirred for 2 hours at ambient temperature. Upon completion, the resulting solution was applied onto a reversed phase C18 column, eluting with 70%~95% (25 min) acetonitrile in water to afford the title compound 179 as a colorless solid (0.70 g, 67%): $^1$H NMR (300 MHz, DMSO-d$_6$) δ 11.26 (s, 2H), 8.78 (d, J=4.0 Hz, 1H), 8.74-8.59 (m, 2H), 8.15-7.96 (m, 5H), 7.73-7.06 (m, 22H), 6.53-6.25 (m, 3H), 6.13 (dq, J=51.3, 4.8 Hz, 1H), Hz, 1H), 2.32 (dt, J=11.3, 6.6 Hz, 1H); $^{19}$F NMR (282 MHz, DMSO-d$_6$) δ −204.01, −204.03, −204.33, −204.40; $^{31}$P NMR (121 MHz, DMSO-d$_6$) δ 74.35, 74.01; LC/MS (ESI, m/z): [(M+1)]$^+$1118.0.

Step 4

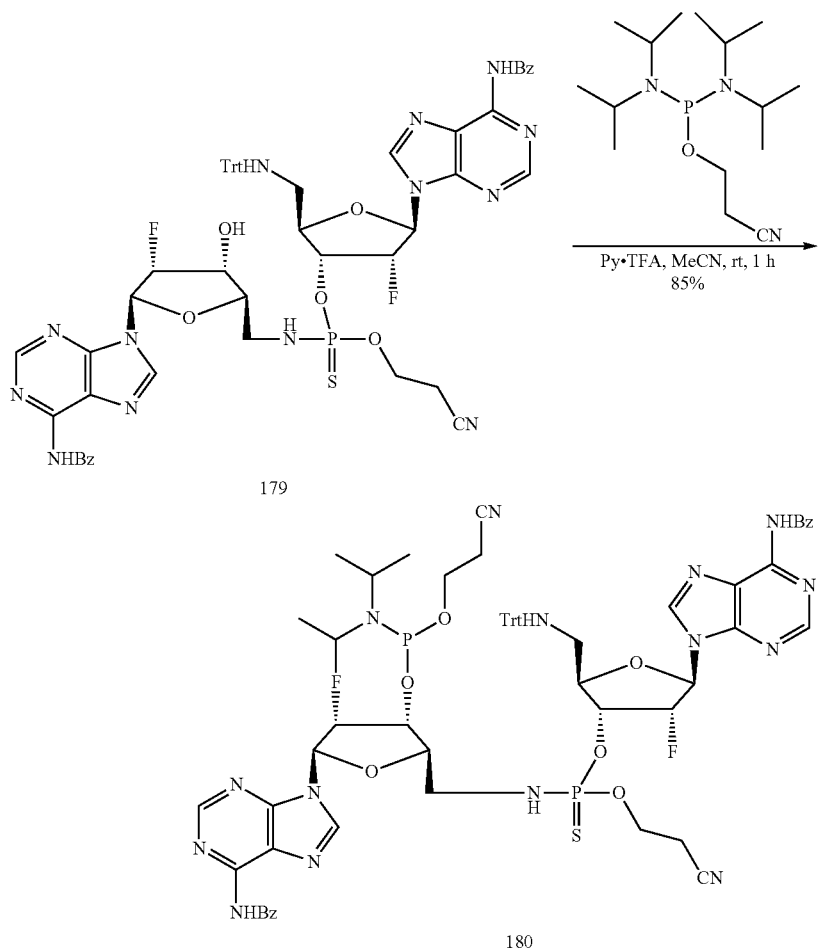

O-((2R,3R,4R,5R)-5-(6-benzamido-9H-purin-9-yl)-4-fluoro-2-((tritylamino methyl)tetrahydrofuran-3-yl)O-(2-cyanoethyl) (((2R,3R,4R,5R)-5-(6-benzamido-9H-purin-9-yl)-3-(((2-cyanoethoxy)(diisopropylamino)phosphino)oxy-4-fluorotetrahydrofuran-2-yl)methyl) phosphoramidothioate (180)

To a solution of O-((2R,3R,4R,5R)-5-(6-benzamido-9H-purin-9-yl)-4-fluoro-2-((tritylamino)methyl)tetrahydrofuran-3-yl)O-(2-cyanoethyl) (((2R,3R,4R,5R)-5-(6-benzamido-9H-purin-9-yl)-4-fluoro-3-hydroxytetrahydrofuran-2-yl)methyl)phosphoramidothioate (179, 0.70 g, 0.63 mmol) in acetonitrile (5 mL) were added pyridinium trifluoroacetate (0.18 g, 0.94 mmol) and 3-([bis[bis(propan-2-yl)amino]phosphanyl]oxy)propanenitrile (0.38 g, 1.25 mol). The resulting solution was stirred for 2 hours at ambient temperature. Upon completion, the resulting solution was applied onto a reversed phase C18 column, eluted with 70%~95% (25 min) acetonitrile in water to afford the title compound 180 as a colorless solid (0.7 g, 85%): $^1$H NMR (300 MHz, DMSO-d$_6$) δ 11.27 (s, 2H), 8.80-8.61 (m, 3H), 8.11-8.04 (m, 5H), 7.70-7.07 (m, 22H), 6.57-6.26 (m, 3H), 6.26-5.98 (m, 1H), 5.95-5.58 (m, 2H), 4.97 (dtt, J=22.5, 10.9, 6.8 Hz, 1H), 4.42 (dt, J=13.3, 4.0 Hz, 1H), 4.33-3.96 (m, 3H), 3.83 (dtd, J=14.6, 6.1, 3.8 Hz, 2H), 3.76-3.57 (m, 2H), 3.32-3.13 (m, 2H), 2.96-2.67 (m, 4H), 2.54 (d, J=9.3 Hz, 1H), 2.40-2.23 (m, 1H), 1.22-1.17 (m, 12H); $^{19}$F NMR (282 MHz, DMSO-d$_6$) δ −200.71, −200.74, −201.16, −201.21, −201.64, −201.67, −201.77, −201.81, −201.99, −202.01, −204.16, −204.33, −204.44, −204.61; $^{31}$P NMR (121 MHz, DMSO-d$_6$) δ 149.99, 149.93, 149.88, 149.85, 149.75, 149.64, 149.54, 74.72, 74.52, 74.14, 74.11; LC/MS (ESI, m/z): [(M+1)]$^+$=1318.0.

Step 5

O-(2R,3R,4R,5R)-5-(6-benzamido-9H-purin-9-yl)-2-{[({[(2R,3R,4R,5R)-5-(6-benzamido-9H-purin-9-yl)-4-fluoro-2-{[(triphenylmethyl)amino]methyl}oxolan-3-yl]oxy}(2-cyanoethoxy)sulfanylidene-λ$^5$-phosphanyl)amino]methyl}-4-fluorooxolan-3-yl O-2-cyanoethyl phosphonothioate (181)

To a mixture of O-((2R,3R,4R,5R)-5-(6-benzamido-9H-purin-9-yl)-4-fluoro-2-((tritylamino)methyl)tetrahydrofuran-3-yl)O-(2-cyanoethyl) (((2R,3R,4R,5R)-5-(6-benzamido-9H-purin-9-yl)-3-(((2-cyanoethoxy)(diisopropylamino)phosphino)oxy)-4-fluorotetrahydrofuran-2-yl)methyl)phosphoramidothioate (180, 0.70 g, 0.53 mmol) and 1H-1,2,3,4-tetrazole (37.2 mg, 0.53 mmol) in acetonitrile (5 mL) was bubbled hydrogen sulfide for 1 min. The resulting solution was sealed and stirred for 2 hours at ambient temperature. Upon completion, the resulting solution was applied onto a reversed phase C18

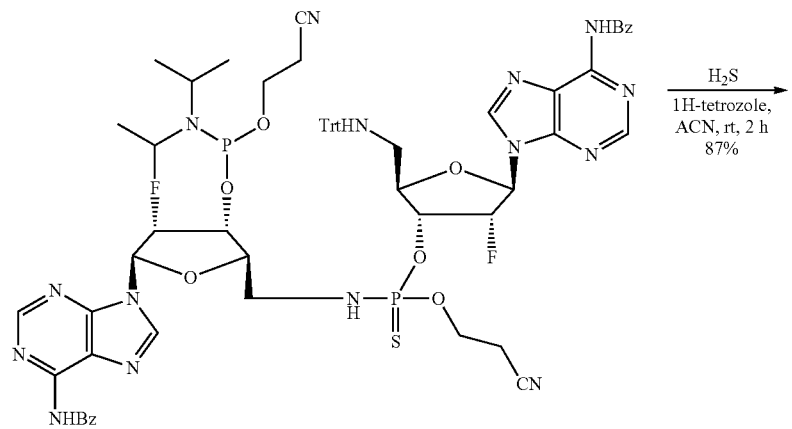

180

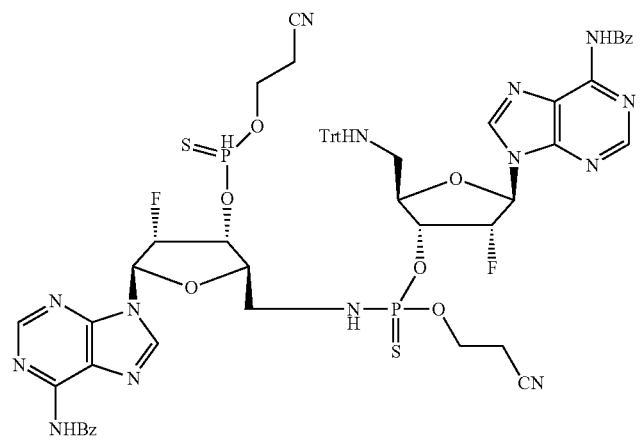

181 column, eluting with 70%~95% (25 min) acetonitrile in water to afford the title compound 181 as a colorless solid (580 mg, 87%): $^1$H NMR (300 MHz, DMSO-d$_6$) δ 11.24 (s, 2H), 8.87-8.55 (m, 3H), 8.20-7.90 (m, 5H), 7.75-6.98 (m, 21H), 6.57-5.44 (m, 8H), 4.72-4.32 (m, 2H), 4.28-3.87 (m, 3H), 3.42 (s, 1H), 3.25 (d, J=27.1 Hz, 3H), 2.85 (dt, J=51.9, 5.8 Hz, 2H), 2.31 (s, 1H); $^{19}$F NMR (282 MHz, DMSO-d$_6$) δ −202.87, −203.12, −203.34, −203.71, −203.95, −204.02, −204.35; $^{31}$P NMR (121 MHz, DMSO-d$_6$) δ 74.43, 74.07, 4.62, 4.62, −1.59, −1.67, −2.54, −2.71, −2.87; LC/MS (ESI, m/z): [(M+1)]$^+$=1251.0.

Step 6

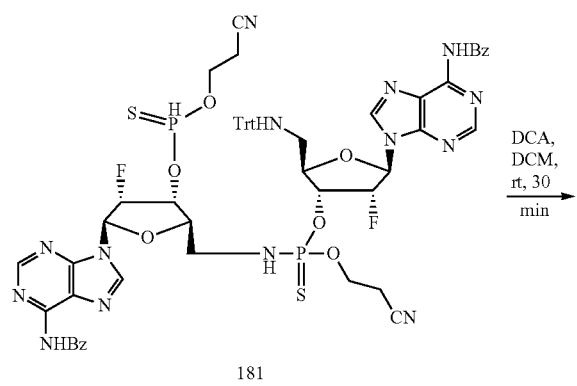

181

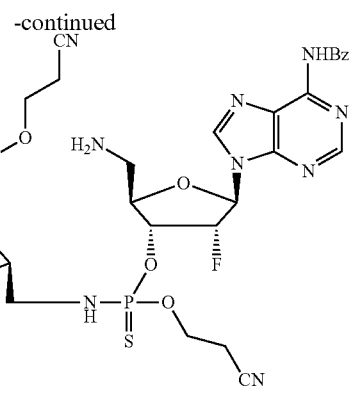

182

O-(2R,3R,4R,5R)-2-{[({[(2R,3R,4R,5R)-2-(aminomethyl)-5-(6-benzamido-9H-purin-9-yl)-4-fluorooxolan-3-yl]oxy}(2-cyanoethoxy)sulfanylidene-λ?-phosphanyl)amino]methyl}-5-(6-benzamido-9H-purin-9-yl)-4-fluorooxolan-3-yl O-2-cyanoethyl phosphonothioate (182)

A solution of O-(2R,3R,4R,5R)-5-(6-benzamido-9H-purin-9-yl)-2-{[({[(2R,3R,4R,5R)-5-(6-benzamido-9H-purin-9-yl)-4-fluoro-2-{[(triphenylmethyl)amino]methyl}oxolan-3-yl]oxy}(2-cyanoethoxy)sulfanylidene-λ$^s$-phosphanyl)amino]methyl}-4-fluorooxolan-3-yl O-2-cyanoethyl phosphonothioate (181, 0.58 g, 0.46 mmol) in dichloromethane (10 mL) was treated with dichloroacetic acid (0.24 g, 1.05 mmol) for 30 min at ambient temperature. The resulting solution was used in the next step without any workup: LC/MS (ESI, m/z): [(M+1)]$^+$=1009.2.

Step 7

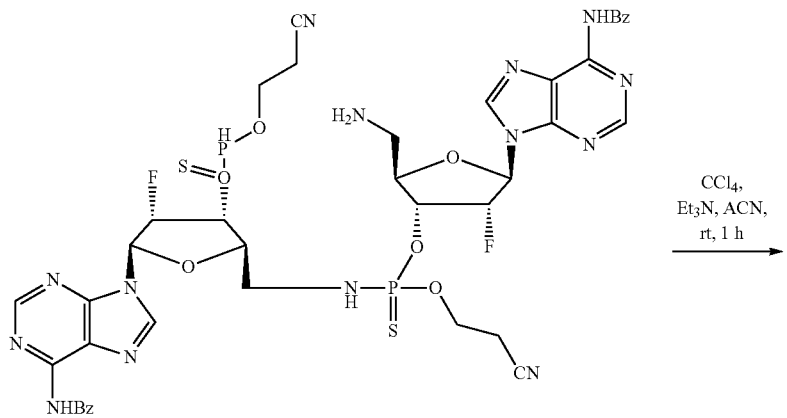

182

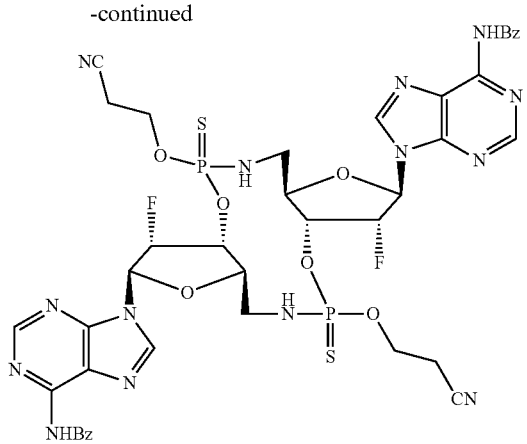

183

N-{9-[(1R,6R,8R,9R,10R,15R,17R,18R)-17-(6-benzamido-9H-purin-9-yl)-3,12-bis(2-cyanoethoxy)-9,18-difluoro-3,12-disulfanylidene-2,7,11,16-tetraoxa-4,13-diaza-3λ$^s$,12λ$^s$-diphosphatricyclo[13.3.0.0$^{6,10}$]octadecan-8-yl]-9H-purin-6-yl}benzamide (183)

To the above reaction solution was added acetonitrile (100 mL) followed by triethylamine (20 mL) and carbon tetrachloride (20 mL). The resulting solution was stirred for 1 h at ambient temperature. Upon completion, the resulting solution was concentrated under reduced pressure to afford the crude title compound 183 which was used directly in the next step without further purification: LC/MS (ESI, m/z): [(M+1)]$^+$=1007.2.

Step 8

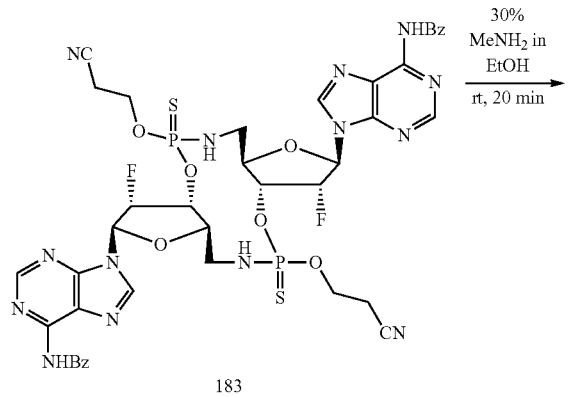

183

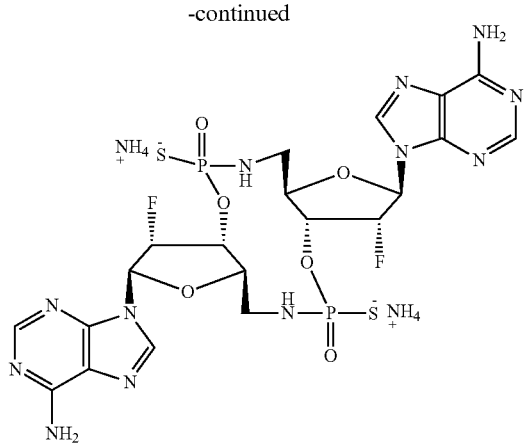

77

Diammonium [(1R,6R,8R,9R,10R,15R,17R,18R)-8,17-bis(6-amino-9H-purin-9-yl)-9,18-difluoro-3,12-dioxo-12-sulfanidyl-2,7,11,16-tetraoxa-4,13-diaza-3λ$^s$,12λ$^s$-diphosphatricyclo[13.3.0.0$^{6,10}$]octadecan-3-yl]sulfanide (77)

The above residue was treated with 30% solution of methanamine in ethanol (5 mL) for 20 min at ambient temperature. The volatile organic compounds were distilled out under reduced pressure. The residue was purified by Prep-HPLC with the following conditions: Column: Atlantis Prep T3 OBD Column, 19×250 mm 10 um; Mobile Phase A: water (plus 10 mmol/L of NH$_4$HCO$_3$), Mobile Phase B: ACN; Flow rate: 20 mL/min; Gradient: 2% B to 6% B in 10 min; Detector: 254/210 nm; to afford the first compound 77 diastereomer as a colorless solid (10.6 mg, retention time: 7.42 min): $^1$H NMR (300 MHz, D$_2$O) δ 8.15 (s, 2H), 8.06 (s, 2H), 6.33 (d, J=22.2 Hz, 2H), 5.80 (dd, J=51.2, 4.8 Hz, 2H), 5.65-5.49 (m, 2H), 4.32 (d, J=9.6 Hz, 2H), 3.49-3.32 (m, 2H), 3.13-2.99 (m, 2H); $^{19}$F NMR (282 MHz, D$_2$O) δ, −195.73; $^{31}$P NMR (121 MHz, D$_2$O) δ 57.00; LC/MS (ESI, m/z): [(M−2NH$_3$−1)]$^+$=690.9. And the slower peak at 8.25 min was a mixture of two isomers of 77 as a colorless solid

243
(12.1 mg): $^1$H NMR (300 MHz, D$_2$O) δ 8.37 (s, 0.34H), 8.14 (s, 1.7H), 7.92 (s, 1H), 7.86 (s, 1H), 6.26-5.91 (m, 3H), 5.71-5.19 (m, 3H), 5.47-5.19 (m, 2H), 4.37 (dd, J=27.2, 9.7 Hz, 3H), 3.54-3.38 (m, 2H), 3.14-2.92 (m, 2H); $^{19}$F NMR (282 MHz, D$_2$O) δ −195.78, −197.35; $^{31}$P NMR (121 MHz, D$_2$O) δ 59.32, 57.59; LC/MS (ESI, m/z): [(M−2NH$_3$−1)]$^−$ =690.9.
Diammonium (1R,6S,8R,9R,10R,15S,17R,18R)-8,17-bis(6-amino-9H-purin-9-yl)-9,18-difluoro-3,12-dioxo-4,7,13,16-tetraoxa-2,11-diaza-3λ$^s$,12λ$^s$-diphosphatricyclo[13.3.0.0$^{6,10}$]octadecane-3,12-bis(olate)
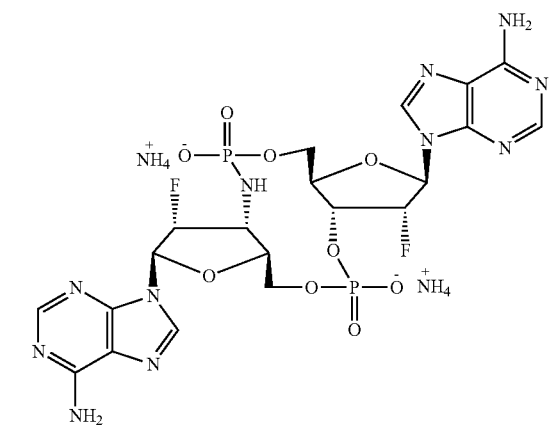
78
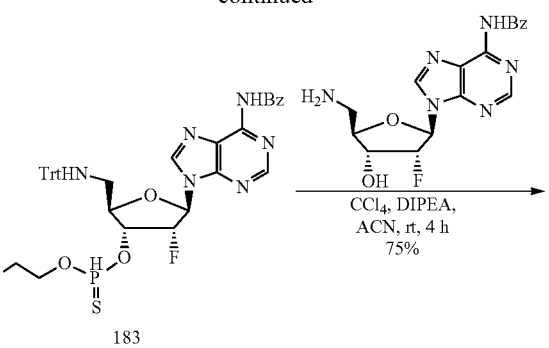
183
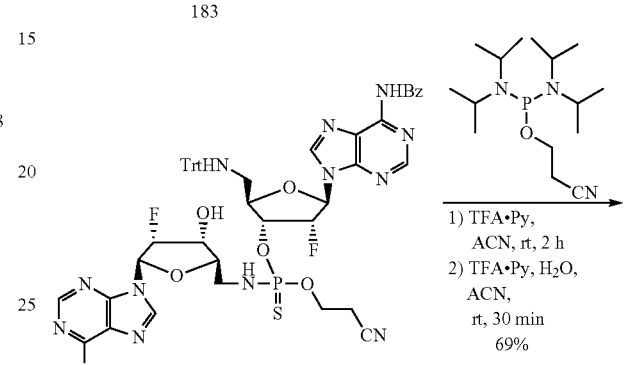
184
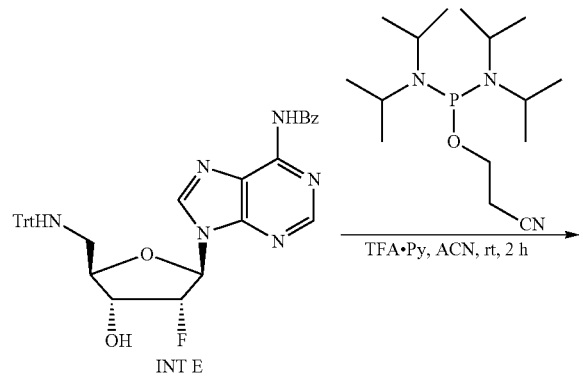
INT E
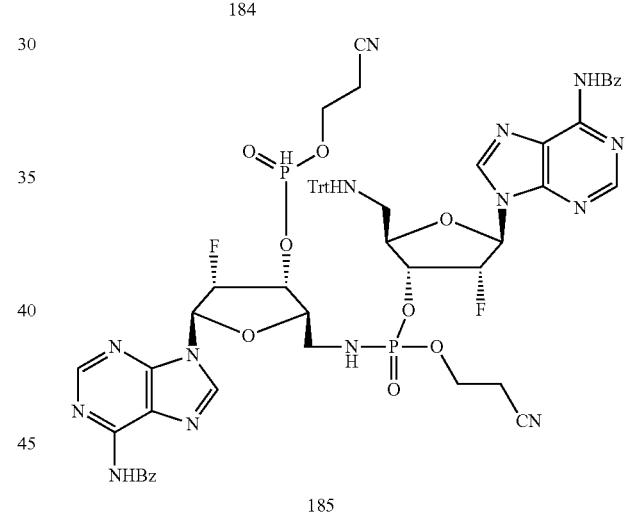
185
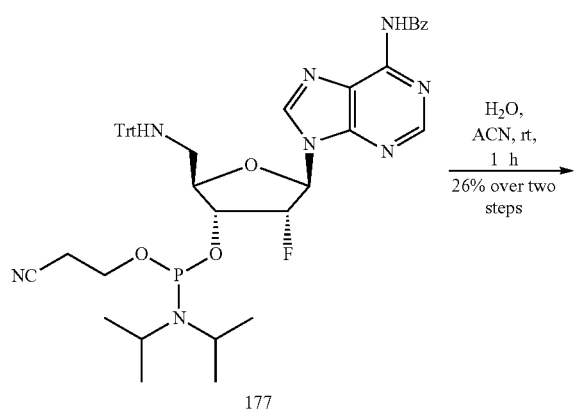
177
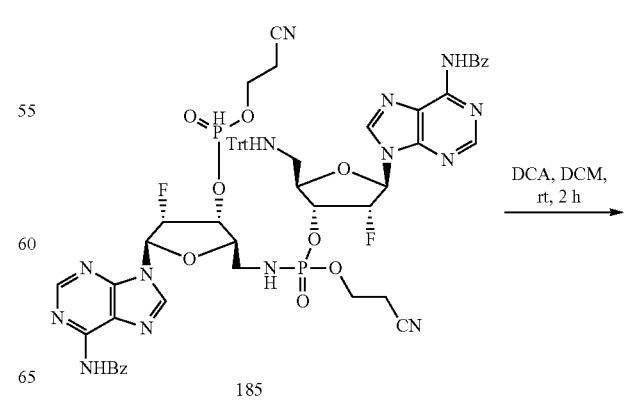
185

245
-continued
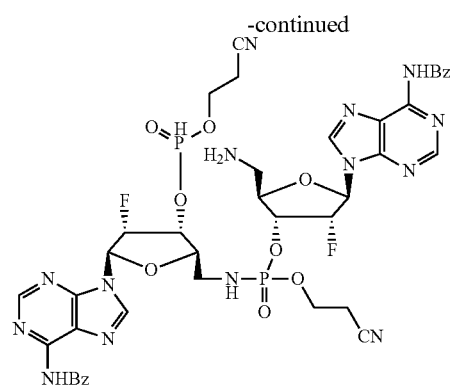
186
CCl4, TEA,
ACN, rt,
2 h
→
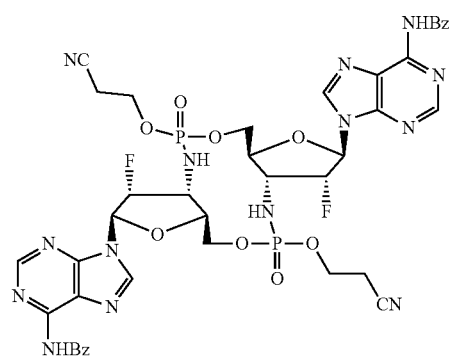
187
30% MeNH2
In EtOH
rt, 4 h
3% over
3 steps
→
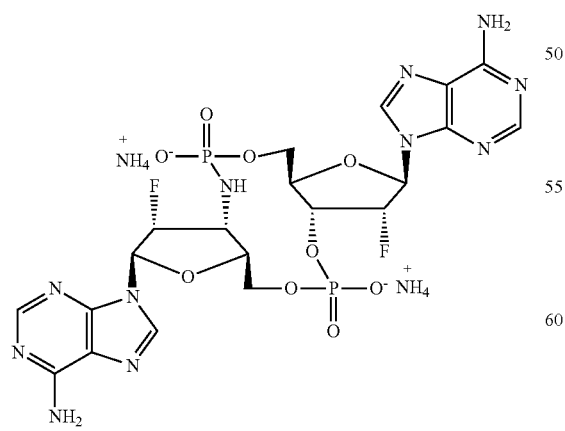
78
246
Step 1
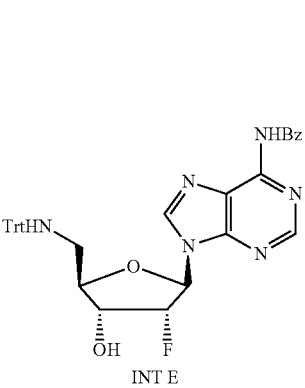 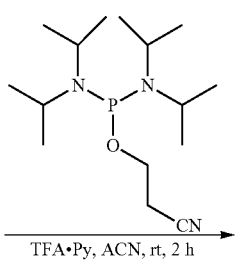
INT E
TFA·Py, ACN, rt, 2 h
→
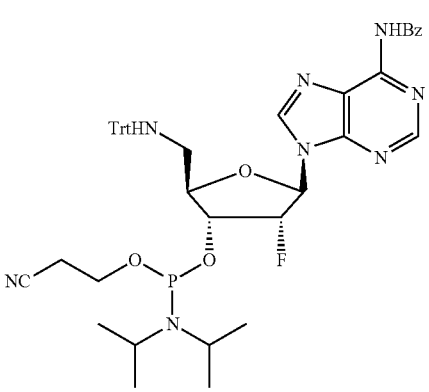
177
H2O,
ACN,
rt, 1 h
26%
over
two
steps
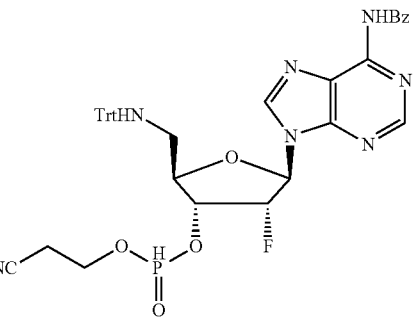
183

247

(2R,3R,4R,5S)-5-(6-benzamido-9H-purin-9-yl)-4-fluoro-2-((tritylamino)methyl)tetrahydrofuran-3-yl (2-cyanoethyl) phosphonate (183)

To a solution of N-(9-((2S,3R,4R,5R)-3-fluoro-4-hydroxy-5-((tritylamino)methyl)tetrahydrofuran-2-yl)-9H-purin-6-yl)benzamide (INT-E, 1.00 g, 1.63 mmol) in acetonitrile (5 mL) were added pyridinium trifluoroacetate (0.47 g, 2.45 mmol) and 3-(bis[bis(propan-2-yl)amino]phosphanyloxy)propanenitrile (0.98 g, 3.26 mmol) at ambient temperature. After stirring for 2 hours, another batch of pyridinium trifluoroacetate (0.63 g, 3.26 mmol) was added followed by the addition of water (0.29 mL, 16.3 mmol). The resulting solution was stirred for 1 h at ambient temperature. Upon completion, the resulting solution was applied onto a reversed phase C18 column, eluted with 5%~80% (30 min) acetonitrile in water to afford the title compound 183 as a colorless solid (0.58 g, 26%): $^1$H NMR (400 MHz, DMSO-$d_6$) δ 11.26-11.23 (m, 1H), 8.75-8.57 (m, 1H), 8.41-8.31 (m, 1H), 8.16-8.00 (m, 2H), 7.70-7.56 (m, 3H), 7.43-7.39 (m, 6H), 7.33-7.23 (m, 6H), 7.19-7.16 (m, 3H), 6.55-6.32 (m, 1H), 6.24-5.64 (m, 2H), 4.43-4.41 (m, 1H), 4.32-4.24 (m, 2H), 3.25-2.91 (m, 2H), 2.53-2.51 (m, 1H), 2.42-2.27 (m, 1H); $^{19}$F NMR (376 MHz, DMSO-$d_6$) δ −203.18; $^{31}$P NMR (162 MHz, DMSO-$d_6$) δ 8.89; LC/MS (ESI, m/z): [(M+1)]$^+$= 815.0.

Step 2

248

(2R,3R,4R,5R)-5-(6-benzamido-9H-purin-9-yl)-4-fluoro-2-((tritylamino)methyl)tetrahydrofuran-3-yl (2-cyanoethyl) (((2R,3R,4R,5R)-5-(6-benzamido-9H-purin-9-yl)-4-fluoro-3-hydroxytetrahydrofuran-2-yl)methyl)phosphoramidate (184)

To a mixture of (2R,3R,4R,5S)-5-(6-benzamido-9H-purin-9-yl)-4-fluoro-2-((tritylamino)methyl)tetrahydrofuran-3-yl (2-cyanoethyl) phosphonate (100 mg, 0.14 mmol) and N-(9-((2S,3R,4R,5R)-5-(aminomethyl)-3-fluoro-4-hydroxytetrahydrofuran-2-yl)-9H-purin-6-yl)benzamide (183, 51 mg, 0.14 mmol) in N-methyl pyrrolidone (1 mL) were added N,N-diisopropylethylamine (45 mg, 0.35 mmol) and carbon tetrachloride (53 mg, 0.34 mmol). The resulting solution was stirred for 4 hours at ambient temperature. Upon completion, the resulting solution was applied onto a silica gel column, eluted with 1%~30% methanol in dichloromethane to afford the title compound 184 as a colorless solid (113 mg, 75%): $^1$H NMR (300 MHz, DMSO-$d_6$) δ 11.21 (s, 2H), 8.78-8.57 (m, 3H), 8.24-8.20 (m, 1H), 8.12-7.96 (m, 4H), 7.71-7.46 (m, 7H), 7.47-7.28 (m, 6H), 7.33-7.03 (m, 9H), 6.48-6.25 (m, 2H), 6.18-5.45 (m, 4H), 4.60-4.45 (m, 1H), 4.38-4.30 (m, 1H), 4.15-3.96 (m, 4H), 3.40-3.00 (m, 2H), 2.91-2.69 (m, 2H); $^{31}$P NMR (162 MHz, DMSO-$d_6$) δ 9.98, 9.93, 6.78; LC/MS (ESI, m/z): [(M+1)]$^+$= 1102.0.

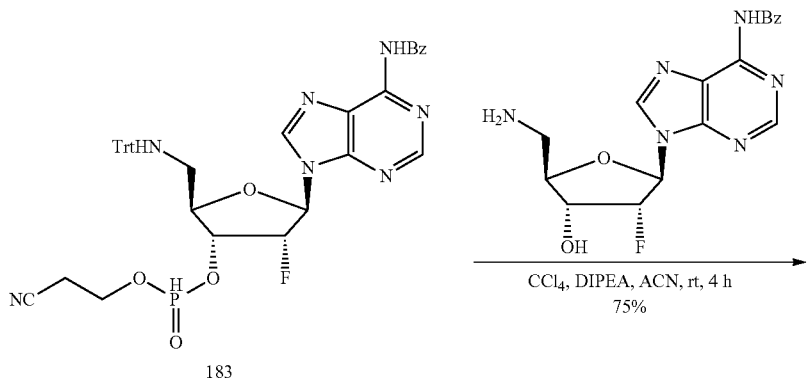

183

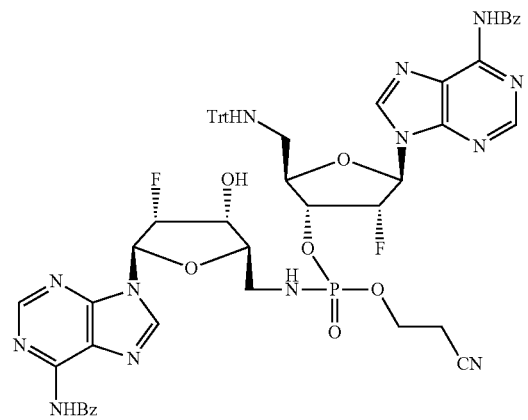

184

Step 3

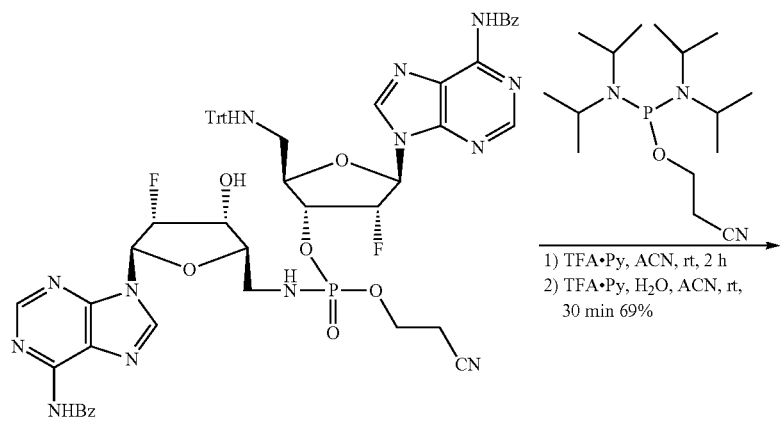

(2R,3R,4R,5R)-5-(6-benzamido-9H-purin-9-yl)-2-{
[({[(2R,3R,4R,5R)-5-(6-benzamido-9H-purin-9-yl)-
4-fluoro-2-{[(triphenylmethyl)amino]
methyl}oxolan-3-yl]oxy}(2-cyanoethoxy)
phosphoryl)amino]methyl}-4-fluorooxolan-3-yl
2-cyanoethyl phosphonate (185)

To a solution of (2R,3R,4R,5R)-5-(6-benzamido-9H-purin-9-yl)-4-fluoro-2-((tritylamino)methyl)tetrahydrofuran-3-yl (2-cyanoethyl) (((2R,3R,4R,5R)-5-(6-benzamido-9H-purin-9-yl)-4-fluoro-3-hydroxytetrahydrofuran-2-yl)methyl)phosphoramidate (184, 200 mg, 0.18 mmol) in acetonitrile (1 mL) were added 3-([bis[bis(propan-2-yl)amino]phosphanyl]oxy)propanenitrile (109 mg, 0.36 mmol) and pyridinium trifluoroacetate (53 mg, 0.27 mmol) at ambient temperature. The resulting solution was stirred for another 2 hours followed by the addition of the second batch of pyridinium trifluoroacetate (106 mg, 0.55 mmol) and water (32.7 mg, 1.8 mmol,). The resulting solution was stirred for 30 min at ambient temperature and applied onto a reversed phase C18 column, eluting with 0-65% (30 min) acetonitrile in water to afford the title compound 185 as a colorless solid (153 mg, 69%): $^1$H NMR (300 MHz, DMSO-d$_6$) δ 11.28-11.23 (m, 2H), 8.82-8.61 (m, 3H), 8.31-8.19 (m, 1H), 8.12-7.99 (m, 4H), 7.72-7.06 (m, 22H), 6.63-6.23 (m, 2H), 6.25-5.31 (m, 4H), 4.46-3.90 (m, 6H), 3.50-3.05 (m, 4H), 3.05-2.70 (m, 4H); $^{19}$F NMR (282 MHz, DMSO-d$_6$) δ −202.92, −202.93, −202.96, −202.97, −203.12, −203.13, −203.68, −203.70, −203.73, −203.93, −203.96, −204.03; $^{31}$P NMR (121 MHz, DMSO-d$_6$) δ 9.98, 9.92, 9.89, 9.84, 9.78, 9.04, 8.91, 8.84; LC/MS (ESI, m/z): [(M+1)]$^+$=1219.4.

Step 4

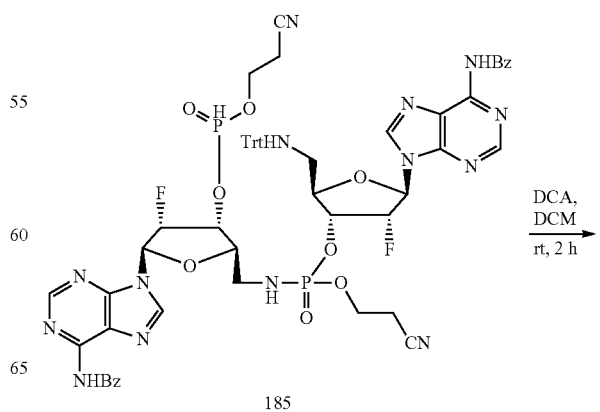

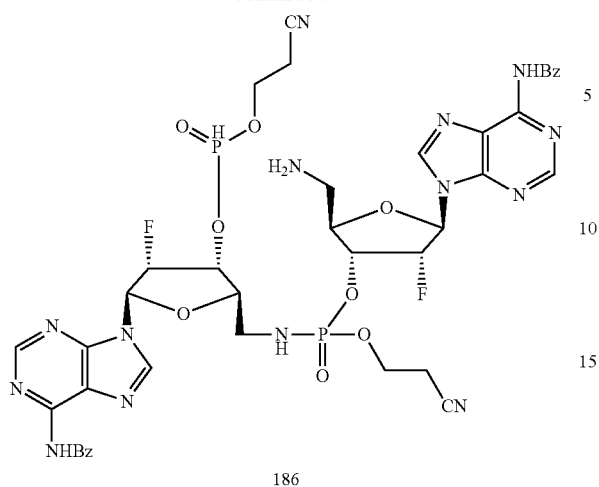

186

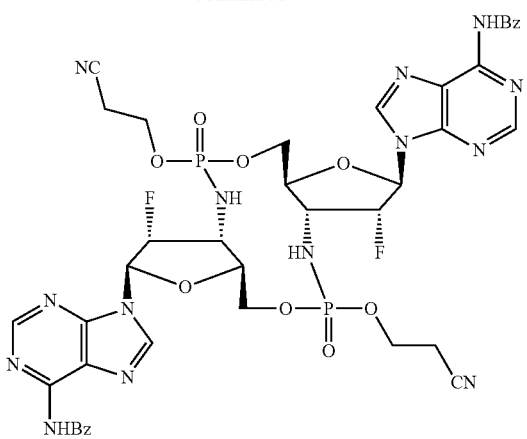

187

(2R,3R,4R,5R)-2-{[({[(2R,3R,4R,5R)-2-(aminomethyl)-5-(6-benzamido-9H-purin-9-yl)-4-fluorooxolan-3-yl]oxy}(2-cyanoethoxy)phosphoryl)amino]methyl}-5-(6-benzamido-9H-purin-9-yl)-4-fluorooxolan-3-yl 2-cyanoethyl phosphonate (186)

N-{9-[(1R,6S,8R,9R,10R,15S,17R,18R)-17-(6-benzamido-9H-purin-9-yl)-3,12-bis(2-cyanoethoxy)-9,18-difluoro-3,12-dioxo-4,7,13,16-tetraoxa-2,11-diaza-3λ$^s$,12λ$^s$-diphosphatricyclo[13.3.0.0$^{6,10}$]octadecan-8-yl]-9H-purin-6-yl}benzamide (187)

A solution of (2R,3R,4R,5R)-5-(6-benzamido-9H-purin-9-yl)-2-{[(({[(2R,3R,4R,5R)-5-(6-benzamido-9H-purin-9-yl)-4-fluoro-2-{[(triphenylmethyl)amino]methyl}oxolan-3-yl]oxy}(2-cyanoethoxy)phosphoryl)amino]methyl}-4-fluorooxolan-3-yl 2-cyanoethyl phosphonate (185, 260 mg, 0.21 mmol) in dichloromethane (10 mL) was treated with 2,2-dichloroacetic acid (109.3 mg, 0.85 mmol) for 2 hours at ambient temperature. Upon completion, the resulting solution was concentrated under reduced pressure and the residue was used in the next step without further purification: LC/MS (ESI, m/z): [(M+1)]$^+$=977.1.

To a solution of the compound 186 in acetonitrile (40 mL) were added triethylamine (0.75 mL, 5.34 mmol) and carbon tetrachloride (0.82 g, 5.34 mmol) at ambient temperature. After stirring for 2 hours, the resulting solution was concentrated under reduced pressure and the residue was used in the next step without further purification: LC/MS (ESI, m/z): [(M+1)]$^+$=975.5.

Step 5

Step 6

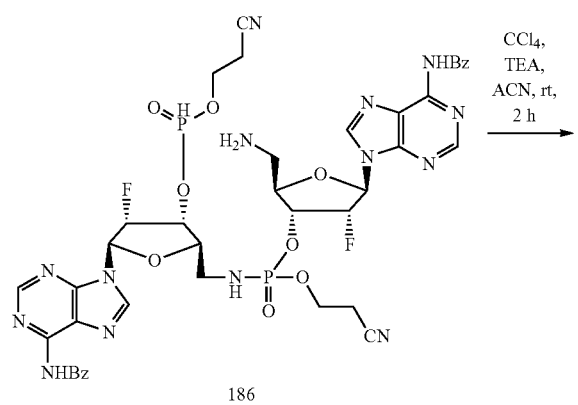

186

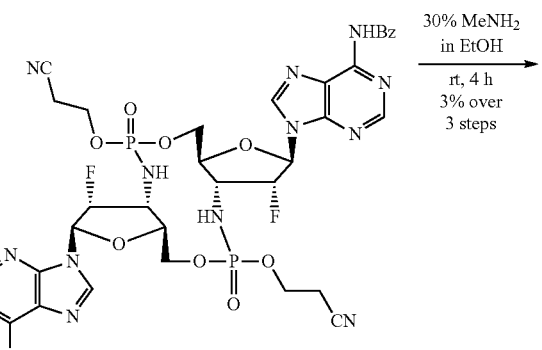

187

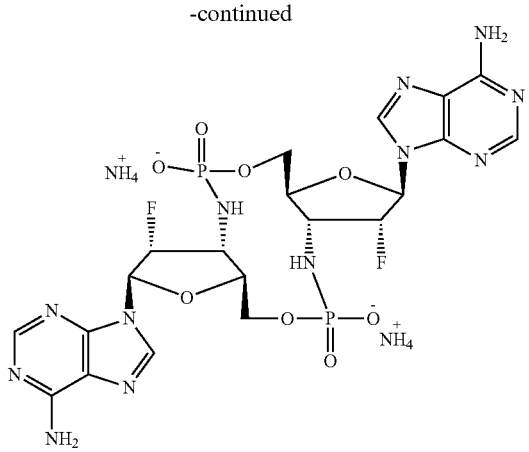

78

Diammonium (1R,6S,8R,9R,10R,15S,17R,18R)-8,17-bis(6-amino-9H-purin-9-yl)-9,18-difluoro-3,12-dioxo-4,7,13,16-tetraoxa-2,11-diaza-3$\lambda^s$,12$\lambda^s$-diphosphatricyclo[13.3.0.0$^{6,10}$]octadecane-3,12-bis (olate) (78)

The above crude compound 187 was treated with a solution of methylamine in ethanol (10 mL, 30%, w/w) for 30 min at ambient temperature. Upon completion, the resulting solution was concentrated under reduced pressure and the residue was purified by Prep-HPLC with the following conditions: Column: Atlantis Prep T3 OBD Column, 19×250 mm, 10 um; Mobile Phase A: water (plus 20 mmol/L of NH$_4$HCO$_3$), Mobile Phase B: ACN; Flow rate: 20 mL/min; Gradient: 0% B to 14% B in 20 min; Detector: 254/220 nm; Retention time: 11.50 min; to afford the title compound 78 as a colorless solid (3.7 mg, 3%): $^1$H NMR (300 MHz, D$_2$O) δ 8.12 (s, 2H), 7.65 (s, 2H), 6.23 (d, J=20.7 Hz, 2H), 5.52-5.22 (m, 4H), 4.36 (d, J=9.3 Hz, 2H), 3.47 (dd, J=13.9, 3.3 Hz, 2H), 3.08 (dd, J=13.8, 7.3 Hz, 2H); $^{19}$F NMR (282 MHz, D$_2$O) δ -196.79; $^{31}$P NMR (121 MHz, D$_2$O) δ 7.98; LC/MS (ESI, m/z): [(M–2NH$_3$–1)]$^-$=659.0

Biological Assays

STING pathway activation by the compounds described herein was measured using THP1-Dual™ cells. These cells are THP1 monocytes that have been modified to be reporters for the NF☐B pathway (by inducing secreted embryonic alkaline phosphatase (SEAP) expression) and the IRF pathway (by inducing secreted luciferase (LUCIA)). Both of these pathways are activated by STING agonists in these cells.

THP1 Dual™ cells (obtained from Invivogen) are maintained in a cell growth medium that includes Roswell Park Memorial Institute medium (RPMI), 10% fetal calf serum (FCS), 100 U/ml Pen/Strep, 2 mM L-glut, 10 mM Hepes, and 1 mM sodium pyruvate. Prior to the assay, the cells were transferred to an assay medium that includes is RPMI, 5% FCS, 100 U/ml Pen/Strep, 2 mM L-glut, 10 mM Hepes, and 1 mM sodium pyruvate. Cells were then counted and evaluated for viability by trypan blue exclusion assay.

Compounds were dissolved in water or DMSO depending, for example, on their solubility in water or DMSO. The compounds were then diluted in the assay medium and plated into wells of a 384-well tissue culture plate in 25 DL portions. Cells are then added in 25 DL assay medium to result in a final cell concentration of 80,000 cells per well.

For each set of compounds, two plates were prepared: one plate that was subjected to a 24-hour assay duration, and one plate that was subjected to a 48-hour assay duration. The plates are incubated during their respective assay durations at 37° C., with 5% CO$_2$.

To carry out the secreted embryonic alkaline phosphatase reporter, 10 ☐L of cell supernatant was mixed with 90 µL of QUANTI-Blue in a flat-bottom 384 well plate. The plates were incubated at 37'C for 1-2 hours. SEAP activity was measured using a spectrophotometer set at 620 nm. In the secreted luciferase (i.e., Lucia) assay, 10 ☐L of THP1-Blue™ WASG cell supernatant was plated, then 50 µL Quanti LUC Solution was added. Luminescence of the wells was then measured.

Table 2 below depicts biological data of the compounds that were assayed using the above procedures.

TABLE 2

| Compound | IRF3 (EC$_{50}$ µM) | NFκB (EC$_{50}$ µM) |
|---|---|---|
| 71 | 1-10 | 1-10 |
| 72-0A1 | 1-10 | <1 |
| 72-0A2 | 1-10 | 1-10 |
| 72-0A3 | 1-10 | <1 |
| 72-0B1 | 1-10 | 50-100 |
| 72-0B2 | 10-49 | 10-49 |
| 73 | 10-49 | 1-10 |
| 74-0A1 | 1-10 | 1-10 |
| 74-0A2 | 1-10 | <1 |
| 74-0B0 | 10-49 | 10-49 |
| 74-0B1 | 10-49 | 50-100 |
| 75 | 10-49 | 10-49 |
| 76-0A1 | 10-49 | 1-10 |
| 76-0A2 | 10-49 | 10-49 |
| 76-0A3 | 1-10 | <1 |
| 76-0B1 | 10-49 | 50-100 |
| 77 | 50-100 | 50-100 |
| 78 | 50-100 | 50-100 |

Compounds can also be assayed using the procedures described in, e.g., WO 2015/077354.

A number of embodiments of the invention have been described. Nevertheless, it will be understood that various modifications may be made without departing from the spirit and scope of the invention. Accordingly, other embodiments are within the scope of the following claims.

What is claimed is:

1. A method for modulating STING activity, the method comprising contacting STING with a compound of the formula

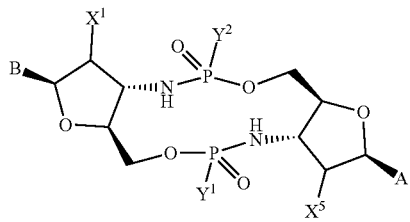

wherein

X$^1$ and X$^5$ are each independently halo or —OH;

Y$^i$ and Y$^2$ are each independently —OH or —SH; and

A and B are each independently

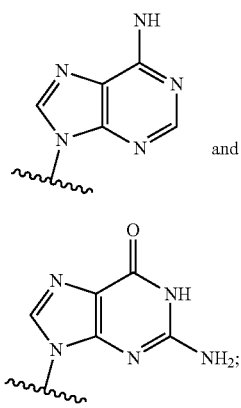

or a stereoisomer or a pharmaceutically acceptable salt thereof.

2. The method of claim 1, wherein the modulating comprises agonizing STING.

3. The method of claim 1, wherein the method comprises administering the compound to a subject having a disease in which repressed or impaired STING signaling contributes to the pathology and/or symptoms and/or progression of the disease.

4. The method of claim 3, wherein the subject is a human.

5. The method of claim 4, wherein the disease is cancer.

6. The method of claim 5, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma.

7. The method of claim 6, wherein the cancer is a refractory cancer.

\* \* \* \* \*

UNITED STATES PATENT AND TRADEMARK OFFICE
CERTIFICATE OF CORRECTION

PATENT NO. : 10,961,270 B2  
APPLICATION NO. : 16/778281  
DATED : March 30, 2021  
INVENTOR(S) : Gary Glick et al.

Page 1 of 1

It is certified that error appears in the above-identified patent and that said Letters Patent is hereby corrected as shown below:

In the Claims

In Claim 1, Column 254, Line 66 (Approx.), delete "$Y^i$" and insert -- $Y^1$ --, therefor.

In Claim 1, Column 255, Line 1-10, delete " 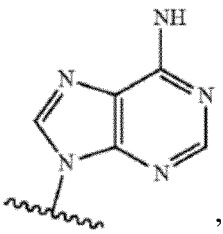 " and insert -- 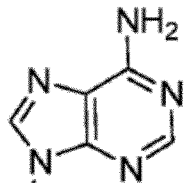 --, therefor.

In Claim 6, Column 256, Line 18, delete "Wilm's tumor," and insert -- Wilms' tumor, --, therefor.

Signed and Sealed this  
Fourteenth Day of December, 2021

Drew Hirshfeld  
*Performing the Functions and Duties of the*  
*Under Secretary of Commerce for Intellectual Property and*  
*Director of the United States Patent and Trademark Office*